(12) United States Patent
Carruthers et al.

(10) Patent No.: US 8,642,583 B2
(45) Date of Patent: Feb. 4, 2014

(54) SEROTONIN RECEPTOR MODULATORS

(75) Inventors: Nicholas I. Carruthers, Poway, CA (US); Wenying Chai, San Diego, CA (US); Jill A. Jablonowski, San Diego, CA (US); Chandravadan R. Shah, San Diego, CA (US); Brock T. Shireman, Poway, CA (US); Devin M. Swanson, San Diego, CA (US); Vi T. Tran, New York, NY (US); Victoria D. Wong, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 44 days.

(21) Appl. No.: 13/126,223

(22) PCT Filed: Oct. 29, 2009

(86) PCT No.: PCT/US2009/062627
§ 371 (c)(1),
(2), (4) Date: Apr. 27, 2011

(87) PCT Pub. No.: WO2010/059393
PCT Pub. Date: May 27, 2010

(65) Prior Publication Data
US 2011/0207714 A1 Aug. 25, 2011

Related U.S. Application Data

(60) Provisional application No. 61/109,903, filed on Oct. 30, 2008.

(51) Int. Cl.
*A61K 31/397* (2006.01)
*C07D 205/04* (2006.01)

(52) U.S. Cl.
USPC ...... 514/210.01; 514/327; 514/429; 546/216; 548/952; 548/577

(58) Field of Classification Search
USPC ............. 514/210.01, 327, 429; 546/216; 548/952, 577
See application file for complete search history.

(56) References Cited

U.S. PATENT DOCUMENTS

| | | | | |
|---|---|---|---|---|
| 3,577,415 | A | | 5/1971 | Cale et al. |
| 4,146,630 | A | | 3/1979 | Kampe et al. |
| 5,130,309 | A | * | 7/1992 | Shanklin et al. ......... 514/210.01 |
| 5,629,325 | A | * | 5/1997 | Lin et al. ....................... 514/318 |
| 6,110,937 | A | * | 8/2000 | Loughhead et al. ......... 514/317 |

FOREIGN PATENT DOCUMENTS

| | | |
|---|---|---|
| DE | 1 964 510 A1 | 7/1970 |
| DE | 27 37 630 A1 | 3/1979 |
| DE | 27 37 630 C2 | 3/1979 |
| EP | 0 600 717 A1 | 11/1993 |
| EP | 0 863 136 A1 | 2/1997 |
| JP | 03 264 583 | 11/1991 |
| WO | WO 99 23073 A1 | 5/1999 |
| WO | WO 02 18333 A1 | 3/2002 |
| WO | WO 2004 113297 A2 | 12/2004 |
| WO | WO 2005 047246 A1 | 5/2005 |
| WO | WO 2006 025517 A1 | 3/2006 |
| WO | WO 2007 038459 A2 | 4/2007 |
| WO | WO 2007 072150 A2 | 6/2007 |
| WO | WO 2007 116230 A1 | 10/2007 |
| WO | WO 2008 009495 A1 | 1/2008 |
| WO | WO 2008 023258 A1 | 2/2008 |
| WO | WO 2008 023720 A1 | 2/2008 |
| WO | WO 2008 077265 A1 | 7/2008 |

OTHER PUBLICATIONS

Glennon et al. "Serotonin/\ . . . " Neuropsychophrammacology:5th generation progress p. 1-17 (2000).*
Hollady et al. "Preparation of hetero . . . " CA131:73563 (1999).*
Improper Markush "supplemental examination guidelines" p. 1, 64-67 (2011).*
Leopoldo et al. "5HT7 receptor . . . " Exp. Opin.ther. patent 20(6) 739-754 (2010).*
Lin et al. "Pyridyloxymethyl . . . " CA137:169427 (2002).*
Lopez-Rodrigues et al. "Serotonin 5HT7 . . . " Curr. Med. Chem. 4, p. 1-12 (2004).*
Patani et al. "Biosisosterism . . . " Chem. Rev. v.96, 3147-3176 (1996).*
International Search Report for Corresponding International Application PCT/US2009/062623 Mailed on Apr. 12, 2010.
International Search Report for Corresponding International Application PCT/US2009/062627 Mailed Apr. 1, 2010.
U.S. Appl. No. 61/109,899, filed Oct. 30, 2008, Carruthers et al.
Bagshawe et al. "Antibody-Directed Enzyme Prodrug Therapy: A Review" Drug Dev Res 1995 vol. 34 pp. 220-230.
Berge et al. "Pharmaceutical Salts". J. Pharm Sci 1977 vol. 66 pp. 1-19.
Bertolini et al."A New Rational Hypothesis for the Pharmacophore of the Active Metabolite of Leflunomide, A Potent Immunosuppressive Drug" J Med Chem 1997 vol. 40 pp. 2011-2016.
Bodor et al. "Novel Approaches to the Design of Safer Drugs: Soft Drugs and Site-Specific Chemical Delivery Systems" Adv Drug Res 1984 vol. 13 pp. 224-331.
Bundgaard et al Design of Prodrugs H Bundgaard Ed. Elsevier 1985.
Fleisher et al "Improved Review Oral Drug Delivery: Solubility Limitations of Prodrugs Overcome by the Use" Adv Drug Delivery Rev 1996 vol. 19 pp. 115-130.

(Continued)

*Primary Examiner* — Celia Chang

(57) ABSTRACT

The biphenyic compounds of formula (I) are serotonin modulators useful in the treatment of serotonin-mediated diseases.

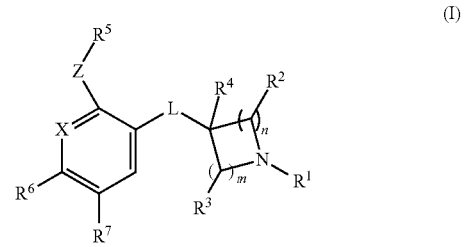

(I)

21 Claims, No Drawings

(56) References Cited

OTHER PUBLICATIONS

Greene et al Protecting Groups in Organic Synthesis 3$^{rd}$ Ed. T.W. Greene and P.G. Wuts John Wiley and Sons 1999.

Harrak et al. The First Synthesis of Spiro (1,4-Benzodioxin-2,4'-Piperidines) and Spiro (1,4-Benzodioxin-2,3'-Pyrrolidines) Synlett 2003 vol. 6 pp. 813-816.

Hoyer et al "Molecular, Pharmacological and Functional Diversity of 5-HT Receptors" Pharmacol Biochem Behav 2002 vol. 71 pp. 533-554.

Larsen et al Design and Application of Prodrugs, Drug Design and Development Krogsgaard-Larsen et al Harwood Academic Publishers 1991.

Nahm et al "N-Methoxy-Methylamides As Effective Acylating Agents" Tetrahderon Letters 1981 vol. 22(39) pp. 3815-3818.

Paulekuhn et al "Trends in Active Pharmaceutical Ingredient Salt Selction Based on Analysis of the Orange Book Database" J Med Chem 2007 vol. 50 pp. 6665-6672.

Robinson et al "Discovery of the Hemifumarate and (A-L-alanyloxy)Methyl Ether As Prodrugs of an Antirheumatic Oxindloe: Prodrugs for the Enolic OH Group" J Med Chem 1996 Vlume 39 pp. 10-18.

Roth et al "The Multiplicity of Serotonin Receptors: Uselessly Diverse Molecules or an Embarassment of Riches?" The Neuroscientist 2000 vol. 6(4) pp. 252-262.

Shan et al "Prodrug Strategies Based on Intramolecular Cyclizaton Reactions" J Pharm Sci 1997 vol. 86(7) pp. 765-767.

Shimizu et al "Industrial Synthesis of Maxacalcitol, The Antihyperparathyroidism and Antipsoriatic Vitamin D3 Analogue Exbiting Low Calcemic Activity" Organic Process Research and Development 2005 vol. 9 pp. 278-287.

Stahl et al Essential Psychopharmacology 2000 2nd Ed Cambridge Univ Press Cambridge UK 2000.

Stahl and Wermuth Eds Handbook of Pharmaceutical Salts, Propeties, Selection, and Use Wiley-VCH and VHCA Zurich 2002.

Chappie et al "Discovery of a Series of 6,7-Dimethoxy-4-Pyrrolidylquinazoline PDE10A Inhibitors" Journal of Medicinal Chemistry 2007 vol. 50(2) pp. 182-185.

\* cited by examiner

SEROTONIN RECEPTOR MODULATORS

CROSS-REFERENCE TO RELATED APPLICATIONS

This application is a national phase of International Application No. PCT/US2009/062627 filed Oct. 29, 2009 and claims benefit of priority under 35 U.S.C. §119(e) of U.S. Provisional Application No. 61/109,903 filed on Oct. 30, 2008.

FIELD OF THE INVENTION

There is provided by the present invention compounds that are serotonin receptor modulators. More particularly, there is provided by the present invention certain compounds that are serotonin receptor modulators useful for the treatment of disease states mediated by serotonin receptor activity.

BACKGROUND OF THE INVENTION

Serotonin (5-hydroxytryptamine, 5-HT) is a major neurotransmitter eliciting effects via a multiplicity of receptors. To date, at least fifteen different 5-HT receptors have been identified, largely as the result of cDNA cloning. These receptors have been grouped into seven families (5-HT$_1$ through 5-HT$_7$) (Hoyer, D. et al. *Pharmacol. Biochem. Behav.*, 2002, 71, 533-554).

Fourteen of the fifteen cloned 5-HT receptors are expressed in the brain. 5-HT is implicated in many disease states, particularly conditions of the central nervous system including; depression, anxiety, schizophrenia, eating disorders, obsessive compulsive disorder, learning and memory dysfunction, migraine, chronic pain, sensory perception, motor activity, temperature regulation, nociception, sexual behavior, hormone secretion, and cognition.

The identification of multiple 5-HT receptors has provided the opportunity to characterize existing therapeutic agents thought to act via the serotonergic system. Consequently, this has led to the realization that many drugs have non-selective properties (Roth, B. L. et al., *Neuroscientist*, 2000, 6(4), 252-262). For example, the antipsychotic drugs, clozapine, chlorpromazine, haloperidol and olanzapine exhibit affinities for multiple serotonin receptors in addition to other families of receptors. Similar behavior has been noted for antidepressants including imipramine, nortriptaline, fluoxetine and sertraline. Similarly, the anti-migraine agent sumatriptan exhibits high affinity for several serotonin receptors. While the lack of selectivity often contributes to a favorable therapeutic outcome, it can also cause undesirable and dose-limiting side effects (Stahl, S. M., *Essential Psychopharmacology*, 2$^{nd}$ ed., Cambridge University Press, Cambridge, U.K., 2000). For example, the inhibition of serotonin and norepinephrine uptake together with 5-HT$_2$ receptor blockade is responsible for the therapeutic effects of the tricyclic antidepressants. In contrast, their blockade of histamine H$_1$, muscarinic and alpha-adrenergic receptors can lead to sedation, blurred vision and orthostatic hypertension respectively. Likewise, the atypical antipsychotics, including olanzapine and clozapine, are considered to have positive therapeutic effects attributable to their actions at 5-HT$_2$, D$_2$ and 5-HT$_7$ receptors. Conversely, their side effect liability is due to their affinities for a range of dopaminergic, serotonergic and adrenergic receptors.

Elucidating selective ligands has the potential to ameliorate untoward pharmacologies and provide novel efficacious therapies. More importantly, the ability to obtain compounds which portray receptor selectivity provides the prospect to target distinct therapeutic mechanisms and improve clinical responses with a single drug. Consequently, there remains a need for potent serotonin receptor modulators with desirable pharmaceutical properties.

SUMMARY OF THE INVENTION

Certain compounds have now been found to have 5HT-modulating activity, in particular 5HT$_7$ and/or serotonin transporter modulating activity. In particular, the invention is directed to the general and preferred embodiments defined, respectively, and by the independent and dependent claims appended hereto, which are incorporated by reference herein.

Thus, in one general aspect, the invention relates to compounds of Formula (I):

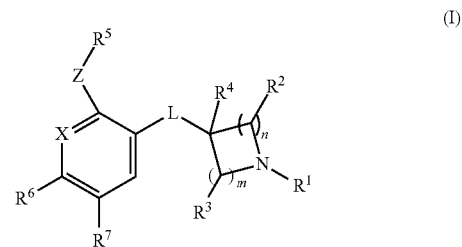

(I)

wherein
R$^1$ is —H, —C$_{1-4}$alkyl, monocyclic cycloalkyl, phenyl, or benzyl;
m is 1, 2 or 3,
n is 1 or 2, with the proviso that if m is 2, then n is not 1;
R$^2$ and R$^3$ are each independently —H or —C$_{1-4}$alkyl;
R$^4$ is —H, F, C$_{1-4}$alkyl, or R$^4$ is —OH when L is —CH$_2$—, —CF$_2$—, or —CHF—, —OCH$_2$—, or —OCH(CH$_3$)—;
L is —O—, —CH$_2$—, —OCH$_2$—, —OCH(CH$_3$)—, —CH$_2$O—, —CF$_2$—, or —CHF—;
Z is —O—, —C(O)—, —OCH(R$^b$)—, or —OCH$_2$C(R$^c$)(R$^d$)—;
  where
  where R$^b$ is —H; a —C$_{1-4}$alkyl group unsubstituted or substituted with OH or halo; —CO$_2$C$_{1-4}$alkyl; or —CO$_2$H; and
  R$^c$ and R$^d$ are each independently —H, —C$_{1-4}$alkyl, —O—C$_{1-4}$alkyl, or halo;
    or R$^c$ and R$^d$ taken together form an oxime, a C$_{1-4}$alkyl oxime, or a carbonyl group;
    or R$^c$ and R$^d$ taken together with the carbon to which they are attached form a C$_{3-6}$cycloalkyl group;
R$^5$ is:
  i) a phenyl or phenoxy group, unsubstituted or substituted with one, two, or three R$^g$ substituents;
    where each R$^g$ substituent is selected from the group consisting of: —C$_{1-6}$alkyl, —OH, —OC$_{1-6}$alkyl, —CN, —NO$_2$, —C(O)C$_{1-6}$alkyl, —S(O)$_{0-2}$—C$_{1-6}$alkyl, —OS(O)$_{0-2}$—C$_{1-6}$alkyl, —SO$_2$CF$_3$, —SCF$_3$, halo, —CF$_3$, —OCF$_3$, —CO$_2$H, —CO$_2$C$_{1-6}$alkyl, —CH$_2$OH, monocyclic cycloalkyl, phenyl, thiophenyl, benzhydryl, and oxadiazolyl;
    or two R$^g$ substituents taken together form —OCH$_2$O—, —OCF$_2$O—, or —OCH$_2$CH$_2$O—;
  ii) a naphthyl group, unsubstituted or substituted with C$_{1-4}$alkyl or halo;
  iii) a monocyclic heteroaryl group, unsubstituted or substituted with one, two, or three R$^g$ substituents;

iv) a fused bicyclic heteroaryl group, unsubstituted or substituted with $C_{1-4}$alkyl or halo;

v) a monocyclic cycloalkyl group, optionally fused to a phenyl ring, and unsubstituted or substituted with one or two substituents selected from the group consisting of: —$C_{1-4}$alkyl, —$OC_{1-4}$alkyl, halo, —$CF_3$, oxime, —$C_{1-4}$alkyl oxime, or phenyl; and vi) a monocyclic heterocycloalkyl group, optionally fused to or substituted with phenyl;

X is C or N; and $R^6$ or $R^7$ are each independently —H, halo, —$CF_3$, thiophene, or —$C(O)N(R^x)R^y$;

wherein $R^x$ and $R^y$ are each independently —H or —$C_{1-4}$alkyl.

The invention also relates to stereoisomeric forms, hydrates, solvates, pharmaceutically acceptable salts, pharmaceutically acceptable prodrugs, and pharmaceutically active metabolites of compounds of Formula (I). In certain preferred embodiments, the compound of Formula (I) is a compound selected from those species described or exemplified in the detailed description below.

In a further general aspect, the invention relates to pharmaceutical compositions each comprising: (a) an effective amount of an agent selected from compounds of Formula (I) and stereoisomeric forms, hydrates, solvates, pharmaceutically acceptable salts, pharmaceutically acceptable prodrugs, and pharmaceutically active metabolites thereof; and (b) a pharmaceutically acceptable excipient.

In another general aspect, the invention is directed to a method of treating a subject suffering from or diagnosed with a disease, disorder, or medical condition (collectively, "indications") mediated by $5HT_7$ activity, comprising administering to the subject in need of such treatment an effective amount of a compound of Formula (I), or a stereoisomeric form, hydrate, solvate, pharmaceutically acceptable salt, pharmaceutically acceptable prodrug, or pharmaceutically active metabolite of such compound. In certain preferred embodiments of the inventive method, the disease, disorder, or medical condition is selected from: cognitive disorders, sleep disorders, psychiatric disorders, and other disorders.

Preferred embodiments, features, and advantages of the invention will be apparent from the following detailed description and through practice of the invention.

DETAILED DESCRIPTION OF THE INVENTION
AND ITS PREFERRED EMBODIMENTS

The invention may be more fully appreciated by reference to the following detailed description, including the following glossary of terms and the concluding examples. For the sake of brevity, the disclosures of the publications, including patents, cited in this specification are herein incorporated by reference.

The terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which may also be structurally depicted by a bond, "/"), ethyl (Et), n-propyl (Pr), isopropyl (iPr), butyl (nBu), isobutyl (iBu), sec-butyl (sBu), tert-butyl (tBu), pentyl, isopentyl, tert-pentyl, hexyl, isohexyl, and so on.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities (depicted without their bonds of attachment):

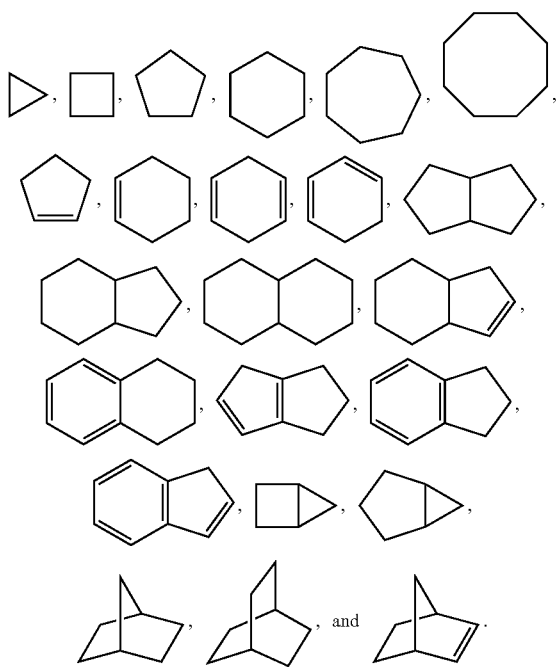

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative examples (depicted without their bonds of attachment) include:

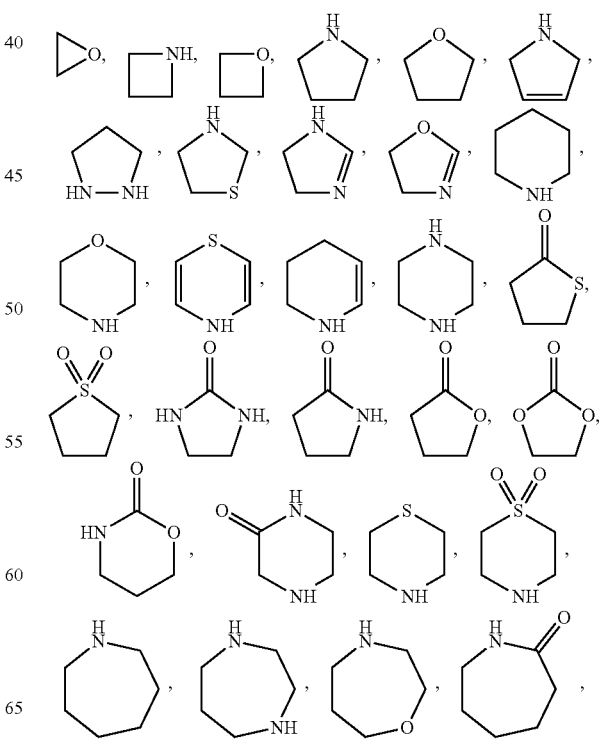

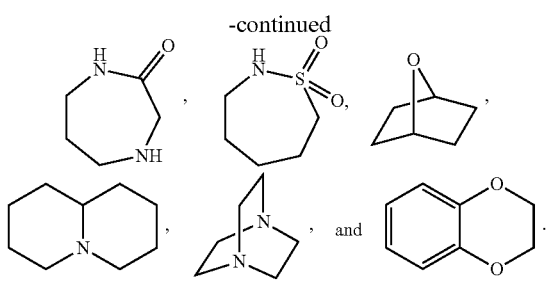

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities (depicted without their bonds of attachment):

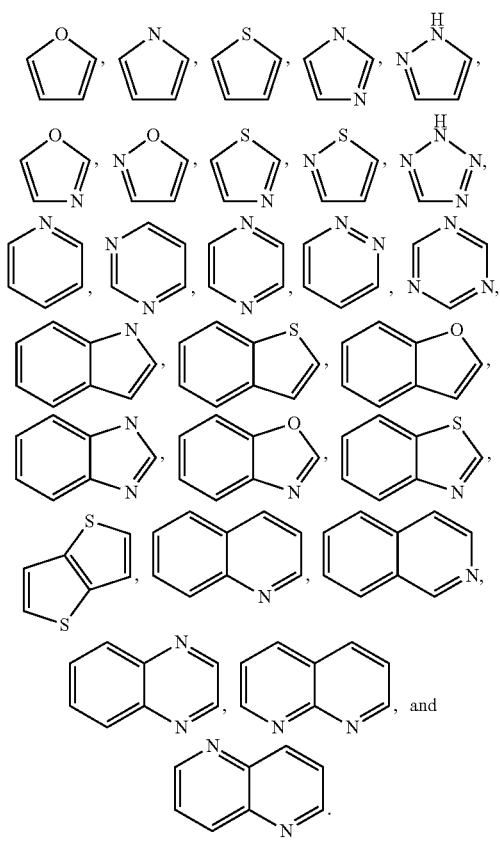

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Any formula given herein is intended to represent compounds having structures depicted by the structural formula as well as certain variations or forms. In particular, compounds of any formula given herein may have asymmetric centers and therefore exist in different enantiomeric forms. It is understood that some compounds referred to herein are chiral and/or have geometric isomeric centers, for example E- and Z-isomers. All optical isomers and stereoisomers of the compounds of any general structural formula, and mixtures thereof, are considered within the scope of the formula. Thus, any general formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any general formula given herein is intended to embrace hydrates, solvates, and polymorphs of such compounds, and mixtures thereof. Furthermore, certain compounds referred to herein can exist in solvated as well as unsolvated forms. It is understood that this invention encompasses all such solvated and unsolvated forms that possess the activity that characterizes the compounds of this invention.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any general formula given herein is also intended to represent unlabeled forms as well as isotopically labeled forms of the compounds. Isotopically labeled compounds have structures of the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{125}$I, respectively. Such isotopically labeled compounds are useful in metabolic studies (preferably with $^{14}$C), reaction kinetic studies (with, for example $^2$H or $^3$H), detection or imaging techniques (such as positron emission tomography (PET) or single-photon emission computed tomography (SPECT) including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to a formula given herein, the selection of a particular moiety from a list of possible species for a specified variable is not intended to define the moiety for the variable appearing elsewhere. In other words, where a variable appears more than once in a formula, the choice of the species from a specified list is independent of the choice of the species for the same variable elsewhere in the formula unless otherwise indicated.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, A, $X^4$, $X^5$, $X^6$, $X^7$, $R^a$, $R^b$, $R^c$, $R^d$, $R^e$, $R^f$, $R^g$, $R^h$, $R^i$, $R^j$, $R^k$, $R^l$, $R^m$, and $R^o$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, A, $X^4$, $X^5$, $X^6$, $X^7$, $R^a$, $R^b$, $R^c$, $R^d$, $R^e$, $R^f$, $R^g$, $R^h$, $R^i$, $R^j$, $R^k$, $R^l$, $R^m$, and $R^o$, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

The compounds of Formula (I) and their pharmaceutically acceptable salts, pharmaceutically acceptable prodrugs, and pharmaceutically active metabolites of the present invention are useful as serotonin receptor modulators in the methods of the invention.

A "pharmaceutically acceptable salt" is intended to mean a salt of a free acid or base of a compound represented by Formula (I) that is non-toxic, biologically tolerable, or otherwise biologically suitable for administration to the subject. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenyl butyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Representative pharmaceutically acceptable amides of the invention include those derived from ammonia, primary $C_{1-6}$ alkyl amines and secondary di($C_{1-6}$alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$alkyl primary amines, and di($C_{1-2}$alkyl) amines. Representative pharmaceutically acceptable esters of the invention include $C_{1-7}$alkyl, $C_{5-7}$cycloalkyl, phenyl, and phenyl($C_{1-6}$)alkyl esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I), which may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites of the present invention are useful as modulators of the serotonin receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize or down-regulate seratonin receptor expression or activity, and "activators" are compounds that increase, activate, facilitate, sensitize, or up-regulate seratonin receptor expression or activity.

Many of the compounds of the present invention are 5-HT$_7$ modulators that act as 5-HT$_7$ antagonists. As such, the compounds are useful in the treatment of 5-HT$_7$-mediated disease in which a decrease, prevention, inactivation, desensitization or down-regulation of serotonin receptor expression or activity is required.

The term "treat" or "treating" as used herein is intended to refer to administration of an active agent or composition of the invention to a subject for the purpose of effecting a therapeutic or prophylactic benefit through modulation of serotonin receptor activity. Treating includes reversing, ameliorating, alleviating, inhibiting the progress of, lessening the severity of, or preventing a disease, disorder, or condition, or one or more symptoms of such disease, disorder or condition mediated through modulation of serotonin receptor activity.

The term "subject" refers to a mammalian patient in need of such treatment, such as a human.

In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician.

The invention may be particularly useful in the treatment or prevention of diseases, disorders, or conditions mediated by serotonin receptor activity, such as: central nervous system disorders such as sleep disorders (including insomnia), depression/anxiety, generalized anxiety disorder, schizophrenia, bipolar disorders, cognitive disorders, mild cognitive impairment, Alzheimer's disease, Parkinson's disease, psychotic disorders, phobic disorders, obsessive-compulsive disorder, mood disorders, post-traumatic stress and other stress-related disorders, migraine, pain, eating disorders, obesity, sexual dysfunction, metabolic disturbances, hormonal imbalance, hot flashes associated with menopause, alcohol abuse, drug abuse, and addictive disorders including drug addiction and alcohol addiction. Further diseases associated with serotonin receptor activity for which the compounds may be useful for treating are nausea, inflammation, centrally mediated hypertension, sleep/wake disturbances, jetlag, and circadian rhythm abnormalities. The compounds may also be used in the treatment and prevention of hypotension, peripheral vascular disorders, cardiovascular shock, renal disorders, gastric motility, diarrhea, spastic colon, irritable bowel disorders, ischemias, septic shock, urinary incontinence and other disorders related to the gastrointestinal and vascular systems. In addition, compounds of the present invention may be used in methods for treating or preventing a range of ocular disorders including glaucoma, optic neuritis, diabetic retinopathy, retinal edema, and age-related macular degeneration. Symptoms or disease states are intended to be included within the scope of "medical conditions, disorders, or diseases."

The compounds of the present invention are $5$-$HT_7$ modulators, many of which are $5$-$HT_7$ antagonists. As such, the compounds are useful in the treatment of $5$-$HT_7$ mediated disease states. Where the compounds possess substantial $5$-$HT_7$ modulating activity, they may be particularly useful in methods for treating depression/anxiety, sleep/wake disturbances, sleep disorders, jet lag, migraine, urinary incontinence, gastric motility, and irritable bowel disorders, hypertension, analgesic, and irritable bowel syndrome.

Particularly, as serotonin receptor modulators, the compounds of the present invention are useful in the treatment or prevention of depression, anxiety, sleep disorders, and circadian rhythm abnormalities.

The compounds of the invention are used, alone or in combination with one or more other active ingredients, to formulate pharmaceutical compositions of the invention. In addition, the compounds of the invention may be used in combination with additional active ingredients in the treatment of the above conditions. In an exemplary embodiment, additional active ingredients are those that are known or discovered to be effective in the treatment of conditions, disorders, or diseases mediated by serotonin receptors or that are active against another target associated with the particular condition, disorder, or disease. Suitable examples include: $H_1$ receptor antagonists, $H_2$ receptor antagonists, $H_3$ receptor antagonists, topiramate (TOPAMAX™), and neurotransmitter modulators such as norepinephrine reuptake inhibitors (NRIs), selective serotonin reuptake inhibitors (SSRIs), noradrenergic reuptake inhibitors, non-selective serotonin re-uptake inhibitors (NSSRIs), acetylcholinesterase inhibitors (such as tetrahydroaminoacridine, Donepezil (ARICEPT™), Rivastigmine, or Galantamine (REMINYL™)), modafinil, anti-psychotics, sedatives, monoamine oxidase inhibitors (MAOs), and tricyclic antidepressants (TCAs). The combination may serve to increase efficacy (e.g., by including in the combination a compound potentiating the potency or effectiveness of a compound according to the invention), decrease one or more side effects, or decrease the required dose of the compound according to the invention. In preferred embodiments, the combination method employs doses containing additional active ingredients in the range of about 20 to 300 mg per dose.

A pharmaceutical composition of the invention comprises: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. It is anticipated that the compounds of the invention can be administered by oral or parenteral routes, including intravenous, intramuscular, intraperitoneal, subcutaneous, rectal and topical administration, and inhalation. For oral administration, the compounds of the invention will generally be provided in the form of tablets or capsules or as an aqueous solution or suspension. Tablets for oral use may include the active ingredient mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate and lactose. Cornstarch and alginic acid are suitable disintegrating agents. Binding agents may include starch and gelatin. The lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and diglycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Effective doses of the compounds of the present invention may be ascertained by conventional methods. The specific dosage level required for any particular patient will depend on a number of factors, including severity of the condition being treated, the route of administration and the weight of the patient. In general, however, it is anticipated that the daily dose (whether administered as a single dose or as divided doses) will be in the range 0.01 to 1000 mg per day, more usually from 1 to 500 mg per day, and most usually from 10 to 200 mg per day. Expressed as dosage per unit body weight, a typical dose will be expected to be between 0.0001 mg/kg and 15 mg/kg, especially between 0.01 mg/kg and 7 mg/kg, and most especially between 0.15 mg/kg and 2.5 mg/kg.

The invention includes also pharmaceutically acceptable salts of the compounds represented by Formula (I), preferably of those described below. Pharmaceutically acceptable salts of the specific compounds exemplified herein are especially preferred.

In certain embodiments of compounds of Formula (I), $R^1$ is —H, —$C_{1-4}$alkyl, monocyclic cycloalkyl, phenyl, or benzyl. In certain embodiments, $R^1$ is —H, —$CH_3$, —$CH_2CH_3$, —$CH_2CH_2CH_3$, —$CH(CH_3)_2$, —$C(CH_3)_3$, cyclopropyl, cyclobutyl, or benzyl. In further embodiments, $R^1$ is —H.

In certain embodiments of compounds of Formula (I), m has the value of 1, 2 or 3 and n has the value of 1 or 2; however, if m is 2 then n is not 1. In preferred embodiments, m is 1 and n is 1. In further embodiments, m is 1 and n is 2. In further embodiments, m is 2 and n is 2. In further embodiments, m is 3 and n is 1.

In certain embodiments of compounds of Formula (I), $R^2$ is —H or —$C_{1-4}$alkyl. In further embodiments, $R^2$ is —H, or —$CH_3$.

In certain embodiments of compounds of Formula (I), $R^3$ is —H or —$C_{1-4}$alkyl. In further embodiments, $R^3$ is —H, or —$CH_3$.

In certain embodiments of compounds of Formula (I), $R^2$ and $R^3$ are each —H.

In certain embodiments of compounds of Formula (I), $R^4$ is —H, F, —$C_{1-4}$alkyl or $R^4$ may be —OH when L is —$CH_2$—, —$CF_2$—, —CHF—, —$OCH_2$—, or —$OCH(CH_3)$—. In further embodiments, $R^4$ is hydrogen.

In certain embodiments of compounds of Formula (I), L is —O—, —$CH_2$—, —$OCH_2$—, —$OCH(CH_3)$—, —$CH_2O$—, —$CF_2$—, or —CHF—. In certain embodiments, L is —O—.

In certain embodiments of compounds of Formula (I), Z is —O—, —C(O)—, —$OCH(R^b)$—, or —$OCH_2C(R^c)(R^d)$—; where $R^b$ is —H; a —$C_{1-4}$alkyl group unsubstituted or substituted with OH or halo; —$CO_2C_{1-4}$alkyl; or —$CO_2H$; and $R^c$ and $R^d$ are each independently —H, —$C_{1-4}$alkyl, —O—$C_{1-4}$alkyl, or halo. In certain embodiments of compounds of Formula (I), $R^c$ and $R^d$ taken together form an oxime, a $C_{1-4}$alkyl oxime, or a carbonyl group. In certain embodiments of compounds of Formula (I), $R^c$ and $R^d$ taken together with the carbon to which they are attached form a $C_{3-6}$cycloalkyl group. In certain embodiments of compounds of Formula (I), Z is —O—, —C(O)—, —$OCH_2$—, —$OCH(CH_3)$—, —$OCH(CH_2CH_3)$—, —$OCH(CH_2OH)$—, —$OCH(CO_2H)$—, —$OCH(CH_2F)$—, —$OCH_2CH_2$—, —$OCH_2CH(F)$—, —$OCH_2CH(OCH_3)$—, —$OCH_2C(NOH)$—, —$OCH_2C(NOCH_3)$—, —$OCH_2CF_2$—, —$OCH_2C(O)$—, or

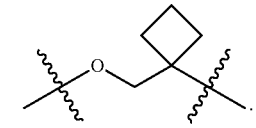 [SMILES: *OCC1(*)CCC1]

In further embodiments, Z is —O—, —$OCH_2$—, or —$OCH(CH_3)$—.

In certain embodiments of compounds of Formula (I), $R^5$ is a phenyl or phenoxy group, unsubstituted or substituted with one, two, or three $R^g$ substituents; where each $R^g$ substituent is selected from the group consisting of —$C_{1-6}$alkyl, —OH, —$OC_{1-6}$alkyl, —CN, —$NO_2$, —$C(O)C_{1-6}$alkyl, —$S(O)_{0-2}$—$C_{1-6}$alkyl, —$OS(O)_{0-2}$—$C_{1-6}$alkyl, —$SO_2CF_3$, —$SCF_3$, halo, —$CF_3$, —$OCF_3$, —$CO_2H$, —$CO_2C_{1-6}$alkyl, —$CH_2OH$, monocyclic cycloalkyl, phenyl, thiophenyl, benzhydryl, and oxadiazolyl. In further embodiments of compounds of Formula (I), two $R^g$ substituents taken together form —$OCH_2O$—, —$OCF_2O$—, or —$OCH_2CH_2O$— group. In further embodiments, $R^5$ is a naphthyl group, unsubstituted or substituted with $C_{1-4}$alkyl or halo. In further embodiments, $R^5$ is a monocyclic heteroaryl group, unsubstituted or substituted with one, two, or three $R^g$ substituents. In further embodiments, $R^5$ is a fused bicyclic heteroaryl group, unsubstituted or substituted with $C_{1-4}$alkyl or halo. In further embodiments, $R^5$ is a monocyclic cycloalkyl group, optionally fused to a phenyl ring, and unsubstituted or substituted with one or two substituents selected from the group consisting of: —$C_{1-4}$alkyl, —$OC_{1-4}$alkyl, halo, —$CF_3$, oxime, —$C_{1-4}$alkyl oxime, or phenyl. In further embodiments, $R^5$ is a monocyclic heterocycloalkyl group, optionally fused to or substituted with phenyl. In further embodiments, $R^5$ is cyclohexyl, 2-indanyl, or furanyl optionally substituted with one or more substituents individually selected from halo, —$CH_3$, —$CF_3$, —$OCF_3$, or —CN.

In certain embodiments, $R^5$ is selected from the group consisting of cyclopropyl, cyclobutyl, 3-phenyl-cyclobutyl, cyclopentyl, cyclohexyl, phenyl, 3- or 4-bromo-phenyl, 2-, 3- or 4-chloro-phenyl, 3,4-dichloro-phenyl, 3- or 4-cyano-phenyl, 2-, 3- or 4-fluoro-phenyl, 3-chloro-4-fluoro-phenyl, 4-chloro-3-fluoro-phenyl, 4-chloro-3-trifluoromethyl-phenyl, 3-chloro-4-trifluoromethoxy-phenyl, 2,4-difluoro-phenyl, 2-fluoro-4-trifluoromethyl-phenyl, 3-fluoro-4-trifluoromethyl-phenyl, 4-fluoro-3-trifluoromethyl-phenyl, 3- or 4-methyl-phenyl, 3- or 4-methylsulfanyl-phenyl, 3- or 4-methoxy-phenyl, 3-chloro-4-methoxy-phenyl, 3-methanesulfonyloxy-phenyl, 3- or 4-methoxy-phenyl, 3-trifluoromethoxy-phenyl, 2-, 3- or 4-trifluoromethyl-phenyl, 4-fluoro-3-trifluoromethyl-phenyl, 3- or 4-trifluoromethylsulfanyl-phenyl, 3-trifluoromethoxy-phenyl,

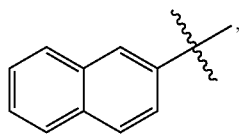 [SMILES: *c1ccc2ccccc2c1]

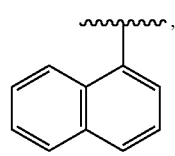 [SMILES: *c1cccc2ccccc12]

3-azetidinyl, 1-benzyl-azetidin-3-yl, 1-benzhydryl-azetidin-3-yl, 1-isopropyl-azetidin-3-yl, benzo[1,3]dioxol-5-yl, 2,2-difluoro-benzo[1,3]dioxol-5-yl, 2-benzofuranyl, 5-benzofuranyl, 2,3-dihydro-benzofuran-2-yl, 2-benzothiazolyl, 6-benzothiazolyl, 1H-benzotriazole-6-yl, 1-methyl-1H-benzotriazole-6-yl, 2- or 3-chromanyl, 2- or 3-furanyl, 5-trifluoromethyl-2-furanyl, 2-indanyl, tetrahydro-3-furanyl, 1-Hydroxyimino-indan-2-yl, 4-methoxy-2-indanyl, 5-fluoro-1-indanyl, 5-methyl-1-indanyl, 5- or 6-chloro-1-indanyl, 6-fluoro-1-indanyl, 6-trifluoromethyl-1-indanyl, 6-methyl-1-indanyl, 5-fluoro-2-indanyl, 5-methoxy-2-indanyl, [1,2,4]oxadiazole-5-yl, 3-cyclopropyl-[1,2,4]oxadiazole-5-yl, 3-cyclobutyl-[1,2,4]oxadiazole-5-yl, 3-isopropyl-[1,2,4]oxadiazole-5-yl, phenoxy, 4-piperidinyl, 2- or 3-pyrrolidinyl, 3-methyl-[1,2,4]oxadiazole-5-yl, 5-oxazolyl, 3-, 4- or 5-pyrazolyl, 4-trifluoromethyl-2-pyridinyl, 2-, 3- or 4-pyridinyl, 6-trifluoromethyl-2-pyridinyl, 1,2,3,4-tetrahydro-naphthalen-1-yl, 1,2,3,4-tetrahydro-naphthalen-2-yl, 1-phenyl-3-azetidinyl, 4- or 5-thiazolyl, 2-methyl-thiazole-4-yl, 2-thiophen-2-yl-thiazole-4-yl,

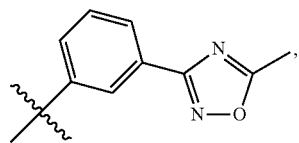 [SMILES: *c1cccc(-c2noc(C)n2)c1]

and 5-methyl-isoxazole-3-yl.

In certain embodiments of compounds of Formula (I), $R^6$ and $R^7$ are each independently —H, halo, —$CF_3$, thiophene, or —C(O)N($R^x$)$R^y$; wherein $R^x$ and $R^y$ are each independently —H or —$C_{1-4}$alkyl. In certain embodiments of compounds of Formula (I), $R^6$ and $R^7$ are each independently —H, halo, —$CF_3$, thiophene-3-yl, or N,N-dimethyl-formamidyl. In certain embodiments, $R^6$ is —H or halo. In certain embodiments, $R^6$ is —H or halo and $R^7$ is —H, halo, —$CF_3$, thiophene-3-yl, or N,N-dimethyl-formamidyl.

Preferred compounds are selected from the group consisting of:

| EX. | Chemical Name |
|---|---|
| 1 | 3-(2-Benzyloxy-5-bromo-phenoxy)-azetidine; |
| 2 | 3-[5-Bromo-2-(3-chloro-benzyloxy)-phenoxy]-azetidine; |
| 3 | 3-[5-Bromo-2-(3-chloro-benzyloxy)-phenoxy]-1-cyclobutyl-azetidine; |
| 4 | 3-[5-Bromo-2-(3-chloro-benzyloxy)-phenoxy]-1-propyl-azetidine; |
| 5 | 3-[5-Bromo-2-(3-chloro-benzyloxy)-phenoxy]-1-isopropyl-azetidine; |
| 6 | 3-[5-Bromo-2-(3-chloro-benzyloxy)-phenoxy]-1-ethyl-azetidine; |
| 7 | 3-[5-Bromo-2-(3-trifluoromethoxy-benzyloxy)-phenoxy]-azetidine; |
| 8 | 3-[5-Bromo-2-(3-trifluoromethyl-benzyloxy)-phenoxy]-azetidine; |
| 9 | 3-[2-(Azetidin-3-yloxy)-4-bromo-phenoxymethyl]-benzonitrile; |
| 10 | 3-[5-Bromo-2-(5-trifluoromethyl-furan-2-ylmethoxy)-phenoxy]-azetidine; |
| 11 | 3-[5-Bromo-2-(3-chloro-4-trifluoromethoxy-benzyloxy)-phenoxy]-azetidine; |
| 12 | 3-[5-Bromo-2-(3-chloro-4-fluoro-benzyloxy)-phenoxy]-azetidine; |
| 13 | 3-[5-Bromo-2-(3-chloro-4-methoxy-benzyloxy)-phenoxy]-azetidine; |
| 14 | 3-[5-Bromo-2-(4-chloro-benzyloxy)-phenoxy]-azetidine; |
| 15 | 3-[5-Bromo-2-(2-chloro-benzyloxy)-phenoxy]-azetidine; |
| 16 | 3-[5-Bromo-2-(2-chloro-benzyloxy)-phenoxy]-1-methyl-azetidine; |
| 17 | 3-[5-Bromo-2-(3-fluoro-benzyloxy)-phenoxy]-azetidine; |
| 18 | 3-[5-Bromo-2-(3-fluoro-benzyloxy)-phenoxy]-1-ethyl-azetidine; |
| 19 | 3-[5-Bromo-2-(3-fluoro-benzyloxy)-phenoxy]-1-propyl-azetidine; |
| 20 | 3-[5-Bromo-2-(3-fluoro-benzyloxy)-phenoxy]-1-isopropyl-azetidine; |
| 21 | 3-[5-Bromo-2-(3-fluoro-benzyloxy)-phenoxy]-1-cyclobutyl-azetidine |
| 22 | 3-[4-Bromo-2-(3-chloro-benzyloxy)-phenoxy]-azetidine; |
| 23 | 3-[4-Bromo-2-(3-chloro-benzyloxy)-phenoxy]-1-cyclobutyl-azetidine; |
| 24 | 3-[4-Bromo-2-(3-chloro-benzyloxy)-phenoxy]-1-isopropyl-azetidine; |
| 25 | 3-[5-Chloro-2-(4-fluoro-benzyloxy)-phenoxy]-azetidine; |
| 26 | 3-[5-Chloro-2-(3-methylsulfanyl-benzyloxy)-phenoxy]-azetidine; |
| 27 | 3-[5-Chloro-2-(3-methanesulfonyl-benzyloxy)-phenoxy]-azetidine; |
| 28 | 4-[2-(Azetidin-3-yloxy)-4-chloro-phenoxymethyl]-2-thiophen-2-yl-thiazole; |
| 29 | 4-[2-(Azetidin-3-yloxy)-4-chloro-phenoxymethyl]-2-methyl-thiazole; |
| 30 | 3-[2-(Azetidin-3-yloxy)-4-chloro-phenoxymethyl]-5-methyl-isoxazole; |
| 31 | 3-[3-[2-(Azetidin-3-yloxy)-4-chloro-phenoxymethyl]-phenyl]-5-methyl-[1,2,4]oxadiazole; |
| 32 | 3-[5-Chloro-2-(2-trifluoromethyl-benzyloxy)-phenoxy]-azetidine; |
| 33 | 3-[5-Chloro-2-(3-methoxy-benzyloxy)-phenoxy]-azetidine; |
| 34 | 3-[2-(Azetidin-3-yloxy)-4-chloro-phenoxymethyl]-benzonitrile; |
| 35 | 3-[5-Chloro-2-(2-chloro-benzyloxy)-phenoxy]-azetidine; |
| 36 | 3-[5-Chloro-2-(4-chloro-benzyloxy)-phenoxy]-azetidine; |
| 37 | 3-[5-Chloro-2-(3-chloro-benzyloxy)-phenoxy]-azetidine; |
| 38 | 3-[5-Chloro-2-(3-chloro-benzyloxy)-phenoxy]-1-methyl-azetidine; |
| 39 | 3-[5-Chloro-2-(3-trifluoromethyl-benzyloxy)-phenoxy]-azetidine; |
| 40 | 3-(2-Benzyloxy-5-chloro-phenoxy)-azetidine; |
| 41 | 3-[5-Chloro-2-(3-chloro-4-trifluoromethoxy-benzyloxy)-phenoxy]-azetidine; |
| 42 | 3-[5-Chloro-2-(4-trifluoromethoxy-benzyloxy)-phenoxy]-azetidine; |
| 43 | 3-[5-Chloro-2-(4-trifluoromethyl-benzyloxy)-phenoxy]-azetidine; |
| 44 | 4-[2-(Azetidin-3-yloxy)-4-chloro-phenoxymethyl]-benzonitrile; |
| 45 | 3-[2-(2,4-Bis-trifluoromethyl-benzyloxy)-5-chloro-phenoxy]-azetidine; |
| 46 | 3-[5-Chloro-2-(4-trifluoromethylsulfanyl-benzyloxy)-phenoxy]-azetidine; |
| 47 | 3-[5-Chloro-2-(4-fluoro-3-trifluoromethyl-benzyloxy)-phenoxy]-azetidine; |
| 48 | 3-[5-Chloro-2-(2-fluoro-4-trifluoromethyl-benzyloxy)-phenoxy]-azetidine; |
| 49 | 3-[5-Chloro-2-(4-chloro-3-trifluoromethyl-benzyloxy)-phenoxy]-azetidine; |
| 50 | 3-[5-Chloro-2-(3,4-dichloro-benzyloxy)-phenoxy]-azetidine; |
| 51 | 2-[2-(Azetidin-3-yloxy)-4-chloro-phenoxymethyl]-pyridine; |
| 52 | 3-[2-(Azetidin-3-yloxy)-4-chloro-phenoxymethyl]-pyridine; |
| 53 | 4-[2-(Azetidin-3-yloxy)-4-chloro-phenoxymethyl]-pyridine; |
| 54 | 3-[5-Chloro-2-(5-trifluoromethyl-furan-2-ylmethoxy)-phenoxy]-azetidine; |
| 55 | 5-[2-(Azetidin-3-yloxy)-4-chloro-phenoxymethyl]-furan-2-carboxylic acid ethyl ester; |

| EX. | Chemical Name |
|---|---|
| 56 | 3-[5-Chloro-2-(4-chloro-2-methanesulfonyl-benzyloxy)-phenoxy]-azetidine; |
| 57 | 3-[5-Chloro-2-(2,4-difluoro-benzyloxy)-phenoxy]-azetidine; |
| 58 | (R)-3-[5-Chloro-2-(3-chloro-benzyloxy)-phenoxy]-pyrrolidine; |
| 59 | (R)-3-[5-Chloro-2-(3-chloro-benzyloxy)-phenoxy]-1-methyl-pyrrolidine; |
| 60 | (R)-3-[5-Chloro-2-(2-chloro-benzyloxy)-phenoxy]-pyrrolidine; |
| 61 | (R)-3-[5-Chloro-2-(2-chloro-benzyloxy)-phenoxy]-1-methyl-pyrrolidine; |
| 62 | 4-(2-Benzyloxy-5-chloro-phenoxy)-piperidine; |
| 63 | 4-[5-Chloro-2-(5-trifluoromethyl-furan-2-ylmethoxy)-phenoxy]-piperidine; |
| 64 | 4-[5-Bromo-2-(5-trifluoromethyl-furan-2-ylmethoxy)-phenoxy]-piperidine; |
| 65 | 4-[5-Bromo-2-(3-chloro-benzyloxy)-phenoxy]-piperidine; |
| 66 | 4-[5-Bromo-2-(3-chloro-benzyloxy)-phenoxy]-1-methyl-piperidine; |
| 67 | 4-[5-Bromo-2-(2-fluoro-benzyloxy)-phenoxy]-piperidine; |
| 68 | 4-[5-Bromo-2-(3-fluoro-benzyloxy)-phenoxy]-piperidine; |
| 69 | (±)-3-[5-Chloro-2-(5-trifluoromethyl-furan-2-ylmethoxy)-phenoxy]-piperidine; |
| 70 | (±)-3-(2-Benzyloxy-5-chloro-phenoxy)-piperidine; |
| 71 | (±)-3-[5-Chloro-2-(3-trifluoromethyl-benzyloxy)-phenoxy]-piperidine; |
| 72 | 3-(5-Chloro-2-cyclopentyloxy-phenoxy)-azetidine; |
| 73 | 3-(5-Chloro-2-cyclohexylmethoxy-phenoxy)-azetidine; |
| 74 | 3-(5-Bromo-2-cyclohexylmethoxy-phenoxy)-azetidine; |
| 75 | 5-[2-(Azetidin-3-yloxy)-4-chloro-phenoxymethyl]-2-trifluoromethyl-furan-3-carboxylic acid; |
| 76 | 5-[2-(Azetidin-3-yloxy)-4-chloro-phenoxymethyl]-2-trifluoromethyl-furan-3-carboxylic acid ethyl ester; |
| 77 | 5-[4-Chloro-2-(1-methyl-azetidin-3-yloxy)-phenoxymethyl]-2-trifluoromethyl-furan-3-yl]-methanol; |
| 78 | 3-[5-Chloro-2-(5-methyl-2-trifluoromethyl-furan-3-ylmethoxy)-phenoxy]-azetidine; |
| 79 | 2-[2-(Azetidin-3-yloxy)-4-chloro-phenoxymethyl]-6-trifluoromethyl-pyridine; |
| 80 | 3-[2-(Azetidin-3-yloxy)-4-chloro-phenoxymethyl]-2-methyl-6-trifluoromethyl-pyridine; |
| 81 | 2-[2-(Azetidin-3-yloxy)-4-chloro-phenoxymethyl]-4-trifluoromethyl-pyridine; |
| 82 | 5-[2-(Azetidin-3-yloxy)-4-chloro-phenoxymethyl]-2-trifluoromethyl-pyridine; |
| 83 | 3-[2-(Benzofuran-5-ylmethoxy)-5-chloro-phenoxy]-azetidine; |
| 84 | 6-[2-(Azetidin-3-yloxy)-4-chloro-phenoxymethyl]-benzothiazole; |
| 85 | 6-[2-(Azetidin-3-yloxy)-4-chloro-phenoxymethyl]-1-methyl-1H-benzotriazole; |
| 86 | 3-[5-Chloro-2-(2,2-difluoro-benzo[1,3]dioxol-5-ylmethoxy)-phenoxy]-azetidine; |
| 87 | 5-[2-(Azetidin-3-yloxy)-4-chloro-phenoxymethyl]-oxazole; |
| 88 | 2-[2-(Azetidin-3-yloxy)-4-chloro-phenoxymethyl]-thiazole; |
| 89 | 3-[2-(Benzofuran-2-ylmethoxy)-5-chloro-phenoxy]-azetidine; |
| 90 | (R)-3-(2-Benzyloxy-4-chloro-phenoxy)-pyrrolidine; |
| 91 | (R)-3-(2-Benzyloxy-4-chloro-phenoxy)-1-methyl-pyrrolidine; |
| 92 | (R)-3-[4-Chloro-2-(3-chloro-benzyloxy)-phenoxy]-pyrrolidine; |
| 93 | (R)-3-[4-Chloro-2-(3-chloro-benzyloxy)-phenoxy]-1-methyl-pyrrolidine; |
| 94 | (S)-3-[4-Chloro-2-(3-chloro-benzyloxy)-phenoxy]-pyrrolidine; |
| 95 | (±)-3-[5-Bromo-2-(3-chloro-benzyloxy)-phenoxy]-1-methyl-pyrrolidine; |
| 96 | (±)-3-[5-Bromo-2-(3-methoxy-benzyloxy)-phenoxy]-1-methyl-pyrrolidine; |
| 97 | (±)-3-[5-Bromo-2-(3-fluoro-benzyloxy)-phenoxy]-1-methyl-pyrrolidine; |
| 98 | (±)-3-(2-Benzyloxy-5-bromo-phenoxy)-1-methyl-pyrrolidine; |
| 99 | (±)-Methanesulfonic acid 3-[4-bromo-2-(1-methyl-pyrrolidin-3-yloxy)-phenoxymethyl]-phenyl ester; |
| 100 | (±)-Methanesulfonic acid 3-[2-(1-methyl-pyrrolidin-3-yloxy)-phenoxymethyl]-phenyl ester; |
| 101 | (S)-3-[5-Chloro-2-[1-(3-trifluoromethyl-phenyl)-ethoxy]-phenoxy]-azetidine; |
| 102 | (S)-3-[5-Chloro-2-[1-(3-trifluoromethyl-phenyl)-ethoxy]-phenoxy]-azetidine; |
| 103 | (S)-3-[5-Chloro-2-[1-(3-trifluoromethyl-phenyl)-ethoxy]-phenoxy]-1-methyl-azetidine; |
| 104 | (S)-1-Benzyl-3-[5-chloro-2-[1-(3-trifluoromethyl-phenyl)-ethoxy]-phenoxy]-azetidine; |
| 105 | (±)-3-[5-Chloro-2-[1-(3-trifluoromethyl-phenyl)-ethoxy]-phenoxy]-azetidine; |
| 106 | (±)-3-[5-Chloro-2-[1-(3-trifluoromethyl-phenyl)-ethoxy]-phenoxy]-1-isopropyl-azetidine; |
| 107 | (±)-3-[5-Chloro-2-[1-(3-trifluoromethyl-phenyl)-ethoxy]-phenoxy]-1-cyclobutyl-azetidine; |
| 108 | (±)-1-Benzyl-3-[5-chloro-2-[1-(3-trifluoromethyl-phenyl)-ethoxy]-phenoxy]-azetidine; |
| 109 | (±)-3-[5-Chloro-2-[1-(3-trifluoromethyl-phenyl)-ethoxy]-phenoxy]-1-methyl-azetidine; |
| 110 | (±)-3-[5-Bromo-2-[1-(3-trifluoromethoxy-phenyl)-ethoxy]-phenoxy]-azetidine; |
| 111 | (±)-3-[5-Bromo-2-[1-(3-chloro-phenyl)-ethoxy]-phenoxy]-azetidine; |
| 112 | (±)-3-[5-Bromo-2-[1-(3-trifluoromethyl-phenyl)-ethoxy]-phenoxy]-azetidine; |
| 113 | (R)-3-[5-Bromo-2-[1-(3-trifluoromethyl-phenyl)-ethoxy]-phenoxy]-azetidine; |
| 114 | (±)-3-[5-Chloro-2-[1-(3-chloro-phenyl)-ethoxy]-phenoxy]-azetidine; |
| 115 | (±)-3-[5-Chloro-2-[1-(3-fluoro-phenyl)-ethoxy]-phenoxy]-azetidine; |
| 116 | (±)-3-[5-Chloro-2-[1-(2-chloro-phenyl)-ethoxy]-phenoxy]-azetidine; |
| 117 | (±)-3-[5-Chloro-2-[1-(4-fluoro-3-trifluoromethyl-phenyl)-ethoxy]-phenoxy]-azetidine; |
| 118 | (±)-3-[5-Chloro-2-[1-(3-fluoro-4-trifluoromethyl-phenyl)-ethoxy]-phenoxy]-azetidine; |
| 119 | (±)-3-[5-Chloro-2-[1-(3-fluoro-5-trifluoromethyl-phenyl)-ethoxy]-phenoxy]-azetidine; |
| 120 | (±)-3-[5-Chloro-2-[1-(3-trifluoromethylsulfanyl-phenyl)-ethoxy]-phenoxy]-azetidine; |
| 121 | (±)-3-[5-Chloro-2-[1-(2-fluoro-phenyl)-ethoxy]-phenoxy]-azetidine; |
| 122 | (±)-3-[5-Chloro-2-[1-(2-trifluoromethyl-phenyl)-ethoxy]-phenoxy]-azetidine; |
| 123 | (±)-3-[5-Chloro-2-[1-(4-chloro-phenyl)-ethoxy]-phenoxy]-azetidine; |
| 124 | (±)-3-[5-Chloro-2-[1-(4-fluoro-phenyl)-ethoxy]-phenoxy]-azetidine; |
| 125 | (±)-3-[1-[2-(Azetidin-3-yloxy)-4-chloro-phenoxy]-ethyl]-benzonitrile; |
| 126 | (±)-3-[5-Chloro-2-[1-(3,4-dichloro-phenyl)-ethoxy]-phenoxy]-azetidine; |
| 127 | (±)-3-[5-Chloro-2-[1-(3-trifluoromethoxy-phenyl)-ethoxy]-phenoxy]-azetidine; |
| 128 | (±)-3-[5-Chloro-2-[1-(3,4-difluoro-phenyl)-ethoxy]-phenoxy]-azetidine; |
| 129 | (±)-3-[5-Chloro-2-[1-(2,5-dichloro-phenyl)-ethoxy]-phenoxy]-azetidine; |
| 130 | (±)-3-[5-Chloro-2-[1-(2,5-difluoro-phenyl)-ethoxy]-phenoxy]-azetidine; |
| 131 | 2-[1-[2-(Azetidin-3-yloxy)-4-chloro-phenoxy]-ethyl]-benzothiazole; |
| 132 | 5-[1-[2-(Azetidin-3-yloxy)-4-chloro-phenoxy]-ethyl]-thiazole; |
| 133 | 2-[1-[2-(Azetidin-3-yloxy)-4-chloro-phenoxy]-ethyl]-thiazole; |
| 134 | 5-[1-[2-(Azetidin-3-yloxy)-4-chloro-phenoxy]-ethyl]-2,4-dimethyl-thiazole; |
| 135 | (R)-4-[5-Chloro-2-[1-(3-trifluoromethyl-phenyl)-ethoxy]-phenoxy]-piperidine; |
| 136 | (±)-4-[5-Chloro-2-[1-(3-chloro-phenyl)-ethoxy]-phenoxy]-piperidine; |
| 137 | (±)-4-[5-Chloro-2-[1-(3-trifluoromethoxy-phenyl)-ethoxy]-phenoxy]-piperidine; |
| 138 | (±)-4-[5-Chloro-2-[1-(3-fluoro-phenyl)-ethoxy]-phenoxy]-piperidine; |
| 139 | (R,S)-3-[5-Chloro-2-[1-((R)-3-trifluoromethyl-phenyl)-ethoxy]-phenoxy]-piperidine; |
| 140 | (±)-3-[5-Chloro-2-[1-(3-trifluoromethyl-phenyl)-propoxy]-phenoxy]-azetidine; |
| 141 | (±)-4-[5-Chloro-2-[1-(3-trifluoromethyl-phenyl)-propoxy]-phenoxy]-piperidine; |
| 142 | 3-[5-Bromo-2-(2-fluoro-1-phenyl-ethoxy)-phenoxy]-azetidine; |
| 143 | 3-[5-Chloro-2-(2-fluoro-1-phenyl-ethoxy)-phenoxy]-azetidine; |
| 144 | (±)-4-[5-Chloro-2-(2-fluoro-1-phenyl-ethoxy)-phenoxy]-piperidine; |
| 145 | (±)-3-[5-Chloro-2-(1-phenyl-ethoxy)-phenoxy]-azetidine; |
| 146 | (±)-3-[5-Chloro-2-[1-(5-trifluoromethyl-furan-2-yl)-ethoxy]-phenoxy]-azetidine; |
| 147 | 3-[5-Chloro-2-(1-phenyl-propoxy)-phenoxy]-azetidine; |
| 148 | 2-[2-(Azetidin-3-yloxy)-4-chloro-phenoxy]-2-phenyl-ethanol; |
| 149 | [2-(Azetidin-3-yloxy)-4-chloro-phenoxy]-phenyl-acetic acid; |
| 150 | (±)-3-[5-Chloro-2-(6-fluoro-indan-1-yloxy)-phenoxy]-azetidine; |
| 151 | (±)-3-[5-Bromo-2-(indan-1-yloxy)-phenoxy]-azetidine; |
| 152 | (±)-3-[5-Bromo-2-(5-chloro-indan-1-yloxy)-phenoxy]-azetidine; |
| 153 | (±)-3-[5-Bromo-2-(6-chloro-indan-1-yloxy)-phenoxy]-azetidine; |
| 154 | (±)-3-[5-Bromo-2-(5-fluoro-indan-1-yloxy)-phenoxy]-azetidine; |
| 155 | (±)-3-[5-Bromo-2-(5-methyl-indan-1-yloxy)-phenoxy]-azetidine; |
| 156 | (±)-3-[5-Bromo-2-(6-methyl-indan-1-yloxy)-phenoxy]-azetidine; |
| 157 | (±)-3-[5-Bromo-2-(6-trifluoromethyl-indan-1-yloxy)-phenoxy]-azetidine; |

| EX. | Chemical Name |
|---|---|
| 158 | (±)-3-[5-Chloro-2-(6-methyl-indan-1-yloxy)-phenoxy]-azetidine; |
| 159 | (±)-3-[5-Chloro-2-(6-chloro-indan-1-yloxy)-phenoxy]-azetidine; |
| 160 | 3-[5-Chloro-2-(6-trifluoromethyl-indan-1-yloxy)-phenoxy]-azetidine; |
| 161 | 3-[5-Chloro-2-(1,2,3,4-tetrahydro-naphthalen-1-yloxy)-phenoxy]-azetidine; |
| 162 | 3-[5-Bromo-2-(5-tert-butyl-indan-1-yloxy)-phenoxy]-azetidine; |
| 163 | 3-[5-Chloro-2-(tetrahydro-furan-3-ylmethoxy)-phenoxy]-azetidine; |
| 164 | 3-[5-Chloro-2-(1,2,3,4-tetrahydro-naphthalen-2-yloxy)-phenoxy]-azetidine; |
| 165 | 3-[5-Chloro-2-(chroman-2-ylmethoxy)-phenoxy]-azetidine; |
| 166 | 3-[5-Chloro-2-(tetrahydro-furan-2-ylmethoxy)-phenoxy]-azetidine; |
| 167 | 3-[5-Chloro-2-(chroman-3-ylmethoxy)-phenoxy]-azetidine; |
| 168 | 3-[5-Chloro-2-(2-methoxy-2-phenyl-ethoxy)-phenoxy]-azetidine; |
| 169 | 3-[5-Chloro-2-(2,3-dihydro-benzofuran-2-ylmethoxy)-phenoxy]-azetidine; |
| 170 | 5-[2-(Azetidin-3-yloxy)-4-chloro-phenoxymethyl]-1,3-dimethyl-1H-pyrazole; |
| 171 | 3-[5-Chloro-2-(2-phenoxy-ethoxy)-phenoxy]-azetidine; |
| 172 | 3-[5-Bromo-2-(3-fluoro-benzyloxy)-phenoxy]-1-phenyl-azetidine; |
| 173 | 3-[5-Chloro-2-(indan-2-yloxy)-phenoxy]-azetidine; |
| 174 | 3-[5-Bromo-2-(indan-2-yloxy)-phenoxy]-azetidine; |
| 175 | 3-[5-Chloro-2-(5-fluoro-indan-2-yloxy)-phenoxy]-azetidine; |
| 176 | 3-[5-Chloro-2-(5-chloro-indan-2-yloxy)-phenoxy]-azetidine; |
| 177 | 3-[5-Chloro-2-(5-methoxy-indan-2-yloxy)-phenoxy]-azetidine; |
| 178 | 3-[5-Chloro-2-(4-methoxy-indan-2-yloxy)-phenoxy]-azetidine; |
| 179 | 2-[2-(Azetidin-3-yloxy)-4-chloro-phenoxy]-indan-1-one oxime; |
| 180 | 2-[2-(Azetidin-3-yloxy)-4-chloro-phenoxy]-indan-1-one O-methyl-oxime; |
| 181 | 2-[2-(Azetidin-3-yloxy)-4-chloro-phenoxy]-1-phenyl-ethanone oxime; |
| 182 | 2-[2-(Azetidin-3-yloxy)-4-chloro-phenoxy]-1-phenyl-ethanone O-methyl-oxime; |
| 183 | 2-[2-(Azetidin-3-yloxy)-4-chloro-phenoxy]-1-(4-chloro-phenyl)-ethanone; |
| 184 | 3-[5-Chloro-2-(2,2-difluoro-2-phenyl-ethoxy)-phenoxy]-azetidine; |
| 185 | 3-[5-Chloro-2-[2-(3-chloro-phenyl)-ethoxy]-phenoxy]-azetidine; |
| 186 | 3-[5-Chloro-2-(3-chloro-benzyloxy)-phenoxy]-azetidine; |
| 187 | 3-[5-Chloro-2-(2-fluoro-2-phenyl-ethoxy)-phenoxy]-azetidine; |
| 188 | 3-[5-Chloro-2-[1-(4-chloro-phenyl)-cyclobutylmethoxy]-phenoxy]-azetidine; |
| 189 | 3-[5-Chloro-2-[1-(3-chloro-phenyl)-cyclobutylmethoxy]-phenoxy]-azetidine; |
| 190 | 3-[5-Chloro-2-[2-(3-methoxy-phenyl)-ethoxy]-phenoxy]-azetidine; |
| 191 | 3-[5-Chloro-2-[2-(3-fluoro-phenyl)-ethoxy]-phenoxy]-azetidine; |
| 192 | 3-[5-Chloro-2-[2-(4-chloro-phenyl)-ethoxy]-phenoxy]-azetidine; |
| 193 | 3-[5-Chloro-2-[2-(4-fluoro-phenyl)-ethoxy]-phenoxy]-azetidine; |
| 194 | 3-[5-Chloro-2-[2-(4-methoxy-phenyl)-ethoxy]-phenoxy]-azetidine; |
| 195 | 3-(5-Bromo-2-phenethyloxy-phenoxy)-azetidine; |
| 196 | 3-(Azetidin-3-yloxy)-2-benzyloxy-5-chloro-pyridine; |
| 197 | 3-(2-Benzyloxy-5-chloro-3-fluoro-phenoxy)-azetidine; |
| 198 | 3-[5-Chloro-3-fluoro-2-(5-trifluoromethyl-furan-2-ylmethoxy)-phenoxy]-azetidine; |
| 199 | 3-[5-Trifluoromethyl-2-(5-trifluoromethyl-furan-2-ylmethoxy)-phenoxy]-azetidine; |
| 200 | 3-[5-Trifluoromethyl-2-[1-(3-trifluoromethyl-phenyl)-ethoxy]-phenoxy]-azetidine; |
| 201 | 3-[2-(1-Phenyl-ethoxy)-5-trifluoromethyl-phenoxy]-azetidine; |
| 202 | 3-[2-(3-Chloro-benzyloxy)-5-fluoro-phenoxy]-azetidine; |
| 203 | 3-[2-(3-Chloro-benzyloxy)-5-fluoro-phenoxy]-1-methyl-azetidine; |
| 204 | 3-[2-(3-Chloro-benzyloxy)-5-fluoro-phenoxy]-1-isopropyl-azetidine; |
| 205 | 3-[2-(3-Chloro-benzyloxy)-5-fluoro-phenoxy]-1-cyclobutyl-azetidine; |
| 206 | 3-[2-(3-Chloro-benzyloxy)-5-fluoro-phenoxy]-1-propyl-azetidine; |
| 207 | 3-[2-(3-Chloro-benzyloxy)-5-fluoro-phenoxy]-1-ethyl-azetidine; |
| 208 | 3-[5-Fluoro-2-(5-trifluoromethyl-furan-2-ylmethoxy)-phenoxy]-azetidine;; |
| 209 | 3-[5-Fluoro-2-(5-trifluoromethyl-furan-2-ylmethoxy)-phenoxy]-1-isopropyl-azetidine; |
| 210 | 3-[2-(3-Chloro-benzyloxy)-5-thiophen-3-yl-phenoxy]-azetidine; |
| 211 | 3-(Azetidin-3-yloxy)-4-(3-chloro-benzyloxy)-N,N-dimethyl-benzamide; |
| 212 | 3-[5-Bromo-2-(3-chloro-benzyloxy)-phenoxy]-3-methyl-azetidine; |
| 213 | 3-[5-Bromo-2-(3-chloro-benzyloxy)-phenoxy]-3-ethyl-azetidine; |
| 214 | 3-[5-Bromo-2-(3-chloro-benzyloxy)-phenoxy]-3-isopropyl-azetidine; |
| 215 | 3-(5-Bromo-2-phenethyloxy-phenoxy)-3-methyl-azetidine; |
| 216 | 3-[5-Bromo-2-(5-trifluoromethyl-furan-2-ylmethoxy)-phenoxy]-azetidine; |
| 217 | 3-[5-Bromo-2-(3-trifluoromethyl-benzyloxy)-phenoxy]-azetidine; |
| 218 | 3-(5-Bromo-2-phenoxy-phenoxy)-3-methyl-azetidine; |
| 219 | (±)-trans-3-[5-Bromo-2-(3-fluoro-benzyloxy)-phenoxy]-2-methyl-azetidine; |
| 220 | cis-1-Benzyl-3-[5-bromo-2-(3-fluoro-benzyloxy)-phenoxy]-2-methyl-azetidine; |
| 221 | trans-1-Benzyl-3-[5-bromo-2-(3-fluoro-benzyloxy)-phenoxy]-2-methyl-azetidine; |
| 222 | 3-[5-Chloro-2-(1-phenyl-azetidin-3-ol)-phenoxy]-azetidine; |
| 223 | (±)-3-[5-Chloro-2-(trans-1-benzyl-2-methyl-azetidin-3-ol)-phenoxy]-azetidine; |
| 224 | 3-[5-Chloro-2-(1-Isopropyl-azetidin-3-ol)-phenoxy]-azetidine; |
| 225 | 3-[5-Chloro-2-(1-benzhydryl-azetidin-3-ol)-phenoxy]-azetidine; |
| 226 | 3-[5-Chloro-2-(1-azetidin-3-ol)-phenoxy]-azetidine; |
| 227 | 3-[5-Chloro-2-(1-Isopropyl-azetidin-3-ol)-phenoxy]-1-isopropyl-azetidine; |
| 228 | 3-[5-Chloro-2-(3-phenyl-cyclobutoxy)-phenoxy]-azetidine; |
| 229 | 3-[5-Bromo-2-(3-fluoro-benzyloxy)-phenoxy]-1-tert-butyl-azetidine; |
| 230 | 1-tert-Butyl-3-[5-chloro-2-(3-trifluoromethyl-benzyloxy)-phenoxy]-azetidine |
| 231 | 1-tert-Butyl-3-[5-chloro-2-[1-(3-trifluoromethyl-phenyl)-ethoxy]-phenoxy]-azetidine |
| 232 | 3-[5-Bromo-2-(5-trifluoromethyl-furan-2-ylmethoxy)-benzyl]-azetidine; |
| 233 | 3-[5-Bromo-2-(3-chloro-benzyloxy)-phenoxymethyl]-azetidine; |
| 234 | 3-[5-Bromo-2-(3-chloro-benzyloxy)-phenoxymethyl]-1-methyl-azetidine; |
| 235 | 3-[5-Bromo-2-(3-chloro-benzyloxy)-phenoxymethyl]-azetidin-3-ol; |
| 236 | 3-[1-[5-Bromo-2-(3-chloro-benzyloxy)-phenoxy]-ethyl]-azetidin-3-ol; |
| 237 | 3-[5-Bromo-2-(3-chloro-benzyloxy)-benzyloxy]-azetidine; |
| 238 | 3-[5-Chloro-2-(3-chloro-benzyloxy)-benzyloxy]-azetidine; |
| 239 | 5-[2-(Azetidin-3-yloxy)-4-chloro-phenoxymethyl]-3-methyl-[1,2,4]oxadiazole; |
| 240 | 5-[2-(Azetidin-3-yloxy)-4-chloro-phenoxymethyl]-3-cyclobutyl-[1,2,4]oxadiazole; |
| 241 | 5-[2-(Azetidin-3-yloxy)-4-chloro-phenoxymethyl]-3-cyclopropyl-[1,2,4]oxadiazole; |
| 242 | 5-[2-(Azetidin-3-yloxy)-4-chloro-phenoxymethyl]-3-isopropyl-[1,2,4]oxadiazole; |
| 243 | 5-[2-(Azetidin-3-yloxy)-4-chloro-phenoxymethyl]-3-ethyl-[1,2,4]oxadiazole; |
| 244 | 3-(5-Bromo-2-phenoxy-phenoxy)-azetidine; |
| 245 | 3-[5-Bromo-2-(3-bromo-phenoxy)-phenoxy]-azetidine; |
| 246 | 3-[5-Bromo-2-(3-fluoro-phenoxy)-phenoxy]-azetidine; |
| 247 | 3-(5-Bromo-2-m-tolyloxy-phenoxy)-azetidine; |
| 248 | 3-[5-Bromo-2-(3-methoxy-phenoxy)-phenoxy]-azetidine; |
| 249 | 3-[5-Bromo-2-(4-fluoro-phenoxy)-phenoxy]-azetidine; |
| 250 | 3-[5-Bromo-2-(4-bromo-phenoxy)-phenoxy]-azetidine; |
| 251 | 3-[5-Bromo-2-(4-chloro-phenoxy)-phenoxy]-azetidine; |
| 252 | 3-[5-Bromo-2-(3-chloro-phenoxy)-phenoxy]-azetidine; |
| 253 | 3-[5-Bromo-2-(3-trifluoromethoxy-phenoxy)-phenoxy]-azetidine; |
| 254 | 3-[5-Bromo-2-(naphthalen-2-yloxy)-phenoxy]-azetidine; |
| 255 | 3-[5-Bromo-2-(naphthalen-1-yloxy)-phenoxy]-azetidine; |
| 256 | 3-(5-Chloro-2-phenoxy-phenoxy)-azetidine; |
| 257 | 3-[5-Chloro-2-(3-chloro-phenoxy)-phenoxy]-azetidine; |
| 258 | 3-[5-Chloro-2-(4-chloro-phenoxy)-phenoxy]-azetidine; |
| 259 | 3-(5-Chloro-2-o-tolyloxy-phenoxy)-azetidine; |
| 260 | 3-[5-Chloro-2-(naphthalen-2-yloxy)-phenoxy]-azetidine; |
| 261 | 2-[2-(Azetidin-3-yloxy)-4-chloro-phenoxy]-benzothiazole; |
| 262 | 2-[2-(Azetidin-3-yloxy)-4-chloro-phenoxy]-benzooxazole; |
| 263 | 2-[2-(Azetidin-3-yloxy)-4-chloro-phenoxy]-[1,8]naphthyridine; |
| 264 | 2-[2-(Azetidin-3-yloxy)-4-chloro-phenoxy]-quinoline; |
| 265 | 4-(5-Chloro-2-phenoxy-phenoxy)-piperidine; |
| 266 | (S)-3-(4-Chloro-2-p-tolyloxy-phenoxy)-pyrrolidine; |
| 267 | (R)-3-(4-Chloro-2-p-tolyloxy-phenoxy)-pyrrolidine; |
| 268 | (R)-3-(4-Chloro-2-p-tolyloxy-phenoxy)-1-methyl-pyrrolidine; |
| 269 | (S)-3-[4-Chloro-2-(4-fluoro-phenoxy)-phenoxy]-pyrrolidine; |
| 270 | (R)-3-[4-Chloro-2-(4-fluoro-phenoxy)-phenoxy]-pyrrolidine; |
| 271 | (R)-3-[4-Chloro-2-(4-fluoro-phenoxy)-phenoxy]-1-methyl-pyrrolidine; |
| 272 | (S)-3-(4-Chloro-2-o-tolyloxy-phenoxy)-pyrrolidine; |
| 273 | (S)-3-(4-Chloro-2-m-tolyloxy-phenoxy)-pyrrolidine; |
| 274 | (S)-3-[4-Chloro-2-(4-fluoro-3-methyl-phenoxy)-phenoxy]-pyrrolidine; |
| 275 | (S)-3-[4-Chloro-2-(4-chloro-phenoxy)-phenoxy]-pyrrolidine; |
| 276 | (S)-3-[4-Chloro-2-(3-chloro-phenoxy)-phenoxy]-pyrrolidine; |
| 277 | (S)-3-[2-(4-Bromo-phenoxy)-4-chloro-phenoxy]-pyrrolidine; |
| 278 | (S)-3-[4-Chloro-2-(4-isopropyl-phenoxy)-phenoxy]-pyrrolidine; |

| EX. | Chemical Name |
|---|---|
| 279 | (±)-3-[5-Bromo-2-(4-bromo-phenoxy)-phenoxy]-1-ethyl-pyrrolidine; |
| 280 | 2-(Azetidin-3-yloxy)-4-bromo-phenyl]-phenyl-methanone; |
| 281 | [2-(Azetidin-3-yloxy)-4-bromo-phenyl]-(4-chloro-phenyl)-methanone; |
| 282 | [2-(Azetidin-3-yloxy)-4-bromo-phenyl]-(3-chloro-phenyl)-methanone; |
| 283 | [4-Bromo-2-(1-methyl-azetidin-3-yloxy)-phenyl]-(3-chloro-phenyl)-methanone; |
| 284 | [2-(Azetidin-3-yloxy)-4-bromo-phenyl]-m-tolyl-methanone; |
| 285 | [2-(Azetidin-3-yloxy)-4-bromo-phenyl]-o-tolyl-methanone; |
| 286 | [2-(Azetidin-3-yloxy)-4-bromo-phenyl]-(3-methoxy-phenyl)-methanone; |
| 287 | [2-(Azetidin-3-yloxy)-4-bromo-phenyl]-naphthalen-2-yl-methanone; |
| 288 | [4-Bromo-2-(1-isopropyl-azetidin-3-yloxy)-phenyl]-naphthalen-2-yl-methanone; |
| 289 | [2-(Azetidin-3-yloxy)-4-bromo-phenyl]-benzo[1,3]dioxol-5-yl-methanone; |
| 290 | Benzo[1,3]dioxol-5-yl-[4-bromo-2-(1-isopropyl-azetidin-3-yloxy)-phenyl]-methanone; |
| 291 | [2-(Azetidin-3-yloxy)-4-bromo-phenyl]-(4-methoxy-phenyl)-methanone; |
| 292 | [2-(Azetidin-3-yloxy)-4-bromo-phenyl]-(4-chloro-3-fluoro-phenyl)-methanone; |
| 293 | [2-(Azetidin-3-yloxy)-4-bromo-phenyl]-(3,4-dichloro-phenyl)-methanone; |
| 294 | [2-(Azetidin-3-yloxy)-4-chloro-phenyl]-naphthalen-2-yl-methanone; |
| 295 | [2-(Azetidin-3-yloxy)-4-chloro-phenyl]-benzo[1,3]dioxol-5-yl-methanone; |
| 296 | Benzo[1,3]dioxol-5-yl-[4-chloro-2-(1-isopropyl-azetidin-3-yloxy)-phenyl]-methanone; |
| 297 | [2-(Azetidin-3-yloxy)-4-chloro-phenyl]-(4-chloro-phenyl)-methanone; and |
| 298 | [2-(Azetidin-3-yloxy)-4-chloro-phenyl]-(3-chloro-phenyl)-methanone; | and stereoisomeric forms, hydrates, solvates, pharmaceutically acceptable salts, prodrugs, and active metabolites thereof.

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables in the formulas depicted in the schemes below are as defined above in reference to Formula (I). Reactions may be performed between the melting point and the reflux temperature of the solvent, and preferably between 0° C. and the reflux temperature of the solvent.

List of abbreviations: Ac=Acetyl, AIBN=azobisisobutyronitrile, Boc=tert-Butylcarbamoyl, m-CPBA=meta-chloroperoxybenzoic acid, DCE=dichloroethane, DEAD=diethyldiazodicarboxylate, DIBAL-H=diisobutyl aluminum hydride, DIEA=N,N-Diisopropylethylamine, DMA=N,N-Dimethylacetamide, DME=Ethylene glycol dimethyl ether, DMF=dimethylformamide, DMSO=Dimethyl sulfoxide, Et$_3$N=triethylamine, Et$_2$O=diethyl ether, EtOAc=Ethyl acetate, MeCN=acetonitrile, MeOH=methanol, MsCl=Methanesulfonyl chloride, TFA=trifluoroacetic acid, TFAA=trifluoroacetic acid anhydride, THF=tetrahydrofuran, TLC=thin layer chromatography, Q-Phos=1,2,3,4,5-pentaphenyl-1'-(di-tert-butylphosphino)ferrocene.

The compounds of formula (I) may be prepared by a number of reaction schemes. The following schemes represent certain synthesis steps for obtaining compounds of the invention. Persons skilled in the art will recognize that certain compounds are more advantageously produced by one scheme as compared to the other.

The amines in the compounds below may be protected, as indicated by $P^1$, as an alkyl or benzyl amine, amide, carbamate or other groups such as described in "Protecting Groups in Organic Synthesis", 3$^{rd}$ ed.; T. W. Greene and P. G. Wuts, John Wiley and Sons, 1999. Preferably, $P^1$ is —C$_{1-6}$Alkyl, —COOC$_{1-6}$Alkyl, —(C=O)C$_{1-6}$Alkyl, benzyl substituted or unsubstituted with —OC$_{1-6}$Alkyl or C$_{1-6}$Alkyl, or benzhydryl substituted or unsubstituted with —OC$_{1-6}$Alkyl or —C$_{1-6}$Alkyl). A further preferred protecting group is t-butyl carbamate (Boc) or trifluoroacetamide. This protecting group ($P^1$) on the nitrogen may be removed or converted directly into the desired compounds using generally accepted methods known to one skilled in the art. More specifically a group such as a Boc group may be removed with an acid such as trifluoroacetic acid or hydrochloric acid and the like in a solvent such as CH$_2$Cl$_2$, EtOAc, THF, 1,4-dioxane, MeOH or EtOH. A group such as trifluoroacetamide was removed using a base such as NH$_3$, NH$_4$OH or K$_2$CO$_3$ in an alcoholic solvent such as MeOH or EtOH and the like.

Scheme A

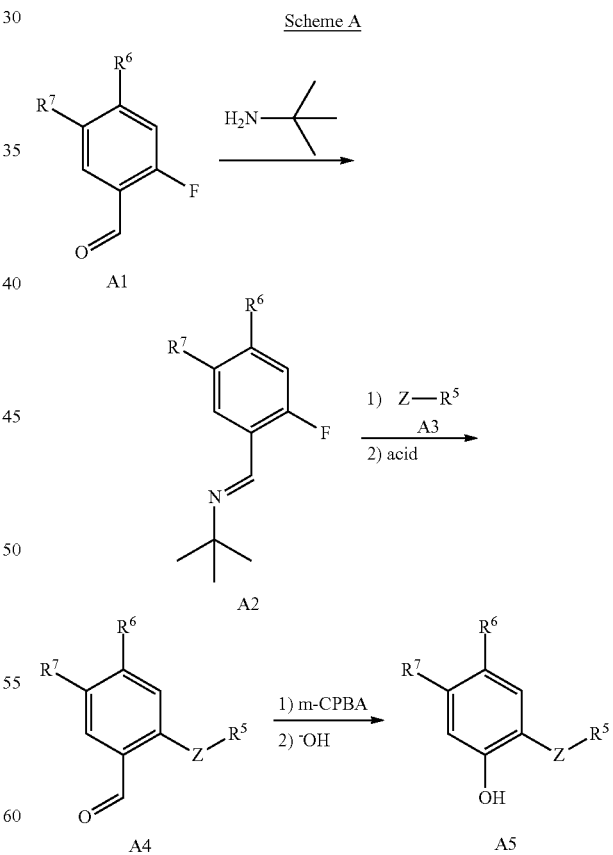

Intermediates of the formula A5 were prepared according to Scheme A. The variable Z in the formula depicted in Scheme 1 are as defined above in reference to Formula (I) except Z cannot be —C(O)— in Scheme 1. Compounds of the formula A1 were treated with tert-butylamine in the presence of a dehydrating agent such as SiO$_2$, CuSO$_4$, Ti(OiPr)$_4$, MgSO$_4$ or molecular sieves in a suitable solvent such as THF, CH$_2$Cl$_2$, benzene, toluene, MeOH or EtOH. A preferred method uses MgSO$_4$ in CH$_2$Cl$_2$ to give compounds of the formula A2. Compounds of the formula A2 were allowed to react with compounds of the formula A3 in a suitable solvent such as DMF, DMSO, NMP or THF in the presence of a base such as NaH, KOtBu or Cs$_2$CO$_3$, preferably NaH in DMF, to produce compounds of formula A4. Compounds of the formula A5 were obtained from compounds of the formula A4 upon basic hydrolysis of the compound obtained from the treatment of compounds of the formula A4 with an oxidant such as m-chloroperoxybenzoic acid (m-CPBA) in CH$_2$Cl$_2$. The hydrolysis is performed using a base such as NaOH or KOH in a solvent such as MeOH, EtOH or H$_2$O.

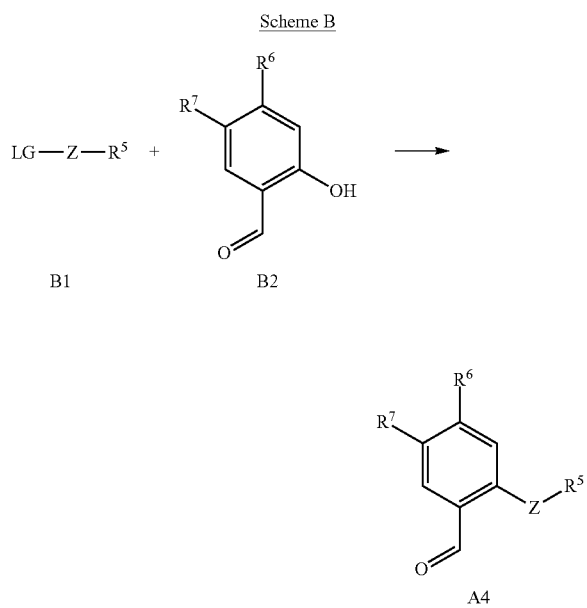

Scheme B

B1     B2

A4

Intermediates of the formula A4 were alternatively prepared according to Scheme B. Compounds of the formula A4 were alternatively obtained from compounds of the formula B1, where LG represents a chloride, bromide, iodide, mesylate or tosylate, upon treatment with a compound of the formula B2. The variable Z in the formulas depicted in Scheme 2 are as defined above in reference to Formula (I) except Z cannot be —C(O)— in Scheme 2. This type of reaction was carried out in a solvent such as DMF, DMA, THF or EtOH in the presence of bases such as NaHCO$_3$, Na$_2$CO$_3$, K$_2$CO$_3$ or Cs$_2$CO$_3$. Alternatively, compounds of the formula A4 may also be obtained from compounds of the formula B1 when LG is OH using PPh$_3$ or similar trialkyl or triaryl phosphine and diethyldiazodicarboxylate (DEAD), diisopropyldiazodicarboxylate (DIAD) or di-tert-butyldiazodicarboxylate (DBAD) in a solvent such as MeCN, DMF, THF or CH$_2$Cl$_2$ and the like. One skilled in the art will recognize this as a Mitsunobu reaction.

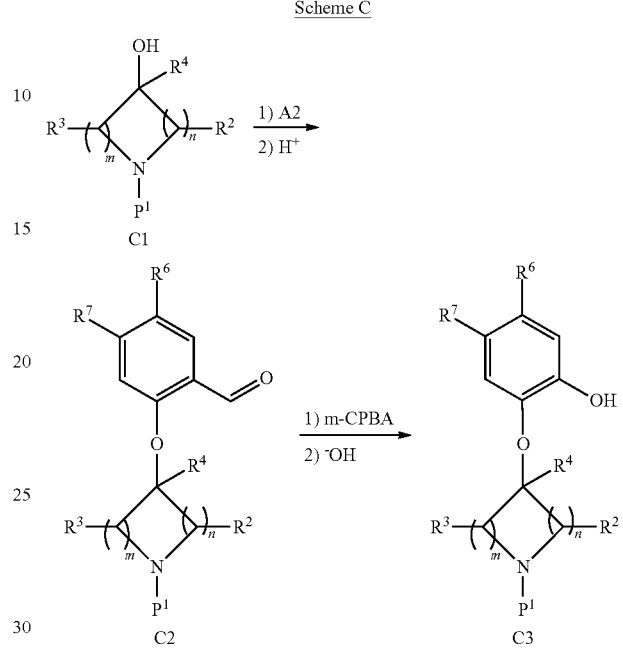

Scheme C

C1

C2     C3

Intermediates of the formula C3 were prepared according to Scheme C. Compounds of the formula C3 were synthesized similar to compounds of the formula A5 (Scheme 1) from compounds of the formula C1. Compounds of the formula C2 were obtained from compounds of the formula C1 and compounds of the formula A2 (Scheme 1) in a suitable solvent such as DMF, DMSO, NMP or THF in the presence of a base such as NaH, KOtBu or Cs$_2$CO$_3$, preferably NaH in DMF. Compounds of the formula C3 were obtained from compounds of the formula C2 upon basic hydrolysis of the compound obtained from the treatment of compounds of the formula C2 with an oxidant such as m-chloroperoxybenzoic acid (m-CPBA) in CH$_2$Cl$_2$. The hydrolysis was performed using a base such as NaOH or KOH in a solvent such as MeOH, EtOH or H$_2$O.

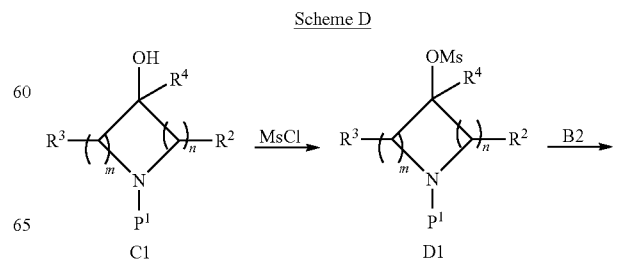

Scheme D

C1     D1

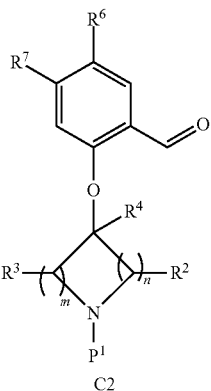

C2

Intermediates of the formula C2 were alternatively prepared according to Scheme D using compounds of the formula D1. The amine in compounds of the formula C2 may be protected with a protecting group, as indicated by $P^1$, with previously described protecting groups. Treatment of compounds of formula D1 with a nucleophile such as a compound of formula B2 (Scheme 2) in the presence of base such as pyridine, triethylamine, diisopropylamine, $K_2CO_3$, $Cs_2CO_3$ or $Na_2CO_3$ in a suitable solvent such as THF, $CH_2Cl_2$, DMF, MeCN, 1,4-dioxane or the like at a temperature ranging from rt to 100° C. provided compounds of the formula C2. Compounds of the formula D1 were obtained from compounds of the formula C1 when treated with methanesulfonyl chloride (MsCl) in the presence of a base such as pyridine, triethylamine or diisopropylamine and the like in a solvent such as $CH_2Cl_2$, THF or DCE.

Scheme E

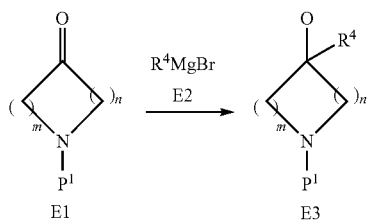

Intermediates of the formula E2 were prepared according to Scheme E. Compounds of the formula E2 were obtained after addition of compounds of the formula E2 to compounds of the formula E1. One skilled in the art will recognize compounds of the formula E2 as Grignard reagents.

Scheme F

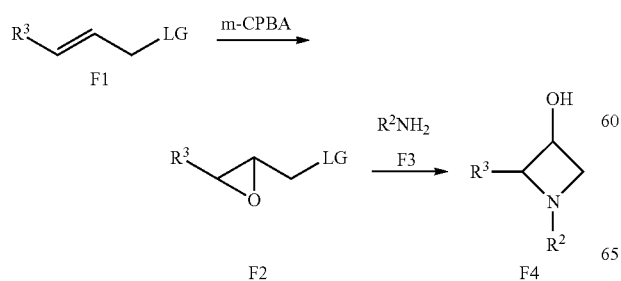

Intermediates of the formula F4 were prepared according to Scheme F. Compounds of the formula F4 were prepared from compounds of the formula F2, where LG represents a Cl or Br, and F3. Compounds of the formula F2 were prepared from compounds of the formula F1 upon treatment with an oxidizing agent such as m-CPBA in a solvent such as $CH_2Cl_2$.

Scheme G

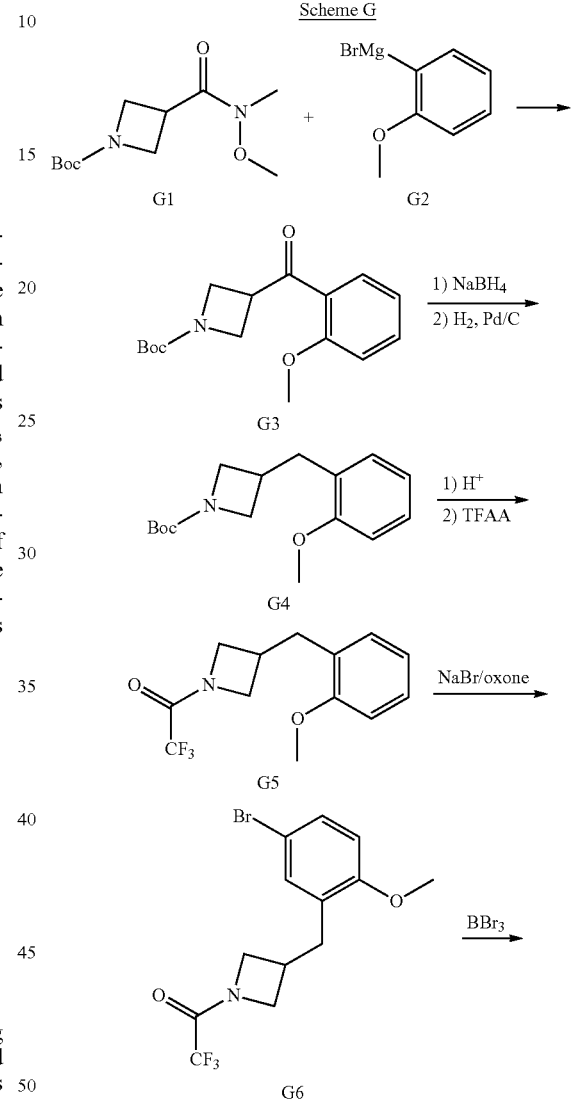

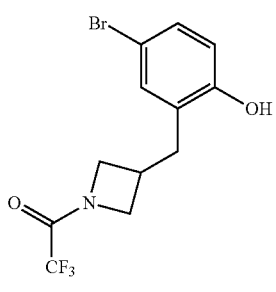

Intermediates of the formula G7 were prepared according to Scheme G. Compounds of the formula G3 were synthesized from compounds of the formula G1 and compounds of the formula G2 using solvents such as $Et_2O$, THF, $CH_2Cl_2$, or dioxane and the like. One skilled in the art will recognize G1 as a Weinreb amide (Nahm, S. et al., *Tet. Lett.*, 1981, 22, 3815-3818) and G2 as a Grignard reagent. Compounds of the formula G4 were obtained from compounds of the formula G3 by partial reduction with hydride donors such as $NaBH_4$ in alcoholic solvents such as MeOH, EtOH or i-PrOH and the like followed by further reduction using $H_2$ in the presence of a hydrogenation catalyst such as Pd/C, $PtO_2$ or $Pd(OH)_2$ and the like at pressures up to 60 psi and temperatures ranging from rt to 60° C. in solvents such as MeOH, EtOH or i-PrOH and the like. The Boc protecting group in compounds of the formula G2 was exchanged for a trifluoroacetamide as shown in compounds of the formula G5 by treatment with acids such as trifluoroacetic acid or hydrochloric acid and the like in a solvent such as $CH_2Cl_2$, EtOAc, THF, 1,4-dioxane, MeOH or EtOH. Treatment of the intermediate from this reaction with trifluoroacetic anhydride (TFAA) in the presence of a base such as pyridine, triethylamine or diisopropylethylamine or the like in a solvent such as $CH_2Cl_2$, THF, DMF, MeOH, EtOH or the like yields compounds of the formula G5. Treatment of compounds of the formula G5 with an electrophilic bromine source such as $Br_2$, NBS, NaBr/oxone or chlorine source such as $Cl_2$, KCl/oxone or NCS and the like in a solvent such as MeOH, $CH_2Cl_2$, EtOH, DMF, acetone, $H_2O$ and the like or mixtures there of produces compounds of the formula G6. Treatment of compounds of the formula G6 with a reagent such as LiI in collidine, HBr in AcOH, or preferably $BBr_3$ in $CH_2Cl_2$, produces compounds of the formula G7.

Scheme H

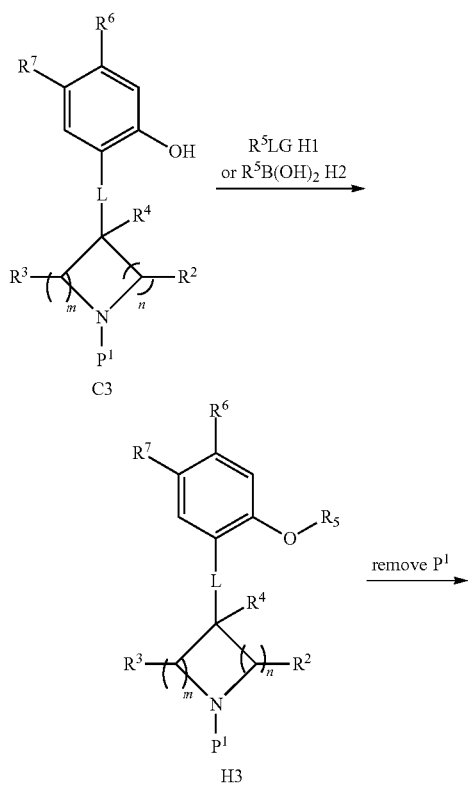

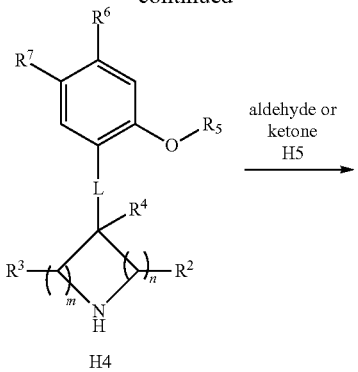

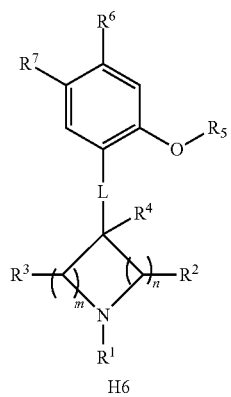

Intermediates of the formula H6 were prepared according to Scheme H. Compounds of the formula H3 were obtained from compounds of the formula C3 upon treatment with compounds of the formula H1, representing an alkyl chloride, bromide, iodide, mesylate or tosylate in a solvent such as DMF, DMA, THF or EtOH in the presence of bases such as $NaHCO_3$, $Na_2CO_3$, $K_2CO_3$ or $Cs_2CO_3$. Alternatively, compounds of the formula H3 may also be obtained from compounds of the formula H2 when X is OH using $PPh_3$ or similar trialkyl or triaryl phosphine and diethyldiazodicarboxylate (DEAD), diisopropyldiazodicarboxylate (DIAD) or di-tert-butyldiazodicarboxylate (DBAD) in a solvent such as MeCN, DMF, THF or $CH_2Cl_2$ and the like. One skilled in the art will recognize this as a Mitsunobu reaction. The transformation when X is OH may also be performed using cyanomethylene-tri-n-butylphosphine in a solvent such as $PhCH_3$ when heated in a microwave reactor at temperatures up to 120° C. When $R_5$ is a substituted aryl or heteroaryl, compounds of the formula H3 were obtained using $Cu(OAc)_2$ and base such as pyridine or $Et_3N$ and the like in the presence of dehydrating agents such as $MgSO_4$ or 4 Å molecular sieves.

Compounds such as H6 were prepared from compounds of the formula H4 using methods such as reductive amination or alkylation. Thus treatment of H4 with a compound of formula H5 containing a carbonyl in the presence of a reductant such as $NaBH_4$, $NaBH_3CN$, $NaBH(OAc)_3$ or hydrogen gas in the presence of a catalyst in a solvent such as $CH_2Cl_2$, THF, DCE, MeOH, EtOH or similar afforded compounds of the formula H6. One skilled in the art will recognize that the presence of Bronsted or Lewis acids may be required. Examples of acids may include AcOH, $Ti(O-iPr)_4$, trifluoroacetic acid or hydrochloric acid and the like. One skilled in the art will also recognize that compounds of the formula H6 may be obtained from H4 upon treatment with an alkyl chloride, bromide, iodide, mesylate or tosylate and the like in a solvent such as DMF, DMA, THF or EtOH in the presence of bases such as NaHCO$_3$, Na$_2$CO$_3$, K$_2$CO$_3$ or Cs$_2$CO$_3$. It will be generally recognized that compounds of the formula H6 represent a subset of compounds of the formula H4 where R$_1$ is equal to H. Compounds of the formula H4 or H6 may be converted to their corresponding salts using methods generally accepted to those skilled in the art.

Scheme I

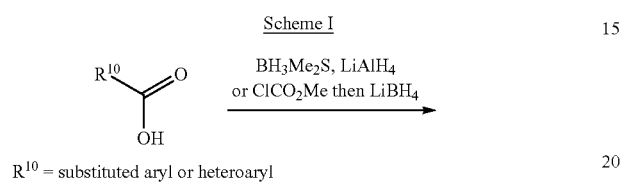

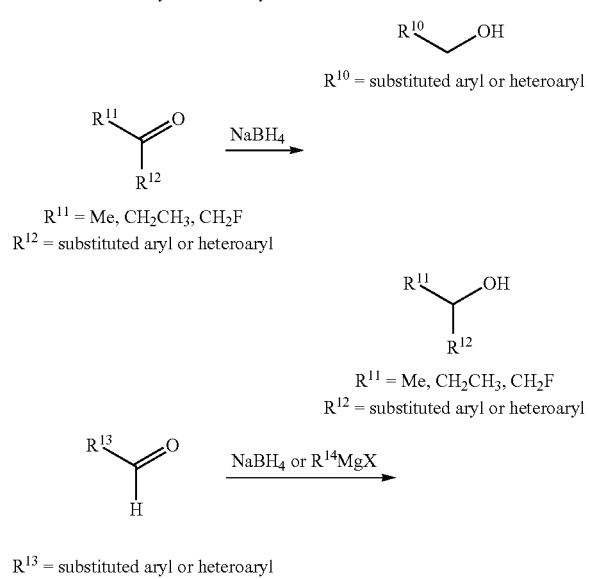

Intermediates of the formula H1 were prepared according to Scheme I when not commercially available.

Scheme J

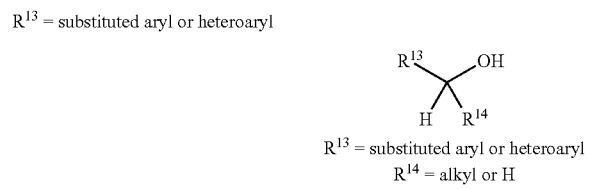

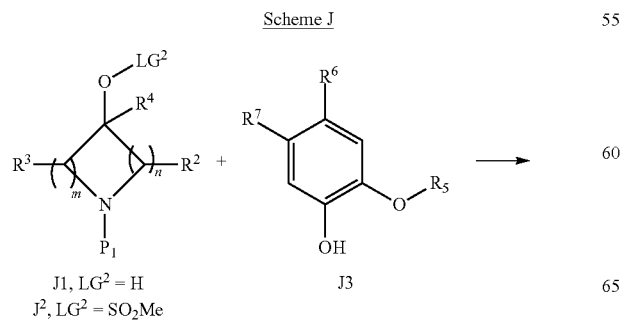

-continued

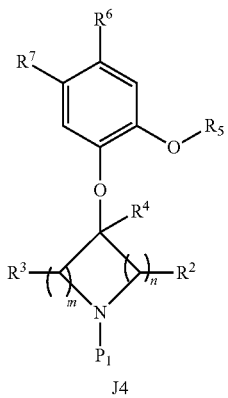

J4

Intermediates of the formula J4 were prepared according to Scheme J. Compounds of the formula J4 were prepared from compounds of the formula J1 and compounds of the formula J3 (prepared as in Scheme A) using cyanomethylene-tri-n-butylphosphine in a solvent such as PhCH$_3$ when heated in a microwave reactor at temperatures up to 120° C. In this reaction scheme, the preferred protecting group, P$^1$ is a benzhydryl group. Alternatively, compounds of the formula J4 were also synthesized from compounds of the formula D1 (Scheme D). Treatment of a compound of formula D1 with a nucleophile such as a compound of formula J3 in the presence of base such as pyridine, triethylamine, diisopropylamine, K$_2$CO$_3$, Cs$_2$CO$_3$ or Na$_2$CO$_3$ in a suitable solvent such as THF, CH$_2$Cl$_2$, DMF, MeCN, 1,4-dioxane or the like at a temperature ranging from rt to 100° C. provided compounds of the formula J4.

Scheme K

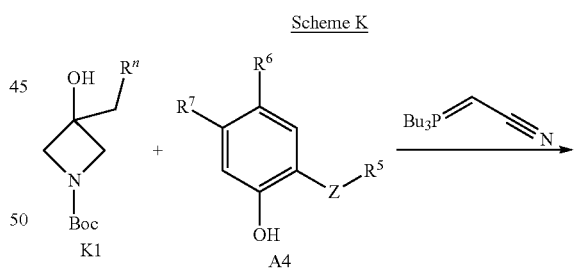

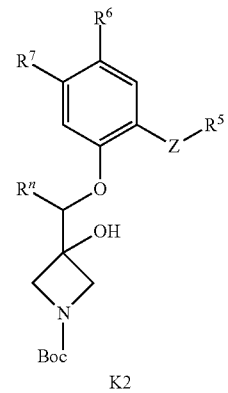

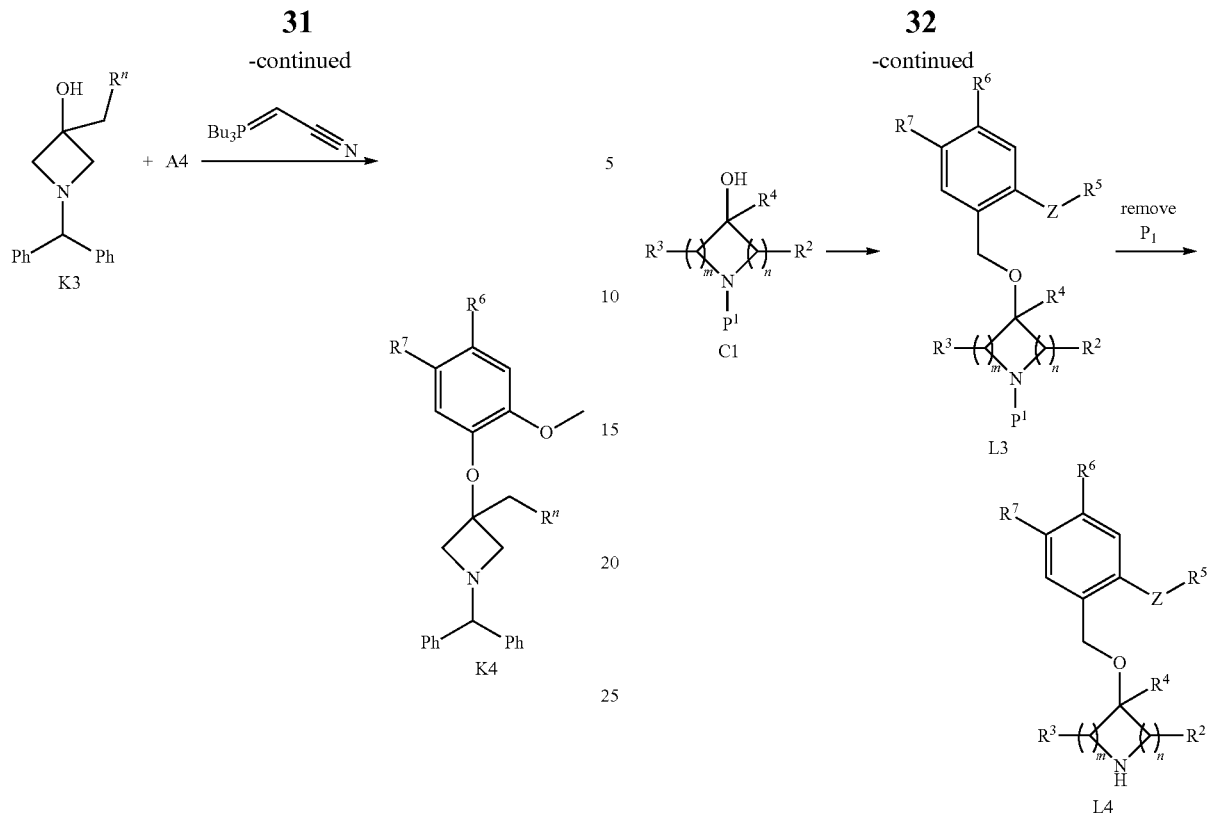

Intermediates of the formula K4 were prepared according to Scheme K. The variable R" in the formulas depicted in Scheme K are —H or —$C_{1-4}$alkyl. The variable Z in the formulas depicted in Scheme K are as defined above in reference to Formula (I) except Z cannot be —C(O)— in Scheme K. Compounds of the formula K2 were obtained from compounds of the formula K1 and compounds of the formula A4 in the presence of cyanomethylene-tri-n-butylphosphine in a solvent such as $PhCH_3$ when heated in a microwave reactor at temperatures up to 120° C. Alternatively, when the protecting group on nitrogen was a benzhydryl as in compounds of the formula K3 compounds of the formula K4 were obtained using similar conditions.

Scheme L

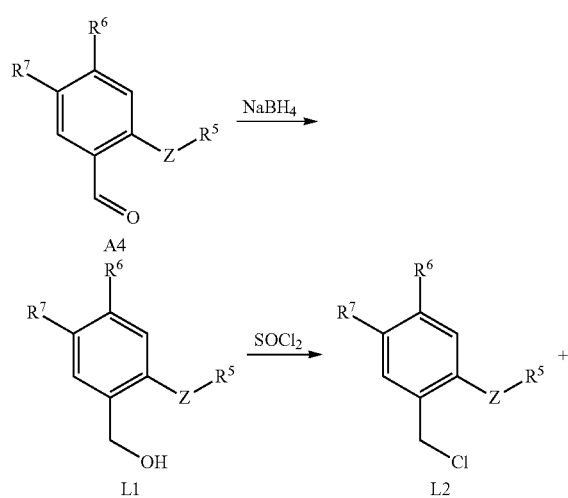

Intermediates of the formula L4 were prepared according to Scheme L. The variable Z in the formulas depicted in Scheme L are as defined above in reference to Formula (I) except Z cannot be —C(O)— in Scheme L. The amine in compounds of the formula L3 may be protected, as indicated by $P^1$, as discussed previously. Compounds of the formula L3 were prepared from compounds of the formula L2 and compounds of the formula C1 in the presence of base such as pyridine, triethylamine, diisopropylamine, $K_2CO_3$, $Cs_2CO_3$ or $Na_2CO_3$ in a suitable solvent such as THF, $CH_2Cl_2$, DMF, MeCN, 1,4-dioxane or the like at a temperature ranging from rt to 100° C. Compounds of the formula L2 were prepared from compounds of the formula L1 by treatment with a chlorinating agent such as $SOCl_2$ in a solvent such as $CH_2Cl_2$. Compounds of the formula L1 were prepared from compounds of the formula A4 using a reducing agent such as $NaBH_4$, $LiBH_4$, Dibal-H, $LiAlH_4$ and the like in a solvent such as $CH_2Cl_2$, THF, DCE, MeOH or EtOH and the like.

Scheme M

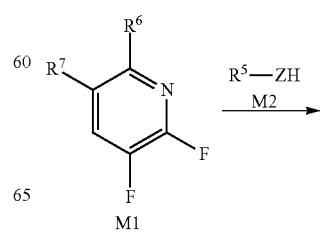

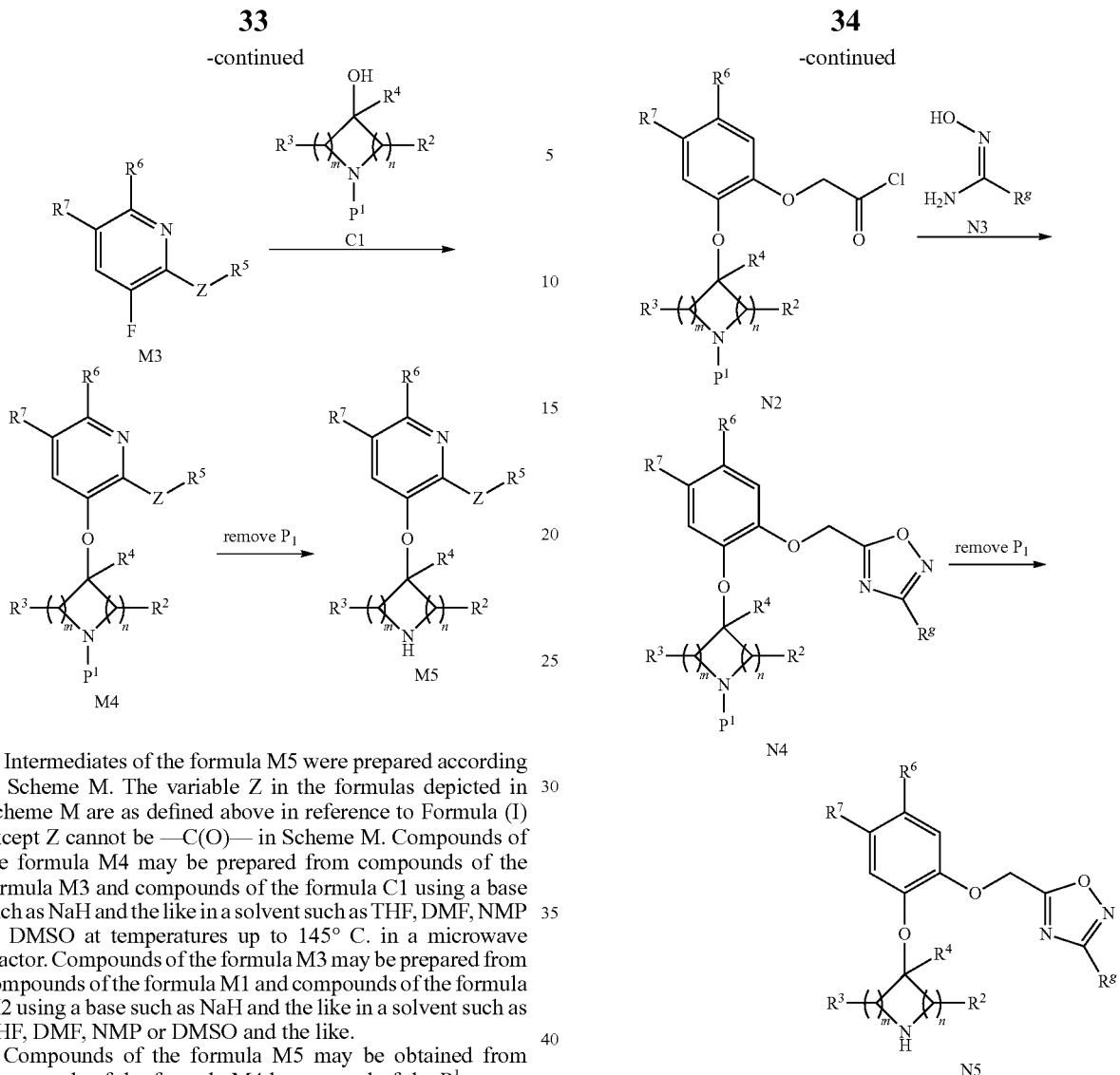

Intermediates of the formula M5 were prepared according to Scheme M. The variable Z in the formulas depicted in Scheme M are as defined above in reference to Formula (I) except Z cannot be —C(O)— in Scheme M. Compounds of the formula M4 may be prepared from compounds of the formula M3 and compounds of the formula C1 using a base such as NaH and the like in a solvent such as THF, DMF, NMP or DMSO at temperatures up to 145° C. in a microwave reactor. Compounds of the formula M3 may be prepared from compounds of the formula M1 and compounds of the formula M2 using a base such as NaH and the like in a solvent such as THF, DMF, NMP or DMSO and the like.

Compounds of the formula M5 may be obtained from compounds of the formula M4 by removal of the $P^1$ group. The amine in compounds of the formula M4 may be protected, as indicated by $P^1$, as described previously. A preferred protecting group is t-butyl carbamate (Boc) or trifluoroacetamide. It will be generally recognized that compounds of the formula M5 may be converted to their corresponding salts using methods generally accepted to those skilled in the art.

Scheme N

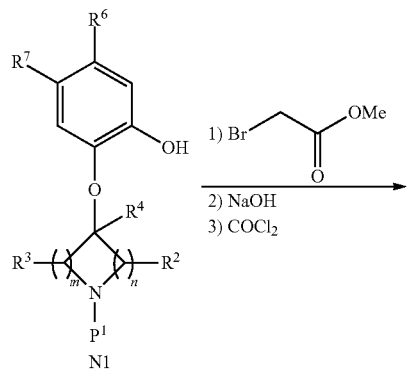

Intermediates of the formula N5 were prepared according to Scheme N. Compounds of the formula N5 may be obtained from compounds of the formula N4 by removal of the $P^1$ group. The amine in compounds of the formula N4 may be protected, as indicated by $P^1$, as described previously. A preferred protecting group is t-butyl carbamate (Boc) or trifluoroacetamide. It will be generally recognized that compounds of the formula N5 may be converted to their corresponding salts using methods generally accepted to those skilled in the art.

Compounds of the formula N4 were prepared from compounds of the formula N2 and compounds of the formula N3 in the presence of a base such as diisopropyethylamine, $Et_3N$ or pyridine and the like upon heating in a microwave reactor at temperatures up to 145° C. Precursors to compounds of the formula N2 were prepared from compounds of the formula N1 and bromomethyl acetate in a solvent such as DMF, DMA, THF or EtOH in the presence of bases such as $NaHCO_3$, $Na_2CO_3$, $K_2CO_3$ or $Cs_2CO_3$. Subsequent hydrolysis using aqueous NaOH followed by formation of compounds of the formula N2 using oxalyl chloride in a solvent such as THF, $CH_2Cl_2$ or $PhCH_3$ in the presence of a catalytic amount of DMF provided compounds of the formula N2.

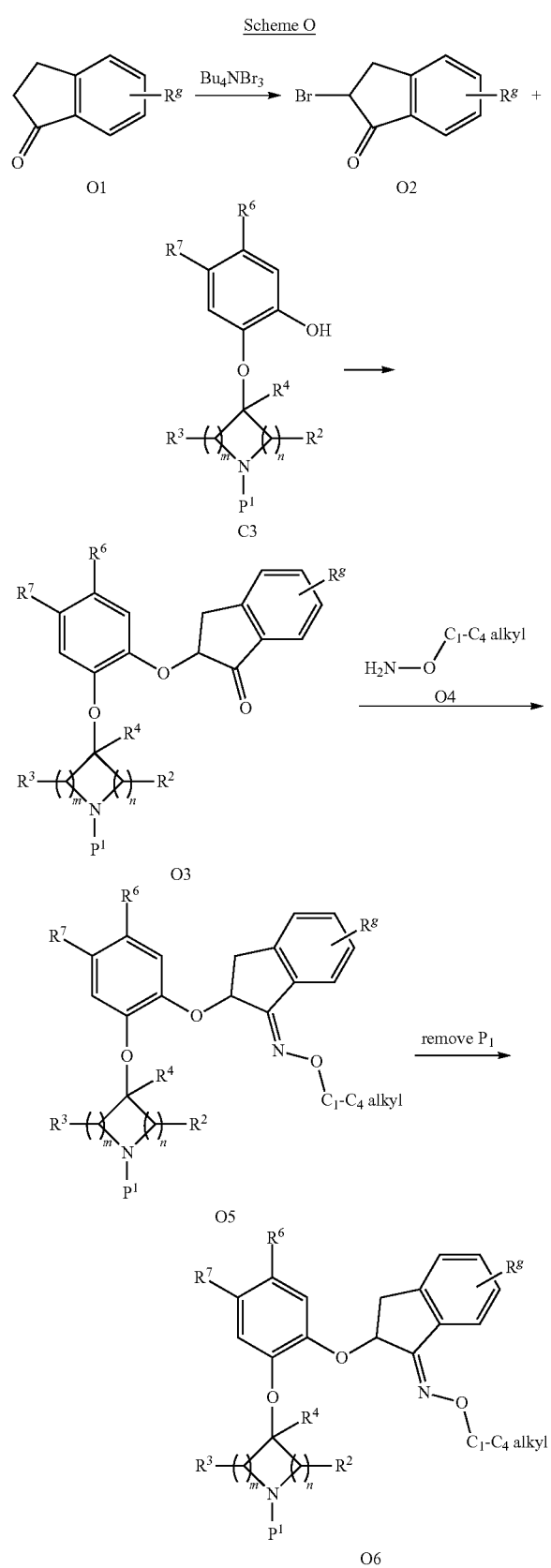

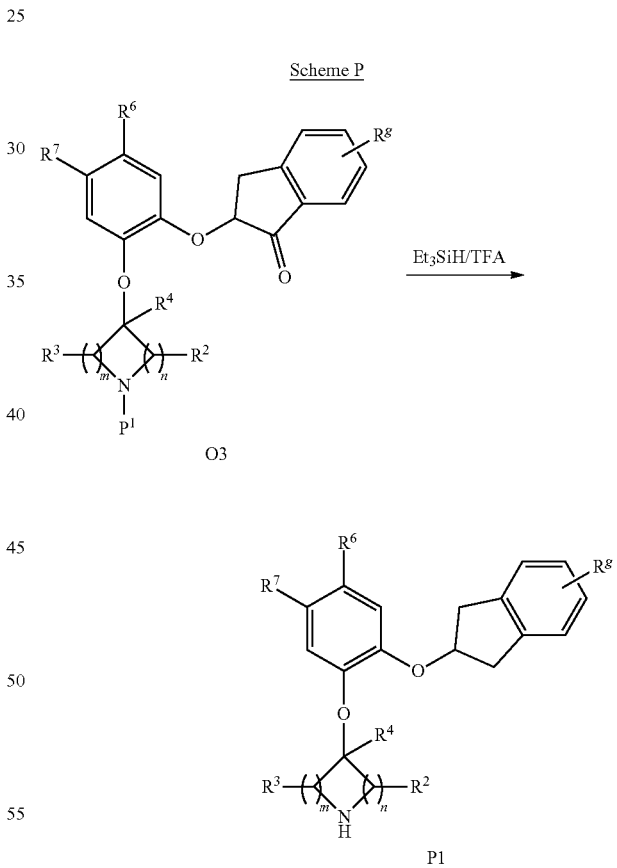

may be protected, as indicated by $P^1$ as described previously. A preferred protecting group is t-butyl carbamate (Boc) or trifluoroacetamide. Compounds of the formula O6 were obtained from compounds of the formula O5 by removal of the $P^1$ group. It will be generally recognized that compounds of the formula O6 may be converted to their corresponding salts using methods generally accepted to those skilled in the art.

Compounds of the formula O5 were prepared form compounds of the formula O3 and compounds of the formula O4 using a base such as $NaHCO_3$, $Na_2CO_3$, $K_2CO_3$ or $Cs_2CO_3$ in solvents such as MeOH, EtOH or iPrOH. Compounds of the formula O3 were prepared from compounds of the formula C3 and compounds of the formula O2 by heating the mixture up to 100° C. in a microwave reactor in a solvent such as DMF, DMA, THF or EtOH in the presence of bases such as $NaHCO_3$, $Na_2CO_3$, $K_2CO_3$ or $Cs_2CO_3$. Compounds of the formula O2 were obtained by bromination of compounds of the formula O1 using $(Bu)N_4Br_3$ ($TBABr_3$) in a solvent mixture of MeOH and $CH_2Cl_2$.

Intermediates of the formula O6 were prepared according to Scheme O. The amine in compounds of the formula O5 may be protected, as indicated by $P^1$ as described previously.

Intermediates of the formula P1 were prepared according to Scheme P. Compounds of the formula P1 were synthesized from compounds of the formula O3 using a hydride donor such as $Et_3SiH$ in the presence of an acid such as trifluoroacetic acid in a solvent such as DCE or $CH_2Cl_2$.

Scheme Q

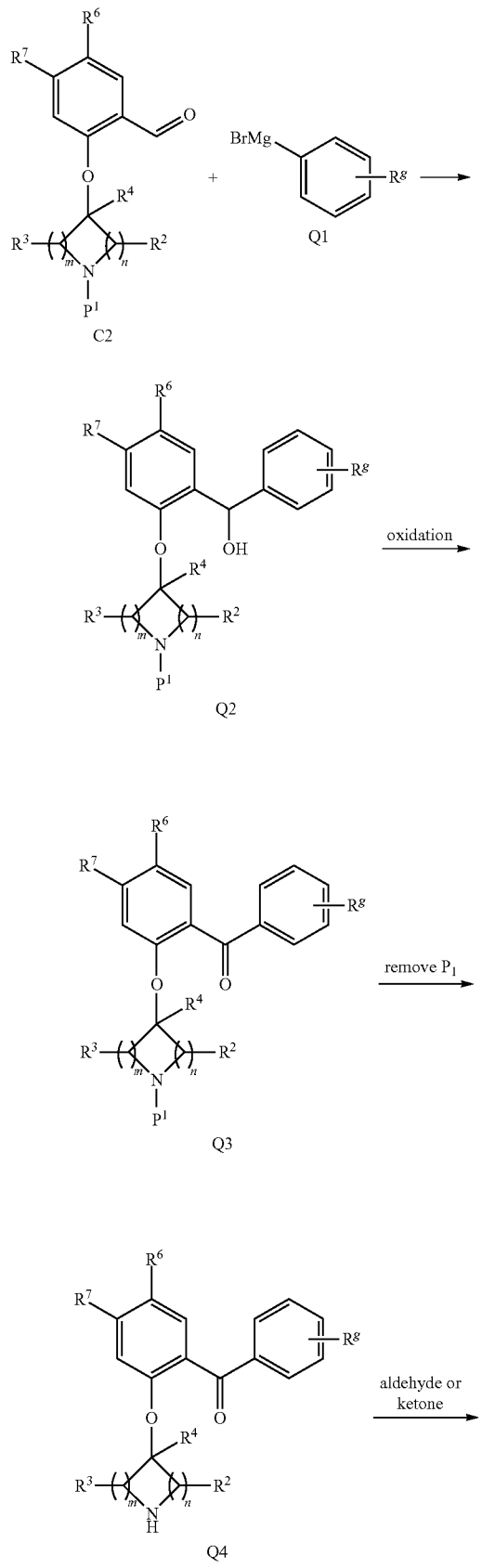

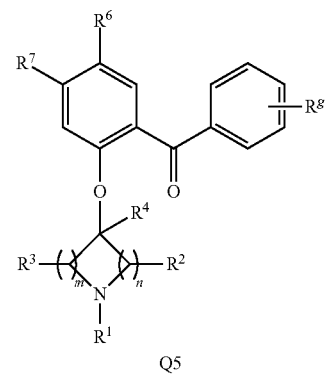

Intermediates of the formula Q5 were prepared according to Scheme Q. Compounds of the formula Q3 were prepared from compounds of the formula Q2 by oxidation with an oxidant such as the Dess-Martin periodinane in a solvent such as $CH_2Cl_2$. Compounds of the formula Q2 were prepared from compounds of the formula C2 (Scheme C) and compounds of the formula Q1 in solvents such as $Et_2O$, THF, $CH_2Cl_2$, or dioxane and the like.

Compounds of the formula Q4 may be obtained from compounds of the formula Q3 by removal of the $P^1$ group. The amine in compounds of the formula Q3 may be protected, as indicated by $P^1$ as described previously. A preferred protecting group is t-butyl carbamate (Boc) or trifluoroacetamide. It will be generally recognized that compounds of the formula Q4 represent a subset of compounds of the formula Q5 where $R_6$ is equal to H. Compounds of the formula Q4 or Q5 may be converted to their corresponding salts using methods generally accepted to those skilled in the art.

Compounds such as Q5 were prepared from compounds of the formula Q4 using methods such as reductive amination or alkylation. Thus treatment of Q4 with a compound containing a carbonyl in the presence of a reductant such as $NaBH_4$, $NaBH_3CN$, $NaBH(OAc)_3$ or hydrogen gas in the presence of a catalyst in a solvent such as $CH_2Cl_2$, THF, DCE, MeOH, EtOH or similar afforded compounds of the formula Q5. One skilled in the art will recognize that the presence of Bronsted or Lewis acids may be required. Examples of acids may include AcOH, $Ti(O-iPr)_4$, trifluoroacetic acid or hydrochloric acid and the like. One skilled in the art will also recognize that compounds of the formula Q5 may be obtained from Q4 upon treatment with an alkyl chloride, bromide, iodide, mesylate or tosylate and the like in a solvent such as DMF, DMA, THF or EtOH in the presence of bases such as $NaHCO_3$, $Na_2CO_3$, $K_2CO_3$ or $Cs_2CO_3$.

Scheme R

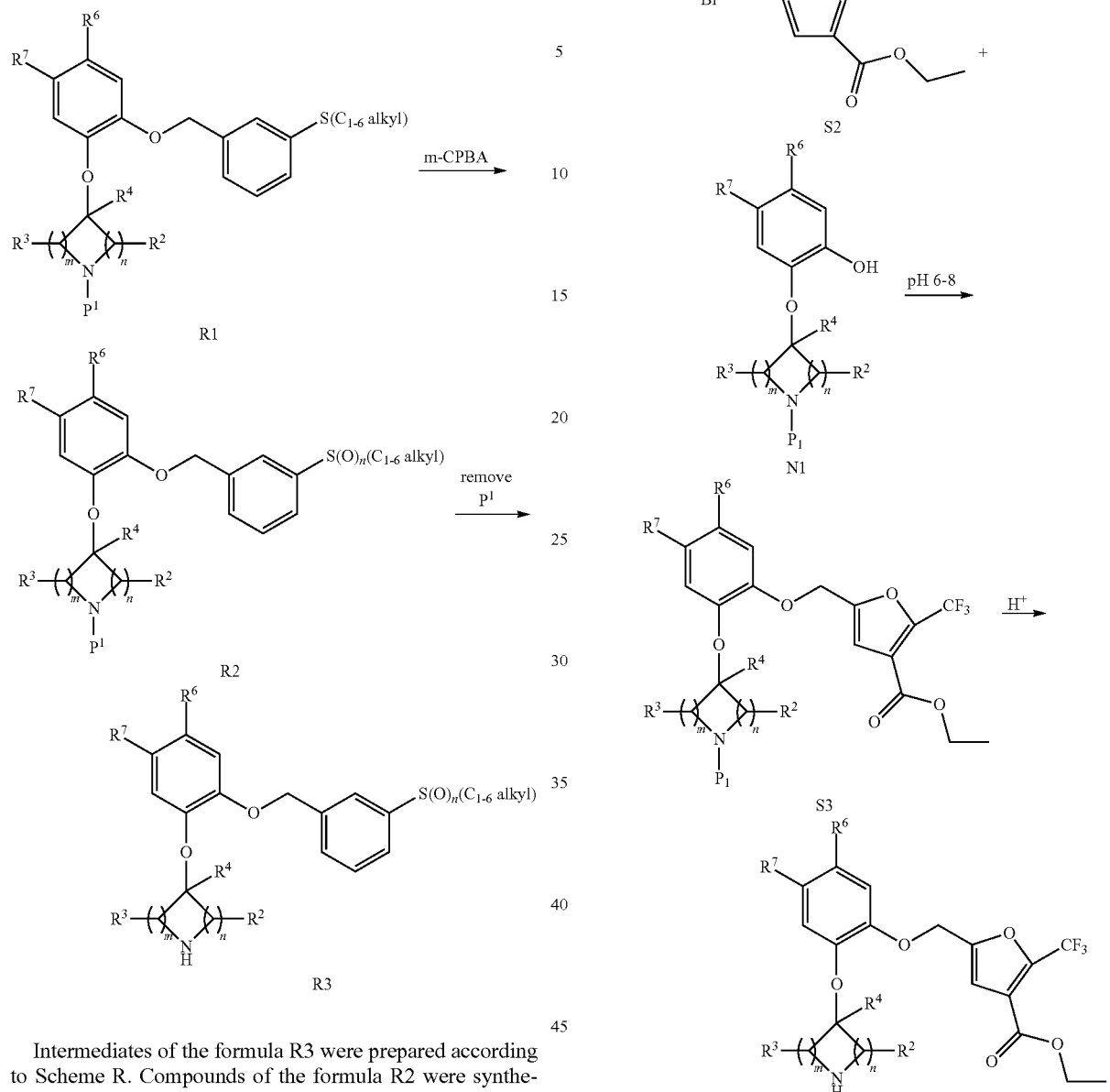

Intermediates of the formula R3 were prepared according to Scheme R. Compounds of the formula R2 were synthesized from compounds of the formula R1 (prepared as outlined in Scheme G) using an oxidant such as m-CPBA in a solvent such as CH$_2$Cl$_2$. Compounds of the formula R3 may be obtained from compounds of the formula R2 by removal of the P$^1$ group. The amine in compounds of the formula R2 may be protected, as indicated by P$^1$ as described previously. A preferred protecting group is t-butyl carbamate (Boc) or trifluoroacetamide.

Scheme S

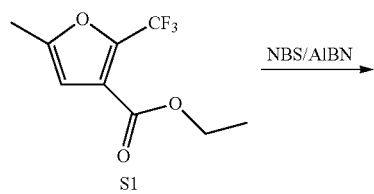

Intermediates of the formula S4 were prepared according to Scheme S. Compounds of the formula S2 were obtained from compounds of the formula S1 by bromination using NBS in the presence of AIBN in solvents such as CCl$_4$ at refluxing temperatures. Compounds of the formula S3 were obtained from compounds of the formula N1 and compounds of the formula S2 in a solvent such as DMF, DMA, THF or EtOH in the presence of bases such as NaHCO$_3$, Na$_2$CO$_3$, K$_2$CO$_3$ or Cs$_2$CO$_3$ followed by a work-up with neutral H$_2$O. A preferred protecting group on compounds of the formula N1 was Boc.

Scheme T

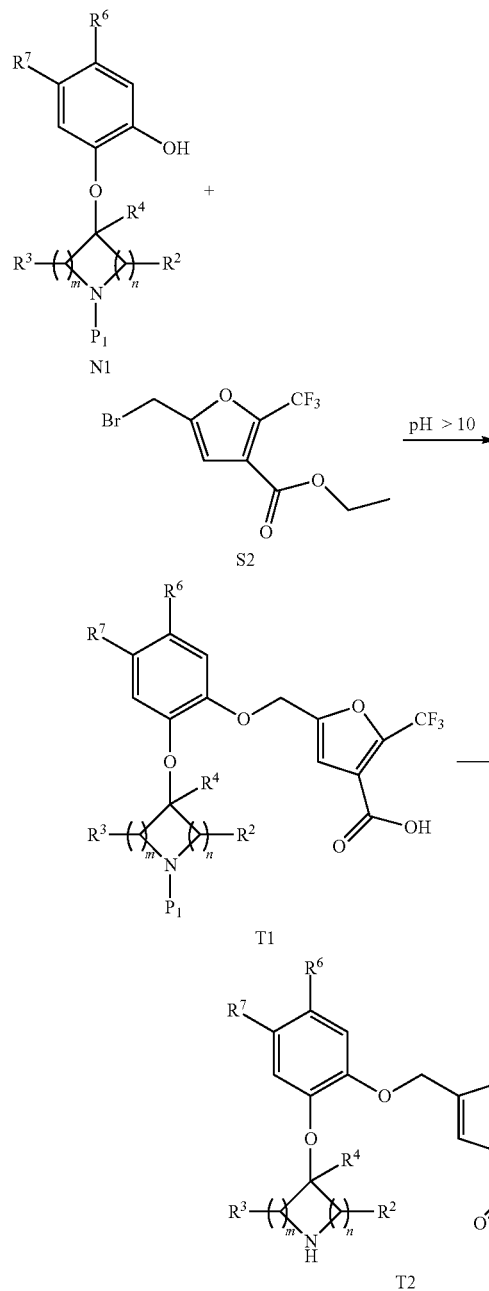

Scheme U

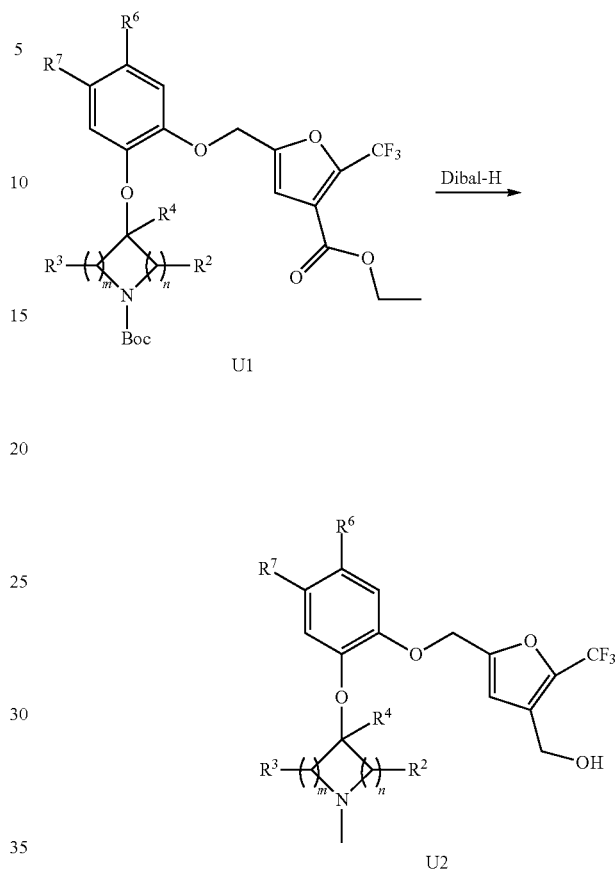

Intermediates of the formula U2 were prepared according to Scheme U. Compounds of the formula U2 were prepared from compounds of the formula U1 using reducing agents such as Dibal-H in solvents such as $CH_2Cl_2$, THF or $PhCH_3$ and the like.

Intermediates of the formula T2 were prepared according to Scheme T. Compounds of the formula T1 were obtained from compounds of the formula N1 and compounds of the formula S2 in a solvent such as DMF, DMA, THF or EtOH in the presence of bases such as $NaHCO_3$, $Na_2CO_3$, $K_2CO_3$ or $Cs_2CO_3$ followed by a work-up with basic $H_2O$ where the pH was >10. A preferred protecting group on compounds of the formula N1 was Boc.

Scheme V

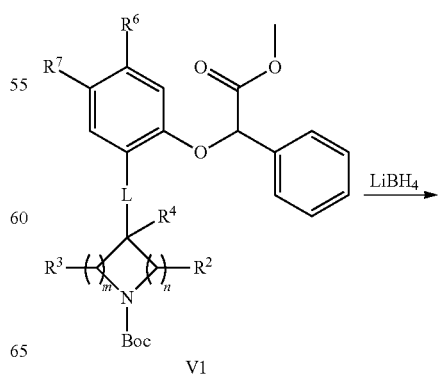

-continued

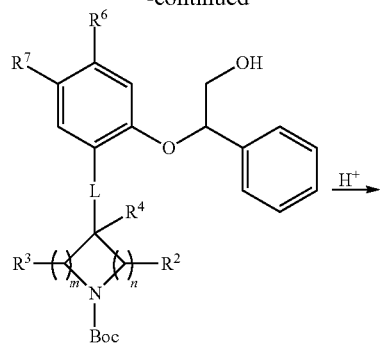

V2

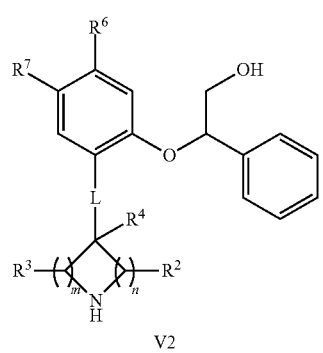

V2

Intermediates of the formula V3 were prepared according to Scheme V. Compounds of the formula V2 were prepared from compounds of the formula V1 using reducing agents such as $LiBH_4$ and the like in solvents such as $CH_2Cl_2$, THF or $PhCH_3$ and the like. Compounds of the formula V3 were prepared from compounds of the formula V2 using acids such as trifluoroacetic acid or hydrochloric acid and the like in a solvent such as $CH_2Cl_2$, EtOAc, THF, 1,4-dioxane, MeOH or EtOH.

Scheme W

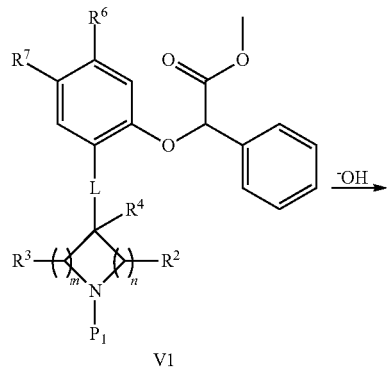

V1

-continued

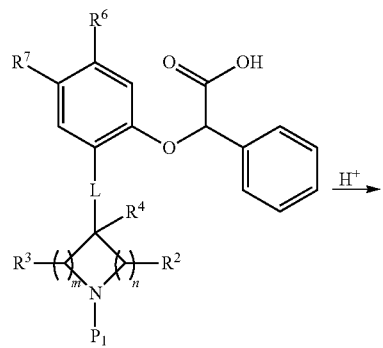

W1

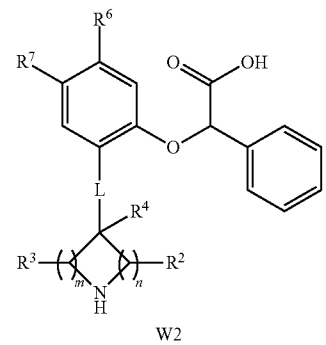

W2

Intermediates of the formula W2 were prepared according to Scheme W. Compounds of the formula W1 were prepared from compounds of the formula V1 by hydrolysis using aqueous hydroxide bases such as NaOH or KOH and the like with an organic co-solvent such as THF or MeOH. A preferred protecting group on compounds of the formula V1 was Boc.

Scheme X

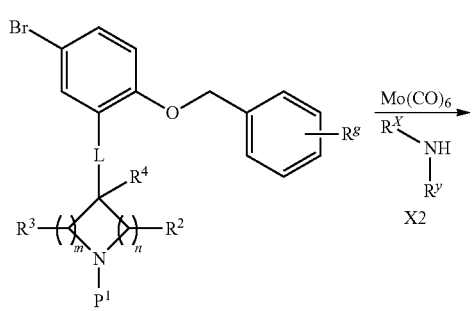

X1

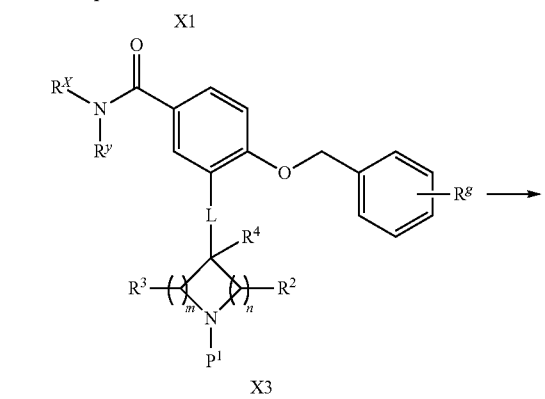

X3

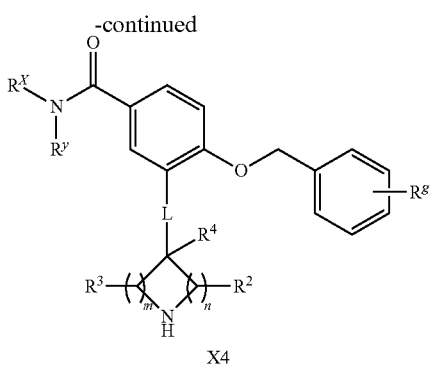

Intermediates of the formula X4 were prepared according to Scheme X. A preferred protecting group on compounds of the formula X1 was Boc. Compounds of the formula X3, were prepared from compounds of the formula X1 and compounds of the formula X2 by heating in a microwave reactor at temperatures up to 170° C. in the presence of Hermann's catalyst, $Mo(CO)_6$ and bases such as $Na_2CO_3$ and the like.

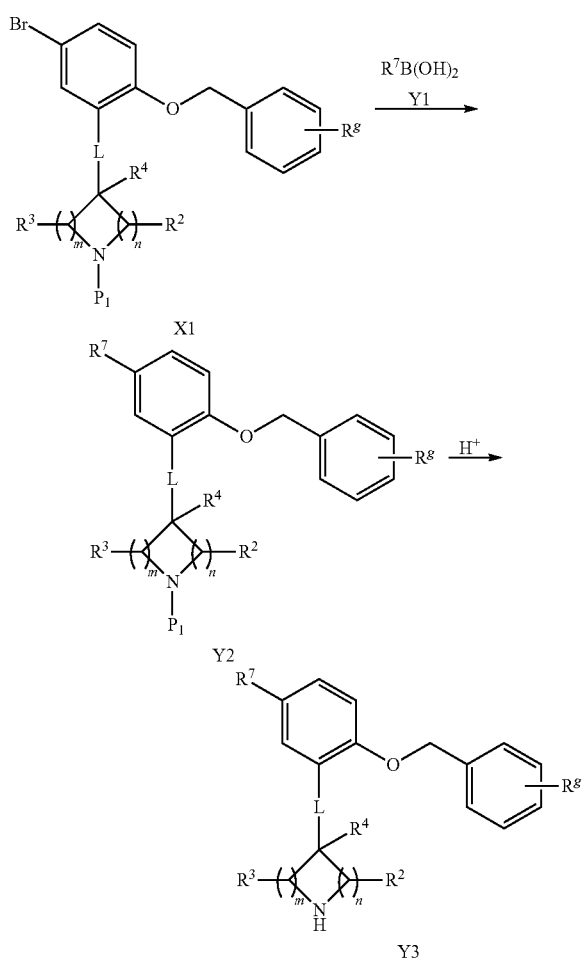

Intermediates of the formula Y3 were prepared according to Scheme Y. A preferred protecting group on compounds of the formula X1 was Boc. Compounds of the formula Y2, were prepared from compounds of the formula X1 by treatment with compounds of the formula Y1 in the presence of a catalyst such as $PdCl_2(dppf)$, $PdCl_2(dppe)$ $Pd_2(dba)_3$, $Pd(dba)_2$, $PdCl_2(PPh_3)_2$, $Pd(PPh_3)_4$ in a solvent such as $PhCH_3$, 1,4-dioxane, THF, DMA, DMF or DME in the presence of a base such as $Na_2CO_3$, $K_2CO_3$, $Cs_2CO_3$, CsF, KF, $K_3PO_4$, KOAc or the like and a ligand typically used in such reactions such as Q-Phos, dppf, dppe or $PPh_3$ and the like at temperatures ranging from rt to 160° C. using conventional or microwave heating.

EXAMPLES

Chemistry

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions were "dried," they were generally dried over a drying agent such as $Na_2SO_4$ or $MgSO_4$ then filtered and concentrated. Where mixtures, solutions, and extracts were "concentrated", they were typically concentrated on a rotary evaporator under reduced pressure.

Thin-layer chromatography (TLC) was performed using Merck silica gel 60 $F_{254}$ 2.5 cm×7.5 cm 250 μm or 5.0 cm×10.0 cm 250 μm pre-coated silica gel plates. Preparative thin-layer chromatography (PTLC) was performed using EM Science silica gel 60 $F_{254}$ 20 cm×20 cm 0.5 mm pre-coated plates with a 20 cm×4 cm concentrating zone.

Normal-phase flash column chromatography (FCC) was performed on silica gel ($SiO_2$) eluting with 2 M $NH_3$ in $MeOH/CH_2Cl_2$ or EtOAc in hexanes, unless otherwise noted.

Preparative reversed-phase HPLC (RP HPLC) was performed on a Hewlett Packard HPLC Series 1100, with a Phenomenex Luna C18 (5 μm, 4.6×150 mm) column. Detection was done at λ=230, 254 and 280 nm. The gradient was 10 to 99% acetonitrile/$H_2O$ (0.05% trifluoroacetic acid) over 5.0 min with a flow rate of 1 mL/min. Alternatively, HPLC was performed on a Dionex APS2000 LC/MS with a Phenomenex Gemini C18 (5 μm, 30×100 mm) column, and a gradient of 5 to 100% acetonitrile/$H_2O$ (20 mM $NH_4OH$) over 16.3 min, and a flow rate of 30 mL/min. Preparative RP HPLC was also performed on an Agilent 1100 preparative system with a Waters X-Bridge C18 (5 μm, 30×100 mm) column, and a gradient of 5 to 99% acetonitrile/$H_2O$ (20 mM $NH_4OH$) over 17 min, and a flow rate of 80 mL/min.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1H$ NMR data below is: chemical shift in ppm downfield of the tetramethylsilane reference or relative to residual protic solvent (multiplicity, coupling constant J in Hz, integration).

Chemical names were generated using ChemDraw Version 6.0.2 (CambridgeSoft, Cambridge, Mass.).

General Procedures

General Procedure 1 (Removal of Boc groups): Boc groups were deprotected using $TFA/CH_2Cl_2$ (1:1) or 4M HCl in dioxane/EtOAc (1:1). The compounds were then either neutralized and extracted with $CH_2Cl_2$ or characterized as the hydrochloride or trifluoroacetate salt where indicated.

General Procedure 2 (Removal of trifluoroacetamide groups): Trifluoroacetamide groups were deprotected using $K_2CO_3$ (1 eq.) in MeOH (0.2 M), 2M $NH_3$ in MeOH or 5N $NH_4OH$ (aq.) in MeOH. After 15 h, $H_2O$ was added and the mixture extracted with EtOAc (2x). The combined organics were dried and concentrated. Purification using silica gel chromatography, reverse-phase HPLC or PTLC then provided the deprotected amines.

General Procedure 3 (Reductive amination): To amine in $CH_2Cl_2$ (0.1 M) was added ketone (1.2-5.0 eq.) and NaBH(OAc)$_3$ (1.2 eq.). After 18 h, the reaction was typically treated with 5% $Na_2CO_3$ (aq.) and extracted with $CH_2Cl_2$ (2x). The combined organics were dried and purified using silica gel chromatography, reverse-phase HPLC or PTLC.

General Procedure 4 (Reductive amination): To amine in MeOH (0.1 M) was added ketone or aldehyde (1.2-5.0 eq.), AcOH (10 mol %) and NaCNBH$_3$ (1.2 eq.). After 18 h, the reaction was typically treated with 5% $Na_2CO_3$ (aq.) and extracted with $CH_2Cl_2$ (2x). The combined organics were dried and purified using silica gel chromatography, reverse-phase HPLC or PTLC.

General Procedure 5 (NH to NMe): To amine in MeOH (0.1 M) was added excess 37 wt % [$H_2CO$]n in $H_2O$ and NaBHOAc$_3$ (1.2 eq.). After 18 h, 5% $Na_2CO_3$ (aq.) was added and the mixture extracted with $CH_2Cl_2$. The combined organics were dried and purified using silica gel chromatography, reverse-phase HPLC or PTLC to yield the corresponding methylated analogs.

General Procedure 6 (Cu(OAc)-2-mediated diaryl ether synthesis): To a phenol in DCE (0.1 M) was added arylboronic acid (2 eq.), Cu(OAc)$_2$ (1 eq.), MgSO$_4$ (2 eq) or 4 Å molecular sieves and Et$_3$N (5 eq). The reactions were allowed to stir open to the air for 12-48 h, then filtered, concentrated and purified using silica gel chromatography, reverse-phase HPLC or PTLC.

General Procedure 7 (Mitsunobu Reaction): To phenol (1 eq), alcohol (1 eq) and either PPh$_3$ (1.2 eq) or resin-bound PPh$_3$ in THF (0.2 M) at 0° C. or rt was added DEAD (1.1 eq) dropwise. After judged complete, the reactions were concentrated and purified using silica gel chromatography, reverse phase HPLC or PTLC.

Example 1

3-(2-Benzyloxy-5-bromo-phenoxy)-azetidine

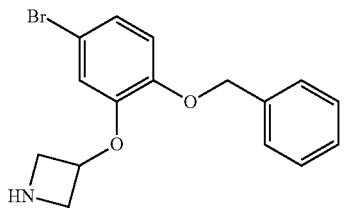

Step A: Preparation of (4-bromo-2-fluoro-benzylidene)-tert-butyl-amine. To a $CH_2Cl_2$ (900 mL) solution of 4-bromo-2-fluoro-benzaldehyde (50.0 g, 246 mmol) was added tert-butylamine (42.3 mL, 29.3 g, 400 mmol) and MgSO$_4$ (60.0 g, 499 mmol). After 48 h, the solution was filtered and concentrated to give 62.0 g (98%) of the title compound as a yellow liquid. $^1$H NMR (CDCl$_3$): 8.48 (s, 1H), 7.89 (t, J=8.1 Hz, 1H), 7.32-7.25 (m, 2H), 1.29 (s, 9H).

Step B: Preparation of 3-(5-bromo-2-formyl-phenoxy)-azetidine-1-carboxylic acid tert-butyl ester. To a 0° C. DMF (720 mL) solution of the title compound of Step A (37.2 g, 144 mmol) and 3-hydroxy-azetidine-1-carboxylic acid tert-butyl ester (25.0 g, 144 mmol) was added NaH (60 wt % in mineral oil, 7.50 g, 188 mmol) portionwise over 2 h. The reaction was then allowed to warm to rt. After 18 h, $H_2O$ was added and the reaction mixture was extracted with EtOAc (2x). The combined organic layers were washed with brine and concentrated to give a yellow liquid that was treated with THF (360 mL), $H_2O$ (360 mL) and AcOH (25 mL). After 5 h, this solution was made basic with 5% $Na_2CO_3$ (aq.) and extracted with EtOAc (2x). The combined organic layers were washed with brine and dried. The resulting solid was then triturated with 20% EtOAc in hexanes to give 41.9 g (82%) of the title compound as a white solid. $^1$H NMR (CDCl$_3$): 10.43 (s, 1H), 7.74 (d, J=8.3 Hz, 1H), 7.26-7.23 (m, 1H), 6.77 (d, J=1.6 Hz, 1H), 5.01-4.95 (m, 1H), 4.39 (ddd, J=9.9, 6.3, 0.8 Hz, 2H), 4.08 (dd, J=6.4, 0.8 Hz, 2H), 1.46 (s, 9H).

Step C: Preparation of 3-(5-Bromo-2-hydroxy-phenoxy)-azetidine-1-carboxylic acid tert-butyl ester. To a $CH_2Cl_2$ (280 mL) solution of the title compound of Step B (24.7 g, 69.4 mmol) was added 77% m-CPBA (23.3 g, 104 mmol). After 15 h, 10% $Na_2S_2O_5$ (aq.) was added and the solution allowed to stir until the aqueous was KI paper negative then extracted with $CH_2Cl_2$ (2x). The combined organic layers were washed with saturated NaHCO$_3$ (aq.), concentrated and treated with MeOH (220 mL) and 1N NaOH (220 mL). After 15 h, the reaction was partially concentrated to remove the MeOH, acidified with 1M KHSO$_4$ (220 mL) and extracted with $CH_2Cl_2$ (2x). The combined organic layers were washed with brine and dried providing a brown solid that was triturated with EtOAc/hexanes giving 17.6 g (74%) of the title compound as a white solid. $^1$H NMR (CDCl$_3$): 7.03 (dd, J=8.5, 2.1 Hz, 1H), 6.84 (d, J=8.5 Hz, 1H), 6.64 (d, J=2.2 Hz, 1H), 4.93-4.89 (m, 1H), 4.34 (dd, J=10.1, 6.8 Hz, 1H), 4.03 (dd, J=9.9, 3.7 Hz, 1H), 1.46 (s, 9H).

Step D: Preparation of 3-(2-benzyloxy-5-bromo-phenoxy)-azetidine-1-carboxylic acid tert-butyl ester. To a DMF (10 mL) solution of the title compound of Step C (0.52 g, 1.5 mmol), Cs$_2$CO$_3$ (0.54 g, 1.7 mmol) and KI (0.20 g, 1.20 mmol) was added benzyl bromide (0.20 mL, 0.29 g, 1.7 mmol). After 48 h, $H_2O$ was added and the mixture extracted with EtOAc (2x). The combined organics were washed with brine (2x) and dried. Silica gel chromatography (5-20% EtOAc in hexanes) gave 0.65 g (99%) of the title compound as a clear oil. $^1$H NMR (CDCl$_3$): 7.42-7.36 (m, 3H), 7.34-7.31 (m, 2H), 7.03 (dd, J=8.6, 2.3 Hz, 1H), 6.81 (d, J=8.6 Hz, 1H), 6.70 (d, J=2.3 Hz, 1H), 5.09 (s, 2H), 4.88-4.83 (m, 1H), 4.26 (ddd, J=9.7, 6.5, 0.9 Hz, 2H), 4.05 (dd, J=9.8, 4.0 Hz, 2H), 1.45 (s, 9H).

Step E: Preparation of 3-(2-Benzyloxy-5-bromo-phenoxy)-azetidine. Synthesized according to general procedure 1 from the title compound of Step D. MS (ESI): mass calcd. for C$_{16}$H$_{16}$BrNO$_2$, 333.0; m/z found, 334.0 [M+H]$^+$. $^1$H NMR (CDCl$_3$): 7.08 (dd, J=8.6, 2.3 Hz, 1H), 6.77 (d, J=8.6 Hz, 1H), 6.67 (d, J=2.2 Hz, 1H), 4.86 (tt, J=6.5, 4.3 Hz, 1H), 4.29 (ddd, J=9.7, 6.5, 0.8 Hz, 2H), 4.08 (dd, J=10.1, 4.2 Hz, 2H), 3.85 (s, 3H), 1.44 (s, 9H).

Unless otherwise specified the compounds in Examples 2-74 were prepared similar to Example 1 using the appropriately substituted phenol and alkyl halide.

Example 2

3-[5-Bromo-2-(3-chloro-benzyloxy)-phenoxy]-azetidine

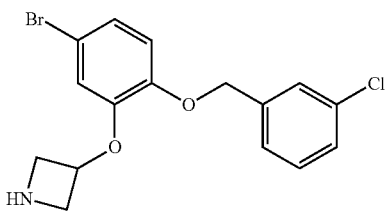 [SMILES: Clc1cccc(COc2ccc(Br)cc2OC2CNC2)c1]

MS (ESI): mass calcd. for $C_{16}H_{15}BrClNO_2$, 367.0; m/z found, 368.1 [M+H]$^+$. $^1$H NMR (CDCl$_3$): 7.47-7.43 (m, 1H), 7.31-7.27 (m, 3H), 7.00 (dd, J=8.6, 2.3 Hz, 1H), 6.78-6.73 (m, 2H), 5.06 (s, 2H), 5.01-4.95 (m, 1H), 3.94-3.83 (m, 4H).

The compounds in Examples 3-6 were prepared from the title compound of Example 2 using general procedure 3 or 4.

Example 3

3-[5-Bromo-2-(3-chloro-benzyloxy)-phenoxy]-1-cyclobutyl-azetidine

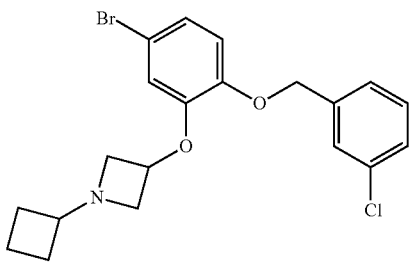 [SMILES: Clc1cccc(COc2ccc(Br)cc2OC2CN(C3CCC3)C2)c1]

MS (ESI): mass calcd. for $C_{20}H_{21}BrClNO_2$, 422.7; m/z found, 423.9 [M+H]$^+$. $^1$H NMR (CDCl$_3$): 7.43 (s, 1H), 7.32-7.26 (m, 3H), 6.98 (dd, J=8.5, 2.3 Hz, 1H), 6.75 (dd, J=13.6, 5.4 Hz, 2H), 5.05 (s, 2H), 4.77-4.72 (m, 1H), 3.78-3.65 (m, 2H), 3.12-3.16 (m, 3H), 2.01-1.95 (m, 2H), 1.87-1.79 (m, 2H), 1.78-1.69 (m, 2H).

Example 4

3-[5-Bromo-2-(3-chloro-benzyloxy)-phenoxy]-1-propyl-azetidine

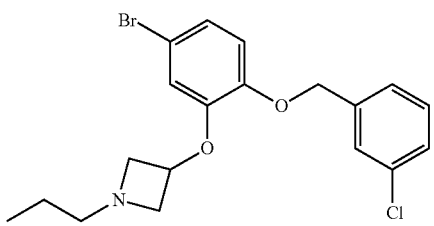 [SMILES: CCCN1CC(Oc2cc(Br)ccc2OCc2cccc(Cl)c2)C1]

MS (ESI): mass calcd. for $C_{19}H_{21}BrClNO_2$, 410.7; m/z found, 411.9 [M+H]$^+$. $^1$H NMR (CDCl$_3$): 7.44 (s, 1H), 7.33-7.27 (m, 3H), 7.02-6.95 (m, 1H), 6.76 (dd, J=13.4, 5.4 Hz, 2H), 5.06 (s, 2H), 4.78-4.74 (m, 1H), 3.88-3.80 (m, 2H), 3.14-3.06 (m, 2H), 2.52-2.44 (m, 2H), 1.45-1.34 (m, 2H), 0.91 (t, J=7.4 Hz, 3H).

Example 5

3-[5-Bromo-2-(3-chloro-benzyloxy)-phenoxy]-1-isopropyl-azetidine

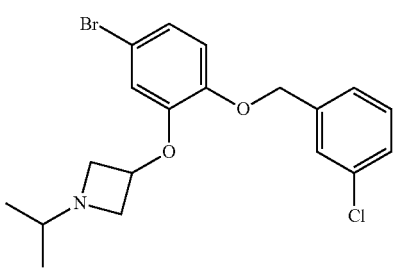 [SMILES: CC(C)N1CC(Oc2cc(Br)ccc2OCc2cccc(Cl)c2)C1]

MS (ESI): mass calcd. for $C_{19}H_{21}BrClNO_2$, 410.7; m/z found, 411.9 [M+H]$^+$. $^1$H NMR (CDCl$_3$): 7.44 (s, 1H), 7.32-7.27 (m, 3H), 6.99 (dd, J=8.6, 2.3 Hz, 1H), 6.79 (d, J=2.3 Hz, 1H), 6.75 (d, J=8.6 Hz, 1H), 4.98 (s, 2H), 4.75-4.70 (m, 1H), 3.88-3.71 (m, 2H), 3.15-2.94 (m, 2H), 2.43-2.38 (m, 1H), 0.99-0.95 (m, 6H).

Example 6

3-[5-Bromo-2-(3-chloro-benzyloxy)-phenoxy]-1-ethyl-azetidine

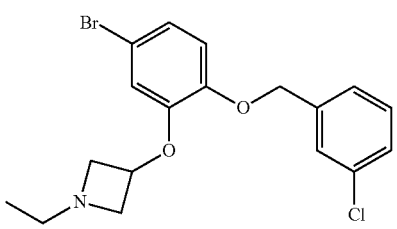 [SMILES: CCN1CC(Oc2cc(Br)ccc2OCc2cccc(Cl)c2)C1]

MS (ESI): mass calcd. for $C_{18}H_{19}BrClNO_2$, 396.7; m/z found, 397.0 [M+H]$^+$. $^1$H NMR (CDCl$_3$): 7.44 (d, J=1.8, 1H), 7.35-7.26 (m, 3H), 6.99 (dd, J=8.6, 2.3 Hz, 1H), 6.76 (dd, J=14.8, 5.4 Hz, 2H), 5.06 (s, 2H), 4.78-4.73 (m, 1H), 3.87-3.79 (m, 2H), 3.11-3.08 (m, 2H), 2.55 (q, J=7.2, 2H), 1.00 (t, J=7.2 Hz, 3H).

Example 7

3-[5-Bromo-2-(3-trifluoromethoxy-benzyloxy)-phenoxy]-azetidine

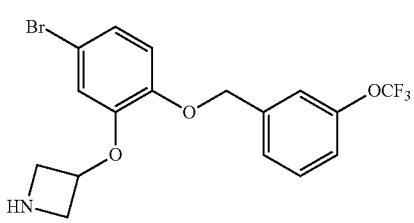 [SMILES: FC(F)(F)Oc1cccc(COc2ccc(Br)cc2OC2CNC2)c1]

MS (ESI): mass calcd. for $C_{17}H_{15}BrF_3NO_3$, 417.0; m/z found, 418.1 [M+H]$^+$. $^1$H NMR (CDCl$_3$): 7.40 (t, J=8.1 Hz, 1H), 7.34-7.33 (m, 2H), 7.18-7.16 (m, 1H), 7.00 (dd, J=8.6, 2.3 Hz, 1H), 6.77 (d, J=8.6 Hz, 1H), 6.73 (d, J=2.3 Hz, 1H), 5.10 (s, 2H), 5.01-4.96 (m, 1H), 3.93-3.86 (m, 4H).

Example 8

3-[5-Bromo-2-(3-trifluoromethyl-benzyloxy)-phenoxy]-azetidine

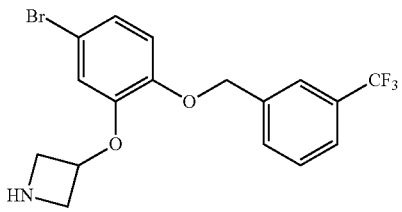

MS (ESI): mass calcd. for $C_{17}H_{15}BrF_3NO_2$, 401.0; m/z found, 401.9 [M+H]$^+$. $^1$H NMR (CDCl$_3$): 7.75 (s, 1H), 7.60 (t, J=7.2 Hz, 2H), 7.51 (t, J=7.7 Hz, 1H), 7.02 (dd, J=8.6, 2.3 Hz, 1H), 6.80 (d, J=8.6 Hz, 1H), 6.74 (d, J=2.3 Hz, 1H), 5.14 (s, 2H), 5.01-4.95 (m, 1H), 3.93-3.86 (m, 4H).

Example 9

3-[2-(Azetidin-3-yloxy)-4-bromo-phenoxymethyl]-benzonitrile

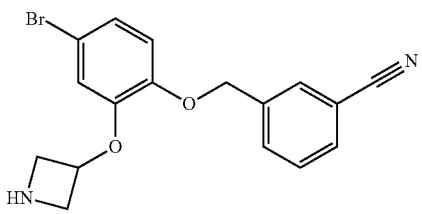 [SMILES: N#Cc1cccc(COc2ccc(Br)cc2OC2CNC2)c1]

$^1$H NMR (CDCl$_3$): 7.78 (s, 1H), 7.67-7.61 (m, 2H), 7.50 (t, J=7.7 Hz, 1H), 7.01 (dd, J=8.6, 2.3 Hz, 1H), 6.76 (d, J=8.6 Hz, 1H), 6.73 (d, J=2.3 Hz, 1H), 5.12 (s, 2H), 5.02-4.96 (m, 1H), 3.95-3.86 (m, 4H).

Example 10

3-[5-Bromo-2-(5-trifluoromethyl-furan-2-yl-methoxy)-phenoxy]-azetidine

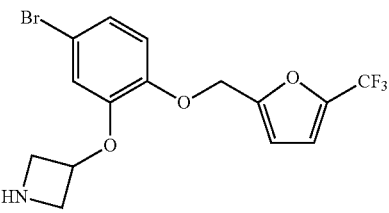

MS (ESI): mass calcd. for $C_{15}H_{13}BrF_3NO_3$, 391.0; m/z found, 392.1 [M+H]$^+$. $^1$H NMR (CDCl$_3$): 7.03 (dd, J=8.6, 2.3 Hz, 1H), 6.84 (d, J=8.6 Hz, 1H), 6.79-6.76 (m, 1H), 6.74 (d, J=2.3 Hz, 1H), 6.47 (d, J=3.3 Hz, 1H), 5.06 (s, 2H), 5.00-4.93 (m, 1H), 3.96-3.89 (m, 2H), 3.88-3.79 (m, 2H).

Example 11

3-[5-Bromo-2-(3-chloro-4-trifluoromethoxy-benzyloxy)-phenoxy]-azetidine

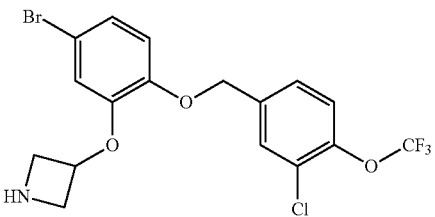

MS (ESI): mass calcd. for $C_{17}H_{14}BrClF_3NO_3$, 451.0; m/z found, 452.0 [M+H]$^+$. $^1$H NMR (CDCl$_3$): 7.62-7.59 (m, 2H), 7.35-7.32 (m, 2H), 7.02 (dd, J=8.6, 2.3 Hz, 1H), 6.78 (d, J=8.6 Hz, 1H), 6.74 (d, J=2.3 Hz, 1H), 5.06 (s, 2H), 5.03-4.96 (m, 1H), 3.98-3.91 (m, 2H), 3.89-3.83 (m, 2H).

Example 12

3-[5-Bromo-2-(3-chloro-4-fluoro-benzyloxy)-phenoxy]-azetidine

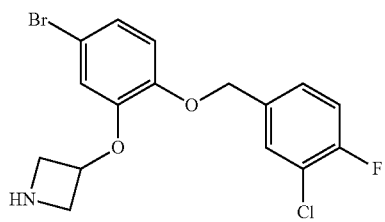 [SMILES: Fc1ccc(COc2ccc(Br)cc2OC2CNC2)cc1Cl]

MS (ESI): mass calcd. for $C_{16}H_{14}BrClFNO_2$, 385.0; m/z found, 386.1 [M+H]$^+$. $^1$H NMR (CDCl$_3$): 7.52 (dd, J=7.0, 2.1 Hz, 1H), 7.31-7.25 (m, 1H), 7.15 (dd, J=8.7, 8.6 Hz, 1H), 7.01 (dd, J=8.6, 2.3 Hz, 1H), 6.77 (d, J=8.6 Hz, 1H), 6.73 (d, J=2.3 Hz, 1H), 5.03 (s, 2H), 5.01-4.95 (m, 1H), 3.99-3.91 (m, 2H), 3.90-3.81 (m, 2H).

Example 13

3-[5-Bromo-2-(3-chloro-4-methoxy-benzyloxy)-phenoxy]-azetidine

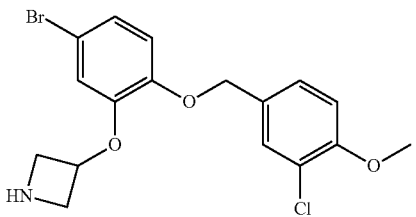 [SMILES: COc1ccc(COc2ccc(Br)cc2OC2CNC2)cc1Cl]

MS (ESI): mass calcd. for $C_{17}H_{17}BrClNO_3$, 397.0; m/z found, 398.1 [M+H]$^+$. $^1$H NMR (CDCl$_3$): 7.48 (d, J=2.1 Hz, 1H), 7.29-7.25 (m, 1H), 7.02 (dd, J=8.6, 2.3 Hz, 1H), 6.92 (d, J=8.4 Hz, 1H), 6.79 (d, J=8.6 Hz, 1H), 6.73 (d, J=2.3 Hz, 1H), 5.01 (s, 2H), 5.00-4.94 (m, 1H), 3.96-3.83 (m, 4H), 3.92 (s, 3H).

Example 14

3-[5-Bromo-2-(4-chloro-benzyloxy)-phenoxy]-azetidine trifluoroacetate

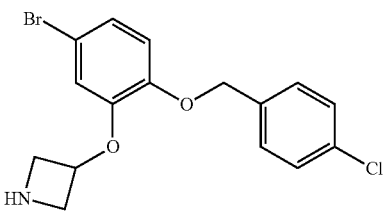 [SMILES: Clc1ccc(COc2ccc(Br)cc2OC2CNC2)cc1]

MS (ESI): mass calcd. for $C_{16}H_{15}BrClNO_2$, 367.00; m/z found, 368.1 [M+H]$^+$. $^1$H NMR (CDCl$_3$): 7.41-7.30 (m, 4H), 7.12 (dd, J=8.7, 2.3 Hz, 1H), 6.87 (d, J=2.3 Hz, 1H), 6.80 (d, J=8.7 Hz, 1H), 5.06-4.99 (m, 3H), 4.31-4.13 (m, 4H).

Example 15

3-[5-Bromo-2-(2-chloro-benzyloxy)-phenoxy]-azetidine trifluoroacetate

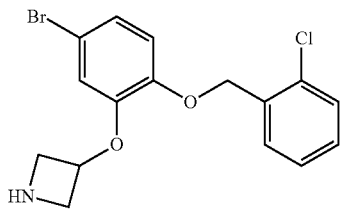 [SMILES: Clc1ccccc1COc1ccc(Br)cc1OC1CNC1]

MS (ESI): mass calcd. for $C_{16}H_{15}BrClNO_2$, 367.0; m/z found, 368.1 [M+H]$^+$. $^1$H NMR (CDCl$_3$): 7.46 (dd, J=5.5, 3.8 Hz, 1H), 7.41 (dd, J=5.6, 3.7 Hz, 1H), 7.32-7.27 (m, 2H), 7.13 (dd, J=8.7, 2.2 Hz, 1H), 6.89 (d, J=2.3 Hz, 1H), 6.83 (d, J=8.7 Hz, 1H), 5.14 (s, 2H), 5.07-4.99 (m, 1H), 4.26-4.21 (m, 4H).

Example 16

3-[5-Bromo-2-(2-chloro-benzyloxy)-phenoxy]-1-methyl-azetidine

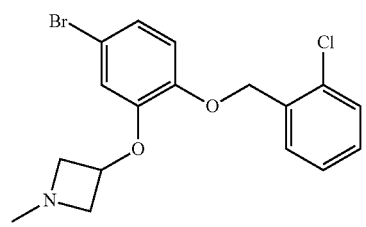 [SMILES: CN1CC(Oc2cc(Br)ccc2OCc2ccccc2Cl)C1]

Synthesized from the title compound of Example 15 according to general procedure 5. MS (ESI): mass calcd. for $C_{17}H_{17}BrClNO_2$, 381.0; m/z found, 382.1 [M+H]$^+$. $^1$H NMR (CDCl$_3$): 7.59-7.51 (m, 1H), 7.39 (dd, J=7.4, 1.7 Hz, 1H), 7.32-7.23 (m, 2H), 7.00 (dd, J=8.6, 2.3 Hz, 1H), 6.78 (dd, J=5.4, 3.1 Hz, 2H), 5.19 (s, 2H), 4.78-4.73 (m, 1H), 3.92-3.78 (m, 2H), 3.21-3.11 (m, 2H), 2.42 (s, 3H).

Example 17

3-[5-Bromo-2-(3-fluoro-benzyloxy)-phenoxy]-azetidine trifluoroacetate

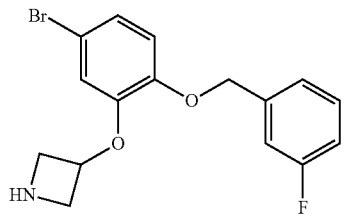 [SMILES: Fc1cccc(COc2ccc(Br)cc2OC2CNC2)c1]

MS (ESI): mass calcd. for $C_{16}H_{15}BrFNO_2$, 351.0; m/z found, 352.1 [M+H]$^+$. $^1$H NMR (CDCl$_3$): 7.36 (dt, J=7.9, 5.9 Hz, 1H), 7.16 (d, J=7.6 Hz, 1H), 7.13-7.08 (m, 2H), 7.03 (dt, J=8.4, 2.1 Hz, 1H), 6.86 (d, J=2.2 Hz, 1H), 6.80 (d, J=8.7 Hz, 1H), 5.04 (s, 3H), 4.29-4.22 (m, 4H).

The compounds in Examples 18-21 were prepared from the title compound of Example 17 using general procedure 3 or 4.

Example 18

3-[5-Bromo-2-(3-fluoro-benzyloxy)-phenoxy]-1-ethyl-azetidine

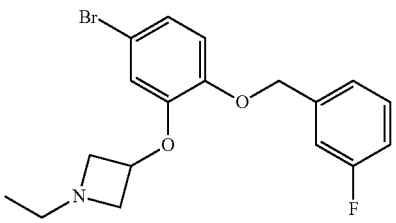 [SMILES: CCN1CC(Oc2cc(Br)ccc2OCc2cccc(F)c2)C1]

MS (ESI): mass calcd. for $C_{18}H_{19}BrFNO_2$, 380.3; m/z found, 381.1 [M+H]$^+$. $^1$H NMR (CDCl$_3$): 7.35-7.31 (m, 1H), 7.17-7.15 (m, 2H), 7.00-6.97 (m, 2H), 6.76 (dd, J=16.1, 5.4 Hz, 2H), 5.08 (s, 2H), 4.78-4.74 (m, 1H), 3.85-3.82 (m, 2H), 3.13-3.05 (m, 2H), 2.57-2.53 (m, 2H), 1.00 (t, J=7.2 Hz, 3H).

Example 19

3-[5-Bromo-2-(3-fluoro-benzyloxy)-phenoxy]-1-propyl-azetidine

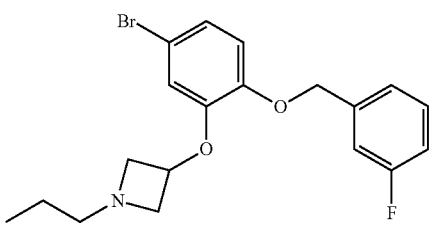 [SMILES: CCCN1CC(Oc2cc(Br)ccc2OCc2cccc(F)c2)C1]

MS (ESI): mass calcd. for $C_{19}H_{21}BrFNO_2$, 394.3; m/z found, 395.1 [M+H]$^+$. $^1$H NMR (CDCl$_3$): 7.34-7.21 (m, 1H), 7.15-7.13 (m, 2H), 7.02-6.92 (m, 2H), 6.74 (dd, J=14.8, 5.4 Hz, 2H), 5.06 (s, 2H), 4.76-4.72 (m, 1H), 3.85-3.77 (m, 2H), 3.11-3.04 (m, 2H), 2.46 (dd, J=8.8, 6.0 Hz, 2H), 1.43-1.32 (m, 2H), 0.89 (t, J=7.4 Hz, 3H).

Example 20

3-[5-Bromo-2-(3-fluoro-benzyloxy)-phenoxy]-1-isopropyl-azetidine

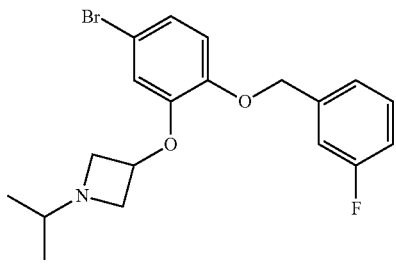 [SMILES: CC(C)N1CC(Oc2cc(Br)ccc2OCc2cccc(F)c2)C1]

MS (ESI): mass calcd. for $C_{19}H_{21}BrFNO_2$, 394.3; m/z found, 395.1 [M+H]$^+$. $^1$H NMR (CDCl$_3$): 7.34-7.30 (m, 1H), 7.18-7.12 (m, 2H), 7.02-6.94 (m, 2H), 6.80-6.71 (m, 2H), 5.07 (s, 2H), 4.74-4.69 (m, 1H), 3.85-3.78 (m, 2H), 3.12-3.06 (m, 2H), 2.43-2.36 (m, 1H), 0.96 (d, J=6.2 Hz, 6H).

Example 21

3-[5-Bromo-2-(3-fluoro-benzyloxy)-phenoxy]-1-cyclobutyl-azetidine

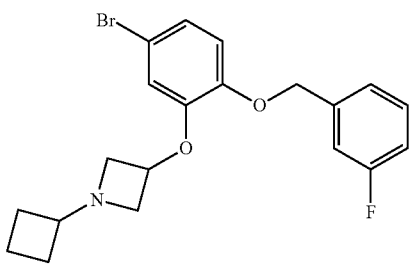 [SMILES: Fc1cccc(COc2ccc(Br)cc2OC2CN(C3CCC3)C2)c1]

MS (ESI): mass calcd. for $C_{20}H_{21}BrFNO_2$, 406.3; m/z found, 407.1 [M+H]$^+$. $^1$H NMR (CDCl$_3$): 7.34-7.30 (m, 1H), 7.19-7.09 (m, 2H), 7.04-6.87 (m, 2H), 6.75 (dd, J=14.4, 5.4 Hz, 2H), 5.07 (s, 2H), 4.77-4.72 (m, 1H), 3.82-3.57 (m, 2H), 3.28-2.99 (m, 3H), 2.03-1.92 (m, 2H), 1.88-1.78 (m, 2H), 1.77-1.70 (m, 2H).

Example 22

3-[4-Bromo-2-(3-chloro-benzyloxy)-phenoxy]-azetidine

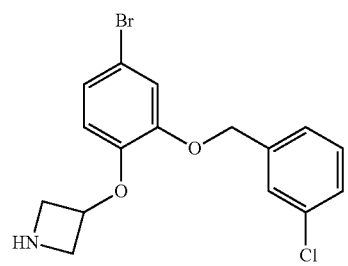 [SMILES: Clc1cccc(COc2cc(Br)ccc2OC2CNC2)c1]

MS (ESI): mass calcd. for $C_{16}H_{15}BrClNO_2$, 368.7; m/z found, 369.1 [M+H]$^+$. $^1$H NMR (CDCl$_3$): 7.47 (s, 1H), 7.33-7.29 (m, 3H), 7.06-6.99 (m, 2H), 6.50 (d, J=8.4 Hz, 1H), 5.07 (s, 2H), 5.00-4.93 (m, 1H), 3.94-3.82 (m, 4H).

Example 23

3-[4-Bromo-2-(3-chloro-benzyloxy)-phenoxy]-1-cyclobutyl-azetidine

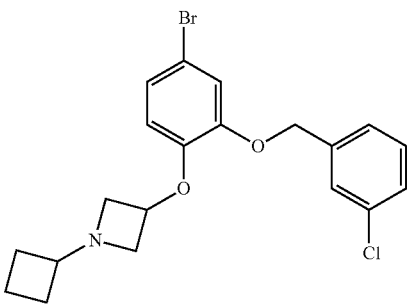 [SMILES: Clc1cccc(COc2cc(Br)ccc2OC2CN(C3CCC3)C2)c1]

Synthesized from the title compound of Example 22 according to general procedure 3. MS (ESI): mass calcd. for $C_{20}H_{21}BrClNO_2$, 422.7; m/z found, 423.9 [M+H]$^+$. $^1$H NMR (CDCl$_3$): 7.46-7.41 (m, 1H), 7.35-7.25 (m, 3H), 7.03-6.95 (m, 2H), 6.53 (d, J=8.6 Hz, 1H), 5.03 (s, 2H), 4.76-4.70 (m, 1H), 3.73-3.65 (m, 2H), 3.22-3.10 (m, 3H), 2.02-1.90 (m, 2H), 1.88-1.57 (m, 4H).

Example 24

3-[4-Bromo-2-(3-chloro-benzyloxy)-phenoxy]-1-isopropyl-azetidine

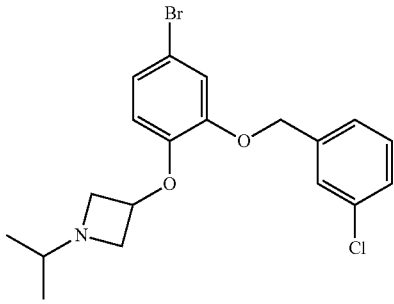 [SMILES: CC(C)N1CC(Oc2ccc(Br)cc2OCc2cccc(Cl)c2)C1]

Synthesized from the title compound of Example 22 according to general procedure 3. MS (ESI): mass calcd. for $C_{19}H_{21}BrClNO_2$, 410.7; m/z found, 412.0 [M+H]$^+$. $^1$H NMR (CDCl$_3$): 7.45 (s, 1H), 7.34-7.22 (m, 3H), 7.04-6.99 (m, 2H), 6.59-6.53 (m, 1H), 5.04 (s, 2H), 4.74-4.68 (m, 1H), 3.83-3.76 (m, 2H), 3.11-3.04 (m, 2H), 2.43-2.34 (m, 1H), 0.99-0.90 (m, 6H).

Example 25

3-[5-Chloro-2-(4-fluoro-benzyloxy)-phenoxy]-azetidine hydrochloride

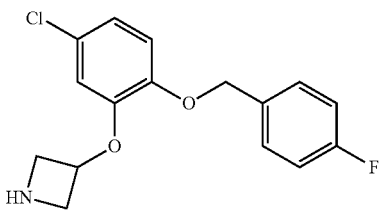 [SMILES: Fc1ccc(COc2ccc(Cl)cc2OC2CNC2)cc1]

MS (ESI): mass calcd. for $C_{16}H_{15}ClFNO_2$, 307.1; m/z found, 308.2 [M+H]$^+$. $^1$H NMR (DMSO-D$_6$): 9.37 (s, 2H), 7.51 (dd, J=8.7, 5.6 Hz, 2H), 7.23 (t, J=8.9 Hz, 2H), 7.1 (d, J=8.7 Hz, 1H), 7.03 (dd, J=8.7, 2.4 Hz, 1H), 6.92 (d, J=2.4 Hz, 1H), 5.11 (s, 2H), 5.08-5.02 (m, 1H), 4.37 (dd, J=12.5, 6.7 Hz, 2H), 3.98 (dd, J=12.5, 5.0 Hz, 2H).

Example 26

3-[5-Chloro-2-(3-methylsulfanyl-benzyloxy)-phenoxy]-azetidine

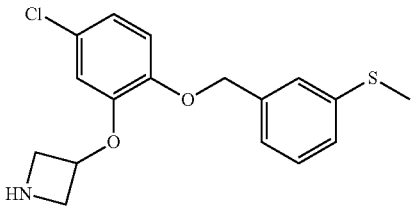 [SMILES: CSc1cccc(COc2ccc(Cl)cc2OC2CNC2)c1]

MS (ESI): mass calcd. for $C_{17}H_{18}ClNO_2S$, 335.1; m/z found, 336.1 [M+H]$^+$. $^1$H NMR (CDCl$_3$): 7.33-7.29 (m, 2H), 7.18 (dd, J=13.3, 7.8 Hz, 2H), 6.86-6.81 (m, 2H), 6.59 (d, J=2.1 Hz, 1H), 5.07 (s, 2H), 5.01-4.95 (m, 1H), 3.94-3.84 (m, 4H), 2.49 (2, 3H).

Example 27

3-[5-Chloro-2-(3-methanesulfonyl-benzyloxy)-phenoxy]-azetidine

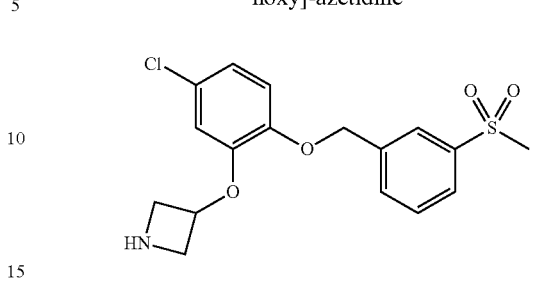

Step A: Preparation of 3-[5-Chloro-2-(3-methanesulfonyl-benzyloxy)-phenoxy]-azetidine-1-carboxylic acid tert-butyl ester. To the title compound of Example 26 (0.050 g, 0.10 mmol) in CH$_2$Cl$_2$ (1 mL) was added 77% m-CPBA (0.06 g, 0.25 mmol). After 18 h, 10% Na$_2$S$_2$O$_5$ (aq.) was added and the mixture extracted with CH$_2$Cl$_2$ (2×). The combined organics were dried. Silica gel chromatography gave 0.038 g (80%) of the title compound as a clear oil. MS (ESI): mass calcd. for $C_{22}H_{26}ClNO_6S$, 467.1; m/z found, 368.1 [M-100]$^+$, 490.1 [M+Na]$^+$. $^1$H NMR (CDCl$_3$): 8.03 (s, 1H), 7.92 (d, J=7.8 Hz, 1H), 7.75 (d, J=7.8 Hz, 1H), 7.62 (t, J=7.8 Hz, 1H), 6.91 (dd, J=8.6, 2.3 Hz, 1H), 6.86 (d, J=8.6 Hz, 1H), 6.57 (d, J=2.3 Hz, 1H), 5.17 (s, 2H), 4.91-4.85 (m, 1H), 4.31 (dd, J=10.4, 6.4 Hz, 2H), 4.08-4.03 (m, 2H), 3.08 (s, 3H), 1.45 (s, 9H).

Step B: Preparation of 3-[5-Chloro-2-(3-methanesulfonyl-benzyloxy)-phenoxy]-azetidine. Prepared from the title compound of Step A using general procedure 1. MS (ESI): mass calcd. for $C_{17}H_{18}ClNO_4S$, 367.1; m/z found, 368.0 [M+H]$^+$. $^1$H NMR (CDCl$_3$): 8.10 (s, 1H), 7.91 (d, J=7.8 Hz, 1H), 7.73 (d, J=7.7 Hz, 1H), 7.60 (t, J=7.8 Hz, 1H), 6.89-6.83 (m, 2H), 6.60 (d, J=2.1 Hz, 1H), 5.17 (s, 2H), 5.03-4.97 (m, 1H), 3.97-3.85 (m, 4H), 3.07 (s, 3H).

Example 28

4-[2-(Azetidin-3-yloxy)-4-chloro-phenoxymethyl]-2-thiophen-2-yl-thiazole

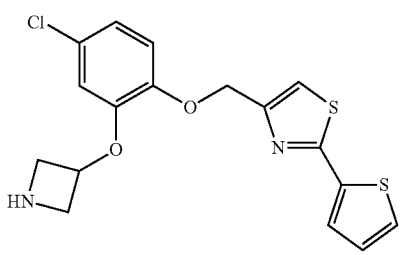 [SMILES: Clc1ccc(OCc2csc(-c3cccs3)n2)c(OC2CNC2)c1]

MS (ESI): mass calcd. for $C_{17}H_{15}ClN_2O_2S_2$, 378.0; m/z found, 379.1 [M+H]$^+$. $^1$H NMR (CDCl$_3$): 7.52 (dd, J=3.7, 0.9 Hz, 1H), 7.40 (dd, J=5.0, 0.9 Hz, 1H), 7.25 (m, 1H), 7.08 (dd, J=5.0, 3.7 Hz, 1H), 6.92-6.86 (m, 2H), 6.60 (d, J=2.3 Hz, 1H), 5.25 (s, 2H), 5.01-4.97 (m, 1H), 3.95-3.85 (m, 4H).

Example 29

4-[2-(Azetidin-3-yloxy)-4-chloro-phenoxymethyl]-2-methyl-thiazole

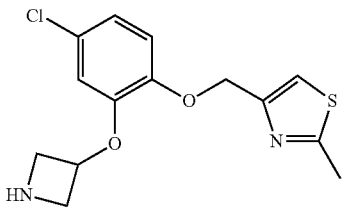 [SMILES: Cc1nc(COc2ccc(Cl)cc2OC2CNC2)cs1]

MS (ESI): mass calcd. for $C_{17}H_{15}ClN_2O_2S$, 310.1; m/z found, 311.2 [M+H]$^+$. $^1$H NMR (CDCl$_3$): 7.15 (d, J=10.2 Hz, 1H), 6.95-6.85 (m, 2H), 6.59 (d, J=2.1 Hz, 1H), 5.18 (d, J=0.8 Hz, 2H), 5.00-4.95 (m, 1H), 3.93-3.87 (m, 4H), 2.73 (s, 3H).

Example 30

3-[2-(Azetidin-3-yloxy)-4-chloro-phenoxymethyl]-5-methyl-isoxazole

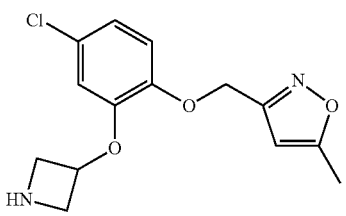 [SMILES: Cc1cc(COc2ccc(Cl)cc2OC2CNC2)no1]

MS (ESI): mass calcd. for $C_{14}H_{16}ClN_2O_3$, 294.1; m/z found, 295.2 [M+H]$^+$. $^1$H NMR (CDCl$_3$): 6.90 (d, J=8.6 Hz, 1H), 6.85 (dd, J=8.6, 2.3 Hz, 1H), 6.58 (d, J=2.3 Hz, 1H), 6.13 (s, 1H), 5.14 (s, 2H), 4.99-4.94 (m, 1H), 3.96-3.89 (m, 2H), 3.87-3.80 (m, 2H), 2.43 (s, 3H).

Example 31

3-[3-[2-(Azetidin-3-yloxy)-4-chloro-phenoxymethyl]-phenyl]-5-methyl-[1,2,4]oxadiazole hydrochloride

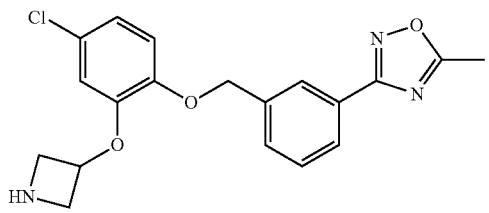 [SMILES: Cc1nc(-c2cccc(COc3ccc(Cl)cc3OC3CNC3)c2)no1]

MS (ESI): mass calcd. for $C_{19}H_{18}ClN_3O_3$, 371.1; m/z found, 372.2 [M+H]$^+$. $^1$H NMR (DMSO-D$_6$): 9.22 (s, 2H), 8.10 (s, 1H), 7.95 (d, J=7.7 Hz, 1H), 7.65 (d, J=7.7 Hz, 1H), 7.59 (t, J=7.7 Hz, 1H), 7.13 (d, J=8.7 Hz, 1H), 7.03 (dd, J=8.7, 2.4 Hz, 1H), 6.93 (d, J=2.4 Hz, 1H), 5.24 (s, 2H), 5.09-5.05 (m, 1H), 4.41 (dd, J=12.5, 6.7 Hz, 2H), 4.02 (dd, J=12.3, 4.9 Hz, 2H), 2.67 (s, 3H).

Example 32

3-[5-Chloro-2-(2-trifluoromethyl-benzyloxy)-phenoxy]-azetidine

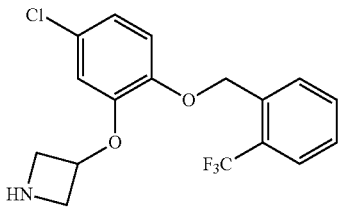 [SMILES: FC(F)(F)c1ccccc1COc1ccc(Cl)cc1OC1CNC1]

MS (ESI): mass calcd. for $C_{17}H_{16}ClF_3NO_2$, 357.1; m/z found, 358.0 [M+H]$^+$. $^1$H NMR (CDCl$_3$): 7.79 (d, J=7.8 Hz, 1H), 7.68 (d, J=7.8 Hz, 1H), 7.57 (t, J=7.6 Hz, 1H), 7.41 (t, J=7.6 Hz, 1H), 6.85 (dd, J=8.6, 2.3 Hz, 1H), 6.80 (d, J=8.6 Hz, 1H), 6.61 (d, J=2.3 Hz, 1H), 5.30 (s, 2H), 5.03-4.97 (m, 1H), 3.96-3.85 (m, 4H).

Example 33

3-[5-Chloro-2-(3-methoxy-benzyloxy)-phenoxy]-azetidine

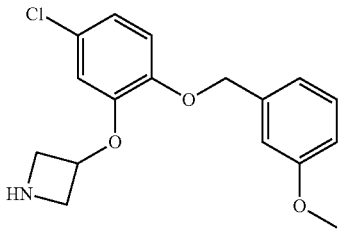 [SMILES: COc1cccc(COc2ccc(Cl)cc2OC2CNC2)c1]

MS (ESI): mass calcd. for $C_{17}H_{18}ClNO_3$, 319.1; m/z found, 320.2 [M+H]$^+$. $^1$H NMR (CDCl$_3$): 7.31-7.22 (m, 1H), 7.00-6.95 (m, 2H), 6.86-6.78 (m, 3H), 6.58 (d, J=2.1 Hz, 1H), 5.07 (s, 2H), 4.99-4.94 (m, 1H), 3.94-3.82 (m, 4H), 3.80 (s, 3H).

Example 34

3-[2-(Azetidin-3-yloxy)-4-chloro-phenoxymethyl]-benzonitrile

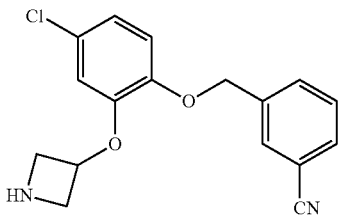

MS (ESI): mass calcd. for $C_{17}H_{15}ClN_2O_2$, 314.1; m/z found, 315.1 [M+H]$^+$. $^1$H NMR (CDCl$_3$): 7.78 (s, 1H), 7.66 (d, J=7.8 Hz, 1H), 7.62 (d, J=7.7 Hz, 1H), 7.49 (t, J=7.8 Hz, 1H), 6.86 (dd, J=8.6, 2.3 Hz, 1H), 6.81 (d, J=8.6 Hz, 1H), 6.60 (d, J=2.3 Hz, 1H), 5.11 (s, 2H), 5.04-4.99 (m, 1H), 3.98-3.91 (m, 2H), 3.89-3.81 (m, 2H).

Example 35

3-[5-Chloro-2-(2-chloro-benzyloxy)-phenoxy]-azetidine trifluoroacetate

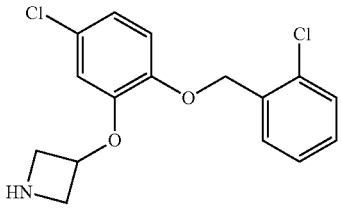

MS (ESI): mass calcd. for $C_{16}H_{15}Cl_2NO_2$, 323.1; m/z found, 324.1 [M+H]$^+$. $^1$H NMR (CDCl$_3$): 7.46 (dd, J=5.5, 3.8 Hz, 1H), 7.43-7.39 (m, 1H), 7.32-7.27 (m, 2H), 6.98 (dd, J=8.7, 2.4 Hz, 1H), 6.87 (d, J=8.7 Hz, 1H), 6.75 (d, J=2.4 Hz, 1H), 5.14 (s, 2H), 5.07-4.99 (m, 1H), 4.34-4.19 (m, 4H).

Example 36

3-[5-Chloro-2-(4-chloro-benzyloxy)-phenoxy]-azetidine trifluoroacetate

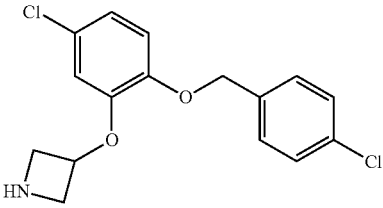

MS (ESI): mass calcd. for $C_{16}H_{15}Cl_2NO_2$, 323.1; m/z found, 324.1 [M+H]$^+$. $^1$H NMR (CDCl$_3$): 7.35 (q, J=8.6 Hz, 4H), 6.95 (dd, J=8.7, 2.4 Hz, 1H), 6.83 (d, J=8.7 Hz, 1H), 6.72 (d, J=2.4 Hz, 1H), 5.08-4.95 (m, 3H), 4.31-4.24 (m, 4H).

Example 37

3-[5-Chloro-2-(3-chloro-benzyloxy)-phenoxy]-azetidine

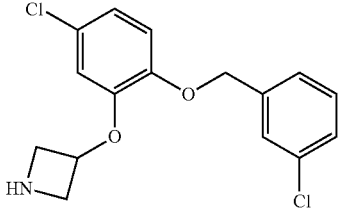 [SMILES: N#Cc1cccc(COc2ccc(Cl)cc2OC2CNC2)c1]

MS (ESI): mass calcd. for $C_{16}H_{15}Cl_2NO_2$, 323.1; m/z found, 324.1 [M+H]$^+$. $^1$H NMR (CDCl$_3$): 7.45 (s, 1H), 7.32-7.27 (m, 3H), 6.85 (td, J=8.5, 1.9 Hz, 1H), 6.81 (dd, J=8.6, 4.6 Hz, 1H), 6.59 (d, J=2.3 Hz, 1H), 5.06 (d, J=3.9 Hz, 2H), 5.00-4.95 (m, 1H), 3.95-3.84 (m, 4H).

Example 38

3-[5-Chloro-2-(3-chloro-benzyloxy)-phenoxy]-1-methyl-azetidine

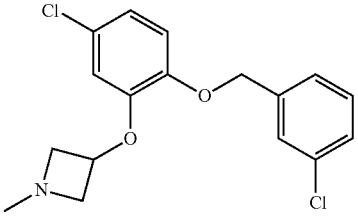 [SMILES: CN1CC(Oc2cc(Cl)ccc2OCc2cccc(Cl)c2)C1]

Synthesized from the title compound of Example 37 according to general procedure 5. MS (ESI): mass calcd. for $C_{17}H_{17}Cl_2NO_2$, 337.1; m/z found, 338.1 [M+H]$^+$. $^1$H NMR (CDCl$_3$): 7.45 (s, 1H), 7.32-7.27 (m, 3H), 6.84 (dd, J=8.6, 2.3 Hz, 1H), 6.80 (d, J=8.6 Hz, 1H), 6.63 (d, J=2.3 Hz, 1H), 5.06 (s, 2H), 4.74-4.69 (m, 1H), 3.88-3.82 (m, 2H), 3.21-3.11 (m, 2H), 2.42 (s, 3H).

Example 39

3-[5-Chloro-2-(3-trifluoromethyl-benzyloxy)-phenoxy]-azetidine

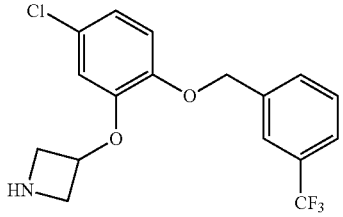

MS (ESI): mass calcd. for $C_{17}H_{15}ClF_3NO_2$, 357.1; m/z found, 358.1 [M+H]$^+$. $^1$H NMR (CDCl$_3$): 7.74 (s, 1H), 7.59 (t, J=8.6 Hz, 2H), 7.50 (t, J=7.7 Hz, 1H), 6.87 (dd, J=8.6, 2.2 Hz, 1H), 6.83 (d, J=8.6 Hz, 1H), 6.60 (d, J=1.7 Hz, 1H), 5.13 (s, 2H), 5.01-4.96 (m, 1H), 3.96-3.85 (m, 4H).

Example 40

3-(2-Benzyloxy-5-chloro-phenoxy)-azetidine

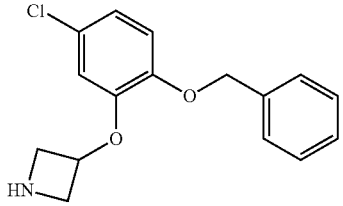

MS (ESI): mass calcd. for $C_{16}H_{16}ClNO_2$, 289.1; m/z found, 290.1 [M+H]$^+$. $^1$H NMR (CDCl$_3$): 7.39 (d, J=4.4 Hz, 4H), 7.36-7.31 (m, 1H), 6.96 (dd, J=8.7, 2.4 Hz, 1H), 6.86 (d, J=8.7 Hz, 1H), 6.74 (d, J=2.4 Hz, 1H), 5.03 (s, 2H), 5.01-4.95 (m, 1H), 4.39-4.15 (m, 4H).

Example 41

3-[5-Chloro-2-(3-chloro-4-trifluoromethoxy-benzy-loxy)-phenoxy]-azetidine

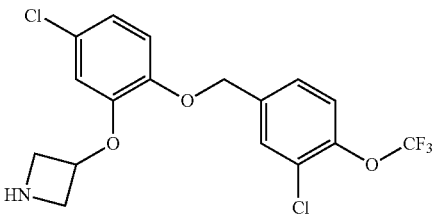 [SMILES: FC(F)(F)Oc1ccc(COc2ccc(Cl)cc2OC2CNC2)cc1Cl]

MS (ESI): mass calcd. for C$_{17}$H$_{14}$Cl$_2$F$_3$NO$_3$, 407.0; m/z found, 408.0 [M+H]$^+$. $^1$H NMR (CD$_3$OD/CDCl$_3$): 7.61-7.59 (m, 1H), 7.38-7.30 (m, 2H), 6.87 (dd, J=8.6, 2.3 Hz, 1H), 6.82 (d, J=8.6 Hz, 1H), 6.59 (d, J=2.3 Hz, 1H), 5.06 (s, 2H), 5.03-4.93 (m, 1H), 4.25-3.60 (m, 4H).

Example 42

3-[5-Chloro-2-(4-trifluoromethoxy-benzyloxy)-phe-noxy]-azetidine

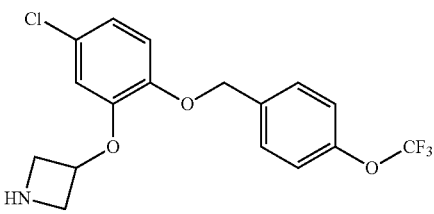 [SMILES: FC(F)(F)Oc1ccc(COc2ccc(Cl)cc2OC2CNC2)cc1]

MS (ESI): mass calcd. for C$_{17}$H$_{15}$ClF$_3$NO$_3$, 373.1; m/z found, 374.0 [M+H]$^+$. $^1$H NMR (CDCl$_3$): 7.46 (d, J=8.7 Hz, 2H), 7.23 (d, J=8.0 Hz, 2H), 6.86 (dd, J=8.6, 2.6 Hz, 1H), 6.82 (d, J=8.6 Hz, 1H), 6.59 (d, J=2.2 Hz, 1H), 5.09 (s, 2H), 5.02-4.94 (m, 1H), 4.00-3.80 (m, 4H).

Example 43

3-[5-Chloro-2-(4-trifluoromethyl-benzyloxy)-phe-noxy]-azetidine

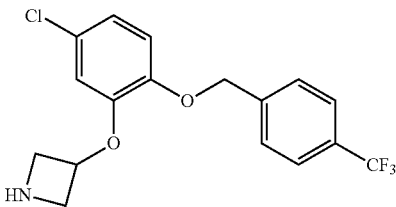 [SMILES: FC(F)(F)c1ccc(COc2ccc(Cl)cc2OC2CNC2)cc1]

MS (ESI): mass calcd. for C$_{17}$H$_{15}$ClF$_3$NO$_2$, 357.1; m/z found, 358.1 [M+H]$^+$. $^1$H NMR (CDCl$_3$): 7.64 (d, J=8.1 Hz, 2H), 7.55 (d, J=8.1 Hz, 2H), 6.85 (dd, J=8.6, 2.3 Hz, 1H), 6.80 (d, J=8.6 Hz, 1H), 6.60 (d, J=2.3 Hz, 1H), 5.15 (s, 2H), 5.02-4.94 (m, 1H), 4.01-3.79 (m, 4H).

Example 44

4-[2-(Azetidin-3-yloxy)-4-chloro-phenoxymethyl]-benzonitrile

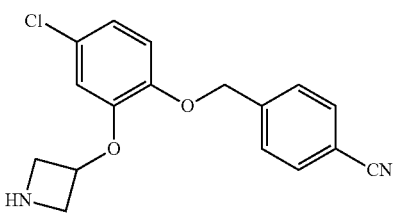 [SMILES: N#Cc1ccc(COc2ccc(Cl)cc2OC2CNC2)cc1]

MS (ESI): mass calcd. for C$_{17}$H$_{15}$ClN$_2$O$_2$, 314.1; m/z found, 315.0 [M+H]$^+$. $^1$H NMR (CDCl$_3$): 7.68 (d, J=8.3 Hz, 2H), 7.55 (d, J=8.0 Hz, 2H), 6.86 (dd, J=8.6, 2.4 Hz, 1H), 6.78 (d, J=8.6 Hz, 1H), 6.60 (d, J=2.3 Hz, 1H), 5.15, (s, 2H), 5.04-4.94 (m, 1H), 4.02-3.79 (m, 4H).

Example 45

3-[2-(2,4-Bis-trifluoromethyl-benzyloxy)-5-chloro-phenoxy]-azetidine

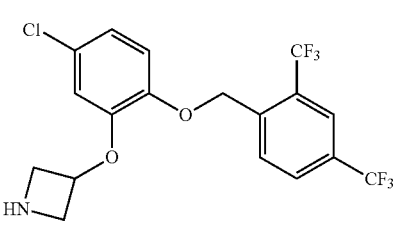 [SMILES: FC(F)(F)c1ccc(COc2ccc(Cl)cc2OC2CNC2)c(C(F)(F)F)c1]

$^1$H NMR (CDCl$_3$, CD$_3$OD): 8.04-7.92 (m, 2H), 7.01 (dd, J=8.7, 2.3 Hz, 1H), 6.94 (d, J=8.7 Hz, 1H), 6.84 (d, J=2.3 Hz, 1H), 5.36, (s, 2H), 5.20-2.11 (m, 1H), 4.49 (dd, J=12.4, 6.7 Hz, 2H), 4.22 (dd, J=12.4, 5.2 Hz, 2H).

Example 46

3-[5-Chloro-2-(4-trifluoromethylsulfanyl-benzy-loxy)-phenoxy]-azetidine

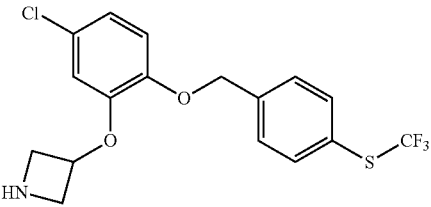 [SMILES: FC(F)(F)Sc1ccc(COc2ccc(Cl)cc2OC2CNC2)cc1]

MS (ESI): mass calcd. for C$_{17}$H$_{15}$ClF$_3$NO$_2$S, 389.1; m/z found, 390.1 [M+H]$^+$. $^1$H NMR (CDCl$_3$): 7.67 (d, J=8.2 Hz, 2H), 7.49 (d, J=8.4 Hz, 2H), 6.86 (dd, J=8.6, 2.3 Hz, 1H), 6.81 (d, J=8.6 Hz, 1H), 6.60 (d, J=2.3 Hz, 1H), 5.13 (s, 2H), 5.05-4.93 (m, 1H), 4.04-3.78 (m, 4H).

Example 47

3-[5-Chloro-2-(4-fluoro-3-trifluoromethyl-benzyloxy)-phenoxy]-azetidine

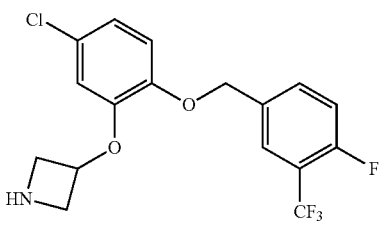 [SMILES: Fc1ccc(COc2ccc(Cl)cc2OC2CNC2)cc1C(F)(F)F]

MS (ESI): mass calcd. for $C_{17}H_{14}ClF_4NO_2$, 375.1; m/z found, 377.0 [M+H]$^+$. $^1$H NMR (CDCl$_3$): 7.77-7.70 (m, 1H), 7.64-7.57 (m, 1H), 7.25-7.18 (m, 1H), 6.88 (dd, J=8.6, 2.3 Hz, 1H), 6.83 (d, J=8.6 Hz, 1H), 6.59 (d, J=8.3 Hz, 1H), 5.08 (s, 2H), 5.02-4.94 (m, 1H), 3.98-3.90 (m, 2H), 3.87-3.80 (m, 2H).

Example 48

3-[5-Chloro-2-(2-fluoro-4-trifluoromethyl-benzyloxy)-phenoxy]-azetidine

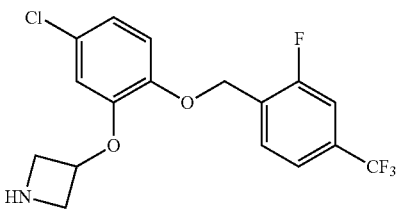 [SMILES: Fc1cc(C(F)(F)F)ccc1COc1ccc(Cl)cc1OC1CNC1]

$^1$H NMR (CDCl$_3$): 7.70 (dd, J=7.6, 7.4 Hz, 1H), 7.45 (d, J=8.0 Hz, 1H), 7.35 (d, J=9.8 Hz, 1H), 6.88-6.84 (m, 2H), 6.61 (d, J=2.0 Hz, 1H), 5.20 (s, 2H), 5.02-4.94 (m, 1H), 3.97-3.90 (m, 2H), 3.88-3.81 (m, 2H).

Example 49

3-[5-Chloro-2-(4-chloro-3-trifluoromethyl-benzyloxy)-phenoxy]-azetidine

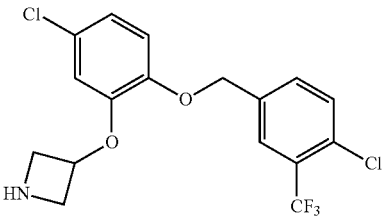 [SMILES: FC(F)(F)c1cc(COc2ccc(Cl)cc2OC2CNC2)ccc1Cl]

MS (ESI): mass calcd. for $C_{17}H_{14}Cl_2F_3NO_2$, 391.0; m/z found, 392.0 [M+H]$^+$. $^1$H NMR (CDCl$_3$): 7.73 (d, J=6.3 Hz, 1H), 7.63-7.58 (m, 1H), 7.21 (dd, J=9.4, 9.2 Hz, 1H), 6.90-6.81 (m, 2H), 6.59 (d, J=1.6 Hz, 1H), 5.10-5.05 (m, 1H), 5.08, (s, 2H), 5.05-4.95 (m, 4H).

Example 50

3-[5-Chloro-2-(3,4-dichloro-benzyloxy)-phenoxy]-azetidine

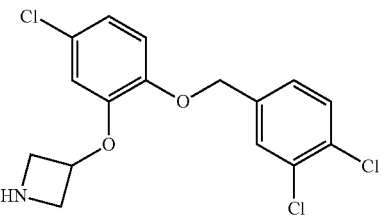 [SMILES: Clc1ccc(OCc2ccc(Cl)c(Cl)c2)c(OC2CNC2)c1]

MS (ESI): mass calcd. for $C_{16}H_{14}Cl_3NO_2$, 357.0; m/z found, 359.9 [M+H]$^+$. $^1$H NMR (CDCl$_3$): 7.56 (d, J=1.8 Hz, 1H), 7.44 (d, J=8.2 Hz, 1H), 7.24 (dd, J=8.3, 1.9 Hz, 1H), 6.85 (dd, J=8.6, 2.3 Hz, 1H), 6.80 (d, J=8.6 Hz, 1H), 6.58 (d, J=2.3 Hz, 1H), 5.04, (s, 2H), 5.05-5.00 (m, 1H), 4.52-3.00 (m, 4H).

Example 51

2-[2-(Azetidin-3-yloxy)-4-chloro-phenoxymethyl]-pyridine

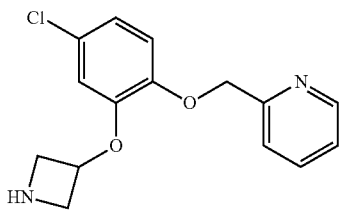 [SMILES: Clc1ccc(OCc2ccccn2)c(OC2CNC2)c1]

MS (ESI): mass calcd. for $C_{15}H_{15}ClN_2O_2$, 290.1; m/z found, 291.1 [M+H]$^+$. $^1$H NMR (CDCl$_3$): 8.62-8.57 (m, 1H), 7.75-7.69 (m, 1H), 7.55 (d, J=7.8 Hz, 1H), 7.25-7.20 (m, 1H), 6.85-6.82 (m, 2H), 6.60 (d, J=1.6 Hz, 1H), 5.24 (s, 2H), 5.09-4.94 (m, 1H), 4.18-3.64 (m, 4H).

Example 52

3-[2-(Azetidin-3-yloxy)-4-chloro-phenoxymethyl]-pyridine

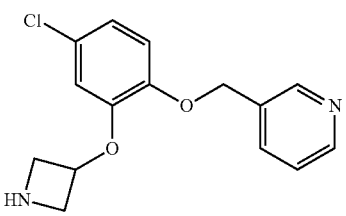 [SMILES: Clc1ccc(OCc2cccnc2)c(OC2CNC2)c1]

MS (ESI): mass calcd. for $C_{15}H_{15}ClN_2O_2$, 290.1; m/z found, 291.1 [M+H]$^+$. $^1$H NMR (CD$_3$OD/CDCl$_3$): 8.68-8.61 (m, 1H), 8.53 (d, J=4.3 Hz, 1H), 7.86 (d, J=7.9 Hz, 1H), 7.45-7.37 (m, 1H), 6.93-6.87 (m, 2H), 6.63-6.60 (m, 1H), 5.13 (s, 2H), 5.04-4.94 (m, 1H), 4.12-3.70 (m, 4H).

Example 53

4-[2-(Azetidin-3-yloxy)-4-chloro-phenoxymethyl]-pyridine

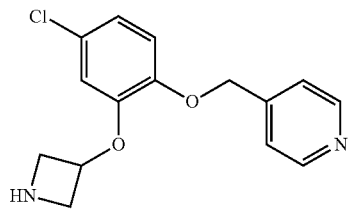 [SMILES: Clc1ccc(OCc2ccncc2)c(OC2CNC2)c1]

MS (ESI): mass calcd. for $C_{15}H_{15}ClN_2O_2$, 290.1; m/z found, 291.1 [M+H]$^+$. $^1$H NMR (CD$_3$OD/CDCl$_3$): 8.56-8.53 (m, 2H), 7.50-7.44 (m, 2H), 6.92-6.86 (m, 2H), 6.66 (d, J=2.1 Hz, 1H), 5.18 (s, 2H), 5.09-5.01 (m, 1H), 4.04-3.94 (m, 2H), 3.88-3.80 (m, 2H).

Example 54

3-[5-Chloro-2-(5-trifluoromethyl-furan-2-yl-methoxy)-phenoxy]-azetidine

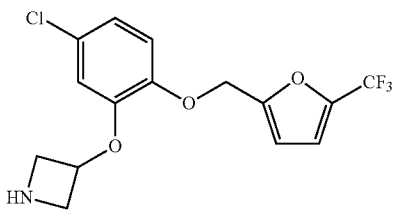 [SMILES: FC(F)(F)c1ccc(COc2ccc(Cl)cc2OC2CNC2)o1]

MS (ESI): mass calcd. for $C_{15}H_{13}ClF_3NO_3$, 347.1; m/z found, 348.2 [M+H]$^+$. $^1$H NMR (CDCl$_3$): 6.90-6.88 (m, 2H), 6.77-6.76 (m, 1H), 6.60 (s, 1H), 6.46-6.45 (m, 1H), 5.05 (s, 2H), 4.98-4.93 (m, 1H), 3.94-3.90 (m, 2H), 3.85-3.82 (m, 2H).

Example 55

5-[2-(Azetidin-3-yloxy)-4-chloro-phenoxymethyl]-furan-2-carboxylic acid ethyl ester

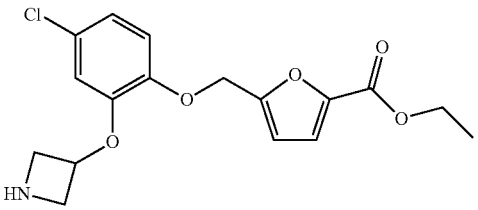 [SMILES: CCOC(=O)c1ccc(COc2ccc(Cl)cc2OC2CNC2)o1]

MS (ESI): mass calcd. for $C_{17}H_{18}ClNO_5$, 351.1; m/z found, 352.2 [M+H]$^+$. $^1$H NMR (CDCl$_3$): 7.13 (d, J=3.4 Hz, 1H), 6.89-6.85 (m, 2H), 6.58 (d, J=1.6 Hz, 1H), 6.50 (d, J=3.4 Hz, 1H), 5.08 (s, 2H), 4.98-4.93 (m, 1H), 4.37 (q, J=7.1 Hz, 1H), 3.94-3.90 (m, 2H), 3.86-3.83 (m, 2H), 1.38 (t, J=7.1 Hz, 1H).

Example 56

3-[5-Chloro-2-(4-chloro-2-methanesulfonyl-benzyloxy)-phenoxy]-azetidine

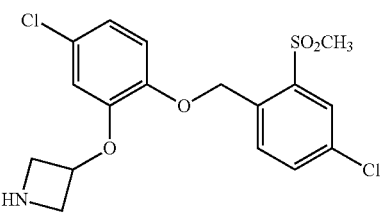 [SMILES: CS(=O)(=O)c1cc(Cl)ccc1COc1ccc(Cl)cc1OC1CNC1]

$^1$H NMR (CD$_3$OD/CDCl$_3$): 7.65 (s, 1H), 7.33-7.27 (m, 2H), 6.64 (d, J=8.7 Hz, 1H), 6.58 (dd, J=8.7, 2.3 Hz, 1H), 6.37 (d, J=2.3 Hz, 1H), 5.03 (s, 2H), 4.71-4.63 (m, 1H), 3.99 (dd, J=12.6, 6.6 Hz, 2H), 3.70 (dd, J=12.5, 5.1 Hz, 2H), 2.84 (s, 3H).

Example 57

3-[5-Chloro-2-(2,4-difluoro-benzyloxy)-phenoxy]-azetidine

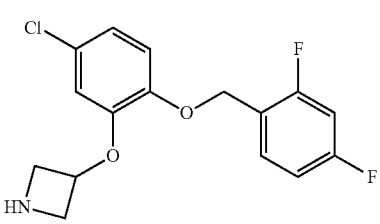 [SMILES: Fc1ccc(COc2ccc(Cl)cc2OC2CNC2)c(F)c1]

MS (ESI): mass calcd. for $C_{16}H_{14}ClF_2NO_2$, 325.1; m/z found, 327.1 [M+H]$^+$. $^1$H NMR (CDCl$_3$): 7.52-7.43 (m, 1H), 6.92-6.80 (m, 4H), 6.60-6.58 (m, 1H), 5.10 (s, 2H), 5.00-4.93 (m, 1H), 4.11-3.69 (m, 4H).

Example 58

(R)-3-[5-Chloro-2-(3-chloro-benzyloxy)-phenoxy]-pyrrolidine

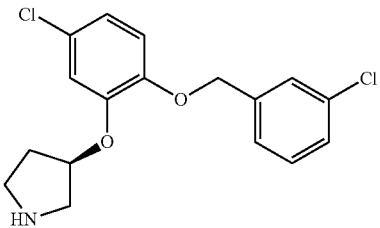 [SMILES: Clc1cccc(COc2ccc(Cl)cc2O[C@@H]2CCNC2)c1]

MS (ESI): mass calcd. for $C_{17}H_{17}Cl_2NO_2$, 337.1; m/z found, 338.1 [M+H]$^+$. $^1$H NMR (CDCl$_3$): 7.43 (s, 1H), 7.30-7.25 (m, 3H), 6.87-6.81 (m, 3H), 5.02 (s, 2H), 4.83-4.81 (m, 1H), 3.23-3.17 (m, 2H), 2.99 (dd, J=12.8, 4.7 Hz, 1H), 2.91 (ddd, J=11.3, 8.5, 5.5 Hz, 1H), 2.11-2.00 (m, 2H).

Example 59

(R)-3-[5-Chloro-2-(3-chloro-benzyloxy)-phenoxy]-1-methyl-pyrrolidine

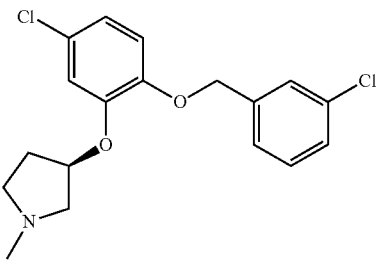 [SMILES: CN1CC[C@@H](Oc2cc(Cl)ccc2OCc2cccc(Cl)c2)C1]

Synthesized from the title compound of Example 58 according to general procedure 5. MS (ESI): mass calcd. for $C_{18}H_{19}Cl_2NO_2$, 351.1; m/z found, 352.1 [M+H]$^+$. $^1$H NMR (CDCl$_3$): 7.45 (s, 1H), 7.29-7.28 (m, 3H), 6.85-6.79 (m, 3H), 5.04 (s, 2H), 4.83-4.80 (m, 1H), 2.96 (dd, J=10.6, 6.1 Hz, 1H), 2.80-2.75 (m, 2H), 2.58-2.54 (m, 1H), 2.41 (s, 3H), 2.32-2.36 (m, 1H), 2.08-2.02 (m, 1H).

Example 60

(R)-3-[5-Chloro-2-(2-chloro-benzyloxy)-phenoxy]-pyrrolidine

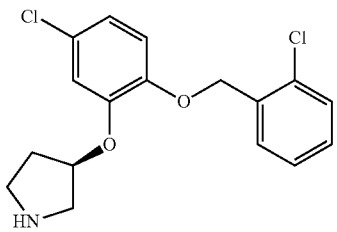 [SMILES: Clc1ccc(OCc2ccccc2Cl)c(O[C@@H]2CCNC2)c1]

MS (ESI): mass calcd. for $C_{17}H_{17}Cl_2NO_2$, 337.1; m/z found, 338.1 [M+H]$^+$. $^1$H NMR (CDCl$_3$): 7.56-7.54 (m, 1H), 7.39-7.37 (m, 1H), 7.30-7.24 (m, 2H), 6.88-6.86 (m, 3H) 5.15 (s, 2H), 4.84-4.82 (m, 1H), 3.23-3.16 (m, 2H), 2.98 (dd, J=12.8, 4.6 Hz, 1H), 2.90 (ddd, J=11.3, 8.5, 5.5 Hz, 1H), 2.12-2.00 (m, 2H).

Example 61

(R)-3-[5-Chloro-2-(2-chloro-benzyloxy)-phenoxy]-1-methyl-pyrrolidine

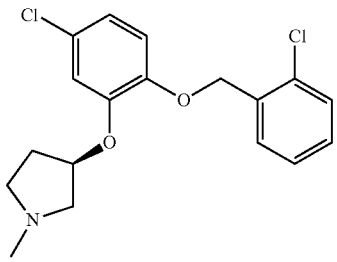 [SMILES: CN1CC[C@@H](Oc2cc(Cl)ccc2OCc2ccccc2Cl)C1]

Synthesized from the title compound of Example 60 according to general procedure 5. MS (ESI): mass calcd. for $C_{18}H_{19}Cl_2NO_2$, 351.1; m/z found, 352.1 [M+H]$^+$. $^1$H NMR (CDCl$_3$): 7.60-7.58 (m, 1H), 7.38-7.37 (m, 1H), 7.29-7.23 (m, 2H), 6.85-6.82 (m, 3H) 5.17 (s, 2H), 4.85-4.81 (m, 1H), 2.95 (dd, J=10.6, 6.1 Hz, 1H), 2.78-2.73 (m, 2H), 2.57-2.53 (m, 1H), 2.39 (s, 3H), 2.32-2.36 (m, 1H), 2.08-2.02 (m, 1H).

Example 62

4-(2-Benzyloxy-5-chloro-phenoxy)-piperidine

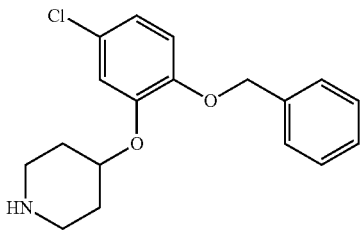 [SMILES: Clc1ccc(OCc2ccccc2)c(OC2CCNCC2)c1]

MS (ESI): mass calcd. for $C_{18}H_{20}ClNO_2$, 317.1; m/z found, 318.3 [M+H]$^+$. $^1$H NMR (CDCl$_3$): 7.42-7.40 (m, 2H), 7.38-7.34 (m, 2H), 7.32-7.29 (m, 1H), 6.93-6.93 (m, 1H), 6.87-6.82 (m, 2H), 5.08 (s, 2H), 4.35-4.29 (m, 1H), 3.17-3.11 (m, 2H), 2.68 (ddd, J=12.6, 9.3, 3.1 Hz, 2H), 2.02-1.96 (m, 2H), 1.74-1.66 (m, 2H).

Example 63

4-[5-Chloro-2-(5-trifluoromethyl-furan-2-yl-methoxy)-phenoxy]-piperidine hydrochloride

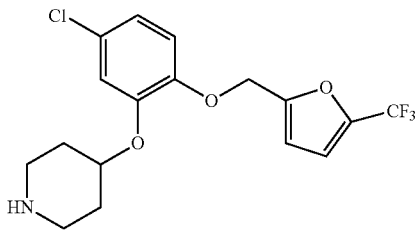 [SMILES: FC(F)(F)c1ccc(COc2ccc(Cl)cc2OC2CCNCC2)o1]

MS (ESI): mass calcd. for $C_{17}H_{17}ClF_3NO_3$, 375.1; m/z found, 378.2. $^1$H NMR (DMSO-D$_6$): 9.10-9.00 (m, 2H), 7.24-7.23 (m, 2H), 7.15 (d, J=8.7 Hz, 1H), 7.01 (d, J=8.7, 2.5 Hz, 1H), 6.80 (d, J=3.2 Hz, 1H), 5.17 (s, 2H), 4.59-4.55 (m, 1H), 3.20-3.17 (m, 2H), 3.03-3.00 (m, 2H), 2.07-2.02 (m, 2H), 1.86-1.82 (m, 2H).

Example 64

4-[5-Bromo-2-(5-trifluoromethyl-furan-2-yl-methoxy)-phenoxy]-piperidine

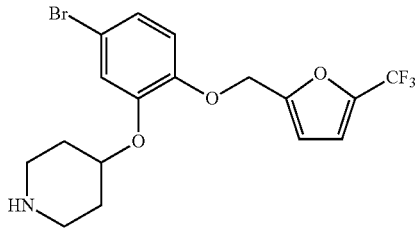 [SMILES: FC(F)(F)c1ccc(COc2ccc(Br)cc2OC2CCNCC2)o1]

MS (ESI): mass calcd. for $C_{17}H_{17}BrF_3NO_3$, 419.0; m/z found, 420.1 [M+H]$^+$. $^1$H NMR (CDCl$_3$): 7.09 (d, J=2.3 Hz, 1H), 7.04 (dd, J=8.5, 2.3 Hz, 1H), 6.84 (d, J=8.6 Hz, 1H), 6.79-6.75 (m, 1H), 6.45 (d, J=3.3 Hz, 1H), 5.06 (s, 2H), 4.37-4.29 (m, 1H), 3.21-3.10 (m, 2H), 2.78-2.66 (m, 2H), 2.06-1.95 (m, 2H), 1.76-1.66 (m, 2H).

Example 65

4-[5-Bromo-2-(3-chloro-benzyloxy)-phenoxy]-piperidine

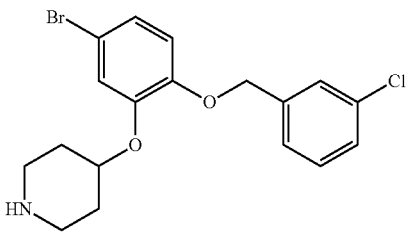 [SMILES: Clc1cccc(COc2ccc(Br)cc2OC2CCNCC2)c1]

MS (ESI): mass calcd. for $C_{18}H_{19}BrClNO_2$, 395.0; m/z found, 396.1 [M+H]$^+$. $^1$H NMR (CDCl$_3$): 7.45 (s, 1H), 7.29-7.27 (m, 3H), 7.07 (d, J=7.1 Hz, 1H), 7.01 (dd, J=8.6, 2.3 Hz, 1H), 6.78 (d, J=8.6 Hz, 1H), 5.04 (s, 2H), 4.36-4.30 (m, 1H), 3.18-3.12 (m, 2H), 2.73-2.67 (m, 2H), 2.02-1.97 (m, 2H), 1.75-1.67 (m, 2H).

Example 66

4-[5-Bromo-2-(3-chloro-benzyloxy)-phenoxy]-1-methyl-piperidine

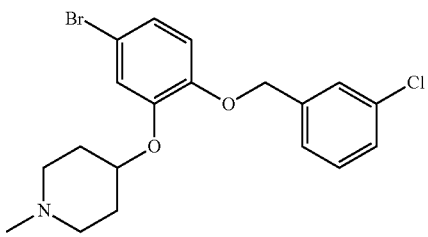 [SMILES: CN1CCC(Oc2cc(Br)ccc2OCc2cccc(Cl)c2)CC1]

Synthesized from the title compound of Example 65 according to general procedure 5. MS (ESI): mass calcd. for $C_{19}H_{21}BrClNO_2$, 409.0; m/z found, 410.1 [M+H]$^+$. $^1$H NMR (CDCl$_3$): 7.46 (s, 1H), 7.30-7.28 (m, 3H), 7.06 (d, J=2.3 Hz, 1H), 7.01 (dd, J=8.6, 2.3 Hz, 1H), 6.79 (d, J=8.6 Hz, 1H), 5.04 (s, 2H), 4.32-4.29 (m, 1), 2.73-2.67 (m, 2H), 2.35-2.27 (m, 4H), 2.02-1.85 (m, 4H).

Example 67

4-[5-Bromo-2-(2-fluoro-benzyloxy)-phenoxy]-piperidine

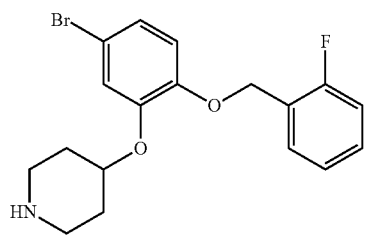 [SMILES: Fc1ccccc1COc1ccc(Br)cc1OC1CCNCC1]

MS (ESI): mass calcd. for $C_{18}H_{19}BrFNO_2$, 379.1; m/z found, 380.2 [M+H]$^+$. $^1$H NMR (CDCl$_3$): 7.52-7.49 (m, 1H), 7.33-7.28 (m, 1H), 7.15 (t, J=7.5 Hz, 1H), 7.09-7.05 (m, 2H), 7.03-7.01 (m, 1H), 6.83 (dd, J=8.6, 2.4 Hz, 1H), 5.12 (s, 2H), 4.34-4.29 (m, 1H), 3.15-3.13 (m, 2H), 2.71-2.62 (m, 2H), 2.00-1.94 (m, 2H), 1.72-1.66 (m, 2H).

Example 68

4-[5-Bromo-2-(3-fluoro-benzyloxy)-phenoxy]-piperidine

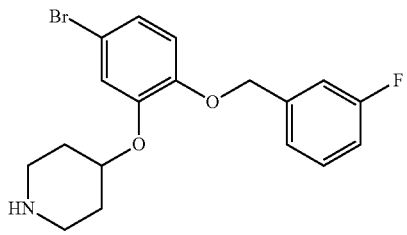 [SMILES: Fc1cccc(COc2ccc(Br)cc2OC2CCNCC2)c1]

MS (ESI): mass calcd. for $C_{18}H_{19}BrFNO_2$, 379.1; m/z found, 380.2 [M+H]$^+$. $^1$H NMR (CDCl$_3$): 7.35-7.31 (m, 1H), 7.18-7.15 (m, 2H), 7.07 (d, J=2.3 Hz, 1H), 7.02-6.98 (m, 2H), 6.78 (d, J=8.6 Hz, 1H), 5.07 (s, 2H), 4.36-4.31 (m, 1H), 3.17-3.14 (m, 2H), 2.71 (t, J=9.6 Hz, 2H), 2.03-2.00 (m, 2H), 1.75-1.67 (m, 2H).

Example 69

(±)-3-[5-Chloro-2-(5-trifluoromethyl-furan-2-yl-methoxy)-phenoxy]-piperidine

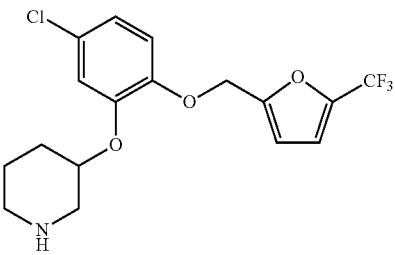 [SMILES: FC(F)(F)c1ccc(COc2ccc(Cl)cc2OC2CCCNC2)o1]

MS (ESI): mass calcd. for $C_{17}H_{17}ClF_3NO_3$, 375.1; m/z found, 376.0 [M+H]$^+$. $^1$H NMR (CDCl$_3$): 6.96-6.95 (m, 1H), 6.88-6.87 (m, 2H), 6.76-6.75 (m, 1H), 6.45-6.44 (m, 1H), 5.04 (s, 2H), 4.22-4.17 (m, 1H), 3.12 (dd, J=2.2, 12.7 Hz, 1H), 2.88-2.82 (m, 2H), 2.78-2.72 (m, 1H), 2.02-1.96 (m, 1H), 1.85-1.74 (m, 2H), 1.53-1.45 (m, 1H).

Example 70

(±)-3-(2-Benzyloxy-5-chloro-phenoxy)-piperidine

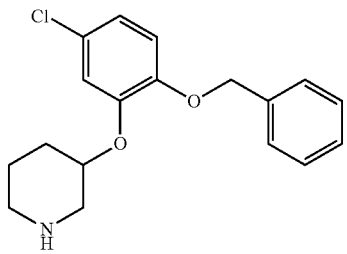

MS (ESI): mass calcd. for $C_{18}H_{20}ClNO_2$, 317.12; m/z found, 318.1 [M+H]$^+$. $^1$H NMR (CDCl$_3$): 7.45-7.28 (m, 5H), 6.95 (d, J=2.1 Hz, 1H), 6.90-6.81 (m, 2H), 5.08 (s, 2H), 4.20

(dq, J=10.2, 3.3 Hz, 1H), 3.11 (dd, J=12.7, 2.3 Hz, 1H), 2.91-2.78 (m, 2H), 2.78-2.69 (m, 1H), 2.05-1.94 (m, 1H), 1.88-1.74 (m, 2H), 1.53-1.41 (m, 1H).

Example 71

(±)-3-[5-Chloro-2-(3-trifluoromethyl-benzyloxy)-phenoxy]-piperidine

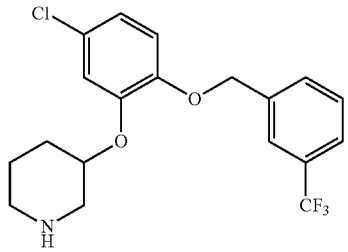 [SMILES: FC(F)(F)c1cccc(COc2ccc(Cl)cc2OC2CCCNC2)c1]

MS (ESI): mass calcd. for $C_{19}H_{19}ClF_3NO_2$, 385.11; m/z found, 386.0 [M+H]$^+$. $^1$H NMR (CDCl$_3$): 7.75 (s, 1H), 7.62-7.56 (m, 2H), 7.50 (t, J=7.7 Hz, 1H), 6.96 (d, J=2.3 Hz, 1H), 6.89 (dd, J=8.6, 2.3 Hz, 1H), 6.84 (d, J=8.6 Hz, 1H), 5.12 (s, 2H), 4.28-4.16 (m, 1H), 3.13 (dd, J=12.6, 2.3 Hz, 1H), 2.91-2.80 (m, 2H), 2.78-2.67 (m, 1H), 2.08-1.94 (m, 1H), 1.88-1.73 (m, 2H), 1.55-1.40 (m, 1H).

Example 72

3-(5-Chloro-2-cyclopentyloxy-phenoxy)-azetidine trifluoroacetate

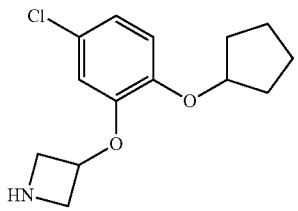 [SMILES: Clc1ccc(OC2CCCC2)c(OC2CNC2)c1]

MS (ESI): mass calcd. for $C_{14}H_{18}ClNO_2$, 267.1; m/z found, 268.2 [M+H]$^+$. $^1$H NMR (CDCl$_3$): 6.97 (dd, J=8.7, 2.5 Hz, 1H), 6.81 (d, J=8.8 Hz, 1H), 6.75 (d, J=2.5 Hz, 1H), 5.04-4.99 (m, 1H), 4.76-4.67 (m, 1H), 4.38-4.27 (m, 4H), 1.96-1.87 (m, 2H), 1.84-1.74 (m, 4H), 1.69-1.59 (m, 2H).

Example 73

3-(5-Chloro-2-cyclohexylmethoxy-phenoxy)-azetidine trifluoroacetate

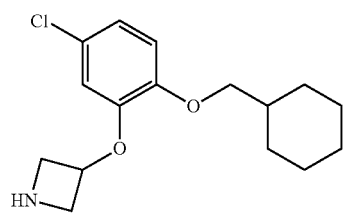 [SMILES: Clc1ccc(OCC2CCCCC2)c(OC2CNC2)c1]

MS (ESI): mass calcd. for $C_{16}H_{22}ClNO_2$, 295.1; m/z found, 296.2 [M+H]$^+$. $^1$H NMR (CDCl$_3$): 6.97 (dd, J=8.7, 2.3 Hz, 1H), 6.80 (d, J=8.7 Hz, 1H), 6.74 (d, J=2.4 Hz, 1H), 5.15-4.97 (m, 1H), 4.44-4.36 (m, 2H), 4.30 (s, 2H), 3.74 (d, J=6.3 Hz, 2H), 1.89-1.65 (m, 6H), 1.36-1.14 (m, 3H), 1.03 (m, 2H).

Example 74

3-(5-Bromo-2-cyclohexylmethoxy-phenoxy)-azetidine

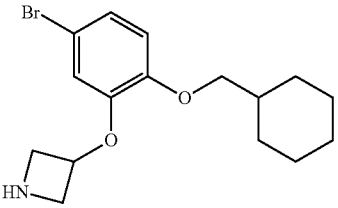

MS (ESI): mass calcd. for $C_{16}H_{22}BrNO_2$, 339.1; m/z found, 340.1 [M+H]$^+$. $^1$H NMR (CDCl$_3$): 7.01 (dd, J=8.6, 2.3 Hz, 1H), 6.74 (d, J=8.6 Hz, 1H), 6.71 (d, J=2.3 Hz, 1H), 4.97-4.92 (m, 1H), 3.92-3.83 (m, 4H), 3.75 (d, J=6.4 Hz, 2H), 1.95-1.63 (m, 6H), 1.36-1.14 (m, 3H), 1.10-0.93 (m, 2H).

Example 75

5-[2-(Azetidin-3-yloxy)-4-chloro-phenoxymethyl]-2-trifluoromethyl-furan-3-carboxylic acid trifluoroacetate

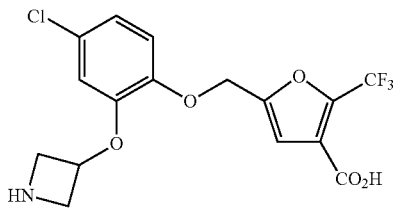 [SMILES: O=C(O)c1cc(COc2ccc(Cl)cc2OC2CNC2)oc1C(F)(F)F]

Step A: Preparation of 5-Bromomethyl-2-trifluoromethyl-furan-3-carboxylic acid ethyl ester. To a solution of 5-methyl-2-trifluoromethyl-furan-3-carboxylic acid ethyl ester (0.95 g, 4.5 mmol) in CCl$_4$ (12 mL) was added N-bromosuccinimide (0.84 g, 4.8 mmol) followed by AIBN (0.004 g, 0.01 mmol). After refluxing for 2 h, analytical HPLC analysis confirmed the reaction was complete. The reaction was cooled to rt, then CH$_2$Cl$_2$ and sat'd NaHCO$_3$ (aq.) were added. The organic portion was separated and dried to provide the crude residue as a yellow oil. This material was purified by RP HPLC to provide the title compound (510 mg, 38%). MS (ESI): mass calcd. for $C_9H_8BrF_3O_3$, 300.0; m/z found, 302.9 [M+H]$^+$. $^1$H NMR (CDCl$_3$): 6.84 (s, 1H), 4.44 (s, 2H), 4.34 (q, J=7.2 Hz, 2H), 1.36 (t, J=7.1 Hz, 3H).

Step B: Preparation of 3-[2-(4-Carboxy-5-trifluoromethyl-furan-2-ylmethoxy)-5-chloro-phenoxy]-azetidine-1-carboxylic acid tert-butyl ester. The title compound was prepared as described in Example 1 Step D using 3-(5-chloro-2-hydroxy-phenoxy)-azetidine-1-carboxylic acid tert-butyl ester (0.15 g, 0.50 mmol), the title compound of Step A (0.18 g, 0.60 mmol), Cs$_2$CO$_3$ (0.41 g, 1.2 mmol), KI (0.12 g, 0.70 mmol) in DMF, except upon completion of the reaction 1N NaOH and EtOAc were added. The organic layer was washed with 1N NaOH and dried. The crude material was purified by RP HPLC to provide the title compound. $^1$H NMR (CDCl$_3$): 7.20-6.92 (m, 1H), 6.91-6.80 (m, 2H), 6.77-6.69 (m, 1H), 6.53 (d, J=2.1 Hz, 1H), 4.87 (s, 2H), 4.79-4.69 (m, 1H), 4.27-4.12 (m, 2H), 4.00-3.88 (m, 2H), 1.38 (s, 9H).

Step C: Preparation of 5-[2-(Azetidin-3-yloxy)-4-chloro-phenoxymethyl]-2-trifluoromethyl-furan-3-carboxylic acid trifluoroacetate: Prepared from the title compound of Step B using general procedure 1. MS (ESI): mass calcd. for $C_{16}H_{13}ClF_3NO_5$ [M-TFA], 391.0; m/z found, 392.9 [M+H]$^+$. $^1$H NMR (CD$_3$OD): 7.10 (d, J=8.7 Hz, 1H), 7.03 (dd, J=8.7, 2.4 Hz, 1H), 6.99 (s, 1H), 6.88 (d, J=2.4 Hz, 1H), 5.14 (s, 2H), 5.11-5.04 (m, 1H), 4.49 (dd, J=12.4, 6.6 Hz, 2H), 4.22 (dd, J=12.4, 4.9 Hz, 2H).

Example 76

5-[2-(Azetidin-3-yloxy)-4-chloro-phenoxymethyl]-2-trifluoromethyl-furan-3-carboxylic acid ethyl ester

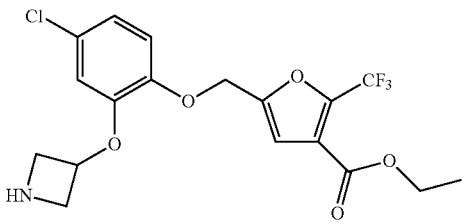 [SMILES: CCOC(=O)c1cc(COc2ccc(Cl)cc2OC2CNC2)oc1C(F)(F)F]

Step A: Preparation of 3-[5-Chloro-2-(4-ethoxycarbonyl-5-trifluoromethyl-furan-2-ylmethoxy)-phenoxy]-azetidine-1-carboxylic acid tert-butyl ester. The title compound was prepared as described in Example 1 Step D using 3-(5-chloro-2-hydroxy-phenoxy)-azetidine-1-carboxylic acid tert-butyl ester (0.3 g, 1.0 mmol), the title compound of Example 75 Step A (0.75 g, 2.5 mmol), Cs$_2$CO$_3$ (0.80 g, 2.4 mmol) and KI (0.23 g, 1.4 mmol) in DMF (15 mL). The crude material was purified by RP HPLC to provide the title compound (0.37 g, 71%). $^1$H NMR (CDCl$_3$): 7.20-6.92 (m, 1H), 6.91-6.80 (m, 2H), 6.77-6.69 (m, 1H), 6.53 (d, J=2.1 Hz, 1H), 4.87 (s, 2H), 4.79-4.69 (m, 1H), 4.27-4.12 (m, 2H), 4.00-3.88 (m, 2H), 1.38 (s, 9H).

Step B: Preparation of 5-[2-(Azetidin-3-yloxy)-4-chloro-phenoxymethyl]-2-trifluoromethyl-furan-3-carboxylic acid ethyl ester: Prepared from the title compound of Step A using general procedure 1. MS (ESI): mass calcd. for $C_{18}H_{17}ClF_3NO_5$, 419.1; m/z found, 420.0 [M+H]$^+$. $^1$H NMR (CDCl$_3$): 6.94-7.80 (m, 3H), 6.65-6.56 (m, 1H), 5.05 (s, 2H), 5.01-4.92 (m, 1H), 4.34 (q, J=7.2 Hz, 2H), 3.97-3.81 (m, 4H), 1.36 (t, J=7.1 Hz, 3H).

Example 77

5-[4-Chloro-2-(1-methyl-azetidin-3-yloxy)-phenoxymethyl]-2-trifluoromethyl-furan-3-yl]-methanol

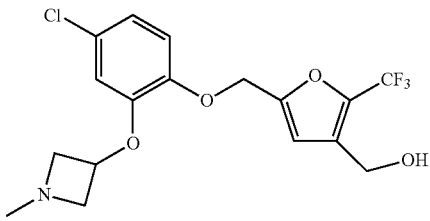 [SMILES: CN1CC(Oc2cc(Cl)ccc2OCc2cc(CO)c(C(F)(F)F)o2)C1]

Step A: Preparation of 5-[4-Chloro-2-(1-methyl-azetidin-3-yloxy)-phenoxymethyl]-2-trifluoromethyl-furan-3-yl]-methanol. To a solution of the title compound of Example 76 Step A (0.05 g, 0.1 mmol) at −78° C. was added DIBAL-H (1.0 M in THF, 0.24 mL). After addition was complete, the bath was replaced with a 0° C. bath and allowed to stir for 1 h. Then, an additional aliquot of DIBAL-H (1.0 M in THF, 1 mL) was added. After 3 h, the reaction was quenched with a saturated solution of sodium potassium tartrate (aq.) and allowed to stir overnight. The mixture was extracted with EtOAc (2×) and the combined organic layers were dried. The product was purified by RP HPLC to provide the title compound (0.004 g, 10%). MS (ESI): mass calcd. for $C_{17}H_{17}ClF_3NO_4$, 391.1; m/z found, 392.1 [M+H]$^+$. $^1$H NMR (CDCl$_3$): 6.94 (d, J=8.6 Hz, 1H), 6.89 (dd, J=8.6, 2.3 Hz, 1H), 6.65 (s, 1H), 6.54 (d, J=2.3 Hz, 1H), 5.02 (s, 2H), 4.73-4.66 (m, 1H), 4.64 (d, J=1.4 Hz, 2H), 3.76-3.69 (m, 2H), 3.27-3.21 (m, 2H), 2.41 (s, 3H).

Example 78

3-[5-Chloro-2-(5-methyl-2-trifluoromethyl-furan-3-ylmethoxy)-phenoxy]-azetidine

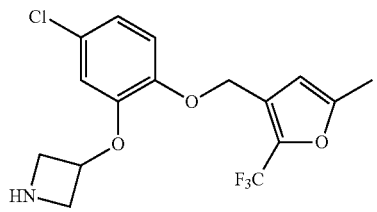 [SMILES: Cc1cc(COc2ccc(Cl)cc2OC2CNC2)c(C(F)(F)F)o1]

Step A: Preparation of (5-Methyl-2-trifluoromethyl-furan-3-yl)-methanol. To a solution of 5-methyl-2-trifluoromethyl-furan-3-carboxylic acid ethyl ester (0.83 g, 3.7 mmol) in Et$_2$O at 0° C., was added DIBAL-H (1.0 M in THF, 1.5 mL). After 10 min, the ice bath was removed and additional DIBAL-H was added (1.0 M in THF, 14.5 mL). After 2 h, the reaction was quenched with a saturated solution of sodium potassium tartrate (aq.) and allowed to stir overnight. After 18 h, EtOAc was added and the organic layer separated and dried provide the title compound (0.39 g, 58%). $^1$H NMR (CDCl$_3$): 6.19 (s, 1H), 4.62 (s, 2H), 2.36-2.28 (m, 3H).

Step B: Preparation of 3-[5-chloro-2-(5-methyl-2-trifluoromethyl-furan-3-ylmethoxy)-phenoxy]-azetidine-1-carboxylic acid tert-butyl ester. Synthesized from the title compound of Step A and 3-(5-chloro-2-hydroxy-phenoxy)-azetidine-1-carboxylic acid tert-butyl ester using general procedure 7. MS (ESI): mass calcd. for $C_{21}H_{23}ClF_3NO_5$, 461.1; m/z found, 485.9 [M+Na]$^+$. $^1$H NMR 6.91 (dd, J=8.6, 2.3 Hz, 1H), 6.84 (d, J=8.6 Hz, 1H), 6.55 (d, J=2.3 Hz, 1H), 6.22 (s, 1H), 5.07-5.00 (m, 2H), 4.90-4.81 (m, 1H), 4.30 (ddd, J=9.7, 6.5, 0.8 Hz, 2H), 4.06 (dd, J=9.8, 4.0 Hz, 2H), 2.34 (s, 3H), 1.45 (s, 9H).

Step C: Preparation of 3-[5-Chloro-2-(5-methyl-2-trifluoromethyl-furan-3-ylmethoxy)-phenoxy]-azetidine. Synthesized from the title compound of Step B using general procedure 1. MS (ESI): mass calcd. for $C_{16}H_{15}ClF_3NO_3$, 361.1; m/z found, 362.1 [M+H]$^+$. $^1$H NMR (CDCl$_3$): 6.86 (dd, J=8.6, 2.2 Hz, 1H), 6.81 (d, J=8.6 Hz, 1H), 6.58 (d, J=2.2 Hz, 1H), 6.23 (s, 1H), 5.03 (s, 2H), 5.01-4.93 (m, 1H), 4.01-3.77 (m, 4H), 2.33 (s, 3H).

Example 79

2-[2-(Azetidin-3-yloxy)-4-chloro-phenoxymethyl]-6-trifluoromethyl-pyridine

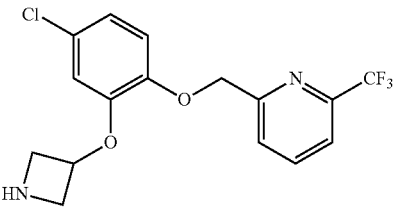

Step A: Preparation of (6-Trifluoromethyl-pyridin-2-yl)-methanol. To a solution of 6-trifluoromethyl-pyridine-2-carboxylic acid (500 mg, 3 mmol) in dry THF at 0° C., was added triethylamine (0.36 mL, 2.6 mmol) followed by ethyl chloroformate (0.25 mL, 2.6 mmol). After 30 min, LiBH$_4$ (2 M in THF, 3.3 mL, 6.5 mmol) was added. After an additional 30 min, the ice bath was removed. After 1 h, the reaction was cooled to 0° C. and quenched with MeOH followed by 1N NaOH and EtOAc. The pH of the solution was adjusted to pH=5 with 1N HCl and the mixture extracted with EtOAc (2×). The combined organic fractions were dried to provide the title compound that was used without further purification. $^1$H NMR (CDCl$_3$): 7.89 (dd, J=7.8, 7.8 Hz, 1H), 7.61 (d, J=7.7 Hz, 1H), 7.51 (d, J=7.9 Hz, 1H), 4.85 (s, 2H).

Step B: Preparation of 3-[5-Chloro-2-(6-trifluoromethyl-pyridin-2-ylmethoxy)-phenoxy]-azetidine-1-carboxylic acid tert-butyl ester. Prepared from the title compound of Step A and 3-(5-Chloro-2-hydroxy-phenoxy)-azetidine-1-carboxylic acid tert-butyl ester using general procedure 7.

Step C: Preparation of 2-[2-(Azetidin-3-yloxy)-4-chloro-phenoxymethyl]-6-trifluoromethyl-pyridine. Prepared from the title compound of Step B according to general procedure 1. MS (ESI): mass calcd. for C$_{16}$H$_{14}$ClF$_3$N$_2$O$_2$, 358.1; m/z found, 359.0 [M+H]$^+$. $^1$H NMR (CDCl$_3$): 7.92 (dd, J=7.8, 7.8 Hz, 1H), 7.81 (d, J=7.9 Hz, 1H), 7.63 (d, J=7.7 Hz, 1H), 6.87 (dd, J=8.6, 2.1 Hz, 1H), 6.61 (d, J=2.1 Hz, 1H), 5.29 (s, 2H), 5.21-4.99 (m, 1H), 4.21-1.15 (br m, 4H).

Examples 80-89 were prepared using the appropriate alcohol and phenol according to general procedure 7.

Example 80

3-[2-(Azetidin-3-yloxy)-4-chloro-phenoxymethyl]-2-methyl-6-trifluoromethyl-pyridine

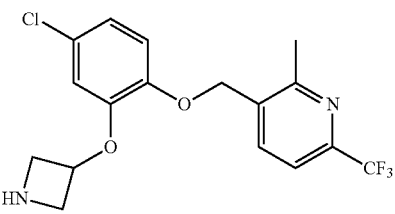 [SMILES: Cc1nc(C(F)(F)F)ccc1COc1ccc(Cl)cc1OC1CNC1]

MS (ESI): mass calcd. for C$_{17}$H$_{16}$ClF$_3$N$_2$O$_2$, 372.1; m/z found, 373.0 [M+H]$^+$. $^1$H NMR (CDCl$_3$): 7.93 (d, J=7.9 Hz, 1H), 7.55 (d, J=7.9 Hz, 1H), 6.89 (dd, J=8.6, 2.2 Hz, 1H), 6.85 (d, J=8.6 Hz, 1H), 6.60 (d, J=2.2 Hz, 1H), 5.11 (s, 2H), 5.03-4.92 (m, 1H), 4.08-3.69 (m, 4H), 2.66 (s, 3H).

Example 81

2-[2-(Azetidin-3-yloxy)-4-chloro-phenoxymethyl]-4-trifluoromethyl-pyridine

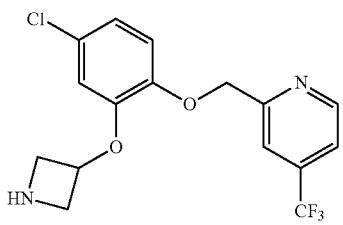 [SMILES: FC(F)(F)c1ccnc(COc2ccc(Cl)cc2OC2CNC2)c1]

MS (ESI): mass calcd. for C$_{16}$H$_{14}$ClF$_3$N$_2$O$_2$, 358.1; m/z found, 358.9 [M+H]$^+$. $^1$H NMR (CDCl$_3$): 8.86 (s, 1H), 7.98 (d, J=7.9 Hz, 1H), 7.73 (d, J=8.2 Hz, 1H), 6.87 (dd, J=8.6, 2.1 Hz, 1H), 6.82 (d, J=8.6 Hz, 1H), 6.61 (d, J=1.9 Hz, 1H), 5.28 (s, 2H), 5.08-4.98 (m, 1H), 4.08-3.97 (m, 2H), 3.96-3.85 (m, 2H).

Example 82

5-[2-(Azetidin-3-yloxy)-4-chloro-phenoxymethyl]-2-trifluoromethyl-pyridine

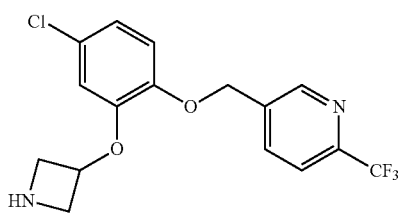 [SMILES: FC(F)(F)c1ccc(COc2ccc(Cl)cc2OC2CNC2)cn1]

MS (ESI): mass calcd. for C$_{16}$H$_{14}$ClF$_3$N$_2$O$_2$, 358.1; m/z found, 359.0 [M+H]$^+$. $^1$H NMR (CDCl$_3$): 8.81 (s, 1H), 7.98 (d, J=8.0 Hz, 1H), 7.72 (d, J=8.1 Hz, 1H), 6.90 (dd, J=8.6, 2.2 Hz, 1H), 6.86 (d, J=8.6 Hz, 1H), 6.60 (d, J=2.2 Hz, 1H), 5.18 (s, 2H), 5.03-4.95 (m, 1H), 4.02-3.95 (m, 2H), 3.89-3.82 (m, 2H).

Example 83

3-[2-(Benzofuran-5-ylmethoxy)-5-chloro-phenoxy]-azetidine

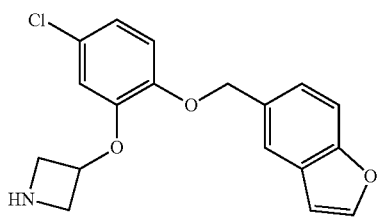

MS (ESI): mass calcd. for C$_{18}$H$_{16}$ClNO$_3$, 329.1; m/z found, 330.1 [M+H]$^+$. $^1$H NMR (CDCl$_3$): 7.65-7.64 (m, 2H) 7.50 (d, J=8.5 Hz, 1H), 7.35 (dd, J=8.5, 1.6 Hz, 1H), 6.87-6.82

(m, 2H), 6.76 (d, J=1.3 Hz, 1H), 6.59 (s, 1H), 5.18 (s, 2H), 5.02-4.92 (m, 1H), 4.06-3.79 (m, 4H).

Example 84

6-[2-(Azetidin-3-yloxy)-4-chloro-phenoxymethyl]-benzothiazole

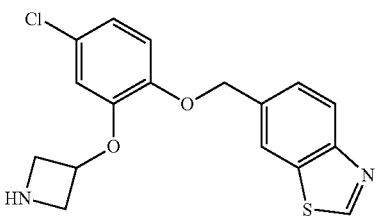 [SMILES: Clc1ccc(OCc2ccc3ncsc3c2)c(OC2CNC2)c1]

MS (ESI): mass calcd. for $C_{17}H_{15}ClN_2O_2S$, 346.1; m/z found, 347.0 [M+H]$^+$. $^1$H NMR (CDCl$_3$): 9.01 (s, 1H), 8.14 (d, J=8.4 Hz, 1H), 8.05 (s, 1H), 7.57 (dd, J=8.4, 1.6 Hz, 1H), 6.85 (d, J=1.2 Hz, 2H), 6.60 (s, 1H), 5.35 (s, 2H), 5.00-4.98 (m, 1H), 3.93-3.87 (m, 4H).

Example 85

6-[2-(Azetidin-3-yloxy)-4-chloro-phenoxymethyl]-1-methyl-1H-benzotriazole

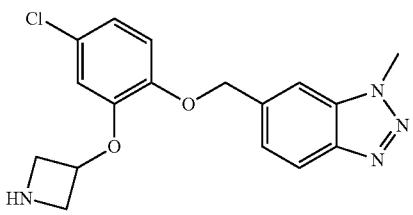 [SMILES: Cn1nnc2ccc(COc3ccc(Cl)cc3OC3CNC3)cc21]

MS (ESI): mass calcd. for $C_{17}H_{17}ClN_4O_2$, 344.1; m/z found, 345.0 [M+H]$^+$. $^1$H NMR (CDCl$_3$): 8.10 (s, 1H), 7.61 (dd, J=8.6, 1.3 Hz, 1H), 7.53 (d, J=8.6 Hz, 1H), 6.88-6.80 (m, 2H), 6.59 (d, J=1.9 Hz, 1H), 5.26 (s, 2H), 5.02-4.96 (m, 1H), 4.31 (s, 3H), 3.97-3.82 (m, 4H).

Example 86

3-[5-Chloro-2-(2,2-difluoro-benzo[1,3]dioxol-5-ylmethoxy)-phenoxy]-azetidine

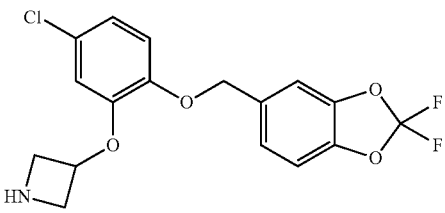 [SMILES: FC1(F)Oc2ccc(COc3ccc(Cl)cc3OC3CNC3)cc2O1]

MS (ESI): mass calcd. for $C_{17}H_{14}ClF_2NO_4$, 369.1; m/z found, 370.0 [M+H]$^+$. $^1$H NMR (CDCl$_3$): 7.20 (d, J=1.2 Hz, 1H), 7.11 (dd, J=8.2, 1.5 Hz, 1H), 7.04 (d, J=8.2 Hz, 1H), 6.86 (dd, J=8.6, 2.3 Hz, 1H), 6.81 (d, J=8.6 Hz, 1H), 6.59 (d, J=2.3 Hz, 1H), 5.06 (s, 2H), 5.01-4.95 (m, 1H), 3.96-3.83 (m, 4H).

Example 87

5-[2-(Azetidin-3-yloxy)-4-chloro-phenoxymethyl]-oxazole

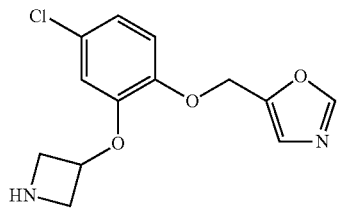 [SMILES: Clc1ccc(OCc2cnco2)c(OC2CNC2)c1]

MS (ESI): mass calcd. for $C_{13}H_{13}ClN_2O_3$, 280.1; m/z found, 281.1 [M+H]$^+$. $^1$H NMR (CDCl$_3$): 7.91 (s, 1H), 7.13 (s, 1H), 6.90-6.87 (m, 2H), 6.59 (d, J=1.9 Hz, 1H), 5.10 (s, 2H), 5.00-4.91 (m, 1H), 3.97-3.89 (m, 2H), 3.87-3.79 (m, 2H).

Example 88

2-[2-(Azetidin-3-yloxy)-4-chloro-phenoxymethyl]-thiazole

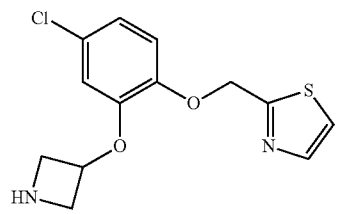 [SMILES: Clc1ccc(OCc2nccs2)c(OC2CNC2)c1]

MS (ESI): mass calcd. for $C_{13}H_{13}ClN_2O_2S$, 296.0; m/z found, 297.0 [M+H]$^+$. $^1$H NMR (CDCl$_3$): 7.80 (t, J=3.1 Hz, 1H), 7.38 (t, J=3.3 Hz, 1H), 6.96-6.84 (m, 2H), 6.63 (dd, J=11.1, 2.3 Hz, 1H), 5.41-5.37 (m, 2H), 5.04-4.78 (m, 1H), 4.01-3.93 (m, 1H), 3.92-3.83 (m, 2H), 3.31-3.23 (m, 1H)

Example 89

3-[2-(Benzofuran-2-ylmethoxy)-5-chloro-phenoxy]-azetidine

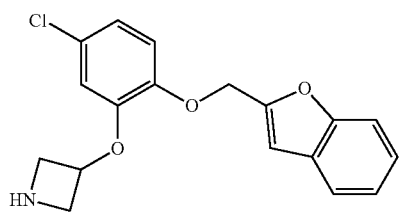 [SMILES: Clc1ccc(OCc2cc3ccccc3o2)c(OC2CNC2)c1]

MS (ESI): mass calcd. for $C_{18}H_{16}ClNO_3$, 329.1; m/z found, 330.0 [M+H]$^+$. $^1$H NMR (CDCl$_3$): 7.56 (d, J=7.7 Hz, 1H), 7.50 (dd, J=8.2, 0.7 Hz, 1H), 7.34-7.28 (m, 1H), 7.23 (dt, J=7.5, 1.0 Hz, 1H), 6.96 (d, J=8.6 Hz, 1H), 6.87 (dd, J=8.6, 2.4 Hz, 1H), 6.73 (d, J=0.5 Hz, 1H), 6.57 (d, J=2.4 Hz, 1H), 5.17 (s, 2H), 4.95-4.89 (m, 1H), 3.93-3.69 (m, 4H).

Example 90

(R)-3-(2-Benzyloxy-4-chloro-phenoxy)-pyrrolidine

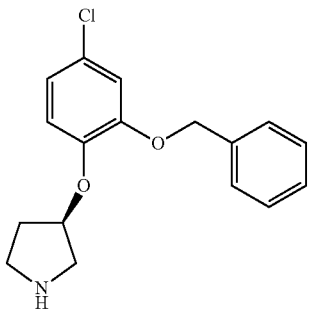 [SMILES: Clc1ccc(O[C@@H]2CCNC2)c(OCc2ccccc2)c1]

Step A: Preparation of 3-(4-chloro-2-formyl-phenoxy)-pyrrolidine-1-carboxylic acid tert-butyl ester. To (S)-3-hydroxy-pyrrolidine-1-carboxylic acid tert-butyl ester (2.0 g, 10.9 mmol) in CH$_2$Cl$_2$ (50 mL) at 0° C. was added Et$_3$N (1.4 g, 1.9 mL, 13.4 mmol) and methanesulfonyl chloride (1.38 g, 0.94 mL, 12.1 mmol). After 1 h, brine was added and the mixture extracted with CH$_2$Cl$_2$ (2×). The combined organics were dried to give 3-methanesulfonyloxy-pyrrolidine-1-carboxylic acid tert-butyl ester that was used without further purification.

To this compound in DMF (50 mL) was added 5-chloro-2-hydroxy-benzaldehyde (1.9 g, 12.1 mmol) and K$_2$CO$_3$ (1.8 g, 13.1 mmol). The reaction was heated at 90° C. for 2 h, then cooled to rt and H$_2$O was added. The mixture was extracted with EtOAc (2×). The combined organics were washed with brine and dried. Silica gel chromatography (10-50% EtOAc in hexanes) gave 1.85 g (52%) of the title compound. $^1$H NMR (CDCl$_3$): 10.36 (s, 1H), 7.81 (s, 1H), 7.50 (s, 1H), 6.90 (d, J=8.9 Hz, 1H), 5.00 (s, 1H), 3.72-3.50 (m, 4H), 2.26-2.18 (m, 2H), 1.47 (s, 9H).

Step B: Preparation of 3-(4-chloro-2-hydroxy-phenoxy)-pyrrolidine-1-carboxylic acid tert-butyl ester. To a CH$_2$Cl$_2$ (25 mL) solution of the title compound of Step A (1.4 g, 4.3 mmol) was added 77% m-CPBA (1.4 g, 6.2 mmol). After 18 h, additional CH$_2$Cl$_2$ was added and the reaction washed with saturated NaHCO$_3$ (aq.) and 10% Na$_2$S$_2$O$_5$ until KI paper negative. The combined organic layers were dried then treated with MeOH (25 mL) and 1N NaOH (25 mL). After 15 h, the reaction was acidified with 1M KHSO$_4$ then extracted with EtOAc (2×). The combined organic layers were washed with brine and dried to give the title compound as a white solid. $^1$H NMR (CDCl$_3$): 6.96 (s, 1H), 6.82-6.80 (m, 1H), 6.73 (d, J=8.6 Hz, 1H), 5.62 (s, 1H), 4.91 (s, 1H), 3.66-3.46 (m, 4H), 2.20-2.11 (m, 2H), 1.47 (s, 9H).

Step C: Preparation of 3-(2-Benzyloxy-4-chloro-phenoxy)-pyrrolidine-1-carboxylic acid tert-butyl ester. Prepared according to Example 1 Step D using the title compound of Step B. MS (ESI): mass calcd. for C$_{22}$H$_{26}$ClNO$_4$, 403.2; m/z found, 426.2 [M+Na]$^+$, 348.2 [M-56]$^+$. $^1$H NMR (CDCl$_3$): 7.43-7.36 (m, 4H), 7.35-7.30 (m, 1H), 6.95 (d, J=2.4 Hz, 1H), 6.88 (dd, J=8.5, 2.4 Hz, 1H), 6.82 (d, J=8.5 Hz, 1H), 5.07 (s, 2H), 4.89-4.85 (m, 1H), 3.71-3.45 (m, 4H), 2.24-2.12 (m, 1H), 2.07-1.94 (m, 1H), 1.46 (s, 9H).

Step D: Preparation of (R)-3-(2-Benzyloxy-4-chloro-phenoxy)-pyrrolidine. Prepared according to general procedure 1 using the title compound of Step C. MS (ESI): mass calcd. for C$_{17}$H$_{18}$ClNO$_2$, 303.1; m/z found, 304.2 [M+H]$^+$. $^1$H NMR (CDCl$_3$): 7.45-7.36 (m, 4H), 7.35-7.30 (m, 1H), 6.94 (d, J=2.4 Hz, 1H), 6.88 (dd, J=8.6, 2.4 Hz, 1H), 6.81 (d, J=8.6 Hz, 1H), 5.06 (s, 2H), 4.86 (s, 1H), 3.25 (d, J=2.1 Hz, 2H), 2.25-1.73 (m, 4H).

Example 91

(R)-3-(2-Benzyloxy-4-chloro-phenoxy)-1-methyl-pyrrolidine

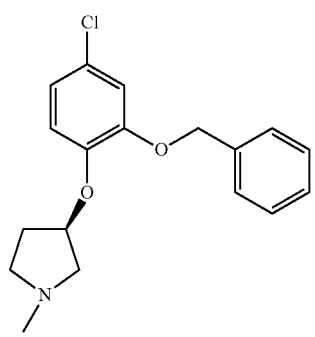 [SMILES: CN1CC[C@@H](Oc2ccc(Cl)cc2OCc2ccccc2)C1]

Synthesized from the title compound of Example 90 according to general procedure 5. MS (ESI): mass calcd. for C$_{18}$H$_{20}$ClNO$_2$, 317.1; m/z found, 318.2 [M+H]$^+$. $^1$H NMR (CDCl$_3$): 7.44-7.32 (m, 5H), 6.91 (d, J=2.3 Hz, 1H), 6.86 (dd, J=8.5, 2.4 Hz, 1H), 6.75 (d, J=8.6 Hz, 1H), 5.08 (s, 2H), 4.81 (td, J=10.4, 5.1 Hz, 1H), 2.90 (dd, J=10.1, 6.1 Hz, 1H), 2.74 (d, J=8.9 Hz, 2H), 2.53 (dd, J=13.8, 7.9 Hz, 1H), 2.38 (s, 3H), 2.28-2.21 (m, 1H), 2.08-1.98 (m, 1H).

Example 92

(R)-3-[4-Chloro-2-(3-chloro-benzyloxy)-phenoxy]-pyrrolidine

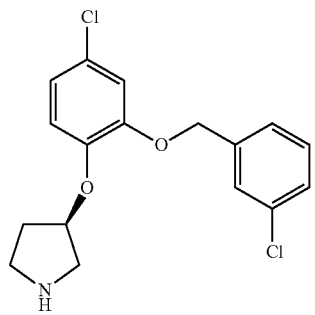 [SMILES: Clc1cccc(COc2cc(Cl)ccc2O[C@@H]2CCNC2)c1]

Synthesized according to Example 90 using 3-chlorobenzyl bromide. MS (ESI): mass calcd. for C$_{17}$H$_{17}$Cl$_2$NO$_2$, 337.1; m/z found, 338.1 [M+H]$^+$. $^1$H NMR (CDCl$_3$): 7.40 (s, 1H), 7.29-7.20 (m, 3H), 6.86 (dd, J=7.1, 2.2 Hz, 2H), 6.79-6.74 (m, 1H), 4.99 (s, 2H), 4.77 (t, J=5.1 Hz, 1H), 3.18-3.13 (m, 2H), 2.92-2.86 (m, 2H), 2.11-1.81 (m, 2H).

Example 93

(R)-3-[4-Chloro-2-(3-chloro-benzyloxy)-phenoxy]-1-methyl-pyrrolidine

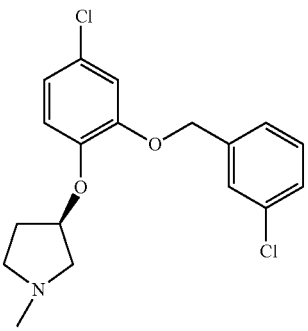 [SMILES: CN1CC[C@@H](Oc2ccc(Cl)cc2OCc2cccc(Cl)c2)C1]

Synthesized from the title compound of Example 92 according to general procedure 5. MS (ESI): mass calcd. for $C_{18}H_{19}Cl_2NO_2$, 351.1; m/z found, 352.2 [M+H]$^+$. $^1$H NMR (CDCl$_3$): 7.47 (s, 1H), 7.30 (s, 3H), 6.88 (dd, J=7.3, 2.2 Hz, 2H), 6.77-6.74 (m, 1H), 5.04 (s, 2H), 4.85-4.73 (m, 1H), 2.96-2.86 (m, 1H), 2.79-2.68 (m, 2H), 2.56-2.50 (m, 1H), 2.39 (s, 3H), 2.31-2.17 (m, 1H), 2.05-1.95 (m, 1H).

Example 94

(S)-3-[4-Chloro-2-(3-chloro-benzyloxy)-phenoxy]-pyrrolidine

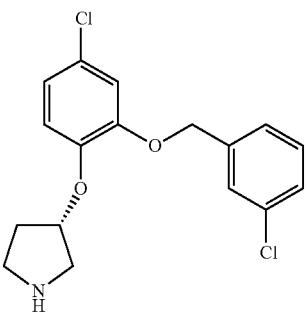 [SMILES: Clc1cccc(COc2cc(Cl)ccc2O[C@H]2CCNC2)c1]

Synthesized according to Example 90 using (R)-3-hydroxy-pyrrolidine-1-carboxylic acid tert-butyl ester and 3-chlorobenzyl bromide. MS (ESI): mass calcd. for $C_{17}H_{17}Cl_2NO_2$, 337.1; m/z found, 338.2 [M+H]$^+$. $^1$H NMR (CDCl$_3$): 7.44 (s, 1H), 7.36-7.24 (m, 3H), 6.94-6.86 (m, 2H), 6.84-6.78 (m, 1H), 5.08 (s, 2H), 4.81 (t, J=5.0 Hz, 1H), 3.26-3.08 (m, 2H), 3.00-2.84 (m, 2H), 2.12-1.91 (m, 2H).

Examples 95-100 were prepared using 1-methyl-pyrrolidin-3-ol and the appropriately substituted phenol (synthesized according to Example 90) according to general procedure 7 using resin bound PPh$_3$.

Example 95

(±)-3-[5-Bromo-2-(3-chloro-benzyloxy)-phenoxy]-1-methyl-pyrrolidine

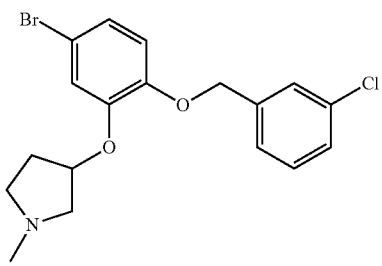 [SMILES: CN1CCC(Oc2cc(Br)ccc2OCc2cccc(Cl)c2)C1]

MS (ESI): mass calcd. for $C_{18}H_{19}BrClNO_2$, 395.0; m/z found, 396.0 [M+H]$^+$. $^1$H NMR (CDCl$_3$): 7.46 (s, 1H), 7.33-7.24 (m, 3H), 6.98 (dd, J=8.5, 2.3 Hz, 1H), 6.94 (d, J=2.3 Hz, 1H), 6.76 (d, J=8.5 Hz, 1H), 5.04 (s, 2H), 4.82 (m, 1H), 2.95 (dd, J=10.5, 6.1 Hz, 1H), 2.82-2.73 (m, 2H), 2.55 (m, 1H), 2.41 (s, 3H), 2.31 (m, 1H), 2.10-2.00 (m, 1H).

Example 96

(±)-3-[5-Bromo-2-(3-methoxy-benzyloxy)-phenoxy]-1-methyl-pyrrolidine

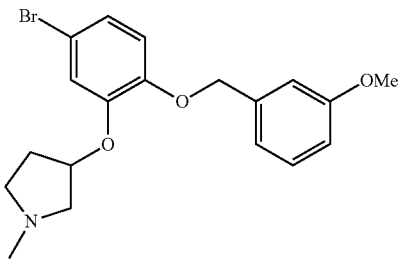 [SMILES: COc1cccc(COc2ccc(Br)cc2OC2CCN(C)C2)c1]

MS (ESI): mass calcd. for $C_{19}H_{22}BrNO_3$, 391.1; m/z found, 391.1 [M+H]$^+$. $^1$H NMR (CDCl$_3$): 7.31-7.23 (m, 1H), 6.99-6.96 (m, 3H), 6.93 (d, J=2.3 Hz, 1H), 6.87-6.82 (m, 1H), 6.76 (d, J=8.5 Hz, 1H), 5.06 (s, 2H), 4.86-4.79 (m, 1H), 3.81 (s, 3H), 2.94 (dd, J=10.6, 6.1 Hz, 1H), 2.79-2.73 (m, 2H), 2.54 (m, 1H), 2.39 (s, 3H), 2.29 (m, 1H), 2.05 (m, 1H).

Example 97

(±)-3-[5-Bromo-2-(3-fluoro-benzyloxy)-phenoxy]-1-methyl-pyrrolidine

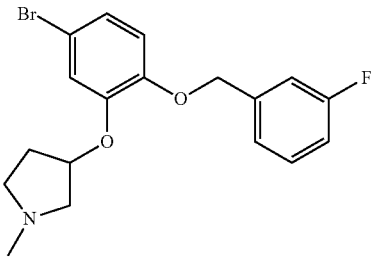 [SMILES: CN1CCC(Oc2cc(Br)ccc2OCc2cccc(F)c2)C1]

MS (ESI): mass calcd. for $C_{18}H_{19}BrFNO_2$, 379.1; m/z found, 380.1 [M+H]$^+$. $^1$H NMR (400 MHz, DMSO-D$_6$): 7.32 (m, 1H), 7.17 (d, J=7.3 Hz, 2H), 7.02-6.96 (m, 2H), 6.94 (d, J=2.3 Hz, 1H), 6.75 (d, J=8.5 Hz, 1H), 5.07 (s, 2H), 4.82 (m, 1H), 2.94 (m, 1H), 2.82-2.73 (m, 2H), 2.55 (m, 1H), 2.40 (s, 3H), 2.31 (m, 1H), 2.07-2.02 (m, 1H).

Example 98

(±)-3-(2-Benzyloxy-5-bromo-phenoxy)-1-methyl-pyrrolidine

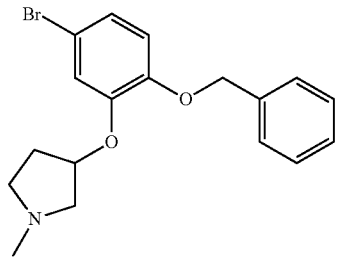 [SMILES: CN1CCC(Oc2cc(Br)ccc2OCc2ccccc2)C1]

MS (ESI): mass calcd. for $C_{18}H_{20}BrNO_2$, 361.1; m/z found, 362.1 [M+H]$^+$. $^1$H NMR (CDCl$_3$): 7.41 (m, 2H), 7.39-7.34 (m, 2H), 7.30 (m, 1H), 6.97 (dd, J=8.5, 2.3 Hz, 1H), 6.93 (d, J=2.3 Hz, 1H), 6.77 (d, J=8.5 Hz, 1H), 5.08 (s, 2H), 4.86-4.76 (m, 1H), 2.93 (m, 1H), 2.80-2.72 (m, 2H), 2.57-2.50 (m, 1H), 2.39 (s, 3H), 2.29 (m, 1H), 2.09-1.99 (m, 1H).

Example 99

(±)-Methanesulfonic acid 3-[4-bromo-2-(1-methyl-pyrrolidin-3-yloxy)-phenoxymethyl]-phenyl ester

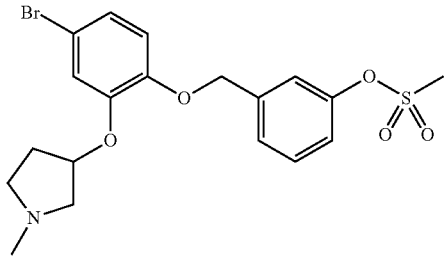 [SMILES: CN1CCC(Oc2cc(Br)ccc2OCc2cccc(OS(C)(=O)=O)c2)C1]

MS (ESI): mass calcd. for $C_{19}H_{22}BrNO_5S$, 455.1; m/z found, 456.1 [M+H]$^+$. $^1$H NMR (CDCl$_3$): 7.46-7.35 (m, 3H), 7.23 (m, 1H), 6.98 (dd, J=8.5, 2.3 Hz, 1H), 6.93 (d, J=2.2 Hz, 1H), 6.75 (d, J=8.5 Hz, 1H), 5.08 (s, 2H), 4.81 (m, 1H), 3.13 (s, 3H), 2.89 (m, 1H), 2.82-2.74 (m, 2H), 2.55-2.46 (m, 1H), 2.39 (s, 3H), 2.31 (m, 1H), 2.03 (m, 1H).

Example 100

(±)-Methanesulfonic acid 3-[2-(1-methyl-pyrrolidin-3-yloxy)-phenoxymethyl]-phenyl ester

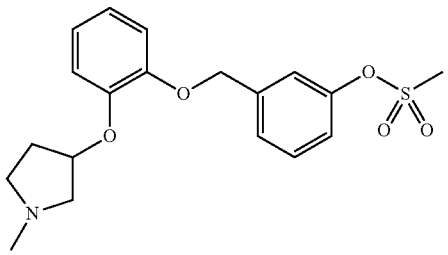 [SMILES: CN1CCC(Oc2ccccc2OCc2cccc(OS(C)(=O)=O)c2)C1]

MS (ESI): mass calcd. for $C_{19}H_{23}NO_5S$, 377.1; m/z found, 378.1 [M+H]$^+$. $^1$H NMR (CDCl$_3$): 7.42 (m, 3H), 7.26-7.20 (m, 1H), 6.98-6.80 (m, 4H), 5.13 (s, 2H), 4.86 (m, 1H), 3.12 (s, 3H), 2.93 (dd, J=10.5, 6.1 Hz, 1H), 2.81-2.71 (m, 2H), 2.60-2.49 (m, 1H), 2.40 (s, 3H), 2.30 (m, 1H), 2.11-2.00 (m, 1H).

Example 101

(S)-3-[5-Chloro-2-[1-(3-trifluoromethyl-phenyl)-ethoxy]-phenoxy]-azetidine

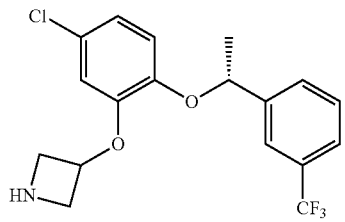

Step A: Preparation of (R)-3-[5-Chloro-2-[1-(3-trifluoromethyl-phenyl)-ethoxy]-phenoxy]-azetidine-1-carboxylic acid tert-butyl ester. To (S)-1-(3-trifluoromethyl-phenyl)-ethanol (2.30 g, 12.1 mmol), 3-(5-chloro-2-hydroxy-phenoxy)-azetidine-1-carboxylic acid tert-butyl ester (3.80 g, 12.7 mmol) and PPh$_3$ (3.80 g, 14.5 mmol) in THF (60 mL) at 0° C. was added DEAD (2.3 g, 2.1 mL, 13 mmol) in THF (10 mL) dropwise over 30 min. After 48 h, the reaction was concentrated and 15% EtOAc in hexanes was added. The flask was cooled to 0° C. and filtered. The filtrate was concentrated and this procedure repeated 2 more times. The resulting oil was then purified using silica gel chromatography (10-40% EtOAc in hexanes) to give 5.17 g (91%) of the title compound as a clear oil. $^1$H NMR (CDCl$_3$): 7.66 (s, 1H), 7.56-7.53 (m, 2H), 7.46 (t, J=7.7 Hz, 1H), 6.79 (dd, J=8.6, 2.4 Hz, 1H), 6.71 (d, J=8.6 Hz, 1H), 6.52 (d, J=2.4 Hz, 1H), 5.29 (q, J=6.5 Hz, 1H), 4.88-4.82 (m, 1H), 4.33-4.29 (m, 2H), 4.08-4.01 (m, 2H), 1.67 (d, J=6.5 Hz, 3H), 1.46 (s, 9H).

Step B: Preparation of (S)-3-[5-Chloro-2-[1-(3-trifluoromethyl-phenyl)-ethoxy]-phenoxy]-azetidine. To the title compound of Step A (5.1 g, 10.8 mmol) in CH$_2$Cl$_2$ (50 mL) at 0° C. was added TFA (50 mL). After 1 h, PhCH$_3$ (50 mL) was added and the mixture concentrated. The resulting oil was neutralized with saturated NaHCO$_3$ (aq.) and extracted with CH$_2$Cl$_2$ (2×). The combined organics were dried and concentrated. Silica gel chromatography (1-7% 2M NH$_3$/MeOH in CH$_2$Cl$_2$) gave 3.38 g (83% yield) of the title compound as a clear oil. MS (ESI): mass calcd. for C$_{18}$H$_{17}$ClF$_3$NO$_2$, 371.1; m/z found, 372.0 [M+H]$^+$. $^1$H NMR (CDCl$_3$): 7.70 (s, 1H), 7.56-7.53 (m, 2H), 7.45 (t, J=7.7 Hz, 1H), 6.77 (dd, J=8.6, 2.3 Hz, 1H), 6.70 (d, J=8.6 Hz, 1H), 6.55 (d, J=2.4 Hz, 1H), 5.30 (q, J=6.3 Hz, 1H), 5.00-4.94 (m, 1H), 3.97-3.93 (m, 2H), 3.89-3.81 (m, 2H), 1.66 (d, J=6.5 Hz, 3H).

Unless otherwise specified the compounds in Examples 102-144 were prepared similar to Example 101 using the appropriately substituted phenols and alcohols.

Example 102

(S)-3-[5-Chloro-2-[1-(3-trifluoromethyl-phenyl)-ethoxy]-phenoxy]-azetidine trifluoroacetate

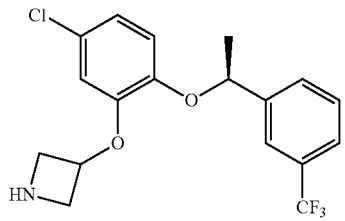 [SMILES: C[C@H](Oc1ccc(Cl)cc1OC1CNC1)c1cccc(C(F)(F)F)c1]

Prepared using (R)-1-(3-trifluoromethyl-phenyl)ethanol. MS (ESI): mass calcd. for C$_{18}$H$_{17}$ClF$_3$NO$_2$, 371.1; m/z found, 372.0 [M+H]$^+$. $^1$H NMR (CDCl$_3$): 7.61 (s, 1H), 7.55-7.45 (m, 3H), 6.86 (dd, J=8.7, 2.2 Hz, 1H), 6.68-6.66 (m, 2H), 5.30 (q, J=6.3 Hz, 1H), 5.11 (s, 1H), 4.44-4.32 (m, 4H), 1.66 (d, J=6.4 Hz, 3H).

Example 103

(5)-3-[5-Chloro-2-[1-(3-trifluoromethyl-phenyl)-ethoxy]-phenoxy]-1-methyl-azetidine

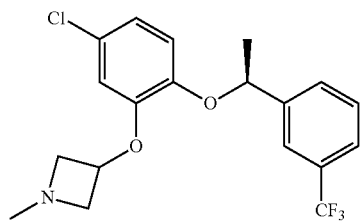 [SMILES: C[C@H](Oc1ccc(Cl)cc1OC1CN(C)C1)c1cccc(C(F)(F)F)c1]

Prepared according to general procedure 5 using the title compound of Example 102. MS (ESI): mass calcd. for C$_{19}$H$_{19}$ClF$_3$NO$_2$, 385.1; m/z found, 386.2 [M+H]$^+$. $^1$H NMR (CDCl$_3$): 7.69 (s, 1H), 7.54 (t, J=8.0 Hz, 2H), 7.45 (t, J=7.7 Hz, 1H), 6.76 (dd, J=8.6, 2.4 Hz, 1H), 6.70 (d, J=8.6 Hz, 1H), 6.59 (d, J=2.3 Hz, 1H), 5.29 (q, J=6.4 Hz, 1H), 4.76-4.65 (m, 1H), 3.85 (s, 2H), 3.14 (s, 2H), 2.42 (s, 3H), 1.66 (d, J=6.5 Hz, 3H).

Example 104

(S)-1-Benzyl-3-[5-chloro-2-[1-(3-trifluoromethyl-phenyl)-ethoxy]-phenoxy]-azetidine

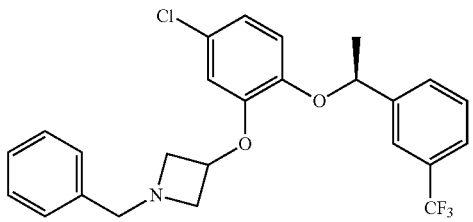 [SMILES: C[C@H](Oc1ccc(Cl)cc1OC1CN(Cc2ccccc2)C1)c1cccc(C(F)(F)F)c1]

Prepared according to general procedure 3 or 4 using the title compound of Example 102. MS (ESI): mass calcd. for C$_{25}$H$_{23}$ClF$_3$NO$_2$, 461.1; m/z found, 462.3 [M+H]$^+$. $^1$H NMR (CDCl$_3$): 7.69 (s, 1H), 7.54 (t, J=7.1 Hz, 2H), 7.45 (t, J=7.7 Hz, 1H), 7.37-7.23 (m, 5H), 6.75 (dd, J=8.6, 2.3 Hz, 1H), 6.69 (d, J=8.6 Hz, 1H), 6.58 (d, J=2.3 Hz, 1H), 5.28 (q, J=6.5 Hz, 1H), 4.80-4.71 (m, 1H), 3.85-3.80 (m, 2H), 3.71 (s, 2H), 3.24-3.14 (m, 2H), 1.66 (d, J=6.5 Hz, 3H).

Example 105

(±)-3-[5-Chloro-2-[1-(3-trifluoromethyl-phenyl)-ethoxy]-phenoxy]-azetidine

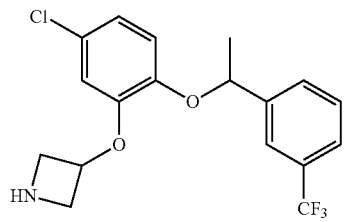

MS (ESI): mass calcd. for C$_{18}$H$_{17}$ClF$_3$NO$_2$, 371.1; m/z found, 372.1 [M+H]$^+$. $^1$H NMR (CDCl$_3$): 7.61 (s, 1H), 7.54 (d, J=7.8 Hz, 2H), 7.51-7.45 (m, 1H), 6.85 (dd, J=8.7, 2.4 Hz, 1H), 6.67 (s, 1H), 6.66 (d, J=7.1 Hz, 1H), 5.31 (q, J=6.4 Hz, 1H), 5.13-5.09 (m, 1H), 4.58-4.30 (m, 4H), 1.67 (d, J=6.5 Hz, 3H).

Example 106

(±)-3-[5-Chloro-2-[1-(3-trifluoromethyl-phenyl)-ethoxy]-phenoxy]-1-isopropyl-azetidine

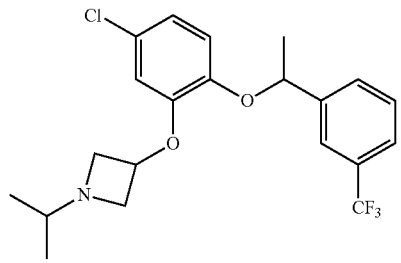 [SMILES: CC(Oc1ccc(Cl)cc1OC1CN(C(C)C)C1)c1cccc(C(F)(F)F)c1]

Synthesized from the title compound of Example 105 according to general procedure 3. MS (ESI): mass calcd. for C$_{21}$H$_{23}$ClF$_3$NO$_2$, 413.1; m/z found, 414.0 [M+H]$^+$. $^1$H NMR (CDCl$_3$): 7.68 (s, 1H), 7.54 (t, J=7.6 Hz, 2H), 7.45 (t, J=7.7 Hz, 1H), 6.76 (dd, J=8.6, 2.4 Hz, 1H), 6.69 (d, J=8.6 Hz, 1H), 6.62 (d, J=2.4 Hz, 1H), 5.28 (q, J=6.5 Hz, 1H), 4.75-4.69 (m, 1H), 3.86-3.82 (m, 2H), 3.11-3.04 (m, 2H), 2.40 (td, J=12.4, 6.2 Hz, 1H), 1.65 (d, J=6.5 Hz, 3H), 0.98 (dd, J=6.2, 0.8 Hz, 6H).

Example 107

(±)-3-[5-Chloro-2-[1-(3-trifluoromethyl-phenyl)-ethoxy]-phenoxy]-1-cyclobutyl-azetidine

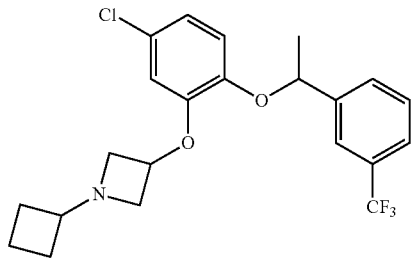 [SMILES: CC(Oc1ccc(Cl)cc1OC1CN(C2CCC2)C1)c1cccc(C(F)(F)F)c1]

Synthesized from the title compound of Example 105 according to general procedure 3. MS (ESI): mass calcd. for C$_{22}$H$_{23}$ClF$_3$NO$_2$, 425.1; m/z found, 426.0 [M+H]$^+$. $^1$H NMR (CDCl$_3$): 7.67 (s, 1H), 7.55 (t, J=8.7 Hz, 2H), 7.45 (t, J=7.7 Hz, 1H), 6.76 (dd, J=8.6, 2.3 Hz, 1H), 6.69 (d, J=8.6 Hz, 1H), 6.61 (d, J=2.3 Hz, 1H), 5.28 (q, J=6.4 Hz, 1H), 4.78-4.72 (m, 1H), 3.75 (dd, J=8.5, 6.1 Hz, 2H), 3.26-3.09 (m, 3H), 2.07-1.94 (m, 2H), 1.92-1.68 (m, 4H), 1.66 (d, J=6.5 Hz, 3H).

Example 108

(±)-1-Benzyl-3-[5-chloro-2-[1-(3-trifluoromethyl-phenyl)-ethoxy]-phenoxy]-azetidine

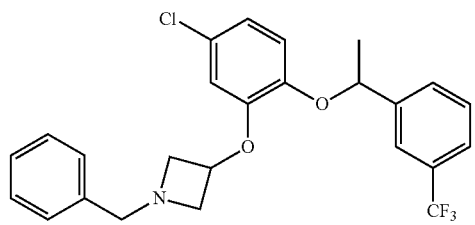 [SMILES: CC(Oc1ccc(Cl)cc1OC1CN(Cc2ccccc2)C1)c1cccc(C(F)(F)F)c1]

Synthesized from the title compound of Example 105 according to general procedure 3. MS (ESI): mass calcd. for C$_{25}$H$_{23}$ClF$_3$NO$_2$, 461.1; m/z found, 462.0 [M+H]$^+$. $^1$H NMR (CDCl$_3$): 7.69 (s, 1H), 7.54 (t, J=7.4 Hz, 2H), 7.44 (t, J=7.7 Hz, 1H), 7.37-7.22 (m, 5H), 6.75 (dd, J=8.6, 2.3 Hz, 1H), 6.69 (d, J=8.6 Hz, 1H), 6.58 (d, J=2.3 Hz, 1H), 5.28 (q, J=6.4 Hz, 1H), 4.79-4.73 (m, 1H), 3.86-3.79 (m, 2H), 3.70 (s, 2H), 3.24-3.13 (m, 2H), 1.66 (d, J=6.5 Hz, 3H).

Example 109

(±)-3-[5-Chloro-2-[1-(3-trifluoromethyl-phenyl)-ethoxy]-phenoxy]-1-methyl-azetidine

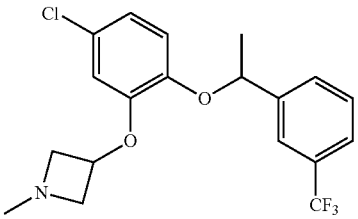 [SMILES: CC(Oc1ccc(Cl)cc1OC1CN(C)C1)c1cccc(C(F)(F)F)c1]

Synthesized from the title compound of Example 105 according to general procedure 5. MS (ESI): mass calcd. for C$_{19}$H$_{19}$ClF$_3$NO$_2$, 385.1; m/z found, 386.0 [M+H]$^+$. $^1$H NMR (CDCl$_3$): 7.69 (s, 1H), 7.54 (t, J=8.5 Hz, 2H), 7.45 (t, J=7.7 Hz, 1H), 6.76 (dd, J=8.6, 2.3 Hz, 1H), 6.70 (d, J=8.6 Hz, 1H), 6.60 (d, J=2.3 Hz, 1H), 5.29 (q, J=6.4 Hz, 1H), 4.74-4.68 (m, 1H), 3.85 (s, 2H), 3.14 (s, 2H), 2.42 (s, 3H), 1.66 (d, J=6.5 Hz, 3H).

Example 110

(±)-3-[5-Bromo-2-[1-(3-trifluoromethoxy-phenyl)-ethoxy]-phenoxy]-azetidine

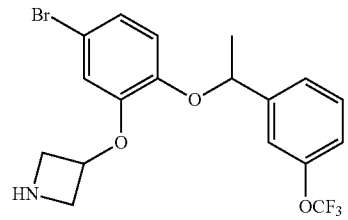 [SMILES: CC(Oc1ccc(Br)cc1OC1CNC1)c1cccc(OC(F)(F)F)c1]

MS (ESI): mass calcd. for C$_{18}$H$_{17}$BrF$_3$NO$_3$, 431.0; m/z found, 431.9 [M+H]$^+$. $^1$H NMR (CDCl$_3$): 7.36 (t, J=8.1 Hz, 1H), 7.27 (d, J=8.1 Hz, 2H), 7.12 (d, J=8.1 Hz, 1H), 6.91 (dd, J=8.6, 2.3 Hz, 1H), 6.70 (d, J=2.3 Hz, 1H), 6.64 (d, J=8.6 Hz, 1H), 5.25 (q, J=6.5 Hz, 1H), 5.01-4.93 (m, 1H), 4.01-3.80 (m, 4H), 1.65 (d, J=6.5 Hz, 3H).

Example 111

(±)-3-[5-Bromo-2-[1-(3-chloro-phenyl)-ethoxy]-phenoxy]-azetidine

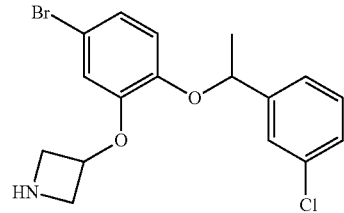

MS (ESI): mass calcd. for C$_{17}$H$_{17}$BrClNO$_2$, 381.0; m/z found, 382.0 [M+H]$^+$. $^1$H NMR (CDCl$_3$): 7.42 (s, 1H), 7.29-7.19 (m, 3H), 6.90 (dd, J=8.6, 2.3 Hz, 1H), 6.69 (d, J=2.3 Hz, 1H), 6.64 (d, J=8.6 Hz, 1H), 5.20 (q, J=6.4 Hz, 1H)), 5.00-4.92 (m, 1H), 3.95-3.80 (m, 4H), 1.64 (d, J=6.5 Hz, 3H).

Example 112

(±)-3-[5-Bromo-2-[1-(3-trifluoromethyl-phenyl)-ethoxy]-phenoxy]-azetidine

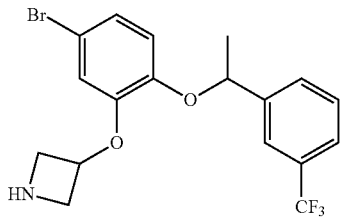

MS (ESI): mass calcd. for $C_{18}H_{17}BrF_3NO_2$, 415.0; m/z found, 416.0 [M+H]$^+$. $^1$H NMR (CDCl$_3$): 7.69 (s, 1H), 7.53 (t, J=7.3 Hz, 2H), 7.44 (t, J=7.7 Hz, 1H), 6.89 (dd, J=8.6, 2.3 Hz, 1H), 6.68 (d, J=2.3 Hz, 1H), 6.65 (d, J=8.6 Hz, 1H), 5.29 (q, J=6.5 Hz, 1H), 4.99-4.93 (m, 1H), 3.95-3.92 (m, 2H), 3.87-3.80 (m, 2H), 1.65 (d, J=6.5 Hz, 3H).

Example 113

(R)-3-[5-Bromo-2-[1-(3-trifluoromethyl-phenyl)-ethoxy]-phenoxy]-azetidine

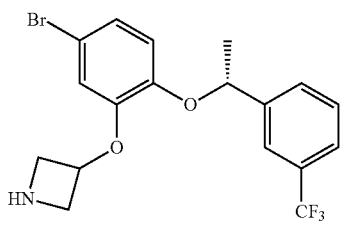

MS (ESI): mass calcd. for $C_{18}H_{17}BrF_3NO_2$, 415.0; m/z found, 418.0 [M+H]$^+$. $^1$H NMR (CDCl$_3$): 7.69 (s, 1H), 7.58-7.50 (m, 2H), 7.45 (t, J=7.7 Hz, 1H), 6.91 (dd, J=8.6, 2.3 Hz, 1H), 6.69 (d, J=2.3 Hz, 1H), 6.66 (d, J=8.6 Hz, 1H), 5.30 (q, J=6.5 Hz, 1H), 4.99-4.93 (m, 1H), 4.01-3.74 (m, 4H), 1.67 (d, J=6.5 Hz, 3H).

Example 114

(±)-3-[5-Chloro-2-[1-(3-chloro-phenyl)-ethoxy]-phenoxy]-azetidine

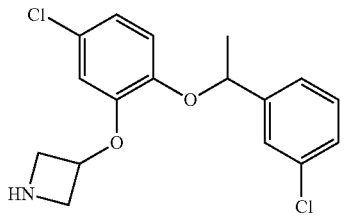 [SMILES: CC(Oc1ccc(Br)cc1OC1CNC1)c1cccc(Cl)c1]

MS (ESI): mass calcd. for $C_{17}H_{17}Cl_2NO_2$, 337.1; m/z found, 338.1 [M+H]$^+$. $^1$H NMR (CDCl$_3$): 7.43 (s, 1H), 7.32-7.17 (m, 3H), 6.76 (dd, J=8.6, 2.4 Hz, 1H), 6.70 (d, J=8.6 Hz, 1H), 6.56 (d, J=2.3 Hz, 1H), 5.20 (q, J=6.5 Hz, 1H), 5.02-4.92 (m, 1H), 3.94 (s, 2H), 3.92-3.78 (m, 2H), 1.65 (d, J=6.5 Hz, 3H).

Example 115

(±)-3-[5-Chloro-2-[1-(3-fluoro-phenyl)-ethoxy]-phenoxy]-azetidine

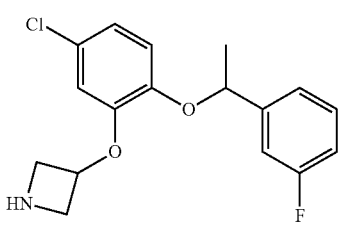

MS (ESI): mass calcd. for $C_{17}H_{17}ClFNO_2$, 321.1; m/z found, 322.1 [M+H]$^+$. $^1$H NMR (CDCl$_3$): 7.35-7.23 (m, 1H), 7.21-7.07 (m, 2H), 7.00-6.91 (m, 1H), 6.71-6.65 (m, 2H), 6.64-6.52 (m, 1H), 5.28-5.18 (m, 1H), 5.05-4.93 (m, 1H), 4.10-3.95 (s, 4H), 1.70-1.60 (s, 3H).

Example 116

(±)-3-[5-Chloro-2-[1-(2-chloro-phenyl)-ethoxy]-phenoxy]-azetidine

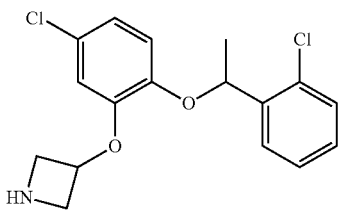 [SMILES: CC(Oc1ccc(Cl)cc1OC1CNC1)c1ccccc1Cl]

MS (ESI): mass calcd. for $C_{17}H_{17}Cl_2NO_2$, 337.1; m/z found, 338.0 [M+H]$^+$. $^1$H NMR (CDCl$_3$): 7.55 (dd, J=7.6, 1.8 Hz, 1H), 7.34 (dd, J=7.8, 1.4 Hz, 1H), 7.28-7.14 (m, 2H), 6.73 (dd, J=8.6, 2.4 Hz, 1H), 6.59 (d, J=8.7 Hz, 1H), 6.56 (d, J=2.4 Hz, 1H), 5.66 (q, J=6.4 Hz, 1H), 5.00-4.94 (m, 1H), 4.02-3.81 (m, 4H), 1.64 (d, J=6.4 Hz, 3H).

Example 117

(±)-3-[5-Chloro-2-[1-(4-fluoro-3-trifluoromethyl-phenyl)-ethoxy]-phenoxy]-azetidine

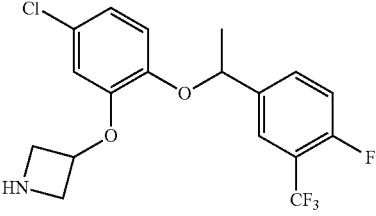 [SMILES: CC(Oc1ccc(Cl)cc1OC1CNC1)c1ccc(F)c(C(F)(F)F)c1]

MS (ESI): mass calcd. for $C_{18}H_{16}ClF_4NO_2$, 389.1; m/z found, 390.0 [M+H]$^+$. $^1$H NMR (CDCl$_3$): 7.68 (dd, J=6.7, 1.9 Hz, 1H), 7.58-7.51 (m, 1H), 7.19-7.14 (m, 1H), 6.78 (dd, J=8.6, 2.4 Hz, 1H), 6.71 (d, J=8.6 Hz, 1H), 6.55 (d, J=2.3 Hz, 1H), 5.27 (q, J=6.4 Hz, 1H), 4.95-4.90 (m, 1H), 3.95-3.84 (m, 4H), 1.65 (d, J=6.5 Hz, 3H).

Example 118

(±)-3-[5-Chloro-2-[1-(3-fluoro-4-trifluoromethyl-phenyl)-ethoxy]-phenoxy]-azetidine

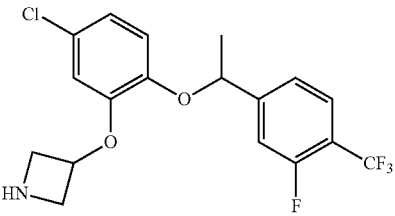 [SMILES: CC(Oc1ccc(Cl)cc1OC1CNC1)c1ccc(C(F)(F)F)c(F)c1]

MS (ESI): mass calcd. for $C_{18}H_{16}ClF_4NO_2$, 389.1; m/z found, 390.0 [M+H]$^+$. $^1$H NMR (CDCl$_3$): 7.57 (t, J=7.6 Hz, 1H), 7.31-7.22 (m, 2H), 6.77 (dd, J=8.6, 2.4 Hz, 1H), 6.68 (d, J=8.6 Hz, 1H), 6.56 (d, J=2.4 Hz, 1H), 5.26 (q, J=6.5 Hz, 1H), 4.99-4.93 (m, 1H), 3.97-3.80 (m, 4H), 1.65 (d, J=6.5 Hz, 3H).

Example 119

(±)-3-[5-Chloro-2-[1-(3-fluoro-5-trifluoromethyl-phenyl)-ethoxy]-phenoxy]-azetidine

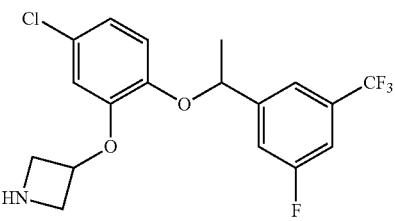 [SMILES: CC(Oc1ccc(Cl)cc1OC1CNC1)c1cc(F)cc(C(F)(F)F)c1]

MS (ESI): mass calcd. for $C_{18}H_{16}ClF_4NO_2$, 389.1; m/z found, 390.0 [M+H]$^+$. $^1$H NMR (CDCl$_3$): 7.33 (d, J=9.3 Hz, 1H), 7.23 (d, J=8.3 Hz, 1H), 6.79 (dd, J=8.6, 2.3 Hz, 1H), 6.73 (d, J=8.6 Hz, 1H), 6.56 (d, J=2.3 Hz, 1H), 5.28 (q, J=6.5 Hz, 1H), 4.99-4.92 (m, 1H), 7.47 (s, 1H), 4.05-3.74 (m, 4H), 1.66 (d, J=6.5 Hz, 3H).

Example 120

(±)-3-[5-Chloro-2-[1-(3-trifluoromethylsulfanyl-phenyl)-ethoxy]-phenoxy]-azetidine

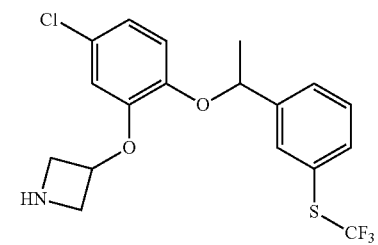 [SMILES: CC(Oc1ccc(Cl)cc1OC1CNC1)c1cccc(SC(F)(F)F)c1]

MS (ESI): mass calcd. for $C_{18}H_{17}ClF_3NO_2S$, 403.1; m/z found, 404.0 [M+H]$^+$. $^1$H NMR (CDCl$_3$): 7.70 (s, 1H), 7.56 (d, J=7.6 Hz, 1H), 7.49 (d, J=7.8 Hz, 1H), 7.39 (t, J=7.7 Hz, 1H), 6.75 (dd, J=8.6, 2.3 Hz, 1H), 6.68 (d, J=8.6 Hz, 1H), 6.55 (d, J=2.2 Hz, 1H), 5.26 (q, J=6.5 Hz, 1H), 4.99-4.93 (m, 1H), 3.94-3.83 (m, 4H), 1.66 (d, J=6.5 Hz, 3H).

Example 121

(±)-3-[5-Chloro-2-[1-(2-fluoro-phenyl)-ethoxy]-phenoxy]-azetidine

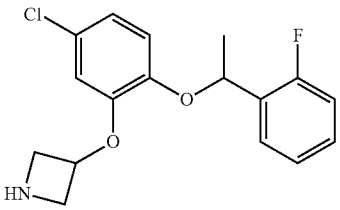

MS (ESI): mass calcd. for $C_{17}H_{17}ClFNO_2$, 321.1; m/z found, 322.0 [M+H]$^+$. $^1$H NMR (CDCl$_3$): 7.50 (dt, J=7.6, 1.7 Hz, 1H), 7.24-7.21 (m, 1H), 7.12 (dt, J=7.6, 1.0 Hz, 1H), 7.06-6.99 (m, 1H), 6.75 (dd, J=8.6, 2.3 Hz, 1H), 6.69 (d, J=8.6 Hz, 1H), 6.56 (d, J=2.3 Hz, 1H), 5.60 (q, J=6.4 Hz, 1H), 5.00-4.94 (m, 1H), 4.00-3.79 (m, 4H), 1.67 (d, J=6.4 Hz, 3H).

Example 122

(±)-3-[5-Chloro-2-[1-(2-trifluoromethyl-phenyl)-ethoxy]-phenoxy]-azetidine

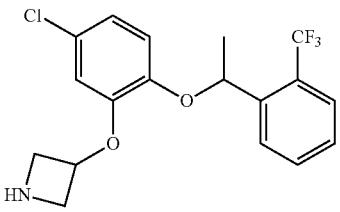

MS (ESI): mass calcd. for $C_{18}H_{17}ClF_3NO_2$, 371.1; m/z found, 372.0 [M+H]$^+$. $^1$H NMR (CDCl$_3$): 7.85 (d, J=7.9 Hz, 1H), 7.61 (d, J=7.9 Hz, 1H), 7.56 (t, J=7.7 Hz, 1H), 7.36 (t, J=7.6 Hz, 1H), 6.72 (dd, J=8.6, 2.3 Hz, 1H), 6.67 (d, J=8.6 Hz, 1H), 6.54 (d, J=2.3 Hz, 1H), 5.68 (q, J=6.2 Hz, 1H), 5.00-4.94 (m, 1H), 4.01-3.79 (m, 4H), 1.66 (d, J=6.3 Hz, 3H).

Example 123

(±)-3-[5-Chloro-2-[1-(4-chloro-phenyl)-ethoxy]-phenoxy]-azetidine

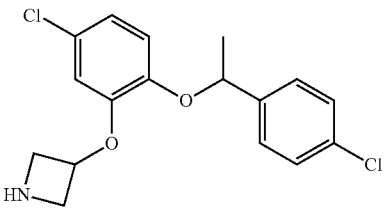 [SMILES: CC(Oc1ccc(Cl)cc1OC1CNC1)c1ccc(Cl)cc1]

MS (ESI): mass calcd. for $C_{17}H_{17}Cl_2NO_2$, 337.1; m/z found, 338.0 [M+H]$^+$. $^1$H NMR (CDCl$_3$): 7.30 (s, 4H), 6.74 (dd, J=8.6, 2.4 Hz, 1H), 6.65 (d, J=8.6 Hz, 1H), 6.55 (d, J=2.4 Hz, 1H), 5.21 (q, J=6.5 Hz, 1H), 4.99-4.93 (m, 1H), 3.96-3.83 (m, 4H), 1.64 (d, J=6.5 Hz, 3H).

Example 124

(±)-3-[5-Chloro-2-[1-(4-fluoro-phenyl)-ethoxy]-phenoxy]-azetidine

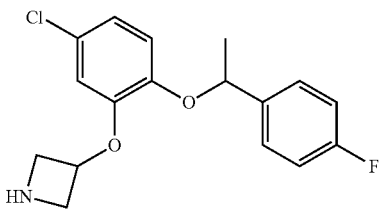

MS (ESI): mass calcd. for $C_{17}H_{17}ClFNO_2$, 321.1; m/z found, 322.0 [M+H]$^+$. $^1$H NMR (CDCl$_3$): 7.39-7.29 (m, 2H), 7.06-6.97 (m, 2H), 6.74 (dd, J=8.6, 2.4 Hz, 1H), 6.66 (d, J=8.6 Hz, 1H), 6.55 (d, J=2.4 Hz, 1H), 5.22 (q, J=6.4 Hz, 1H), 4.99-4.93 (m, 1H), 3.99-3.78 (m, 4H), 1.64 (d, J=6.4 Hz, 3H).

Example 125

(±)-3-[1-[2-(Azetidin-3-yloxy)-4-chloro-phenoxy]-ethyl]-benzonitrile

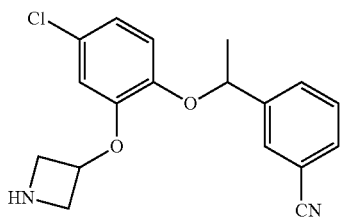 [SMILES: CC(Oc1ccc(Cl)cc1OC1CNC1)c1cccc(C#N)c1]

MS (ESI): mass calcd. for $C_{18}H_{17}ClN_2O_2$, 328.1; m/z found, 329.1 [M+H]$^+$. $^1$H NMR (CDCl$_3$): 7.76 (s, 1H), 7.61 (d, J=7.8 Hz, 1H), 7.57 (td, J=7.7, 1.3 Hz, 1H), 7.45 (t, J=7.7 Hz, 1H), 6.76 (dd, J=8.6, 2.4 Hz, 1H), 6.69 (d, J=8.6 Hz, 1H), 6.56 (d, J=2.4 Hz, 1H), 5.27 (q, J=6.6 Hz, 1H), 5.01-4.95 (m, 1H), 4.02-3.76 (m, 4H), 1.65 (d, J=6.5 Hz, 3H).

Example 126

(±)-3-[5-Chloro-2-[1-(3,4-dichloro-phenyl)-ethoxy]-phenoxy]-azetidine

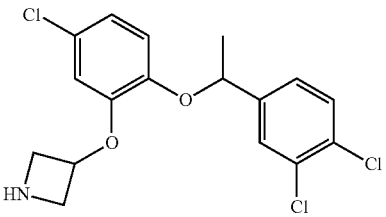 [SMILES: CC(Oc1ccc(Cl)cc1OC1CNC1)c1ccc(Cl)c(Cl)c1]

MS (ESI): mass calcd. for $C_{17}H_{16}Cl_3NO_2$, 371.0; m/z found, 372.0 [M+H]$^+$. $^1$H NMR (CDCl$_3$): 7.52 (d, J=2.0 Hz, 1H), 7.40 (d, J=8.3 Hz, 1H), 7.19 (dd, J=8.3, 2.0 Hz, 1H), 6.77 (dd, J=8.6, 2.4 Hz, 1H), 6.69 (d, J=8.6 Hz, 1H), 6.55 (d, J=2.4 Hz, 1H), 5.18 (q, J=6.5 Hz, 1H), 4.99-4.93 (m, 1H), 4.00-3.76 (m, 4H), 1.63 (d, J=6.5 Hz, 3H).

Example 127

(±)-3-[5-Chloro-2-[1-(3-trifluoromethoxy-phenyl)-ethoxy]-phenoxy]-azetidine

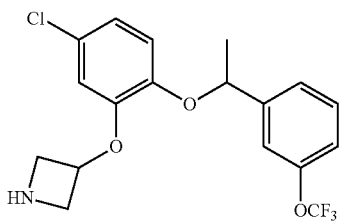

MS (ESI): mass calcd. for $C_{18}H_{17}ClF_3NO_3$, 387.1; m/z found, 388.0 [M+H]$^+$. $^1$H NMR (CDCl$_3$): 7.36 (t, J=8.1 Hz, 1H), 7.30-7.27 (m, 2H), 7.16-7.08 (m, 1H), 6.76 (dd, J=8.6, 2.4 Hz, 1H), 6.69 (d, J=8.6 Hz, 1H), 6.55 (d, J=2.4 Hz, 1H), 5.25 (q, J=6.4 Hz, 1H), 5.00-4.93 (m, 1H), 3.98-3.77 (m, 4H), 1.65 (d, J=6.5 Hz, 3H).

Example 128

(±)-3-[5-Chloro-2-[1-(3,4-difluoro-phenyl)-ethoxy]-phenoxy]-azetidine trifluoroacetate

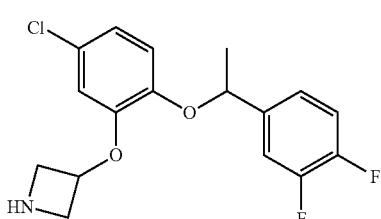

MS (ESI): mass calcd. for $C_{17}H_{16}ClF_2NO_2$, 339.1; m/z found, 340.1 [M+H]$^+$. $^1$H NMR (CDCl$_3$): 7.21-7.09 (m, 2H), 7.08-7.02 (m, 1H), 6.85 (dd, J=8.7, 2.4 Hz, 1H), 6.68 (d, J=2.4 Hz, 1H), 6.65 (d, J=8.8 Hz, 1H), 5.20 (q, J=6.4 Hz, 1H), 5.13-5.05 (m, 1H), 4.44-4.32 (m, 4H), 1.62 (d, J=6.4 Hz, 3H).

Example 129

(±)-3-[5-Chloro-2-[1-(2,5-dichloro-phenyl)-ethoxy]-phenoxy]-azetidine trifluoroacetate

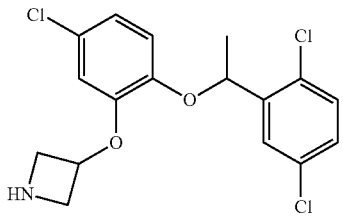

MS (ESI): mass calcd. for $C_{17}H_{16}Cl_3NO_2$, 371.0; m/z found, 372.0 [M+H]$^+$. $^1$H NMR (CDCl$_3$): 7.43 (d, J=2.5 Hz, 1H), 7.30 (d, J=8.5 Hz, 1H), 7.19 (dd, J=8.5, 2.5 Hz, 1H), 6.86 (dd, J=8.7, 2.4 Hz, 1H), 6.69 (d, J=2.4 Hz, 1H), 6.57 (d, J=8.8 Hz, 1H), 5.59 (q, J=6.3 Hz 1H), 5.14 (s, 1H), 4.49-4.37 (m, 4H), 1.63 (d, J=6.4 Hz, 3H).

Example 130

(±)-3-[5-Chloro-2-[1-(2,5-difluoro-phenyl)-ethoxy]-phenoxy]-azetidine trifluoroacetate

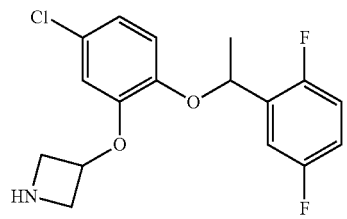 [SMILES: CC(Oc1ccc(Cl)cc1OC1CNC1)c1cc(F)ccc1F]

MS (ESI): mass calcd. for C$_{17}$H$_{16}$ClF$_2$NO$_2$, 339.1; m/z found, 340.0 [M+H]$^+$. $^1$H NMR (CDCl$_3$): 7.43 (d, J=2.5 Hz, 1H), 7.30 (d, J=8.5 Hz, 1H), 7.19 (dd, J=8.5, 2.5 Hz, 1H), 6.86 (dd, J=8.7, 2.4 Hz, 1H), 6.69 (d, J=2.4 Hz, 1H), 6.57 (d, J=8.8 Hz, 1H), 5.59 (q, J=6.3 Hz, 1H), 5.14 (s, 1H), 4.47-4.34 (m, 4H), 1.63 (d, J=6.4 Hz, 3H).

Example 131

2-[1-[2-(Azetidin-3-yloxy)-4-chloro-phenoxy]-ethyl]-benzothiazole

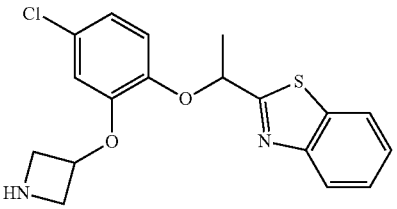 [SMILES: CC(Oc1ccc(Cl)cc1OC1CNC1)c1nc2ccccc2s1]

MS (ESI): mass calcd. for C$_{18}$H$_{17}$ClN$_2$O$_2$S, 360.1; m/z found, 361.0 [M+H]$^+$. $^1$H NMR (CDCl$_3$): 8.01-7.99 (m, 1H), 7.92-7.86 (m, 1H), 7.48 (ddd, J=8.3, 7.3, 1.3 Hz, 1H), 7.39 (ddd, J=8.3, 7.3, 1.2 Hz, 1H), 6.93 (d, J=8.6 Hz, 1H), 6.80 (dd, J=8.6, 2.4 Hz, 1H), 6.59 (d, J=2.4 Hz, 1H), 5.66 (q, J=6.5 Hz, 1H), 5.01-4.95 (m, 1H), 3.95-3.88 (m, 2H), 3.86-3.80 (m, 2H), 1.86 (d, J=6.5 Hz, 3H).

Example 132

5-[1-[2-(Azetidin-3-yloxy)-4-chloro-phenoxy]-ethyl]-thiazole

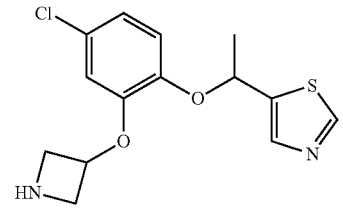 [SMILES: CC(Oc1ccc(Cl)cc1OC1CNC1)c1cncs1]

MS (ESI): mass calcd. for C$_{14}$H$_{15}$ClN$_2$O$_2$S, 310.1; m/z found, 311.0 [M+H]$^+$. $^1$H NMR (CDCl$_3$): 8.77 (s, 1H), 7.73 (s, 1H), 6.83-6.77 (m, 2H), 6.57-6.56 (m, 1H), 5.56 (q, J=6.4 Hz, 1H), 5.02-4.89 (m, 1H), 3.98-3.90 (m, 2H), 3.87-3.75 (m, 2H), 1.77 (d, J=6.4 Hz, 3H).

Example 133

2-[1-[2-(Azetidin-3-yloxy)-4-chloro-phenoxy]-ethyl]-thiazole

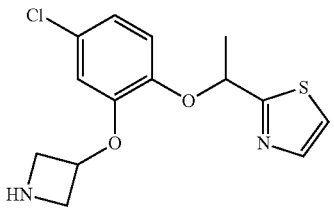

MS (ESI): mass calcd. for C$_{14}$H$_{15}$ClN$_2$O$_2$S, 310.1; m/z found, 311.1 [M+H]$^+$. $^1$H NMR (CDCl$_3$): 7.74 (d, J=3.2 Hz, 1H), 7.33 (d, J=3.2 Hz, 1H), 6.88 (d, J=8.6 Hz, 1H), 6.81 (dd, J=8.6, 2.3 Hz, 1H), 6.59 (d, J=2.3 Hz, 1H), 5.59 (q, J=6.5 Hz, 1H), 5.02-4.92 (m, 1H), 4.04-3.72 (m, 4H), 1.79 (dd, J=6.4, 2.2 Hz, 3H).

Example 134

5-[1-[2-(Azetidin-3-yloxy)-4-chloro-phenoxy]-ethyl]-2,4-dimethyl-thiazole

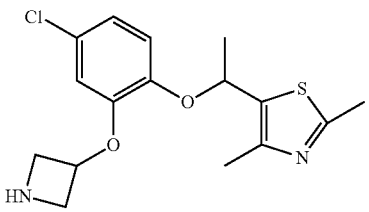 [SMILES: Cc1nc(C)c(C(C)Oc2ccc(Cl)cc2OC2CNC2)s1]

MS (ESI): mass calcd. for C$_{16}$H$_{19}$ClN$_2$O$_2$S, 338.1; m/z found, 339.1 [M+H]$^+$. $^1$H NMR (CDCl$_3$): 6.78 (dd, J=8.5, 2.4 Hz, 1H), 6.70 (d, J=8.6 Hz, 1H), 6.55 (d, J=2.4 Hz, 1H), 5.48 (q, J=6.4 Hz, 1H), 5.00-4.90 (m, 1H), 4.02-3.76 (m, 4H), 2.63 (s, 3H), 2.19 (s, 3H), 1.69 (d, J=6.4 Hz, 3H).

Example 135

(R)-4-[5-Chloro-2-[1-(3-trifluoromethyl-phenyl)-ethoxy]-phenoxy]-piperidine

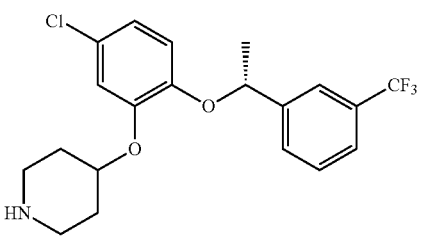 [SMILES: C[C@@H](Oc1ccc(Cl)cc1OC1CCNCC1)c1cccc(C(F)(F)F)c1]

MS (ESI): mass calcd. for C$_{20}$H$_{21}$ClF$_3$NO$_2$, 399.1; m/z found, 400.0 [M+H]$^+$. $^1$H NMR (CDCl$_3$): 7.68 (s, 1H), 7.57-7.52 (m, 2H), 7.45 (t, J=7.7 Hz, 1H), 6.90 (d, J=2.4 Hz, 1H), 6.77 (d, J=8.6, 2.4 Hz, 1H), 6.69 (d, J=8.6 Hz, 1H), 5.30 (q, J=6.4 Hz, 1H), 4.36-4.32 (m, 1H), 3.17 (br s, 2H), 2.74 (br s, 2H), 2.02 (br s, 2H), 1.72 (br s, 2H), 1.64 (d, J=6.4 Hz, 3H).

Example 136

(±)-4-[5-Chloro-2-[1-(3-chloro-phenyl)-ethoxy]-phenoxy]-piperidine

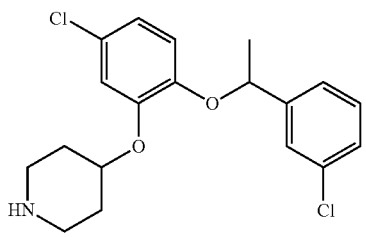 [SMILES: CC(Oc1ccc(Cl)cc1OC1CCNCC1)c1cccc(Cl)c1]

MS (ESI): mass calcd. for $C_{19}H_{21}Cl_2NO_2$, 349.1; m/z found, 350.1 [M+H]$^+$. $^1$H NMR (CDCl$_3$): 7.40 (s, 1H), 7.29-7.19 (m, 3H), 6.89 (d, J=2.4 Hz, 1H), 6.76 (dd, J=8.6, 2.4 Hz, 1H), 6.68 (d, J=8.6 Hz, 1H), 5.21 (q, J=6.4 Hz, 1H), 4.38-4.27 (m, 1H), 3.17 (td, J=7.8, 4.6 Hz, 2H), 2.72 (ddd, J=12.5, 9.3, 3.2 Hz, 2H), 2.09-1.93 (m, 2H), 1.79-1.66 (m, 2H), 1.62 (d, J=6.5 Hz, 3H).

Example 137

(±)-4-[5-Chloro-2-[1-(3-trifluoromethoxy-phenyl)-ethoxy]-phenoxy]-piperidine

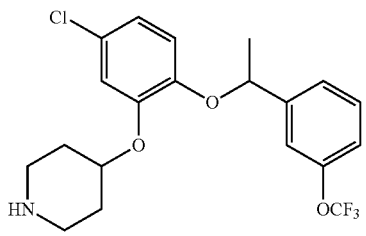 [SMILES: CC(Oc1ccc(Cl)cc1OC1CCNCC1)c1cccc(OC(F)(F)F)c1]

MS (ESI): mass calcd. for $C_{20}H_{21}ClF_3NO_3$, 415.1; m/z found, 416.0 [M+H]$^+$. $^1$H NMR (CDCl$_3$): 7.36 (t, J=7.9 Hz, 1H), 7.28 (d, J=8.8 Hz, 2H), 7.12 (d, J=8.0 Hz, 1H), 6.90 (d, J=2.4 Hz, 1H), 6.76 (dd, J=8.6, 2.4 Hz, 1H), 6.68 (d, J=8.6 Hz, 1H), 5.26 (q, J=6.4 Hz, 1H), 4.43-4.24 (m, 1H), 3.22-3.09 (m, 2H), 2.73 (ddd, J=12.5, 9.2, 3.1 Hz, 2H), 2.02 (d, J=9.1 Hz, 2H), 1.72 (dt, J=12.7, 9.0, 2H), 1.63 (d, J=6.4 Hz, 3H).

Example 138

(±)-4-[5-Chloro-2-[1-(2-fluoro-phenyl)-ethoxy]-phenoxy]-piperidine

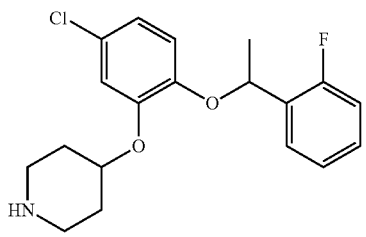 [SMILES: CC(Oc1ccc(Cl)cc1OC1CCNCC1)c1ccccc1F]

MS (ESI): mass calcd. for $C_{19}H_{21}ClFNO_2$, 349.1; m/z found, 350.0 [M+H]$^+$. $^1$H NMR (CDCl$_3$): 7.50 (dt, J=7.6, 1.7 Hz, 1H), 7.26-7.20 (m, 1H), 7.12 (dt, J=7.5, 1.0 Hz, 1H), 7.02 (ddd, J=10.2, 8.2, 1.1 Hz, 1H), 6.89 (d, J=2.4 Hz, 1H), 6.76 (dd, J=8.7, 2.4 Hz, 1H), 6.69 (d, J=8.7 Hz, 1H), 5.59 (q, J=6.4 Hz, 1H), 4.38-4.27 (m, 1H), 3.16 (td, J=9.8, 4.6 Hz, 2H), 2.71 (ddd, J=12.4, 9.3, 3.1 Hz, 2H), 2.01 (ddd, J=13.2, 5.0, 3.0 Hz, 2H), 1.72 (ddt, J=11.7, 8.3, 3.1 Hz, 2H), 1.64 (d, J=6.4 Hz, 3H).

Example 139

(R,S)-3-[5-Chloro-2-[1-((R)-3-trifluoromethyl-phenyl)-ethoxy]-phenoxy]-piperidine

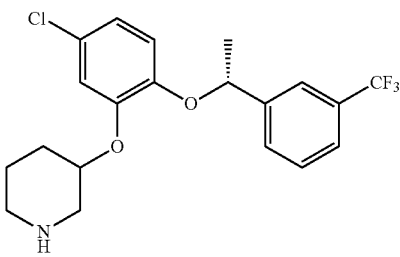 [SMILES: C[C@@H](Oc1ccc(Cl)cc1OC1CCCNC1)c1cccc(C(F)(F)F)c1]

MS (ESI): mass calcd. for $C_{20}H_{21}ClF_3NO_2$, 399.1; m/z found, 400.0 [M+H]$^+$. $^1$H NMR (CDCl$_3$): 7.68 (s, 1H), 7.57-7.53 (m, 2H), 7.48-7.44 (m, 1H), 6.92 (dd, J=2.4, 1.1 Hz, 1H), 6.79-6.76 (m, 1H), 6.69 (dd, J=8.6, 6.1 Hz, 1H), 5.33-5.26 (m, 1H), 4.24-4.17 (m, 1H), 3.14-3.11 (m, 1H), 2.89-2.73 (m, 3H), 2.05-1.98 (m, 1H), 1.87-1.73 (m, 2H), 1.64 (d, J=6.5 Hz, 3H), 1.54-1.45 (m, 1H).

Example 140

(±)-3-[5-Chloro-2-[1-(3-trifluoromethyl-phenyl)-propoxy]-phenoxy]-azetidine

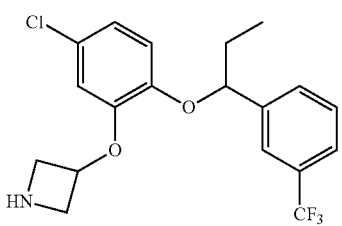

MS (ESI): MS (ESI): mass calcd. for $C_{19}H_{19}ClF_3NO_2$, 385.1; m/z found, 386.0 [M+H]$^+$. $^1$H NMR (CDCl$_3$): 7.66 (s, 1H), 7.52 (t, J=7.5 Hz, 2H), 7.44 (t, J=7.7 Hz, 1H), 6.73 (dd, J=8.6, 2.4 Hz, 1H), 6.65 (d, J=8.6 Hz, 1H), 6.54 (d, J=2.4 Hz, 1H), 5.05-5.00 (m, 1H), 4.99-4.92 (m, 1H), 4.01-3.72 (m, 4H), 2.31-1.97 (m, 1H), 1.97-1.83 (m, 1H), 1.02 (t, J=7.4 Hz, 3H).

Example 141

(±)-4-[5-Chloro-2-[1-(3-trifluoromethyl-phenyl)-propoxy]-phenoxy]-piperidine

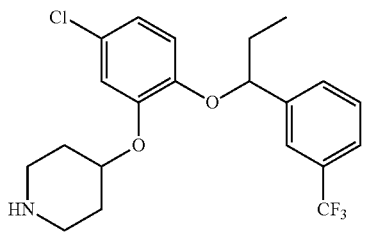 [SMILES: CCC(Oc1ccc(Cl)cc1OC1CCNCC1)c1cccc(C(F)(F)F)c1]

MS (ESI): mass calcd. for C$_{21}$H$_{23}$ClF$_3$NO$_2$, 413.1; m/z found, 414.0 [M+H]$^+$. $^1$H NMR (CDCl$_3$): 7.61 (s, 1H), 7.51 (dd, J=7.4, 4.4 Hz, 2H), 7.47-7.40 (m, 1H), 6.88 (d, J=2.5 Hz, 1H), 6.72 (dd, J=8.6, 2.5 Hz, 1H), 6.61 (d, J=8.7 Hz, 1H), 5.05 (t, J=6.3 Hz, 1H), 4.37-4.28 (m, 1H), 3.23-3.10 (m, 2H), 2.71 (ddd, J=12.6, 9.4, 3.2 Hz, 2H), 2.13-1.97 (m, 3H), 1.96-1.84 (m, 1H), 1.76-1.65 (m, 2H), 0.98 (t, J=7.4 Hz, 3H).

Example 142

3-[5-Bromo-2-(2-fluoro-1-phenyl-ethoxy)-phenoxy]-azetidine

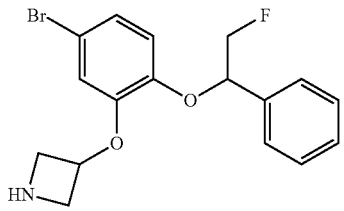 [SMILES: FCC(Oc1ccc(Br)cc1OC1CNC1)c1ccccc1]

MS (ESI): mass calcd. for C$_{17}$H$_{17}$BrFNO$_2$, 365.0; m/z found, 366.0 [M+H]$^+$. $^1$H NMR (CDCl$_3$): 7.41-7.30 (m, 5H), 6.88 (dd, J=8.6, 2.3 Hz, 1H), 6.69 (dd, J=13.3, 5.4 Hz, 2H), 5.35 (ddd, J=14.3, 7.7, 3.3 Hz, 1H), 5.00-4.93 (m, 1H), 4.75 (ddd, J=48.0, 10.1, 7.7 Hz, 1H), 4.59 (ddd, J=46.7, 10.1, 3.4 Hz, 1H), 3.93-3.79 (m, 4H).

Example 143

3-[5-Chloro-2-(2-fluoro-1-phenyl-ethoxy)-phenoxy]-azetidine

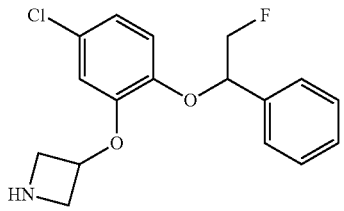 [SMILES: FCC(Oc1ccc(Cl)cc1OC1CNC1)c1ccccc1]

MS (ESI): mass calcd. for C$_{17}$H$_{17}$ClFNO$_2$, 321.1; m/z found, 322.1 [M+H]$^+$. $^1$H NMR (CDCl$_3$): 7.42-7.31 (m, 5H), 6.75-6.71 (m, 2H), 6.56 (s, 1H), 5.35 (ddd, J=14.3, 7.7, 3.3 Hz, 1H), 5.00 (s, 1H), 4.75 (ddd, J=48.0, 10.0, 7.7, Hz, 1H), 4.59 (ddd, J=46.7, 10.1, 3.3 Hz, 1H), 4.26-3.53 (m, 4H).

Example 144

(±)-4-[5-Chloro-2-(2-fluoro-1-phenyl-ethoxy)-phenoxy]-piperidine

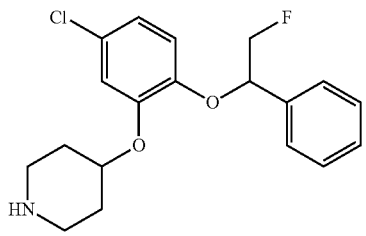 [SMILES: FCC(Oc1ccc(Cl)cc1OC1CCNCC1)c1ccccc1]

MS (ESI): mass calcd. for C$_{19}$H$_{21}$ClFNO$_2$, 349.1; m/z found, 350.1 [M+H]$^+$. $^1$H NMR (CDCl$_3$): δ 7.45-7.28 (m, 5H), 6.90 (d, J=2.2 Hz, 1H), 6.77-6.67 (m, 2H), 5.36 (ddd, J=14.5, 7.6, 3.3 Hz, 1H), 4.80-4.50 (m, 2H), 4.35 (dt, J=12.3, 4.0 Hz, 1H), 3.14 (dd, J=12.0, 4.9 Hz, 2H), 2.70 (dd, J=11.9, 9.7 Hz, 2H), 2.00 (dd, J=7.9, 3.9 Hz, 2H), 1.77-1.62 (m, 2H).

Example 145

(±)-3-[5-Chloro-2-(1-phenyl-ethoxy)-phenoxy]-azetidine

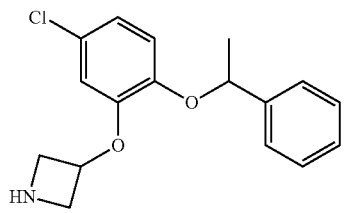 [SMILES: CC(Oc1ccc(Cl)cc1OC1CNC1)c1ccccc1]

Step A: Preparation of 1-[3-(5-Chloro-2-hydroxy-phenoxy)-azetidin-1-yl]-2,2,2-trifluoro-ethanone. To 3-(5-Chloro-2-hydroxy-phenoxy)-azetidine-1-carboxylic acid tert-butyl ester (0.80 g, 2.7 mmol) in EtOAc (2 mL) was added 4M HCl in dioxane (5 mL). After 18 h, EtOAc was added and the resulting white solid filtered to give 2-(azetidin-3-yloxy)-4-chloro-phenol hydrochloride as a white solid. To a CH$_2$Cl$_2$ (25 mL) solution of this compound was added Et$_3$N (0.30 g, 0.42 mL, 3.0 mmol) and TFAA (0.58 g, 0.38 mL, 2.8 mmol). After 18 h, H$_2$O was added and the reaction extracted with CH$_2$Cl$_2$ (2×). The combined organics were dried and concentrated to give 0.54 g (74% yield 2 steps) of the title compound as a brown oil that was used in the next step without further purification.

Step B: Preparation of (±)-1-[3-[5-Chloro-2-(1-phenyl-ethoxy)-phenoxy]-azetidin-1-yl]-2,2,2-trifluoro-ethanone. To the title compound of Step A (0.17 g, 0.56 mmol) in DMF (3 mL) was added Cs$_2$CO$_3$ (0.25 g, 0.80 mmol), KI (0.09 g, 0.55 mmol) and (1-bromoethyl)-benzene (0.10 g, 0.08 mL, 0.56 mmol). After 15 h, H$_2$O was added and the mixture extracted with EtOAc (2×). The combined organics were washed with brine and dried. Silica gel chromatography (5-25% EtOAc in hexanes) gave 0.14 g (64%) of the title compound. $^1$H NMR (CDCl$_3$): 7.37-7.27 (m, 5H), 6.82 (dd, J=8.7, 2.4 Hz, 1H), 6.72 (d, J=2.4 Hz, 1H), 6.60 (d, J=2.4 Hz, 1H), 5.2 (q, J=6.5 Hz, 1H), 5.0-4.9 (m, 1H), 4.75-4.69 (m, 1H), 4.52-4.42 (m, 2H), 4.32-4.21 (m, 1H), 1.67 (d, J=6.4 Hz, 3H).

Step C: Preparation of (±)-3-[5-Chloro-2-(1-phenyl-ethoxy)-phenoxy]-azetidine. To the title compound of Step B in MeOH (4 mL) was added $K_2CO_3$ (0.10 g, 0.72 mmol). After 15 h, $H_2O$ was added and the mixture extracted with EtOAc (2×). The combined organics were dried and concentrated. Silica gel chromatography (1-7 2M $NH_3$/MeOH in $CH_2Cl_2$) gave 0.75 g (68% yield) of the title compound. MS (ESI): mass calcd. for $C_{17}H_{18}ClNO_2$, 303.10; m/z found, 304.1 [M+H]$^+$. $^1$H NMR (CDCl$_3$): 7.38-7.31 (m, 4H), 7.28-7.24 (m, 1H), 6.72 (dd, J=8.6, 2.4 Hz, 1H), 6.67 (d, J=8.6 Hz, 1H), 6.55 (d, J=2.4 Hz, 1H), 5.23 (q, J=6.4 Hz, 1H), 4.99-4.93 (m, 1H), 3.95-3.81 (m, 4H), 1.66 (d, J=6.5 Hz, 3H).

Example 146

(±)-3-[5-Chloro-2-[1-(5-trifluoromethyl-furan-2-yl)-ethoxy]-phenoxy]-azetidine

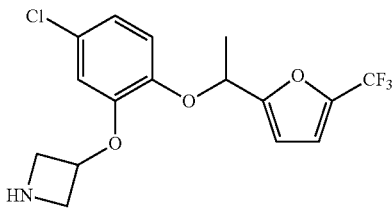 [SMILES: CC(Oc1ccc(Cl)cc1OC1CNC1)c1ccc(C(F)(F)F)o1]

Step A: Preparation of 1-(5-Trifluoromethyl-furan-2-yl)-ethanol. To 5-trifluoromethyl-furan-2-carbaldehyde (0.76 g, 4.6 mmol) in THF (20 mL) at 0° C. was added MeMgBr (3M in $Et_2O$, 3 mL, 6 mmol) dropwise over 1 h. After an additional 1 h, ½ saturated $NH_4Cl$ (aq.) was added and the mixture extracted with EtOAc (2×). The combined organics were washed with brine and dried to give 0.81 g (97%) of the title compound. $^1$H NMR (CDCl$_3$): 6.74-6.73 (m, 1H), 6.32-6.31 (m, 1H), 4.91 (q, J=6.5 Hz, 1H), 1.57 (d, J=6.6 Hz, 3H).

Step B: Preparation of 1-(3-[5-Chloro-2-[1-(5-trifluoromethyl-furan-2-yl)-ethoxy]-phenoxy]-azetidin-1-yl)-2,2,2-trifluoro-ethanone: Prepared from the title compound of Step A and the title compound of Example 145 Step A using general procedure 7. $^1$H NMR (CDCl$_3$): 6.94 (dd, J=8.6, 2.3 Hz, 1H), 6.88 (dd, J=8.7, 1.4 Hz, 1H), 6.73 (m, 1H), 6.62 (d, J=2.3 Hz, 1H), 6.33 (d, J=3.3 Hz, 1H), 5.27-5.22 (m, 1H), 5.01-4.94 (m, 1H), 4.76-4.69 (m, 1H), 4.52-4.44 (m, 2H), 4.27-4.21 (m, 1H), 1.74 (d, J=6.6 Hz, 3H).

Step C: Preparation of (±)-3-[5-Chloro-2-[1-(5-trifluoromethyl-furan-2-yl)-ethoxy]-phenoxy]-azetidine: Prepared from the title compound of Step B according to Example 145 Step C. MS (ESI): mass calcd. for $C_{16}H_{15}ClF_3NO_3$, 361.1; m/z found, 362.0 [M+H]$^+$. $^1$H NMR (CDCl$_3$): 6.84-6.79 (m, 2H), 6.72-6.71 (m, 1H), 6.57 (d, J=1.9 Hz, 1H), 6.32 (d, J=3.4 Hz, 1H), 5.24 (q, J=6.6 Hz, 1H), 4.98-4.92 (m, 1H), 3.93-3.82 (m, 4H), 1.72 (d, J=6.6 Hz, 3H).

Example 147

3-[5-Chloro-2-(1-phenyl-propoxy)-phenoxy]-azetidine

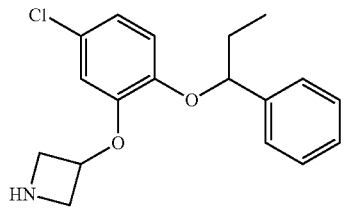

Synthesized according to Example 146 using 1-phenyl-propan-1-ol. MS (ESI): mass calcd. for $C_{18}H_{20}ClNO_2$, 317.1; m/z found, 318.1 [M+H]$^+$. $^1$H NMR (CDCl$_3$): 7.33-7.23 (m, 5H), 6.70 (dd, J=8.6, 2.4 Hz, 1H), 6.62 (d, J=8.6 Hz, 1H), 6.54 (d, J=2.3 Hz, 1H), 4.97-4.92 (m, 2H), 4.03-3.78 (m, 4H), 2.11-2.02 (m, 1H), 1.95-1.85 (m, 1H), 1.01 (t, J=7.4 Hz, 3H).

Example 148

2-[2-(Azetidin-3-yloxy)-4-chloro-phenoxy]-2-phenyl-ethanol

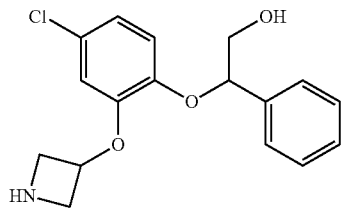 [SMILES: OCC(Oc1ccc(Cl)cc1OC1CNC1)c1ccccc1]

Step A: Preparation of 3-[5-Chloro-2-(methoxycarbonyl-phenyl-methoxy)-phenoxy]-azetidine-1-carboxylic acid tert-butyl ester. To 3-(5-Chloro-2-hydroxy-phenoxy)-azetidine-1-carboxylic acid tert-butyl ester (1.1 g, 3.7 mmol) in DMF (18 mL) was added $Cs_2CO_3$ (1.5 g, 4.4 mmol) and bromophenylacetic acid methyl ester (0.92 g, 0.63 mL, 4.0 mmol). After 15 h, $H_2O$ was added and the mixture extracted with EtOAc (2×). The combined organics were washed with brine and dried. Silica gel chromatography (5-25% EtOAc in hexanes) gave 1.6 g (96%) of the title compound. $^1$H NMR (CDCl$_3$): 7.55-7.33 (m, 2H), 7.43-7.36 (m, 3H), 6.85 (d, J=1.2, 2H), 6.51 (t, J=1.2 Hz, 1H), 5.58 (s, 1H), 4.91-4.85 (m, 1H), 4.31-4.26 (m, 2H), 3.98-3.93 (m, 2H), 3.89-3.74 (m, 3H), 1.46 (s, 9H).

Step B: Preparation of 3-[5-Chloro-2-(methoxycarbonyl-phenyl-methoxy)-phenoxy]-azetidine-1-carboxylic acid tert-butyl ester. To the title compound of Step A (0.22 g, 0.50 mmol) in THF at 0° C. was added LiBH$_4$ (2M in THF, 0.4 mL, 0.8 mmol). After 2 h, 1N KHSO$_4$ (aq.) was added and the mixture extracted with EtOAc (2×). The combined organic layers were washed with brine and dried. Silica gel chromatography (5-25% EtOAc in hexanes) gave 0.17 g (82%) of the title compound. $^1$H NMR (CDCl$_3$): 7.36-7.30 (m, 5H), 6.75 (dd, J=8.6, 2.3 Hz, 1H), 6.68 (d, J=8.7 Hz, 1H), 6.51 (d, J=2.3 Hz, 1H), 5.09 (dd, J=8.7, 3.4 Hz, 1H), 4.90-4.85 (m, 1H), 4.35-4.30 (m, 2H), 4.15-3.94 (m, 4H), 3.80-3.77 (m, 1H), 1.47 (s, 9H).

Step C: Preparation of 2-[2-(Azetidin-3-yloxy)-4-chloro-phenoxy]-2-phenyl-ethanol. Prepared from the title compound of Step B according to general procedure 1. MS (ESI): mass calcd. for $C_{17}H_{18}ClNO_3$, 319.1; m/z found, 320.1 [M+H]$^+$. $^1$H NMR (DMSO-D$_6$): 7.40 (m, 5H), 6.94-6.69 (m, 3H), 5.32-5.28 (m, 1H), 5.11-4.79 (m, 2H), 3.80-3.75 (m, 3H), 3.61 (dd, J=11.4, 4.1 Hz, 1H), 3.54-3.20 (m, 2H).

Example 149

[2-(Azetidin-3-yloxy)-4-chloro-phenoxy]-phenyl-acetic acid hydrochloride

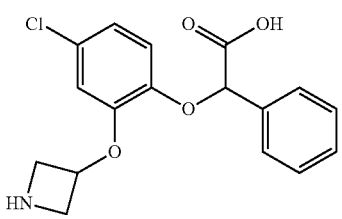 [SMILES: O=C(O)C(Oc1ccc(Cl)cc1OC1CNC1)c1ccccc1]

Step A: Preparation of 3-[2-(Carboxy-phenyl-methoxy)-5-chloro-phenoxy]-azetidine-1-carboxylic acid tert-butyl ester. To the title compound of Example 148 Step A (0.16 g, 0.36 mmol) in MeOH (3 mL) was added 1N NaOH (3 mL). After 18 h, the solution was acidified with 1N KHSO$_4$ and extracted with EtOAc (2×). The combined organics were washed with brine and dried to give 0.16 g (>98%) of the title compound. $^1$H NMR (CDCl$_3$): 8.56-8.19 (broad s, 1H), 7.55-7.51 (m, 2H), 7.41-7.36 (m, 3H), 6.85-6.84 (m, 2H), 6.54 (s, 1H), 5.55 (s, 1H), 4.88-4.83 (m, 1H), 4.29-4.24 (m, 2H), 4.06-3.97 (m, 2H), 1.44 (s, 9H).

Step B: Preparation of [2-(Azetidin-3-yloxy)-4-chloro-phenoxy]-phenyl-acetic acid hydrochloride. Prepared from the title compound of Step A according to general procedure 1. MS (ESI): mass calcd. for $C_{17}H_{16}ClNO_4$, 333.1; m/z found, 334.1 [M+H]$^+$. $^1$H NMR (DMSO-D$_6$): 13.3 (s, 1H), 9.27 (s, 2H), 7.58-7.56 (m, 2H), 7.46-7.37 (m, 3H), 7.05-6.99 (m, 2H), 6.96 (d, J=2.2 Hz, 1H), 5.86 (s, 1H), 5.11-5.06 (m, 1H), 4.45-4.37 (m, 2H), 4.05-3.98 (m, 2H).

Example 150

(±)-3-[5-Chloro-2-(6-fluoro-indan-1-yloxy)-phenoxy]-azetidine

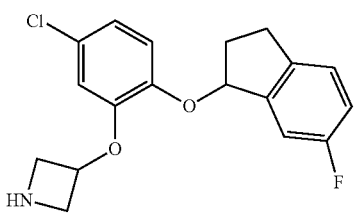

Step A: Preparation of (±)-6-fluoro-indan-1-ol. To a solution of 6-fluoro-indan-1-one (0.50 g, 3.3 mmol) in DCE (10 mL) and MeOH (10 mL) was added NaBH$_4$ (0.25 g, 6.6 mmol). After 30 min the reaction was quenched with H$_2$O (10 mL) and extracted with CH$_2$Cl$_2$ (3×20 mL). The organic layers were combined and dried to give the title compound (0.49 g, 97%). MS (ESI): mass calcd. for $C_9H_7FO$, 150.1; m/z found, 151.4 [M+H]$^+$. $^1$H NMR (CDCl$_3$): 7.23-7.13 (m, 1H), 7.09 (dd, J=8.6, 2.5 Hz, 1H), 6.99-6.90 (m, 1H), 5.21 (t, J=6.3 Hz, 1H), 3.13-2.91 (m, 1H), 2.85-2.68 (m, 1H), 2.63-2.44 (m, 1H), 2.09-1.74 (m, 2H).

Step B: Preparation of 1-[3-[5-Chloro-2-(6-fluoro-indan-1-yloxy)-phenoxy]-azetidin-1-yl]-2,2,2-trifluoro-ethanone. Prepared from the title compound of Step A and the title compound of Example 145 Step A according to the general procedure 7.

Step C: Preparation of 3-[5-Chloro-2-(6-fluoro-indan-1-yloxy)-phenoxy]-azetidine. Prepared from the title compound of Step B using general procedure 2. MS (ESI): mass calcd. for $C_{18}H_{17}ClFNO_2$, 333.1; m/z found, 334.1 [M+H]$^+$. $^1$H NMR (CDCl$_3$): 7.23 (dd, J=8.2, 5.0 Hz, 1H), 7.10-6.87 (m, 4H), 6.65 (s, 1H), 5.68-5.53 (m, 1H), 4.94 (s, 1H), 4.15-4.06 (m, 4H), 3.19-2.99 (m, 1H), 2.97-2.66 (m, 1H), 2.67-2.43 (m, 1H), 2.40-2.17 (m, 1H).

Unless otherwise specified the compounds in Examples 151-161 were prepared according to Example 150 using the appropriately substituted phenol and alcohol.

Example 151

(±)-3-[5-Bromo-2-(indan-1-yloxy)-phenoxy]-azetidine

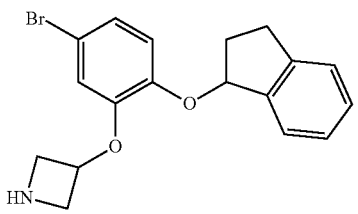 [SMILES: Brc1ccc(OC2CCc3ccccc32)c(OC2CNC2)c1]

MS (ESI): mass calcd. for $C_{18}H_{18}BrNO_2$, 359.1; m/z found, 360.0 [M+H]$^+$. $^1$H NMR (CDCl$_3$): 7.40-7.16 (m, 4H), 7.11 (d, J=8.5 Hz, 1H), 7.05-6.90 (m, 2H), 5.67 (d, J=3.4 Hz, 1H), 4.05-3.84 (m, 2H), 3.82-3.52 (m, 2H), 3.24-3.10 (m, 1H), 2.93 (d, J=4.5 Hz, 1H), 2.65-2.43 (m, 1H), 2.34-2.17 (m, 2H).

Example 152

(±)-3-[5-Bromo-2-(5-chloro-indan-1-yloxy)-phenoxy]-azetidine

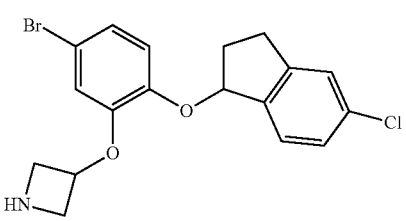 [SMILES: Clc1ccc2c(c1)CCC2Oc1ccc(Br)cc1OC1CNC1]

MS (ESI): mass calcd. for $C_{18}H_{17}BrClNO_2$, 393.0; m/z found, 394.0 [M+H]$^+$. $^1$H NMR (CDCl$_3$): 7.36-7.12 (m, 4H), 7.00-6.87 (m, 1H), 6.79 (s, 1H), 5.65 (s, 1H), 4.98-4.74 (m, 1H), 4.46-4.29 (m, 1H), 4.29-4.04 (m, 2H), 3.25-3.10 (m, 1H), 3.03-2.83 (m, 1H), 2.60-2.46 (m, 1H), 2.36-2.20 (m, 2H).

Example 153

(±)-3-[5-Bromo-2-(6-chloro-indan-1-yloxy)-phenoxy]-azetidine

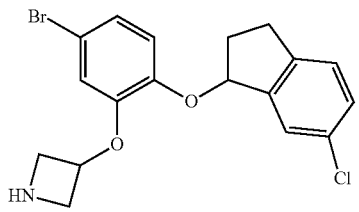 [SMILES: Clc1ccc2c(c1)C(Oc1ccc(Br)cc1OC1CNC1)CC2]

MS (ESI): mass calcd. for C$_{18}$H$_{17}$BrClNO$_2$, 393.0; m/z found, 394.0 [M+H]$^+$. $^1$H NMR (CDCl$_3$): 7.42-7.09 (m, 5H), 7.02-6.83 (m, 1H), 5.62 (s, 1H), 4.38 (s, 1H), 4.27-3.90 (m, 2H), 3.73-3.54 (m, 1H), 3.12 (s, 1H), 2.90 (s, 1H), 2.53 (s, 1H), 2.35-2.14 (m, 2H).

Example 154

(±)-3-[5-Bromo-2-(5-fluoro-indan-1-yloxy)-phenoxy]-azetidine

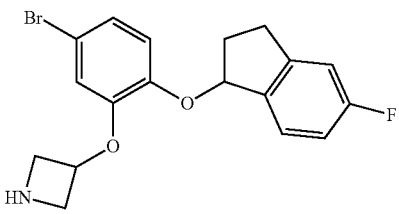 [SMILES: Fc1ccc2c(c1)CCC2Oc1ccc(Br)cc1OC1CNC1]

MS (ESI): mass calcd. for C$_{18}$H$_{17}$BrFNO, 377.0; m/z found, 378.0 [M+H]$^+$. $^1$H NMR (CDCl$_3$): 7.23 (d, J=5.2, 1H), 7.13-7.03 (m, 1H), 6.98-6.79 (m, 4H), 4.95-4.68 (m, 1H), 4.37-3.96 (m, 4H), 3.08 (s, 1H), 2.86 (s, 1H), 2.53-2.38 (m, 1H), 2.31-2.11 (m, 2H).

Example 155

(±)-3-[5-Bromo-2-(5-methyl-indan-1-yloxy)-phenoxy]-azetidine

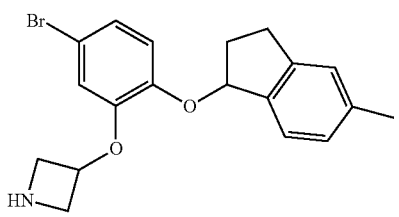 [SMILES: Cc1ccc2c(c1)CCC2Oc1ccc(Br)cc1OC1CNC1]

MS (ESI): mass calcd. for C$_{19}$H$_{20}$BrNO$_2$, 373.1; m/z found, 374.0 [M+H]$^+$. $^1$H NMR (CDCl$_3$): 7.25-7.10 (m, 4H), 7.04-6.78 (m, 2H), 5.65 (s, 2H), 4.31 (s, 1H), 4.12 (s, 2H), 3.10 (s, 1H), 2.89 (s, 1H), 2.46 (s, 2H), 2.35 (d, J=6.6 Hz, 4H).

Example 156

(±)-3-[5-Bromo-2-(6-methyl-indan-1-yloxy)-phenoxy]-azetidine

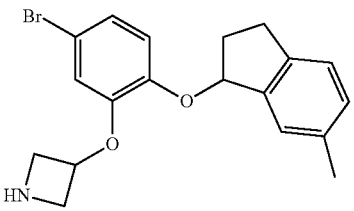 [SMILES: Cc1ccc2c(c1)C(Oc1ccc(Br)cc1OC1CNC1)CC2]

MS (ESI): mass calcd. for C$_{19}$H$_{20}$BrNO$_2$, 373.1; m/z found, 374.0 [M+H]$^+$. $^1$H NMR (CDCl$_3$): 7.36-7.18 (m, 3H), 7.08 (d, J=8.2, 1H), 7.02-6.92 (m, 2H), 5.67 (d, J=3.4 Hz, 1H), 4.02-3.84 (m, 2H), 3.80-3.53 (m, 2H), 3.24-3.10 (m, 1H), 2.93 (d, J=4.5 Hz, 1H), 2.65-2.46 (m, 1H), 2.37-2.18 (m, 5H).

Example 157

(±)-3-[5-Bromo-2-(6-trifluoromethyl-indan-1-yloxy)-phenoxy]-azetidine

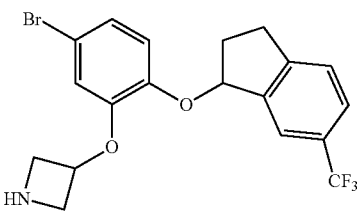 [SMILES: FC(F)(F)c1ccc2c(c1)C(Oc1ccc(Br)cc1OC1CNC1)CC2]

MS (ESI): mass calcd. for C$_{19}$H$_{17}$BrF$_3$NO$_2$, 427.1; m/z found, 429.0 [M+H]$^+$. $^1$H NMR (CDCl$_3$): 7.69-7.35 (m, 3H), 7.07 (dd, J=8.5, 2.3 Hz, 1H), 6.91 (d, J=8.5 Hz, 1H), 6.76 (d, J=2.3 Hz, 1H), 5.72-5.56 (m, 1H), 4.95 (s, 1H), 3.91 (s, 4H), 3.21 (d, J=9.4 Hz, 1H), 3.07-2.85 (m, 1H), 2.61-2.46 (m, 1H), 2.42-2.22 (m, 1H).

Example 158

(±)-3-[5-Chloro-2-(6-methyl-indan-1-yloxy)-phenoxy]-azetidine

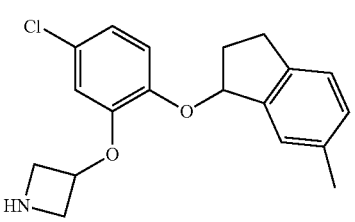

MS (ESI): mass calcd. for C$_{19}$H$_{20}$ClNO$_2$, 329.1; m/z found, 330.4 [M+H]$^+$. $^1$H NMR (CDCl$_3$): 7.22-7.08 (m, 3H), 7.02-6.89 (m, 2H), 6.67-6.60 (m, 1H), 5.63 (dd, J=6.5, 4.1 Hz, 1H), 4.96-4.86 (m, 1H), 4.04-3.72 (m, 4H), 3.21-3.02 (m, 1H), 2.94-2.77 (m, 1H), 2.57-2.40 (m, 1H), 2.33 (d, J=8.2 Hz, 3H), 2.29-2.17 (m, 1H).

Example 159

(±)-3-[5-Chloro-2-(6-chloro-indan-1-yloxy)-phenoxy]-azetidine

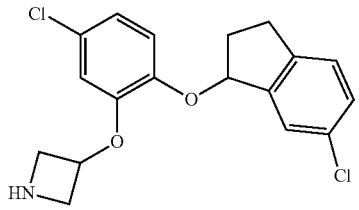

MS (ESI): mass calcd. for $C_{18}H_{17}Cl_2NO_2$, 349.1; m/z found, 350.0 [M+H]$^+$. $^1$H NMR (CDCl$_3$): 7.38-7.19 (m, 3H), 7.06-6.93 (m, 2H), 6.76-6.59 (m, 1H), 5.74-5.54 (m, 1H), 5.05-4.78 (m, 1H), 4.30-3.89 (m, 3H), 3.13 (d, J=8.2 Hz, 1H), 2.91 (d, J=5.1 Hz, 1H), 2.63-2.45 (m, 1H), 2.27 (s, 1H), 2.19 (s, 1H).

Example 160

3-[5-Chloro-2-(6-trifluoromethyl-indan-1-yloxy)-phenoxy]-azetidine

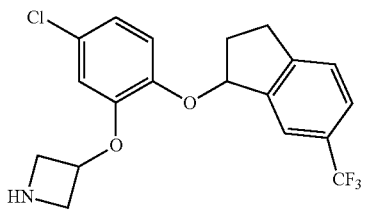

MS (ESI): mass calcd. for $C_{19}H_{17}ClF_3NO_2$, 383.1; m/z found, 384.1 [M+H]$^+$. $^1$H NMR (CDCl$_3$): 7.74-7.40 (m, 3H), 7.03-6.88 (m, 2H), 6.65 (d, J=2.2 Hz, 1H), 5.73-5.59 (m, 1H), 4.99 (s, 1H), 4.33-3.65 (m, 2H), 3.23 (s, 1H), 3.01 (s, 2H), 2.68-2.48 (m, 2H), 2.44-2.31 (m, 1H).

Example 161

3-[5-Chloro-2-(1,2,3,4-tetrahydro-naphthalen-1-yloxy)-phenoxy]-azetidine

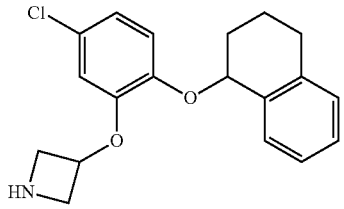 [SMILES: Clc1ccc(OC2CCCc3ccccc32)c(OC2CNC2)c1]

MS (ESI): mass calcd. for $C_{19}H_{20}ClNO_2$, 329.1; m/z found, 330.2 [M+H]$^+$. $^1$H NMR (CDCl$_3$): 7.29-7.13 (m, 4H), 7.01 (d, J=8.7 Hz, 3H), 5.27 (s, 1H), 4.96-4.71 (m, 1H), 4.08 (s, 3H), 2.91 (s, 1H), 2.79 (s, 1H), 2.19-2.04 (m, 4H), 1.86 (s, 1H).

Example 162

3-[5-Bromo-2-(5-tert-butyl-indan-1-yloxy)-phenoxy]-azetidine

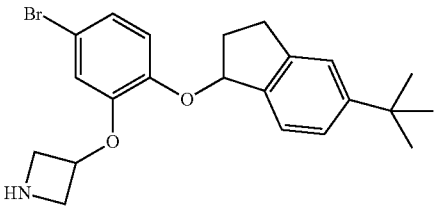 [SMILES: CC(C)(C)c1ccc2c(c1)CCC2Oc1ccc(Br)cc1OC1CNC1]

Step A: Preparation of 1-(4-tert-Butyl-phenyl)-3-chloro-propan-1-one. To a solution of tert-butyl benzene (1.0 g, 7.5 mmol) and 3-chloropropionyl chloride (0.7 mL, 7.5 mmoL) in CH$_2$Cl$_2$ (20 mL) was added dropwise to a suspension of AlCl$_3$ (1.1 g, 8.2 mmol) in CH$_2$Cl$_2$ (10 mL) at 0° C. The reaction was allowed to warm to rt. After 15 h, the reaction was quenched with H$_2$O (10 mL) and extracted with CH$_2$Cl$_2$ (2×20 mL). The organic layers were combined and dried to give the title compound that was used without further purification (1.3 g).

Step B.: Preparation of 5-tert-butyl-indan-1-one. The title compound of Step A (1.3 g, 5.8 mmol) was dissolved in conc. H$_2$SO$_4$ (10 mL) and heated at 95° C. for 3 h. The reaction mixture was cooled to rt, poured onto ice, and extracted with Et$_2$O (3×25 mL). The combined organic extracts were washed with sat'd NaHCO$_3$ (aq.) and dried to provide the title compound (0.74 g, 68%). MS (ESI): mass calcd. for $C_{13}H_{16}O$, 188.1; m/z found, 189.2 [M+H]$^+$. $^1$H NMR (CDCl$_3$): 7.67-7.58 (m, 1H), 7.44-7.32 (m, 2H), 3.09-3.02 (m, 2H), 2.65-2.68 (m, 2H), 1.27 (d, J=8.5 Hz, 9H).

Step B.: Preparation of 3-[5-Bromo-2-(5-tert-butyl-indan-1-yloxy)-phenoxy]-azetidine. MS (ESI): mass calcd. for $C_{22}H_{26}BrNO_2$, 415.1; m/z found, 418.1 [M+H]$^+$. $^1$H NMR (CDCl$_3$): 7.38-7.13 (m, 4H), 7.08-6.84 (m, 2H), 5.71 (s, 1H), 4.32 (s, 2H), 3.71-3.50 (m, 2H), 3.14 (s, 1H), 2.94 (s, 1H), 2.53 (s, 1H), 2.24 (s, 2H), 1.43-1.20 (m, 9H).

Example 163

3-[5-Chloro-2-(tetrahydro-furan-3-ylmethoxy)-phenoxy]-azetidine

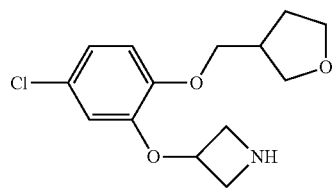 [SMILES: Clc1ccc(OCC2CCOC2)c(OC2CNC2)c1]

A mixture of 3-(5-chloro-2-hydroxy-phenoxy)-azetidine-1-carboxylic acid tert-butyl ester (0.5 mmol), tetrahydro-furan-3-yl-methanol (0.5 mmol), and cyanomethylenetri-n-butylphosphorane (0.5 mmol) in toluene (3 mL) was heated at 120° C. in a microwave reactor for 1 h. The mixture was cooled to rt and purified via PTLC providing 3-[5-chloro-2-(tetrahydro-furan-3-ylmethoxy)-phenoxy]-azetidine-1-carboxylic acid tert-butyl ester (120 mg). To this compound was added CH$_2$Cl$_2$ (20 mL) and TFA (3 mL). After 4 h at rt the mixture was concentrated to give the title compound (161 mg). MS (ESI): mass calcd. for C$_{14}$H$_{18}$ClNO$_3$, 283.1; m/z found, 284.0 [M+H]$^+$. $^1$H NMR (MeOD): 7.05-6.96 (m, 2H), 6.88 (d, J=1.9 Hz, 1H), 5.15-5.05 (m, 1H), 4.57-4.48 (m, 2H), 4.28-4.19 (m, 2H), 4.04-3.88 (m 4H), 3.82-3.70 (m 2H), 2.82-2.70 (m, 1H), 2.20-2.09 (m, 1H), 1.84-1.73 (m, 1H).

The compounds in Examples 164-174 were prepared according to Example 163 with the appropriate alcohols.

Example 164

3-[5-Chloro-2-(1,2,3,4-tetrahydro-naphthalen-2-yloxy)-phenoxy]-azetidine

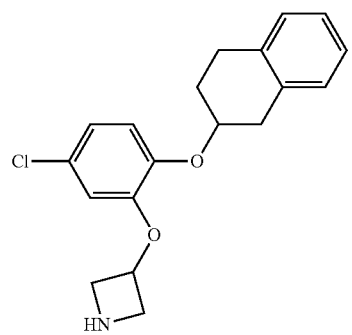 [SMILES: Clc1ccc(OC2CCc3ccccc3C2)c(OC2CNC2)c1]

MS (ESI): mass calcd. for C$_{19}$H$_{20}$ClNO$_2$, 329.1; m/z found, 330.0 [M+H]$^+$. $^1$H NMR (MeOD): 7.18-6.90 (m, 7H), 4.98-4.89 (m, 1H), 4.87-4.78 (m, 1H), 4.35-4.25 (m, 2H), 4.12-3.95 (m, 2H), 3.30-2.80 (m, 4H), 2.18-2.02 (m, 2H).

Example 165

3-[5-Chloro-2-(chroman-2-ylmethoxy)-phenoxy]-azetidine

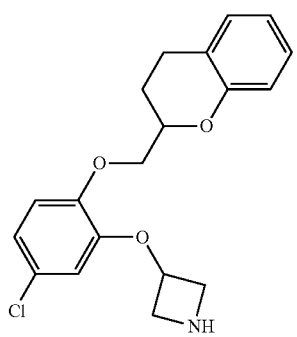 [SMILES: Clc1ccc(OCC2CCc3ccccc3O2)c(OC2CNC2)c1]

MS (ESI): mass calcd. for C$_{19}$H$_{20}$ClNO$_3$, 345.1; m/z found, 346.1 [M+H]$^+$. $^1$H NMR (400 MHz, CDCl$_3$): 7.13-6.75 (m, 7H), 5.15-4.98 (m, 1H), 4.55-4.09 (m, 7H), 3.00-2.75 (m, 2H), 2.18-1.85 (m, 2H).

Example 166

3-[5-Chloro-2-(tetrahydro-furan-2-ylmethoxy)-phenoxy]-azetidine

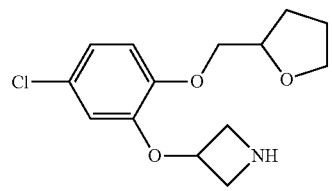 [SMILES: Clc1ccc(OCC2CCCO2)c(OC2CNC2)c1]

MS (ESI): mass calcd. for C$_{14}$H$_{18}$ClNO$_3$, 283.1; m/z found, 284.0 [M+H]$^+$. $^1$H NMR (MeOD): 7.05-6.86 (m, 3H), 5.12-5.02 (m, 1H), 4.60-4.46 (m, 2H), 4.32-4.20 (m, 3H), 4.09-4.00 (m, 1H), 3.95-3.87 (m, 2H), 3.86-3.70 (m, 1H), 2.20-1.90 (m, 3H), 1.80-1.68 (m, 1H).

Example 167

3-[5-Chloro-2-(chroman-3-ylmethoxy)-phenoxy]-azetidine

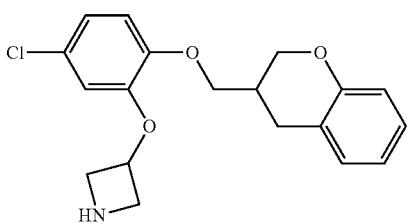 [SMILES: Clc1ccc(OCC2COc3ccccc3C2)c(OC2CNC2)c1]

MS (ESI): mass calcd. for C$_{19}$H$_{20}$ClNO$_3$, 345.1; m/z found, 346.1 [M+H]$^+$. $^1$H NMR (MeOD): 7.15-6.63 (m, 7H), 5.15-4.98 (m, 1H), 4.60-3.90 (m, 8H), 3.10-2.93 (m, 1H), 2.78-2.50 (m, 2H).

Example 168

3-[5-Chloro-2-(2-methoxy-2-phenyl-ethoxy)-phenoxy]-azetidine

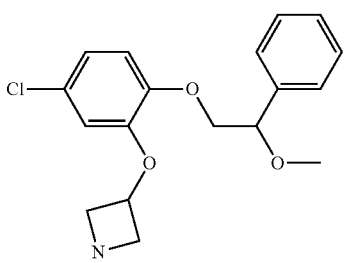 [SMILES: COC(COc1ccc(Cl)cc1OC1CNC1)c1ccccc1]

MS (ESI): mass calcd. for C$_{18}$H$_{20}$ClNO$_3$, 333.1; m/z found, 334.1 [M+H]$^+$. $^1$H NMR (CDCl$_3$): 7.45-7.25 (m, 5H), 7.04-6.88 (m, 3H), 5.05-4.96 (m, 1H), 4.63-4.57 (m, 1H), 4.53-4.42 (m, 2H), 4.26-4.05 (m, 4H), 4.33 (s, 3H).

Example 169

3-[5-Chloro-2-(2,3-dihydro-benzofuran-2-yl-methoxy)-phenoxy]-azetidine

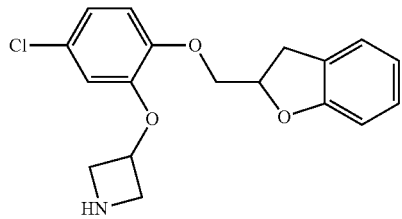 [SMILES: Clc1ccc(OCC2Cc3ccccc3O2)c(OC2CNC2)c1]

MS (ESI): mass calcd. for $C_{18}H_{18}ClNO_3$, 331.1; m/z found, 332.1 [M+H]$^+$. $^1$H NMR (CDCl$_3$): 7.20-6.66 (m, 7H), 5.20-5.05 (m, 1H), 4.98-4.88 (m, 1H), 4.35-4.03 (m, 6H), 3.42-3.32 (m, 1H), 3.12-3.03 (m, 1H).

Example 170

5-[2-(Azetidin-3-yloxy)-4-chloro-phenoxymethyl]-1,3-dimethyl-1H-pyrazole

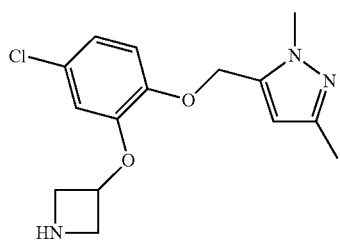 [SMILES: Cc1cc(COc2ccc(Cl)cc2OC2CNC2)n(C)n1]

MS (ESI): mass calcd. for $C_{15}H_{18}ClN_3O_2$, 307.1; m/z found, 308.1 [M+H]$^+$. $^1$H NMR (MeOD): 7.12 (d, J=8.7 Hz, 1H), 7.00 (dd, J=8.7, 2.1 Hz, 1H), 6.87 (d, J=2.1 Hz, 1H), 6.17 (s, 1H), 5.13-5.05 (m, 3H), 4.48-4.39 (m, 2H), 4.18-4.12 (m, 2H), 3.85 (s, 3H), 2.20 (s, 3H).

Example 171

3-[5-Chloro-2-(2-phenoxy-ethoxy)-phenoxy]-azetidine

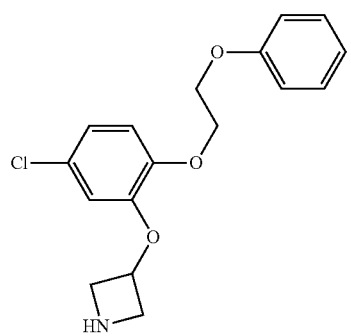 [SMILES: Clc1ccc(OCCOc2ccccc2)c(OC2CNC2)c1]

MS (ESI): mass calcd. for $C_{17}H_{18}ClNO_3$, 319.1; m/z found, 320.0 [M+H]$^+$. $^1$H NMR (MeOD): 7.34-7.26 (m, 2H), 7.12-6.92 (m, 6H), 5.14-4.95 (m, 2H), 4.83-4.74 (m, 1H), 4.48-4.42 (m, 1H), 4.39-4.30 (m, 4H), 4.24-4.16 (m, 1H).

Example 172

3-[5-Bromo-2-(3-fluoro-benzyloxy)-phenoxy]-1-phenyl-azetidine

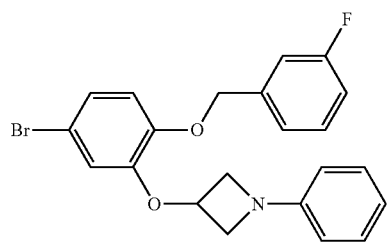 [SMILES: Fc1cccc(COc2ccc(Br)cc2OC2CN(c3ccccc3)C2)c1]

Prepared by the procedure of Example 163 using 5-bromo-2-(3-fluoro-benzyloxy)-phenol and 1-phenyl-azetidin-3-ol. MS (ESI): mass calcd. for $C_{22}H_{19}BrFNO_2$, 427.1; m/z found, 428.2 [M+H]$^+$. $^1$H NMR (CDCl$_3$): 7.34-6.47 (m, 12H), 5.11-5.03 (m, 3H), 4.36-4.28 (m, 2H), 3.98-3.91 (m, 2H).

Example 173

3-[5-Chloro-2-(indan-2-yloxy)-phenoxy]-azetidine

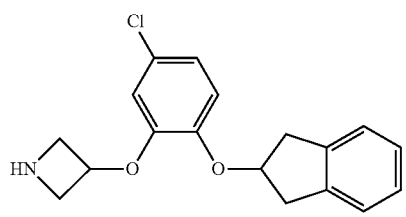 [SMILES: Clc1ccc(OC2Cc3ccccc3C2)c(OC2CNC2)c1]

MS (ESI): mass calcd. for $C_{18}H_{18}ClNO_2$, 315.1; m/z found, 316.1 [M+H]$^+$.
$^1$H NMR (MeOD): 7.35-7.06 (m, 6H), 6.93-6.90 (m, 1H), 5.28-5.21 (m, 1H), 4.86-4.78 (m, 1H), 4.28-4.18 (m, 2H), 4.08-3.98 (m, 2H), 3.42-3.35 (m, 2H), 3.18-3.08 (m, 2H).

Example 174

3-[5-Bromo-2-(indan-2-yloxy)-phenoxy]-azetidine

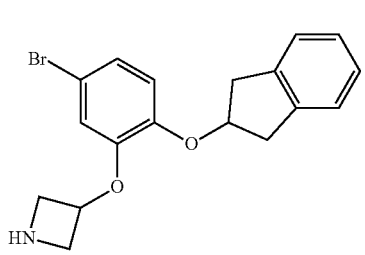 [SMILES: Brc1ccc(OC2Cc3ccccc3C2)c(OC2CNC2)c1]

MS (ESI): mass calcd. for $C_{18}H_{18}BrNO_2$, 359.1; m/z found, 359.9 [M+H]$^+$. $^1$H NMR (MeOD): 7.33-7.02 (m, 7H), 5.28-5.21 (m, 1H), 4.86-4.78 (m, 1H), 4.28-4.16 (m, 2H), 4.08-3.98 (m, 2H), 3.42-3.35 (m, 2H), 3.18-3.08 (m, 2H).

Example 175

3-[5-Chloro-2-(5-fluoro-indan-2-yloxy)-phenoxy]-azetidine

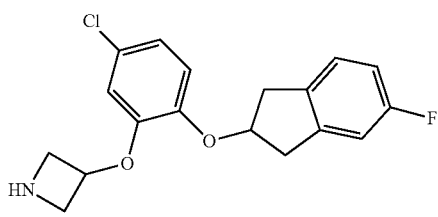 [SMILES: Fc1ccc2c(c1)CC(Oc1ccc(Cl)cc1OC1CNC1)C2]

Step A: Preparation of 2-Bromo-5-fluoro-indan-1-one. To the solution of 5-fluoro-indan-1-one (10 mmol) in MeOH/CH$_2$Cl$_2$ (40 mL/120 mL) was added Bu$_4$NBr$_3$ (11 mmol). The mixture was stirred at 25° C. for 16 h, concentrated and partitioned between CH$_2$Cl$_2$/H$_2$O (150 mL/80 mL). The organic layer was concentrated and purified providing the title compound (2 g).

Step B: Preparation of 3-[5-Chloro-2-(5-fluoro-indan-2-yloxy)-phenoxy]-azetidine. The mixture of 3-(5-chloro-2-hydroxy-phenoxy)-azetidine-1-carboxylic acid tert-butyl ester (0.5 mmol), the title compound of Step A (0.5 mmol), and K$_2$CO$_3$ (1 mmol) in acetonitrile (3 mL) was heated at 100° C. in a microwave reactor for 1 h. The mixture was cooled to rt and purified via PTLC providing the title compound (150 mg). To this product was added DCE (5 mL), Et$_3$SiH (1 mL) and TFA (3 mL). The mixture was stirred at 80° C. for 16 h. After concentration, the title compound was obtained (91 mg). MS (ESI): mass calcd. for C$_{18}$H$_{17}$ClFNO$_2$, 333.1; m/z found, 334.1 [M+H]$^+$. $^1$H NMR (CDCl$_3$): 7.20-7.13 (m, 1H), 6.96-6.60 (m, 5H), 5.18-5.08 (m, 1H), 4.93-4.83 (m, 1H), 3.98-3.70 (m, 4H), 3.38-3.05 (m, 4H).

The compounds in Examples 176-178 were prepared according to Example 175 using the appropriately substituted indanone.

Example 176

3-[5-Chloro-2-(5-chloro-indan-2-yloxy)-phenoxy]-azetidine

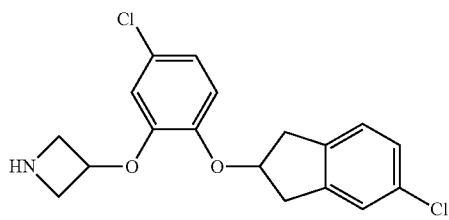 [SMILES: Clc1ccc2c(c1)CC(Oc1ccc(Cl)cc1OC1CNC1)C2]

MS (ESI): mass calcd. for C$_{18}$H$_{17}$Cl$_2$NO$_2$, 349.1; m/z found, 350.0 [M+H]$^+$. $^1$H NMR (CDCl$_3$): 7.26-6.63 (m, 6H), 5.20-5.05 (m, 1H), 4.93-4.83 (m, 1H), 4.10-3.85 (M, 4H), 3.45-3.05 (m, 4H).

Example 177

3-[5-Chloro-2-(5-methoxy-indan-2-yloxy)-phenoxy]-azetidine

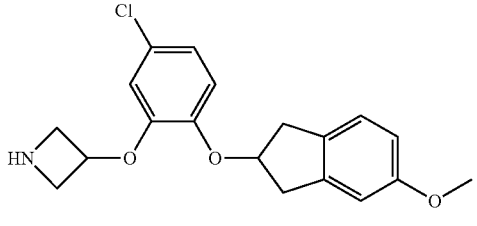 [SMILES: COc1ccc2c(c1)CC(Oc1ccc(Cl)cc1OC1CNC1)C2]

MS (ESI): mass calcd. for C$_{19}$H$_{20}$ClNO$_3$, 345.1; m/z found, 346.0 [M+H]$^+$. $^1$H NMR (MeOD): 7.15 (d, J=8.2 Hz, 1H), 7.08-7.03 (m, 2H), 6.94-6.73 (m, 3H), 5.25-5.17 (m, 1H), 4.90-4.81 (m, 1H), 4.80-4.70 (m, 2H), 4.12-4.02 (m, 2H), 3.77 (s, 3H), 3.37-3.24 (m, 2H), 3.12-2.98 (m, 2H).

Example 178

3-[5-Chloro-2-(4-methoxy-indan-2-yloxy)-phenoxy]-azetidine

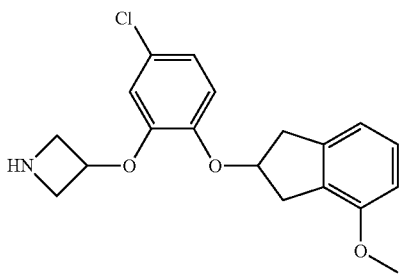 [SMILES: COc1cccc2c1CC(Oc1ccc(Cl)cc1OC1CNC1)C2]

MS (ESI): mass calcd. for C$_{19}$H$_{20}$ClNO$_3$, 345.1; m/z found, 346.1 [M+H]$^+$. $^1$H NMR (MeOD): 7.22-6.76 (m, 6H), 5.26-5.18 (m, 1H), 4.94-4.83 (m, 1H), 4.18-4.10 (m, 2H), 3.98-3.88 (m, 2H), 3.83 (s, 3H), 3.40-3.20 (m, 2H), 3.15-3.02 (m, 2H).

Example 179

2-[2-(Azetidin-3-yloxy)-4-chloro-phenoxy]-indan-1-one oxime

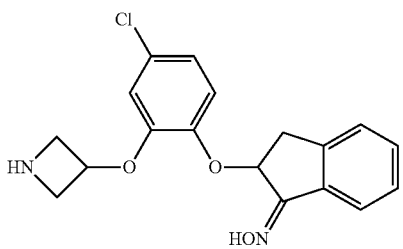

Step A: Preparation of 3-[5-chloro-2-(6-fluoro-1-oxo-indan-2-yloxy)-phenoxy]-azetidine-1-carboxylic acid tert-butyl ester. The mixture of 3-(5-chloro-2-hydroxy-phenoxy)- azetidine-1-carboxylic acid tert-butyl ester (0.5 mmol), 1-bromo-indan-2-one (0.5 mmol), and K₂CO₃ (1 mmol) in acetonitrile (3 mL) was heated at 100° C. in a microwave reactor for 1 h. The mixture was cooled down and separated through PTLC providing the title compound (150 mg).

Step B: Preparation of 3-[5-Chloro-2-(1-hydroxyimino-indan-2-yloxy)-phenoxy]-azetidine-1-carboxylic acid tert-butyl ester. The title compound of Step A was dissolved into MeOH (2 mL), then NH₂OH HCl (1 mmol) and K₂CO₃ (2 mmol) were added. The mixture was heated at 100° C. using a microwave reactor for 1 h. The mixture was cooled to rt and purified by PTLC providing the title compound (120 mg).

Step C: Preparation of 2-[2-(Azetidin-3-yloxy)-4-chloro-phenoxy]-indan-1-one oxime. The title compound from Step B was dissolved in CH₂Cl₂ (20 mL), and CF₃COOH (3 mL) was added. The mixture was stirred at 25° C. for 4 h. After concentration and purification via PTLC, the title compound was obtained (91 mg). MS (ESI): mass calcd. for $C_{18}H_{17}ClN_2O_3$, 344.1; m/z found, 345.0 [M+H]⁺. ¹H NMR (MeOD): 8.40 (d, J=8.0 Hz, 1H), 7.50-6.80 (m, 6H), 5.48-5.46 (m, 1H), 5.18-5.10 (m, 1H), 4.45-4.32 (m, 2H), 4.18-4.08 (m, 2H), 3.62-3.52 (m, 1H), 3.16-3.08 (m, 1H).

Example 180-183 were prepared by the procedure of example 179 using the appropriate α-bromo-ketone and NH₂OH or NH₂OCH₃.

Example 180

2-[2-(Azetidin-3-yloxy)-4-chloro-phenoxy]-indan-1-one O-methyl-oxime

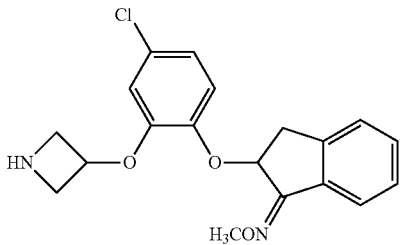

MS (ESI): mass calcd. for $C_{19}H_{19}ClN_2O_3$, 358.1; m/z found, 359.0 [M+H]⁺. ¹H NMR (MeOD): 8.70 (d, J=8.0 Hz, 1H), 7.60-6.90 (m, 6H), 6.03-5.98 (m, 1H), 5.15-5.05 (m, 1H), 4.56-4.43 (m, 2H), 4.22-1.18 (m, 2H), 3.93 (s, 3H), 3.76-3.64 (m, 1H), 3.24-3.16 (m, 1H).

Example 181

2-[2-(Azetidin-3-yloxy)-4-chloro-phenoxy]-1-phenyl-ethanone oxime

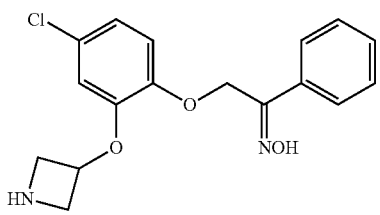

MS (ESI): mass calcd. for $C_{17}H_{17}ClN_2O_3$, 332.1; m/z found, 333.0 [M+H]⁺. ¹H NMR (MeOD): 8.12-6.80 (m, 8H), 5.56-5.30 (m, 2H), 5.25-4.80 (m, 1H), 4.60-3.98 (m, 4H).

Example 182

2-[2-(Azetidin-3-yloxy)-4-chloro-phenoxy]-1-phenyl-ethanone O-methyl-oxime

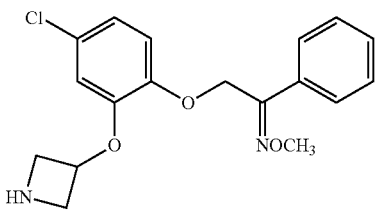

MS (ESI): mass calcd. for $C_{18}H_{19}ClN_2O_3$, 346.1; m/z found, 347.0 [M+H]⁺. ¹H NMR (MeOD): 8.18-6.80 (m, 8H), 5.56-5.33 (m, 2H), 5.32-4.80 (m, 1H), 4.60-3.98 (m, 7H).

Example 183

2-[2-(Azetidin-3-yloxy)-4-chloro-phenoxy]-1-(4-chloro-phenyl)-ethanone

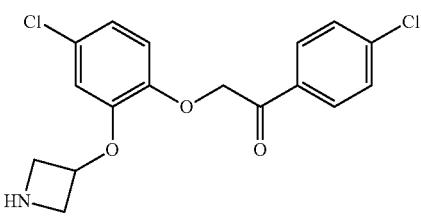 [SMILES: O=C(COc1ccc(Cl)cc1OC1CNC1)c1ccc(Cl)cc1]

¹H NMR (CDCl₃): 7.97 (d, J=8.6 Hz, 2H), 7.48 (d, J=8.6 Hz, 2H), 6.85 (dd, J=8.6, 2.3 Hz, 1H), 6.78 (d, J=8.6 Hz, 1H), 6.59 (d, J=8.6 Hz, 1H), 5.25 (s, 2H), 5.00-4.97 (m, 1H), 3.98-3.80 (m, 4H).

Example 184

3-[5-Chloro-2-(2,2-difluoro-2-phenyl-ethoxy)-phenoxy]-azetidine

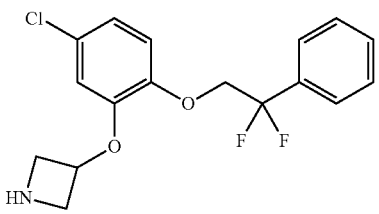 [SMILES: FC(F)(COc1ccc(Cl)cc1OC1CNC1)c1ccccc1]

The mixture of 3-(5-chloro-2-hydroxy-phenoxy)-azetidine-1-carboxylic acid tert-butyl ester (0.5 mmol), (2-bromo-1,1-difluoro-ethyl)-benzene (1 mmol), and K₂CO₃ (1 mmol) in acetonitrile (3 mL) was heated at 180° C. in a microwave reactor for 1 h. The mixture was cooled to rt and purified via PTLC providing 3-[5-chloro-2-(2,2-difluoro-2-phenylethoxy)-phenoxy]-azetidine-1-carboxylic acid tert-butyl ester (90 mg). To this compound was added CH$_2$Cl$_2$ (20 mL) and CF$_3$COOH (3 mL). The mixture was stirred at rt for 4 h and concentrated to give the title compound (50 mg). MS (ESI): mass calcd. for C$_{17}$H$_{16}$ClF$_2$NO$_2$, 339.1; m/z found, 340.0 [M+H]$^+$. $^1$H NMR (MeOD): 7.66-7.46 (m, 5H), 7.02-6.83 (m, 3H), 5.05-4.95 (m, 1H), 4.50 (t, J=12.7 Hz, 2H), 4.30-4.20 (m, 2H), 4.10-3.98 (m, 2H).

Example 185

3-[5-Chloro-2-[2-(3-chloro-phenyl)-ethoxy]-phenoxy]-azetidine

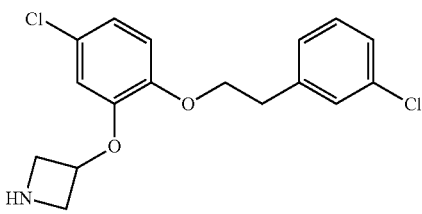 [SMILES: Clc1cccc(CCOc2ccc(Cl)cc2OC2CNC2)c1]

Step A. Preparation of Methanesulfonic acid 2-(3-chlorophenyl)-ethyl ester. To a solution of 2-(3-chloro-phenyl)-ethanol (566 mg, 3.6 mmol) in CH$_2$Cl$_2$ (10 mL) was added methanesulfonyl chloride (310 μL, 4.0 mmol). After min, Et$_3$N (756 μL, 5.4 mmol) was added and the reaction was allowed to stir for 18 h. The reaction was then diluted with H$_2$O. The organic layer was separated and washed with H$_2$O, brine, then dried and concentrated to give a yellow oil (770 mg, 91%). $^1$H NMR (CDCl$_3$): 7.27-7.23 (m, 3H), 7.14-7.11 (m, 1H), 4.41 (t, J=6.8 Hz, 2H), 3.04 (t, J=6.8 Hz, 2H), 2.90 (s, 3H).

Step B. Preparation of 3-[5-Chloro-2-[2-(3-chloro-phenyl)-ethoxy]-phenoxy]-azetidine-1-carboxylic acid tert-butyl ester. To a solution of 3-(5-chloro-2-hydroxy-phenoxy)-azetidine-1-carboxylic acid tert-butyl ester (60 mg, 0.20 mmol) in DMF (2 mL) was added NaH (10 mg, 0.24 mmol). After 5 min, the title compound of Step A (56 mg, 0.24 mmol) was added and the resulting mixture was heated at 65° C. for 18 h. The reaction was diluted with H$_2$O and extracted EtOAc (3×). The organics were dried and purified by RP HPLC (Agilent) to give the title compound as an oil (47 mg, 54%). MS (ESI): mass calcd. for C$_{22}$H$_{25}$Cl$_2$NO$_4$, 438.3; m/z found, 382.0 [M-56+H]$^+$. $^1$H NMR (CDCl$_3$): 7.34-7.32 (m, 1H), 7.25-7.22 (m, 2H), 7.19-7.16 (m, 1H), 6.90 (dd, J=8.8, 2.0 Hz, 1H), 6.78 (d, J=8.8 Hz, 1H), 6.54 (d, J=2.4 Hz, 1H), 4.85-4.79 (m, 1H), 4.30-4.25 (m, 2H), 4.16 (t, J=6.7 Hz, 2H), 4.07-4.03 (m, 2H), 3.10 (t, J=6.7 Hz, 2H), 1.46 (s, 9H).

Step C: Preparation of 3-[5-Chloro-2-[2-(3-chloro-phenyl)-ethoxy]-phenoxy]-azetidine. Prepared from title compound of Step B using general procedure 1. MS (ESI): mass calcd. for C$_{17}$H$_{17}$Cl$_2$NO$_2$, 338.2; m/z found, 338.1 [M+H]$^+$. $^1$H NMR (CDCl$_3$): 7.35-7.34 (m, 1H), 7.25-7.21 (m, 3H), 7.18-7.16 (m, 1H), 6.88-6.85 (m, 1H), 6.77 (d, J=8.8 Hz, 1H), 6.57 (d, J=2.4 Hz, 1H), 4.98-4.91 (m, 1H), 4.17 (t, J=6.8 Hz, 2H), 3.96-3.85 (m, 4H), 3.10 (t, J=6.7 Hz, 2H).

The compounds in Examples 186-195 were synthesized according to Example 185 using the appropriately substituted mesylates as prepared in Example 185 Step A.

Example 186

3-[5-Chloro-2-(3-chloro-benzyloxy)-phenoxy]-azetidine

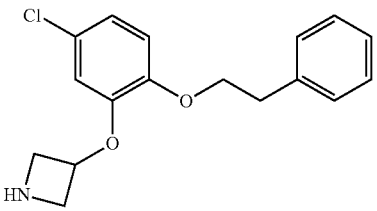 [SMILES: Clc1ccc(OCCc2ccccc2)c(OC2CNC2)c1]

MS (ESI): mass calcd. for C$_{17}$H$_{18}$ClNO$_2$, 303.8; m/z found, 304.1 [M+H]$^+$. $^1$H NMR (CDCl$_3$): 7.39-7.19 (m, 7H), 6.93-6.73 (m, 2H), 6.58 (d, J=2.4 Hz, 1H), 4.94 (s, 1H), 4.18 (t, J=7.3 Hz, 2H), 3.91 (s, 3H), 3.14 (t, J=7.3 Hz, 2H).

Example 187

3-[5-Chloro-2-(2-fluoro-2-phenyl-ethoxy)-phenoxy]-azetidine

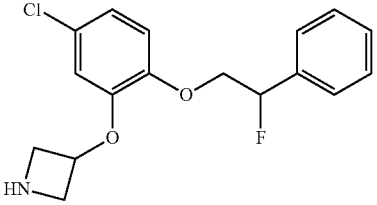 [SMILES: FC(COc1ccc(Cl)cc1OC1CNC1)c1ccccc1]

MS (ESI): mass calcd. for C$_{17}$H$_{17}$ClFNO$_2$, 321.8; m/z found, 322.1 [M+H]$^+$. $^1$H NMR (CDCl$_3$): 7.42 (s, 5H), 6.87-6.61 (m, 2H), 6.62 (d, J=2.2 Hz, 1H), 5.85 (dd, J=48.0, 8.0 Hz, 1H), 5.02 (bs, 1H), 4.40-4.08 (m, 7H).

Example 188

3-[5-Chloro-2-[1-(4-chloro-phenyl)-cyclobutylmethoxy]-phenoxy]-azetidine

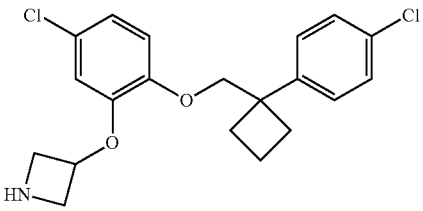 [SMILES: Clc1ccc(C2(COc3ccc(Cl)cc3OC3CNC3)CCC2)cc1]

MS (ESI): mass calcd. for C$_{20}$H$_{21}$Cl$_2$NO$_2$, 378.3; m/z found, 378.0 [M+H]$^+$. $^1$H NMR (CDCl$_3$): 7.34-7.27 (m, 5H), 7.21-7.20 (m, 1H), 7.19-7.18 (m 1H), 6.81 (s, 1H), 6.70 (d, J=8.6, 1H), 6.54 (d, J=2.4 Hz, 1H), 4.97-4.87 (m, 1H), 4.01 (s, 2H), 3.94-3.90 (m, 2H), 3.82-3.78 (m, 2H), 2.42 (t, J=7.7 Hz, 4H).

Example 189

3-[5-Chloro-2-[1-(3-chloro-phenyl)-cyclobutyl-methoxy]-phenoxy]-azetidine

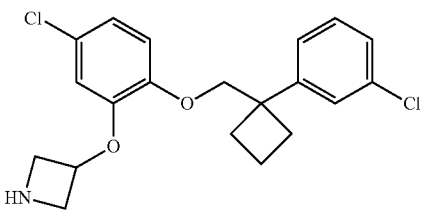 [SMILES: Clc1cccc(C2(COc3ccc(Cl)cc3OC3CNC3)CCC2)c1]

MS (ESI): mass calcd. for $C_{20}H_{21}Cl_2NO_2$, 378.3; m/z found, 378.0. $^1$H NMR (CDCl$_3$): 7.28-7.22 (m, 5H), 7.19-7.16 (m, 1H), 7.13-7.10 (m, 1H), 6.82 (dd, J=8.6, 2.4 Hz, 1H), 6.70 (d, J=8.6 Hz, 1H), 6.54 (d, J=2.4, 1H), 4.92 (m, 1H), 4.03 (s, 2H), 3.94-3.76 (m, 3H), 2.42 (d, J=8.8 Hz, 3H), 2.17 (s, 2H).

Example 190

3-[5-Chloro-2-[2-(3-methoxy-phenyl)-ethoxy]-phenoxy]-azetidine

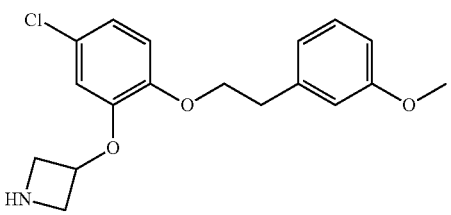 [SMILES: COc1cccc(CCOc2ccc(Cl)cc2OC2CNC2)c1]

MS (ESI): mass calcd. for $C_{18}H_{20}ClNO_3$, 333.8; m/z found, 334.1 [M+H]$^+$. $^1$H NMR (CDCl$_3$): 7.24-7.22 (m, 2H), 6.90-6.86 (m, 3H), 6.81-6.77 (m, 2H), 6.60 (d, J=2.4, 1H), 5.00-4.87 (m, 1H), 4.18 (t, J=7.2, 2H), 4.03-3.94 (m, 2H), 3.90-3.86 (m, 2H), 3.80 (s, 3H), 3.11 (t, J=7.1 Hz, 2H).

Example 191

3-[5-Chloro-2-[2-(3-fluoro-phenyl)-ethoxy]-phenoxy]-azetidine

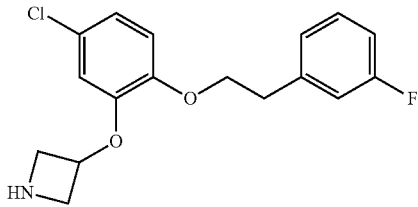 [SMILES: Fc1cccc(CCOc2ccc(Cl)cc2OC2CNC2)c1]

MS (ESI): mass calcd. for $C_{17}H_{17}ClFNO_2$, 321.8; m/z found, 322.0 [M+H]$^+$. $^1$H NMR (CDCl$_3$): 7.30-7.24 (m, 2H), 7.09-7.05 (m, 2H), 6.96-6.91 (m, 1H), 6.88-6.85 (m, 1H), 6.77 (d, J=8.8 Hz, 1H), 6.57 (d, J=2.4, 1H), 4.95 (s, 1H), 4.18 (t, J=6.8 Hz, 2H), 3.95-3.84 (m, 4H), 3.12 (t, J=6.8 Hz, 2H).

Example 192

3-[5-Chloro-2-[2-(4-chloro-phenyl)-ethoxy]-phenoxy]-azetidine

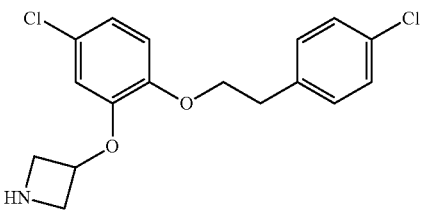 [SMILES: Clc1ccc(CCOc2ccc(Cl)cc2OC2CNC2)cc1]

MS (ESI): mass calcd. for $C_{17}H_{17}Cl_2NO_2$, 338.2; m/z found, 338.0. $^1$H NMR (CDCl$_3$): 7.34-7.17 (m, 5H), 6.89 (dd, J=8.6, 2.4 Hz, 1H), 6.77 (d, J=8.7 Hz, 1H), 6.60 (d, J=2.4 Hz, 1H), 4.95 (t, J=6.2 Hz, 1H), 4.16-4.13 (m, 2H), 4.04-3.99 (m, 2H), 3.93-3.89 (m, 2H), 3.09 (t, J=6.9 Hz, 2H).

Example 193

3-[5-Chloro-2-[2-(4-fluoro-phenyl)-ethoxy]-phenoxy]-azetidine

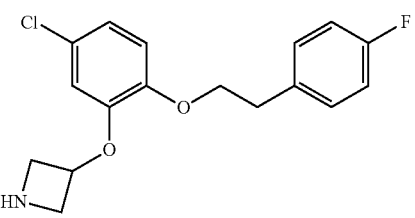 [SMILES: Fc1ccc(CCOc2ccc(Cl)cc2OC2CNC2)cc1]

MS (ESI): mass calcd. for $C_{17}H_{17}ClFNO_2$, 321.8; m/z found, 322.1 [M+H]$^+$. $^1$H NMR (CDCl$_3$): 7.32-7.20 (m, 4H), 7.00 (t, J=8.7 Hz, 1H), 6.87-6.85 (m, 1H), 6.77 (d, J=8.8 Hz, 1H), 6.57 (d, J=2.4 Hz, 1H), 5.00-4.87 (m, 1H), 4.15 (t, J=7.0 Hz, 2H), 3.94-3.90 (m, 2H), 3.85-3.81 (m, 2H), 3.10 (t, J=7.0 Hz, 2H).

Example 194

3-[5-Chloro-2-[2-(4-methoxy-phenyl)-ethoxy]-phenoxy]-azetidine

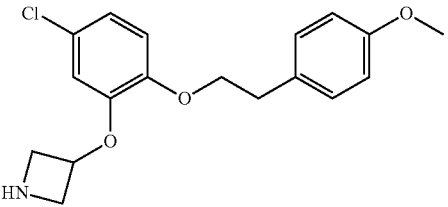 [SMILES: COc1ccc(CCOc2ccc(Cl)cc2OC2CNC2)cc1]

MS (ESI): mass calcd. for $C_{18}H_{20}ClNO_3$, 333.8; m/z found, 334.1 [M+H]$^+$. $^1$H NMR (CDCl$_3$): 7.22-7.20 (m, 2H), 6.93-6.85 (m, 3H), 6.77 (d, J=8.4 Hz, 1H), 6.58 (d, J=2.4 Hz, 1H), 4.98-4.91 (m, 1H), 4.13 (t, J=7.3 Hz, 2H), 3.96-3.92 (m, 2H), 3.89-3.85 (m, 2H), 3.79 (s, 3H), 3.07 (t, J=7.3 Hz, 2H).

Example 195

3-(5-Bromo-2-phenethyloxy-phenoxy)-azetidine

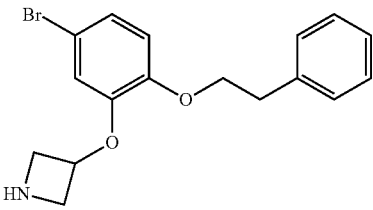 [SMILES: Brc1ccc(OCCc2ccccc2)c(OC2CNC2)c1]

Prepared according to Example 185 using 3-(5-Bromo-2-hydroxy-phenoxy)-azetidine-1-carboxylic acid tert-butyl ester. MS (ESI): mass calcd. for $C_{17}H_{18}BrNO_2$, 348.2; m/z found, 348.0. $^1$H NMR (CDCl$_3$): 7.39-7.20 (m, 6H), 7.05 (dd, J=8.6, 2.3 Hz, 1H), 6.76 (dd, J=6.8, 5.5 Hz, 2H), 4.99-4.87 (m, 1H), 4.18 (t, J=7.2 Hz, 2H), 4.03-3.98 (m, 2H), 3.95-3.91 (m, 2H), 3.13 (t, J=7.2 Hz, 2H).

Example 196

3-(Azetidin-3-yloxy)-2-benzyloxy-5-chloro-pyridine

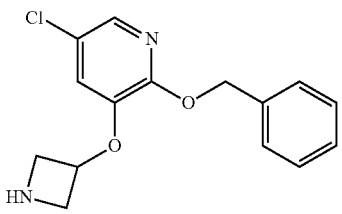 [SMILES: Clc1cnc(OCc2ccccc2)c(OC2CNC2)c1]

Step A: Preparation of 2-benzyloxy-5-chloro-3-fluoro-pyridine. To 60% NaH in mineral oil (1.0 g, 25.0 mmol) in THF (25 mL) was added benzyl alcohol (2.7 g, 2.6 mL, 25.0 mmol) dropwise. After 1 h, 5-chloro-2,3-difluoro-pyridine (3.73 g, 25.0 mmol) was added in THF (5 mL). After an additional 18 h, H$_2$O was added and the mixture extracted with EtOAc (2×). The combined organics were washed with brine and dried. Silica gel chromatography (1-15% EtOAc in hexanes) gave 4.02 g (67% yield) of the title compound as a clear oil. $^1$H NMR (CDCl$_3$): 7.91 (d, J=2.2 Hz, 1H), 7.48-7.46 (m, 2H), 7.39-7.32 (m, 4H), 5.44 (s, 2H).

Step B: Preparation of 3-(2-Benzyloxy-5-chloro-pyridin-3-yloxy)-azetidine-1-carboxylic acid tert-butyl ester. To 3-hydroxy-azetidine-1-carboxylic acid tert-butyl ester (0.35 g, 2.0 mmol) in NMP (3 mL) was added 60% NaH in mineral oil (0.08 g, 2.0 mmol). After 20 min at rt, the reaction was heated to 50° C. for 20 min, cooled to rt and the title compound from step A (0.40 g, 1.7 mmol) in NMP (1 mL) was added. The reaction was then heated in a microwave reactor at 145° C. for 1 h, cooled to rt, poured into H$_2$O and extracted with EtOAc (2×). The combined organics were washed with brine and dried. Silica gel chromatography (2-15% EtOAc in hexanes) gave 0.34 g (51% yield) of the title compound as a white solid. $^1$H NMR (CDCl$_3$): 7.74 (d, J=2.1 Hz, 1H), 7.46 (d, J=7.0 Hz, 2H), 7.39-7.30 (m, 3H), 6.77 (d, J=2.1 Hz, 1H), 5.42 (s, 2H), 4.87-4.82 (m, 1H), 4.26 (dd, J=10.5, 6.4 Hz, 2H), 4.05 (dd, J=10.3, 4.2 Hz, 2H), 1.44 (s, 9H).

Step C: Preparation of 3-(Azetidin-3-yloxy)-2-benzyloxy-5-chloro-pyridine. Prepared from the title compound of Step B using general procedure 1. MS (ESI): mass calcd. for $C_{15}H_{15}ClN_2O_2$, 290.1; m/z found, 291.1 [M+H]$^+$. $^1$H NMR (CDCl$_3$): 7.70 (d, J=2.2 Hz, 1H), 7.46 (d, J=7.3 Hz, 2H), 7.37 (t, J=7.2 Hz, 2H), 7.33-7.29 (m, 1H), 6.77 (d, J=2.2 Hz, 1H), 5.43 (s, 2H), 4.99-4.93 (m, 1H), 3.96-3.81 (m, 4H).

Example 197

3-(2-Benzyloxy-5-chloro-3-fluoro-phenoxy)-azetidine

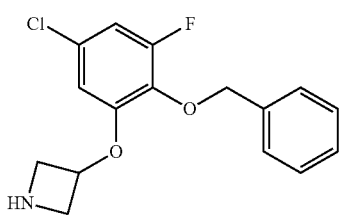 [SMILES: Fc1cc(Cl)cc(OC2CNC2)c1OCc1ccccc1]

Step A: Preparation of 4-Chloro-2,6-difluoro-benzaldehyde. To a −78° C. solution of 1-chloro-3,5-difluoro-benzene (5.0 g, 34 mmol) in THF (70 mL) was added n-butyl lithium (1.6 M in hexane, 19 mL). After 50 min, DMF (5.2 mL, 67 mmol) was added and the reaction was allowed to warm to rt over 18 h. After the addition of 0.5 M HCl (150 mL) and ether (150 mL), the aqueous layer was extracted with Et$_2$O (3×). The combined organic extracts were dried and concentrated to provide a yellow solid. The crude material was dissolved in warm hexanes and a small amount of white solid formed upon cooling. This white solid was filtered off and discarded. The filtrate was concentrated to provide the title compound as a light yellow solid (2.5 g, 41%). $^1$H NMR (CDCl$_3$): 10.3 (s, 1H), 7.06 (d, J=8.1 Hz, 2H).

Step B: Preparation of 3-(5-Chloro-3-fluoro-2-formyl-phenoxy)-azetidine-1-carboxylic acid tert-butyl ester. To a solution of the title compound of Step A (270 mg, 1.5 mmol) and 3-hydroxy-azetidine-1-carboxylic acid tert-butyl ester (270 mg, 1.5 mmol) in dry DMF (10 mL) at 0° C. was added NaH (60% in mineral oil, 22 mg, 1.5 mmol). After 18 h, H$_2$O and EtOAc were added and the aqueous layer was extracted with EtOAc. The combined organic extracts were dried and concentrated. The crude residue was purified by RP HPLC to provide the title compound (75 mg, 15%). MS (ESI): mass calcd. for $C_{15}H_{17}ClFNO_4$, 329.1; m/z found, 274.0 [M+H−56]$^+$. $^1$H NMR (CDCl$_3$): 10.4 (s, 1H), 6.84 (dd, J=10.0, 1.6 Hz, 1H), 6.39 (dd, J=1.4, 1.3 Hz, 1H), 5.00-4.92 (m, 1H), 4.38 (dd, J=9.9, 6.3 Hz, 2H), 4.08 (dd, J=10.7, 4.0 Hz, 2H), 1.46 (s, 9H).

Step C: Preparation of 3-(5-Chloro-3-fluoro-2-hydroxy-phenoxy)-azetidine-1-carboxylic acid tert-butyl ester. To a solution of the title compound of Step B (650 mg, 2.0 mmol) in CH$_2$Cl$_2$ (100 mL) was added 77% m-CPBA (510 mg, 3.0 mmol). After stirring for 72 h, the starting aldehyde remained as determined by analytical HPLC analysis. Thus an additional portion of m-CPBA (790 mg, 4.6 mmol) was added. After 18 h, analytical HPLC analysis indicated that the reaction was complete. A solution of 10% aqueous sodium bisulfite (100 mL) was added to the reaction mixture. After an additional 18 h, CH$_2$Cl$_2$ was added and the aqueous portion extracted three times with CH$_2$Cl$_2$. The combined organic extracts were washed with saturated NaHCO$_3$ (2×) and concentrated. The residue was then treated with MeOH (500 mL) and 1 N NaOH (250 mL). The solution immediately turned dark brown. After 2 h, the MeOH was removed by rotary evaporation and 1 M KHSO$_4$ was added to the residue until the pH of the solution reached pH=4. The reaction mixture was then extracted with EtOAc (3×). The combined organic layers were washed with brine and dried. The residue was purified by RP HPLC to provide the desired phenol (290 mg, 46%). $^1$H NMR (CDCl$_3$): 6.74 (dd, J=10.1, 2.3 Hz, 1H), 6.30 (dd, J=2.0, 2.1 Hz, 1H), 4.87-4.80 (m, 1H), 4.26 (dd, J=9.9, 6.4 Hz, 2H), 4.00 (dd, J=9.9, 3.8 Hz, 2H), 3.29-3.13 (m, 1H), 1.40 (s, 9H).

Step D: Preparation of 3-(2-Benzyloxy-5-chloro-3-fluoro-phenoxy)-azetidine-1-carboxylic acid tert-butyl ester. Prepared from the title compound of Step C using according to Example 1 Step D. MS (ESI): mass calcd. for C$_{21}$H$_{23}$ClFNO$_4$, 407.1; m/z found, 430.0 [M+Na]$^+$. $^1$H NMR (CDCl$_3$): 7.46-7.29 (m, 5H), 6.79 (dd, J=9.9, 2.4 Hz, 1H), 6.29 (dd, J=2.1, 2.1 Hz, 1H), 5.06 (s, 2H), 4.82-4.72 (m, 1H), 4.25 (ddd, J=9.7, 6.4, 1.0 Hz, 2H), 3.92 (dd, J=9.8, 3.9 Hz, 2H), 1.46 (s, 9H).

Step E: Preparation of 3-(2-Benzyloxy-5-chloro-3-fluoro-phenoxy)-azetidine. Prepared from the title compound of Step D using general procedure 1. MS (ESI): mass calcd. for C$_{16}$H$_{15}$ClFNO$_2$, 307.1; m/z found, 308.0 [M+H]$^+$. $^1$H NMR (CDCl$_3$): 7.47-7.41 (m, 2H), 7.37-7.30 (m, 3H), 6.76 (dd, J=9.9, 2.4 Hz, 1H), 6.34 (dd, J=2.1, 2.1 Hz, 1H), 5.06 (s, 2H), 4.97-4.86 (m, 1H), 4.05-3.63 (m, 4H), 2.27-2.00 (m, 1H).

Example 198

3-[5-Chloro-3-fluoro-2-(5-trifluoromethyl-furan-2-ylmethoxy)-phenoxy]-azetidine

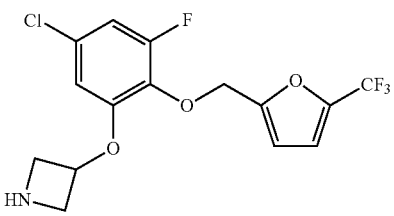 [SMILES: Fc1cc(Cl)cc(OC2CNC2)c1OCc1ccc(C(F)(F)F)o1]

Prepared according to Example 199 using 2-bromomethyl-5-trifluoromethyl-furan. MS (ESI): mass calcd. for C$_{15}$H$_{12}$ClF$_4$NO$_3$, 365.0; m/z found, 367.0 [M+H]$^+$. $^1$H NMR (CDCl$_3$): 6.78-6.72 (m, 2H), 6.42 (d, J=3.3 Hz, 1H), 6.36 (dd, J=2.1, 2.1 Hz, 1H), 5.04 (s, 2H), 4.98-4.85 (m, 1H), 4.05-3.69 (m, 4H), 2.20-1.99 (m, 1H).

Example 199

3-[5-Trifluoromethyl-2-(5-trifluoromethyl-furan-2-ylmethoxy)-phenoxy]-azetidine

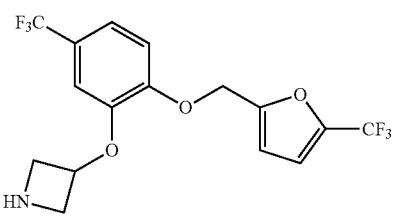 [SMILES: FC(F)(F)c1ccc(OCc2ccc(C(F)(F)F)o2)c(OC2CNC2)c1]

Prepared according to Example 1 using 3-(2-hydroxy-5-trifluoromethyl-phenoxy)-azetidine-1-carboxylic acid tert-butyl ester and 2-bromomethyl-5-trifluoromethyl-furan. MS (ESI): mass calcd. for C$_{16}$H$_{13}$F$_6$N$_3$O$_3$, 381.1; m/z found, 382.0 [M+H]$^+$. $^1$H NMR (CDCl$_3$): 7.21 (dd, J=8.4, 1.2 Hz, 1H), 7.03 (d, J=8.4 Hz, 1H), 6.83 (d, J=2.0 Hz, 1H), 6.79-6.78 (m, 1H), 6.51 (d, J=3.1 Hz, 1H), 5.13 (s, 2H), 5.05-4.99 (m, 1H), 3.94-3.87 (m, 4H).

Example 200

3-[5-Trifluoromethyl-2-[1-(3-trifluoromethyl-phenyl)-ethoxy]-phenoxy]-azetidine

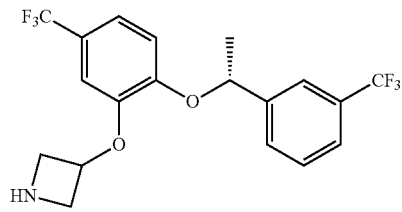 [SMILES: C[C@@H](Oc1ccc(C(F)(F)F)cc1OC1CNC1)c1cccc(C(F)(F)F)c1]

Prepared according to Example 101 using 3-(2-hydroxy-5-trifluoromethyl-phenoxy)-azetidine-1-carboxylic acid tert-butyl ester. MS (ESI): mass calcd. for C$_{19}$H$_{17}$F$_6$NO$_2$, 405.1; m/z found, 406.0 [M+H]$^+$. $^1$H NMR (CDCl$_3$): 7.70 (s, 1H), 7.56 (t, J=7.6 Hz, 2H), 7.47 (t, J=7.7 Hz, 1H), 7.08 (d, J=8.4 Hz, 1H), 6.83-6.80 (m, 2H), 5.41 (q, J=6.4 Hz, 1H), 5.07 (br s, 1H), 4.33-3.64 (m, 4H), 1.70 (d, J=6.5 Hz, 3H).

Example 201

3-[2-(1-Phenyl-ethoxy)-5-trifluoromethyl-phenoxy]-azetidine hydrochloride

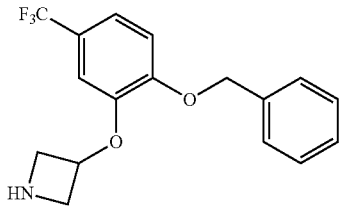

Prepared according to Example 1 using 3-(2-hydroxy-5-trifluoromethyl-phenoxy)-azetidine-1-carboxylic acid tert-butyl ester and benzyl bromide. MS (ESI): mass calcd. for C$_{17}$H$_{16}$F$_3$NO$_2$, 323.1; m/z found, 324.1 [M+H]$^+$. $^1$H NMR (DMSO-D$_6$): 9.39 (s, 2H), 7.49-7.48 (m, 2H), 7.44-7.34 (m, 2H), 7.30 (d, J=8.5 Hz, 1H), 7.13 (d, J=1.9 Hz, 1H), 5.23 (s, 2H), 5.14-5.10 (m, 1H), 4.39-4.34 (m, 2H), 4.01-3.98 (m, 2H).

Example 202

3-[2-(3-Chloro-benzyloxy)-5-fluoro-phenoxy]-azetidine hydrochloride

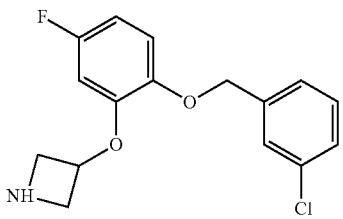 [SMILES: Fc1ccc(OCc2cccc(Cl)c2)c(OC2CNC2)c1]

Step A: Preparation of 2-(3-Chloro-benzyloxy)-5-fluoro-benzaldehyde. A mixture of 5-fluorosalicyladehyde (5.0 g, 36 mmol), 3-chloro-benzyl bromide (7.34 g, 35.7 mmol), K$_2$CO$_3$ (6.0 g, 43 mmol) in DMF (50 mL) was heated at 65° C. for 18 h. The reaction mixture was cooled to rt and diluted with a mixture of EtOAc (500 mL) and H$_2$O (300 mL). The organic phase was separated, washed with H$_2$O (3×250 mL), and dried to give the title compound (9.4 g, 99%) that was used without further purification.

Step B: Preparation of 2-(3-Chloro-benzyloxy)-5-fluoro-phenol. To the title compound from Step A (9.4 g, 36 mmol) in CH$_2$Cl$_2$ (200 mL) was added 77% m-CPBA (12.0 g, 54.0 mmol). The mixture was allowed to stir for 36 h at rt and 10 wt % NaHSO$_3$ (aq.) solution was added. After 48 h, the reaction mixture was washed with H$_2$O (2×250 mL). The organic layer was dried and treated with 1N NaOH (100 mL) and MeOH (100 mL). After 48 h, the MeOH was removed and 1N H$_2$SO$_4$ was added slowly to adjust the pH to 1.5. The resulting solution was extracted with CH$_2$Cl$_2$ (3×150 mL). The combined extracts were washed with H$_2$O and dried to give a red oil (8.4 g). Chromatography (SiO$_2$, 0-20% EtOAc/hexane) gave the title compound (5.0 g, 56%). $^1$H NMR (CDCl$_3$) 7.50-7.16 (m, 4H), 6.87-6.57 (m, 2H), 6.50 (t, J=8.6, 3.0 Hz, 1H), 5.80 (s, 1H), 5.05-4.89 (m, 2H).

Step C: Preparation of 3-[2-(3-Chloro-benzyloxy)-5-fluoro-phenoxy]-azetidine-1-carboxylic acid tert-butyl ester. To the title compound of Step B (200 mg, 0.79 mmol) in DMF (5.0 mL) was added 60 wt % NaH (34.3 mg, 0.86 mmol). The mixture was heated to 50° C. for 1 h then cooled to rt and 3-methanesulfonyloxy-azetidine-1-carboxylic acid tert-butyl ester (Example 90 Step A, 229 mg, 0.91 mmol) in DMF was added. This mixture was heated to 80° C. for 18 h, cooled to rt and treated with EtOAc (50 mL) and H$_2$O (100 mL). The organic layer was separated, washed with H$_2$O (2×50 mL) and dried to give a solid (400 mg). This solid was purified on RP HPLC to yield the title compound (90 mg, 28%). $^1$H NMR (CDCl$_3$) 7.44 (s, 1H), 7.36-7.23 (m, 3H), 6.86 (dd, J=8.9, 5.4 Hz, 1H), 6.60 (dd, J=8.0, 2.9 Hz, 1H), 6.33 (dd, J=9.6, 2.9 Hz, 1H), 5.03 (s, 2H), 4.90-4.80 (m, 1H), 4.33-4.22 (m, 2H), 4.07-4.02 (m, 2H), 1.54-1.28 (m, 9H).

Step D: Preparation of 3-[2-(3-Chloro-benzyloxy)-5-fluoro-phenoxy]-azetidine hydrochloride. The title compound from step C (85 mg) was dissolved in MeOH (5 mL) and 4M HCl in dioxane (3 mL) was added. The mixture was stirred at rt for 18 h. The reaction was concentrated and dried under vacuum to yield the title compound (75 mg). MS (ESI): mass calcd. for C$_{16}$H$_{15}$ClFNO$_2$, 307.8; m/z found, 310.2 [M+H]$^+$. $^1$H NMR (MeOD): 7.46 (s, 1H), 7.37-7.28 (m, 3H), 7.04 (dd, J=9.0 Hz, 5.3, 1H), 6.75-6.61 (m, 2H), 5.09-5.00 (m, 3H), 4.42 (dd, J=12.7, 6.6 Hz, 2H), 4.14 (dd, J=12.7, 4.9 Hz, 2H).

Example 203

3-[2-(3-Chloro-benzyloxy)-5-fluoro-phenoxy]-1-methyl-azetidine

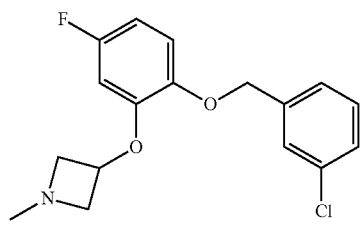 [SMILES: CN1CC(Oc2cc(F)ccc2OCc2cccc(Cl)c2)C1]

Prepared according to general procedure 5 using the title compound from Example 202. MS (ESI): mass calcd. for C$_{17}$H$_{17}$ClFNO$_2$, 321.8; m/z found, 322.2 [M+H]$^+$. $^1$H NMR (CDCl$_3$): 7.47-7.39 (m, 1H), 7.31-7.25 (m, 3H), 6.81 (dd, J=8.9, 5.5 Hz, 1H), 6.56-6.52 (m, 1H), 6.38 (dd, J=9.9, 2.9 Hz, 1H), 5.02 (s, 2H), 4.72-4.67 (m, 1H), 3.87-3.78 (m, 2H), 3.17-3.08 (m, 2H), 2.40 (s, 3H).

Example 204

3-[2-(3-Chloro-benzyloxy)-5-fluoro-phenoxy]-1-isopropyl-azetidine

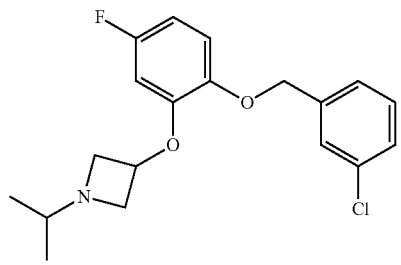 [SMILES: CC(C)N1CC(Oc2cc(F)ccc2OCc2cccc(Cl)c2)C1]

Prepared according to general procedure 3 or 4 using the title compound from Example 202. MS (ESI): mass calcd. for C$_{19}$H$_{21}$ClFNO$_2$, 349.8; m/z found, 350.2 [M+H]$^+$. $^1$H NMR (CDCl$_3$): 7.44 (s, 1H), 7.29-7.26 (m, 3H), 6.81 (dd, J=8.9, 5.5 Hz, 1H), 6.54-6.52 (m, 1H), 6.41 (dd, J=9.9, 2.9, 1H), 5.01 (s, 2H), 4.73-4.68 (m, 1H), 3.85-3.77 (m, 2H), 3.11-3.04 (m, 2H), 2.43-2.36 (m, 1H), 0.95 (d, J=6.2 Hz, 6H).

Example 205

3-[2-(3-Chloro-benzyloxy)-5-fluoro-phenoxy]-1-cyclobutyl-azetidine

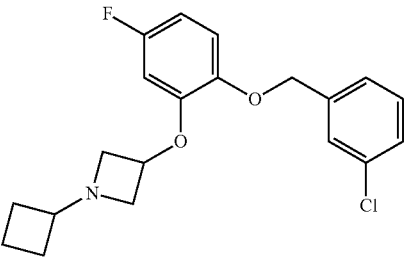 [SMILES: Fc1ccc(OCc2cccc(Cl)c2)c(OC2CN(C3CCC3)C2)c1]

Prepared according to general procedure 3 or 4 using the title compound from Example 202. MS (ESI): mass calcd. for C$_{20}$H$_{21}$ClFNO$_2$, 361.8; m/z found, 362.2 [M+H]$^+$. $^1$H NMR (CDCl$_3$): 7.44 (s, 1H), 7.32-7.22 (m, 3H), 6.82 (dd, J=8.9, 5.5 Hz, 1H), 6.57-6.53 (m, 1H), 6.41 (dd, J=9.8, 2.9 Hz, 1H), 5.02 (s, 2H), 4.77-4.72 (m, 1H), 3.77-3.69 (m, 2H), 3.23-3.12 (m, 3H), 2.01-1.95 (m, 2H), 1.87-1.62 (m, 4H).

Example 206

3-[2-(3-Chloro-benzyloxy)-5-fluoro-phenoxy]-1-propyl-azetidine

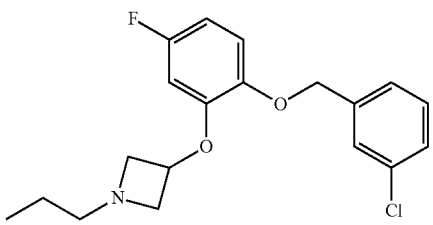 [SMILES: CCCN1CC(Oc2cc(F)ccc2OCc2cccc(Cl)c2)C1]

Prepared according to general procedure 3 or 4 using the title compound from Example 202. MS (ESI): mass calcd. for $C_{19}H_{21}ClFNO_2$, 349.8; m/z found, 350.2 [M+H]⁺. ¹H NMR (CDCl₃): 7.46 (s, 1H), 7.30 (m, 3H), 6.83 (dd, J=8.9, 5.5 Hz, 1H), 6.59-6.51 (m, 1H), 6.42 (dd, J=9.9, 2.9 Hz, 1H), 5.04 (s, 2H), 4.78-4.73 (m, 1H), 3.8-3.80 (m, 2H), 3.13-3.05 (m, 2H), 2.52-2.44 (m, 2H), 1.45-1.34 (m, 2H), 0.91 (t, J=7.4 Hz, 3H).

Example 207

3-[2-(3-Chloro-benzyloxy)-5-fluoro-phenoxy]-1-ethyl-azetidine

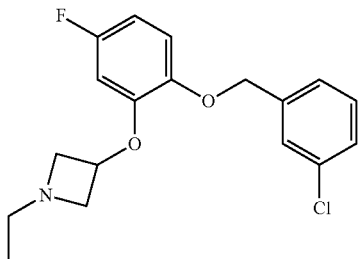 [SMILES: CCN1CC(Oc2cc(F)ccc2OCc2cccc(Cl)c2)C1]

Prepared according to general procedure 3 or 4 using the title compound from Example 202. MS (ESI) mass calcd. for $C_{18}H_{19}ClFNO_2$, 335.8; m/z found, 338.2 [M+H]⁺. ¹H NMR (CDCl₃) 7.47 (s, 1H), 7.32-7.28 (m, 3H), 6.84 (dd, J=8.9, 5.5 Hz, 1H), 6.59-6.55 (m, 1H), 6.43 (dd, J=9.8, 2.9 Hz, 1H), 5.04 (s, 2H), 4.79-4.74 (m, 1H), 3.87-3.80 (m, 2H), 3.15-3.06 (m, 2H), 2.59-2.54 (m, 2H), 1.01 (dd, J=8.8, 5.6 Hz, 3H).

Example 208

3-[5-Fluoro-2-(5-trifluoromethyl-furan-2-yl-methoxy)-phenoxy]-azetidine

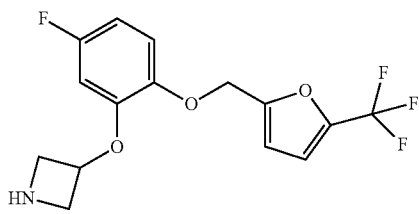 [SMILES: Fc1ccc(OCc2ccc(C(F)(F)F)o2)c(OC2CNC2)c1]

Prepared according top Example 202 using 2-bromomethyl-5-trifluoromethyl-furan. MS (ESI): mass calcd. for $C_{15}H_{13}F_4NO_3$, 331.26; m/z found, 332.2 [M+H]⁺. ¹H NMR (CDCl₃): 6.91 (dd, J=8.9, 5.5 Hz, 1H), 6.77 (d, J=2.3, 1H), 6.66-6.53 (m, 1H), 6.49-6.29 (m, 2H), 5.04 (s, 2H), 5.00-4.92 (m, 1H), 3.98-3.94 (m, 4H), 2.44 (s br, 1H).

Example 209

3-[5-Fluoro-2-(5-trifluoromethyl-furan-2-yl-methoxy)-phenoxy]-1-isopropyl-azetidine

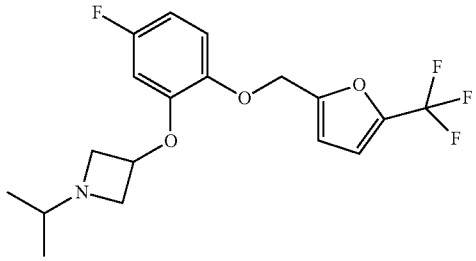 [SMILES: CC(C)N1CC(Oc2cc(F)ccc2OCc2ccc(C(F)(F)F)o2)C1]

Prepared according to general procedure 3 or 4 using the title compound from Example 208. MS (ESI): mass calcd. for $C_{18}H_{19}F_4NO_3$, 373.3; m/z found, 374.1 [M+H]⁺. ¹H NMR (CDCl₃): 6.89 (dd, J=8.9, 5.5 Hz, 1H), 6.77-6.75 (m, 1H), 6.63-6.51 (m, 1H), 6.44-6.41 (m, 2H), 5.01 (s, 2H), 4.78-4.58 (m, 1H), 3.83 (dd, J=8.8, 6.0 Hz, 2H), 3.09 (dd, J=8.8, 6.0 Hz, 2H), 2.47-2.31 (m, 1H), 0.97 (d, J=6.2 Hz, 6H).

Example 210

3-[2-(3-Chloro-benzyloxy)-5-thiophen-3-yl-phenoxy]-azetidine

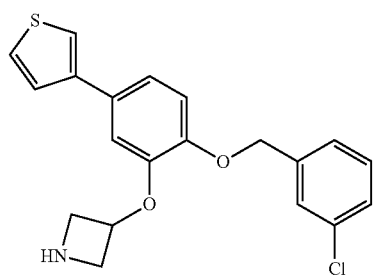 [SMILES: Clc1cccc(COc2ccc(-c3ccsc3)cc2OC2CNC2)c1]

3-[5-Bromo-2-(3-chloro-benzyloxy)-phenoxy]-azetidine-1-carboxylic acid tert-butyl ester (188 mg, 0.4 mmol), 3-thiophene boronic acid (53 mg, 0.41 mmol), Q-Phos (23 mg, 0.032 mmol), Pd(dba)₂ (9.2 mg, 0.016 mmol) and K₃PO₄ (255 mg, 1.2 mmol) were taken into toluene (3 mL) and heated at 80° C. After the reaction was complete it was cooled to rt, diluted with CH₂Cl₂ (20 mL), filtered, washed with H₂O (2×25 mL) and concentrated to give 3-[2-(3-chloro-benzyloxy)-5-thiophen-3-yl-phenoxy]-azetidine-1-carboxylic acid tert-butyl ester. To this compound was added MeOH (10 mL) followed by 4M HCl in dioxane (4 mL). After 4 h the reaction was concentrated and purified on RP HPLC (basic) to yield the title compound (12 mg). MS (ESI): mass calcd. for $C_{20}H_{18}ClNO_2S$, 371.9; m/z found, 372.2 [M+H]⁺. ¹H NMR (CDCl₃): 10.30-9.57 (m, 1H), 7.43 (s, 1H), 7.40-7.28 (m, 6H), 7.24 (dd, J=8.4, 2.1 Hz, 1H), 7.01 (d, J=2.1 Hz, 1H), 6.96 (d, J=8.5 Hz, 1H), 5.24-4.99 (m, 3H), 4.40-4.11 (m, 4H).

Example 211

3-(Azetidin-3-yloxy)-4-(3-chloro-benzyloxy)-N,N-dimethyl-benzamide

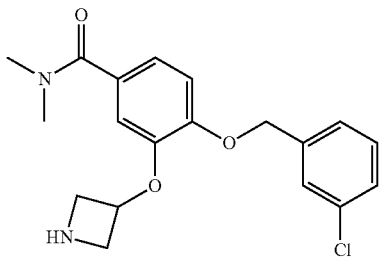 [SMILES: CN(C)C(=O)c1ccc(OCc2cccc(Cl)c2)c(OC2CNC2)c1]

A suspension of 3-[5-bromo-2-(3-chloro-benzyloxy)-phenoxy]-azetidine-1-carboxylic acid tert-butyl ester (94 mg, 0.2 mmol), Na$_2$CO$_3$ (53 mg, 0.5 mmol), 40% Me$_2$NH in H$_2$O (0.17 mmol), Hermann's catalyst (8 mg, 0.008 mmol) and Mo(CO)$_6$ (22 mg, 0.083 mmol) in H$_2$O (2 mL) was heated to 170° C. in a microwave reactor for 10 min. The reaction was cooled rt, and saturated NaHCO$_3$ (aq.) was added. This solution was extracted with CH$_2$Cl$_2$ (3×). The combined organic layers were concentrated to give a solid (30 mg) that was dissolved in MeOH (2 mL) and treated with 4M HCl in dioxane (1 mL). After 3 h, the mixture was concentrated to give a residue that was purified on RP HPLC providing the title compound (5 mg). MS (ESI): mass calcd. for C$_{19}$H$_{21}$ClN$_2$O$_3$, 360.8; m/z found, 361.1 [M+H]$^+$. $^1$H NMR (CDCl$_3$): 7.45 (s, 1H), 7.29-7.27 (m, 3H), 6.96 (dd, J=8.2, 1.9 Hz, 1H), 6.87 (d, J=8.3 Hz, 1H), 6.72 (d, J=1.9 Hz, 1H), 5.11 (s, 2H), 5.05-4.95 (m, 1H), 3.92-3.85 (m, 4H), 3.00 (s br, 6H).

Example 212

3-[5-Bromo-2-(3-chloro-benzyloxy)-phenoxy]-3-methyl-azetidine

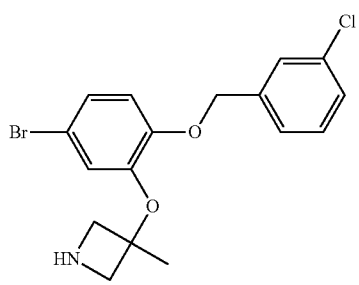 [SMILES: CC1(Oc2cc(Br)ccc2OCc2cccc(Cl)c2)CNC1]

Step A: Preparation of 1-benzhydryl-3-methyl-azetidin-3-ol. To 1-benzhydryl-azetidin-3-one (1.0 g, 4.2 mmol) in ether (100 mL) at 0° C. was added CH$_3$MgBr (1.5 mL, 3M in ether). The mixture was warmed to rt over 1 h and 1N NaOH (3 mL) was added. The organic layer was concentrated providing the title compound (1.1 g). MS (ESI): mass calcd. for C$_{17}$H$_{19}$NO, 253.2; m/z found, 254.2 [M+H]$^+$. $^1$H NMR (CDCl$_3$): 7.42-7.11 (m, 10H), 4.32 (s, 1H), 3.14 (d, J=8.5 Hz, 2H), 2.96 (d, J=8.5 Hz, 2H), 1.43 (s, 3H).

Step B: Preparation of 1-benzhydryl-3-[5-bromo-2-(3-chloro-benzyloxy)-phenoxy]-3-methyl-azetidine. The mixture of the title compound from Step A (0.5 mmol), 5-bromo-2-(3-chloro-benzyloxy)-phenol (0.5 mmol), and cyanomethylenetri-n-butylphosphorane (0.5 mmol) in toluene (3 mL) was heated at 150° C. in a microwave reactor for 1 h. The mixture was cooled to rt and purified via PTLC providing the title compound (120 mg). MS (ESI): mass calcd. for C$_{30}$H$_{27}$BrClNO$_2$, 547.1; m/z found, 548.0 [M+H]$^+$.

Step C: Preparation of 3-[5-Bromo-2-(3-chloro-benzyloxy)-phenoxy]-3-methyl-azetidine. The title compound from Step B (60 mg) was dissolved in DCE (10 mL) and chloroethylformate (0.2 mmol) was added. The mixture was heated at 80-100° C. for 1 h and concentrated. The residue was dissolved in MeOH (3 mL) and heated at 150° C. in a microwave reactor for another 1 h. The mixture was cooled to rt and purified via PTLC providing the title compound (30 mg). MS (ESI): mass calcd. for C$_{17}$H$_{17}$BrClNO$_2$, 381.0; m/z found, 382.0 [M+H]$^+$. $^1$H NMR (CDCl$_3$): 7.43-7.23 (m, 4H), 7.12-7.06 (m, 1H), 6.86-6.78 (m, 2H), 5.12 (s, 2H), 4.24-4.16 (m, 2H), 3.78-3.67 (m, 2H), 1.67 (s, 3H).

Example 213

3-[5-Bromo-2-(3-chloro-benzyloxy)-phenoxy]-3-ethyl-azetidine

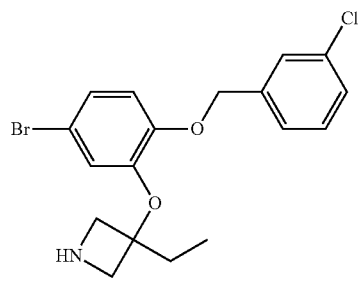 [SMILES: CCC1(Oc2cc(Br)ccc2OCc2cccc(Cl)c2)CNC1]

Prepared according to Example 212 using the ethylmagnesium bromide in Step A. MS (ESI): mass calcd. for C$_{18}$H$_{19}$BrClNO$_2$, 395.0; m/z found, 396.1 [M+H]$^+$. $^1$H NMR (CDCl$_3$): 7.41-7.25 (m, 4H), 7.15-7.05 (m, 1H), 6.84-6.73 (m, 2H), 5.13 (s, 2H), 4.26-4.19 (m, 2H), 3.85-3.74 (m, 2H), 2.19-2.00 (m, 2H), 1.00-0.90 (m, 3H).

Example 214

3-[5-Bromo-2-(3-chloro-benzyloxy)-phenoxy]-3-isopropyl-azetidine

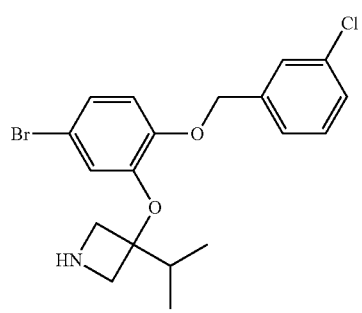 [SMILES: CC(C)C1(Oc2cc(Br)ccc2OCc2cccc(Cl)c2)CNC1]

Prepared according to Example 212 using the isopropylmagnesium bromide in Step A. MS (ESI): mass calcd. for $C_{19}H_{21}BrClNO_2$, 409.0; m/z found, 409.9 [M+H]$^+$. $^1$H NMR (CDCl$_3$): 7.43-7.23 (m, 4H), 7.14-6.78 (m, 3H), 5.13 (s, 2H), 3.98-3.85 (m, 2H), 3.48-3.33 (m, 2H), 1.45-1.36 (m, 1H), 0.63-0.50 (m, 6H).

Example 215

3-(5-Bromo-2-phenethyloxy-phenoxy)-3-methyl-azetidine

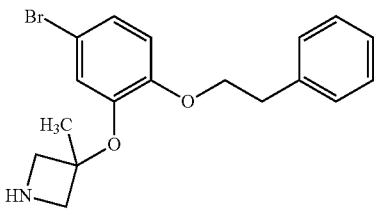 [SMILES: CC1(Oc2cc(Br)ccc2OCCc2ccccc2)CNC1]

Step A: Preparation of (4-Bromo-2-fluoro-benzylidene)-tert-butyl-amine. A mixture of 4-bromo-2-fluorobenzaldehyde (10 g, 47 mmol), tert-butyl amine (6.1 mL, 57 mmol) and 4 Å powder molecular sieves (8.0 g) in 160 mL CH$_2$Cl$_2$ (160 mL) was stirred at rt for 18 h. The reaction mixture was filtered through a pad of celite and concentrated to give the title compound (9.9 g, 78%). MS (ESI): mass calcd. for $C_{11}H_{13}BrFNO$, 258.1; m/z found, 260.0 [M+H]$^+$. $^1$H NMR (CDCl$_3$): 10.32 (s, 1H), 8.48 (s, 1H), 7.89 (t, J=8.1 Hz, 1H), 7.50-7.20 (m, 1H), 1.49-1.08 (m, 9H).

Step B: Preparation of 3-hydroxy-3-methyl-azetidine-1-carboxylic acid tert-butyl ester. A solution of 1-Boc-azetidin-3-one (3.5 g, 20 mmol) in 50 mL and Et$_2$O was cooled to 0° C. and 3M MeMgBr in Et$_2$O (10 mL, 30 mmol) was added dropwise over 1 h. After 45 min, the reaction was allowed to warm to rt and stir an additional for 18 h. Then ½ sat'd NH$_4$Cl (aq.) was added and the mixture extracted with EtOAc (2×). The combined organic layers were dried and the resulting semisolid was purified by RP HPLC (Agilent) to give the title compound as a white solid (3.2 g, 84%). $^1$H NMR (CDCl$_3$): 3.84 (q, J=9.2 Hz, 4H), 1.97 (bs, 1H), 1.52 (s, 3H), 1.44 (m, 9H).

Step C: Preparation of 3-(5-Bromo-2-formyl-phenoxy)-3-methyl-azetidine-1-carboxylic acid tert-butyl ester. To a solution of the title compound from Step B (400 mg, 2.2 mmol) in DMSO (8 mL) was added 60% NaH (120 mg, 3.0 mmol). After 30 min, the title compound from Step A was added and the resulting mixture was heated at 125° C. for 1 h in a microwave reactor. An additional quantity of the title compound from Step B (100 mg) and 60% NaH (32 mg) were added to the reaction. Heating was then resumed at 125° C. for another 1 h in a microwave reactor. The reaction was diluted with H$_2$O and extracted with EtOAc (3×) followed by methanolic EtOAc (2×). The organics were dried, then THF (5 mL), H$_2$O (5 mL) and AcOH (3 mL) were added. After 18 h at rt, the reaction was diluted with H$_2$O and extracted with CH$_2$Cl$_2$. The organics were dried and purified by PTLC to give the title compound as an off white solid (247 mg, 31%). $^1$H NMR (CDCl$_3$): 10.36 (s, 1H), 7.74 (d, J=8.3 Hz, 1H), 7.22-7.20 (m, 1H), 6.68 (d, J=1.6 Hz, 1H), 4.25 (d, J=9.2 Hz, 2H), 4.03 (d, J=9.8 Hz, 2H), 1.55 (s, 3H), 1.46 (m, 9H).

Step D: Preparation of 3-(5-Bromo-2-hydroxy-phenoxy)-3-methyl-azetidine-1-carboxylic acid tert-butyl ester. Prepared according to Example 1 Step C using the title compound from Step C. Purification was accomplished by PTLC to give the title compound as a peach solid (152 mg, 64%). $^1$H NMR (CDCl$_3$): 7.02 (dd, J=8.5, 2.2 Hz, 1H), 6.84 (d, J=8.5 Hz, 1H), 6.63 (d, J=2.2 Hz, 1H), 4.22 (d, J=9.2 Hz, 2H), 3.98 (d, J=9.5 Hz, 2H), 3.49 (s, 1H), 1.69 (s, 3H), 1.46 (s, 9H).

Step E. Preparation of 3-(5-Bromo-2-phenethyloxy-phenoxy)-3-methyl-azetidine-1-carboxylic acid tert-butyl ester. A mixture of 3-(5-bromo-2-hydroxy-phenoxy)-3-methyl-azetidine-1-carboxylic acid tert-butyl ester (30 mg, 0.08 mmol), (2-bromoethyl)benzene (29 µL, 0.21 mmol), KI (42 mg, 0.25 mmol) and Cs$_2$CO$_3$ (82 mg, 0.25 mmol) in 3 mL DMF was stirred at rt for 18 h. The reaction mixture was diluted with H$_2$O and extracted with EtOAc (3×). The organic layers were dried and purified by RP HPLC (Agilent) to give the title compound as an oil (22 mg, 58%). MS (ESI): mass calcd. for $C_{23}H_{28}BrNO_4$, 462.4; m/z found, 408.0 [M-56+H]$^+$. $^1$H NMR (CDCl$_3$): 7.38-7.18 (m, 5H), 7.07 (dd, J=8.6, 2.3 Hz, 1H), 6.76-6.74 (m, 2H), 4.24-4.08 (m, 4H), 3.84 (d, J=9.7 Hz, 2H), 3.11 (t, J=7.1 Hz, 2H), 1.58 (s, 3H), 1.45 (s, 9H).

Step F: Preparation of 3-(5-Bromo-2-phenethyloxy-phenoxy)-3-methyl-azetidine. A mixture of 3-(5-bromo-2-phenethyloxy-phenoxy)-3-methyl-azetidine-1-carboxylic acid tert-butyl ester (20 mg) and TFA (1 mL) in CH$_2$Cl$_2$ (2 mL) was stirred at rt for 2 h. The reaction was concentrated in vacuo and purified by PTLC followed by additional purification using RP HPLC (Agilent) to give the title compound as an oil (12 mg, 77%). MS (ESI): mass calcd. for $C_{18}H_{20}BrNO_2$, 362.3; m/z found, 362.0 [M+H]$^+$. $^1$H NMR (CDCl$_3$): 7.38-7.18 (m, 5H), 7.04 (dd, J=8.6, 2.3 Hz, 1H), 6.74 (dd, J=5.5, 3.1, 2H), 4.15 (t, J=7.2 Hz, 2H), 3.97 (d, J=8.9 Hz, 2H), 3.45 (d, J=9.2 Hz, 2H), 3.11 (t, J=7.1 Hz, 2H), 1.98 (s, 1H), 1.65 (s, 3H).

The compounds in Examples 216-217 were prepared according to Example 215 using the appropriate alkyl halide in Step E.

Example 216

3-[5-Bromo-2-(5-trifluoromethyl-furan-2-yl-methoxy)-phenoxy]-azetidine

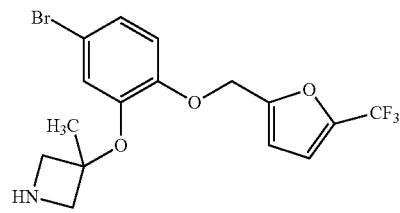 [SMILES: CC1(Oc2cc(Br)ccc2OCc2ccc(C(F)(F)F)o2)CNC1]

MS (ESI): mass calcd. for $C_{16}H_{15}BrF_3NO_3$, 406.2; m/z found, 407.9 [M+H]$^+$. $^1$H NMR (CDCl$_3$): 7.05 (dd, J=8.6, 2.3 Hz, 1H), 6.83 (d, J=8.8 Hz, 1H), 6.76-6.75 (m, 2H), 6.45-6.44 (m, 1H), 5.02 (s, 2H), 4.00 (d, J=9.0 Hz, 2H), 3.59-3.43 (m, 2H), 2.35 (br s, 1H), 1.67 (s, 3H).

Example 217

3-[5-Bromo-2-(3-trifluoromethyl-benzyloxy)-phenoxy]-azetidine

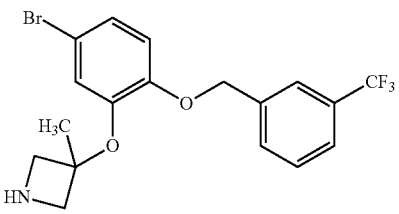 [SMILES: CC1(Oc2cc(Br)ccc2OCc2cccc(C(F)(F)F)c2)CNC1]

MS (ESI): mass calcd. for $C_{18}H_{17}BrF_3NO_2$, 416.2; m/z found, 416.0 [M+H]$^+$. $^1$H NMR (CDCl$_3$): 7.72 (bs, 1H), 7.59-7.57 (m, 2H), 7.51-7.46 (m, 2H), 7.03 (dd, J=8.6, 2.3 Hz, 1H), 6.79 (d, J=8.4 Hz, 1H), 6.74 (d, J=2.4 Hz, 1H), 5.11 (s, 2H), 4.03 (br s, 2H), 3.54 (bs, 2H), 1.71 (s, 3H).

Example 218

3-(5-Bromo-2-phenoxy-phenoxy)-3-methyl-azetidine

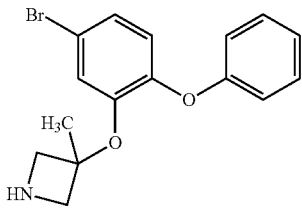 [SMILES: CC1(Oc2cc(Br)ccc2Oc2ccccc2)CNC1]

Prepared according to general procedure 6 using the title compound of Example 215 Step D. MS (ESI): mass calcd. for $C_{16}H_{16}BrNO_2$, 334.2; m/z found, 334.0 [M+H]$^+$. $^1$H NMR (CDCl$_3$): 7.34-7.24 (m, 2H), 7.08-7.04 (m, 2H), 6.94-6.86 (m, 3H), 6.80 (d, J=2.3, 1H), 3.88 (d, J=8.3 Hz, 2H), 3.46 (d, J=8.7 Hz, 2H), 1.85 (br s, 1H), 1.65 (s, 3H).

Example 219

(±)-trans-3-[5-Bromo-2-(3-fluoro-benzyloxy)-phenoxy]-2-methyl-azetidine

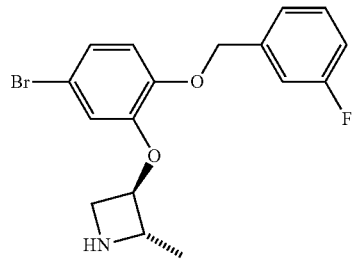 [SMILES: C[C@@H]1NC[C@H]1Oc1cc(Br)ccc1OCc1cccc(F)c1]

Step A. Preparation of (±)-2-bromomethyl-3-methyl-oxirane. See Shimizu et al., *Organic Process & Research Development*, 2005, Vol 9(3), pp. 278-287. To a stirred solution of crotyl bromide (10 g, 63 mmol) in CH$_2$Cl$_2$ (200 mL) was slowly added 77% m-CPBA (19.8 g, 88 mmol) portionwise over 45 min. After stirring at rt for 18 h, the solids were removed by filtration. The filtrate was treated with aqueous 10% aq. NaHSO$_3$ (150 mL) and stirred at rt for 5 h. The organic layer was separated, washed with sat'd NaHCO$_3$ (3×), brine (2×) and dried to give the title compound as a colorless oil (6.6 g, 70%). $^1$H NMR (CDCl$_3$): 3.43-3.39 (m, 1H), 3.35-3.18 (m, 1H), 3.04-2.89 (m, 2H), 1.35 (d, J=5.2 Hz, 3H).

Step B. Preparation of cis and trans 1-benzhydryl-2-methyl-azetidin-3-ol. See PCT pat appl. WO 01/01988. A mixture of 2-bromomethyl-3-methyl-oxirane (3.6 g, 23.8 mmol) and aminodiphenylmethane (4.1 mL, 23.8 mmol) in 12 mL MeOH was stirred at rt for 72 h. Next, the reaction was heated at reflux for 72 h. After cooling to rt, the reaction was purified by reverse phase basic HPLC (Agilent) to give the cis and trans isomers of the title compound. Trans isomer as an oil (424 mg), $^1$H NMR (CDCl$_3$): 7.44-7.35 (m, 4H), 7.28-7.12 (m, 7H), 4.34 (s, 1H), 3.93-3.90 (m, 1H), 3.67-3.64 (m, 1H), 3.03-2.99 (m, 1H), 2.57-2.55 (m, 1H), 0.75 (d, J=6.1, 3H). Cis isomer as an off white solid (914 mg), $^1$H NMR (CDCl$_3$): 7.42-7.36 (m, 4H), 7.28-7.22 (m, 4H), 7.18-7.16 (m, 2H), 4.37 (s, 1H), 4.30-4.27 (m, 1H), 3.46-3.42 (m, 1H), 3.26-3.24 (m, 1H), 3.06-3.04 (m, 1H), 0.74 (d, J=6.5 Hz, 3H).

Step C. Preparation of (±)-trans-1-3-[5-Bromo-2-(3-fluoro-benzyloxy)-phenoxy]-2-methyl-azetidine. Prepared according to Example 212 Steps B-C using the trans-isomer from Step B. MS (ESI): mass calcd. for $C_{17}H_{17}BrFNO_2$, 365.0; m/z found, 366.1 [M+H]$^+$. $^1$H NMR (MeOD): 7.43-6.95 (m, 7H), 5.12 (s, 2H), 4.68-4.62 (m, 1H), 4.32-4.25 (m, 1H), 3.98-3.92 (m, 1H), 3.75-3.68 (m, 1H), 1.44 (d, J=6.7 Hz, 3H).

Example 220 cis-1-Benzyl-3-[5-bromo-2-(3-fluoro-benzyloxy)-phenoxy]-2-methyl-azetidine

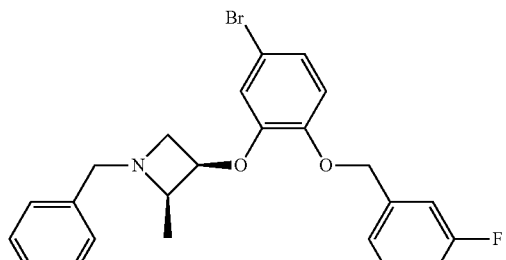

Prepared from cis-(±)-1-benzyl-2-methyl-azetidin-3-ol according to Example 219. MS (ESI): mass calcd. for $C_{24}H_{23}BrFNO_2$, 455.1; m/z found, 456.0 [M+H]$^+$. $^1$H NMR (CDCl$_3$): 7.39-6.94 (m, 11H), 6.78-6.69 (m, 2H), 5.08 (s, 2H), 4.78-4.72 (m, 1H), 3.76-3.62 (m, 3H), 3.54-3.48 (m, 1H), 3.34-3.26 (m, 1H), 1.20 (d, J=6.4 Hz, 3H).

Example 221 trans-1-Benzyl-3-[5-bromo-2-(3-fluoro-benzyloxy)-phenoxy]-2-methyl-azetidine

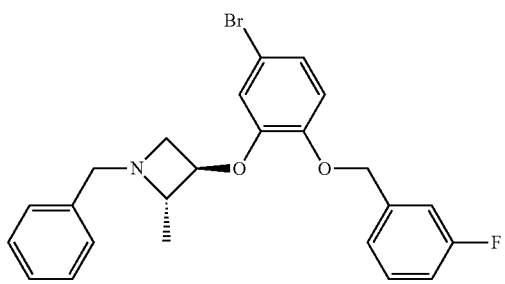 [SMILES: C[C@H]1[C@H](Oc2cc(Br)ccc2OCc2cccc(F)c2)CN1Cc1ccccc1]

Prepared from trans-(±)-1-benzyl-2-methyl-azetidin-3-ol according to Example 219. MS (ESI): mass calcd. for $C_{24}H_{23}BrFNO_2$, 455.1; m/z found, 456.0 [M+H]+. 1H NMR (CDCl3): 7.38-7.22 (m, 5H), 7.17-7.16 (m, 2H), 7.05-6.96 (m, 2H), 6.84 (d, J=2.2 Hz, 1H), 6.74 (d, J=8.6 Hz, 1H), 5.07 (s, 2H), 4.33 (q, J=6.0 Hz, 1H), 3.82-3.80 (m, 2H), 3.57 (d, J=6.9 Hz, 1H), 3.41-3.39 (m, 1H), 2.87 (t, J=7.0 Hz, 1H), 1.21 (d, J=6.2 Hz, 3H).

Example 222

3-[5-Chloro-2-(1-phenyl-azetidin-3-ol)-phenoxy]-azetidine

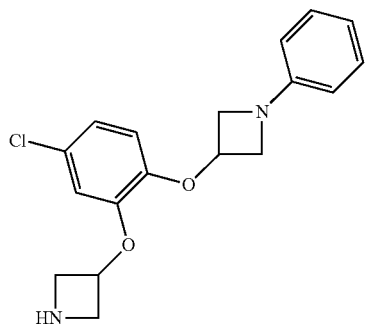 [SMILES: Clc1ccc(OC2CN(c3ccccc3)C2)c(OC2CNC2)c1]

Step A: Preparation of 1-phenyl-azetidin-3-ol. The mixture of azetidin-3-ol (2 mmol), bromobenzene (2 mmol), Pd(OAc)2 (0.1 mmol), 2-(di-tert-butylphosphino)biphenyl (0.2 mmol) and NaOtBu (3 mmol) in toluene (3 mL) was heated at 100° C. for 1 h. The mixture was cooled to rt and purified via PTLC providing the title compound (15 mg).

Step B: Preparation of 3-[5-Chloro-2-(1-phenyl-azetidin-3-ol)-phenoxy]-azetidine. The mixture of the title compound of Step A (15 mg), 3-(5-chloro-2-hydroxy-phenoxy)-azetidine-1-carboxylic acid tert-butyl ester (0.2 mmol) and cyanomethylenetri-n-butylphosphorane (0.2 mmol) in toluene (2 mL) was heated at 120° C. in a microwave reactor for 1 h. The mixture was cooled to rt and purified via PTLC providing the title compound (20 mg). This compound was dissolved in CH2Cl2 (5 mL) and TFA (1 mL) was added. The mixture was stirred at rt for 4 h and concentrated to provide the title compound (25 mg). MS (ESI): mass calcd. for $C_{18}H_{19}ClN_2O_2$, 330.1; m/z found, 331.1 [M+H]+. 1H NMR (MeOD): 7.26-6.58 (m, 8H), 5.20-5.05 (m, 2H), 4.55-4.45 (m, 2H), 4.37-4.28 (m, 2H), 4.25-4.16 (m, 2H), 3.88-3.85 (m, 2H).

Examples 223-225 were prepared similar to Example 222 using the appropriately substituted hydroxyazetidine.

Example 223

(±)-3-[5-Chloro-2-(trans-1-benzyl-2-methyl-azetidin-3-ol)-phenoxy]-azetidine

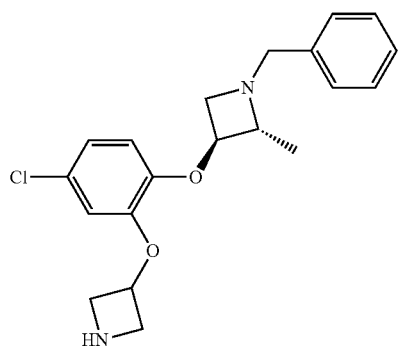 [SMILES: C[C@@H]1[C@@H](Oc2ccc(Cl)cc2OC2CNC2)CN1Cc1ccccc1]

Prepared from trans-(±)-1-benzyl-2-methyl-azetidin-3-ol. MS (ESI): mass calcd. for $C_{20}H_{23}ClN_2O_2$, 358.1; m/z found, 359.1 [M+H]+. 1H NMR (MeOD): 7.61-7.43 (m, 5H), 7.03-6.87 (m, 3H), 5.23-5.16 (m, 1H), 4.88-4.78 (m, 1H), 4.76-4.65 (m, 1H), 4.63-4.45 (m, 5H), 4.29-4.19 (m, 2H), 4.18-4.09 (m, 1H), 1.40 (d, J=6.7 Hz, 3H).

Example 224

3-[5-Chloro-2-(1-Isopropyl-azetidin-3-ol)-phenoxy]-azetidine

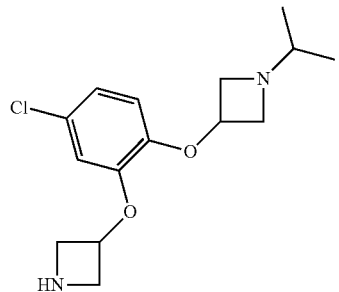 [SMILES: CC(C)N1CC(Oc2ccc(Cl)cc2OC2CNC2)C1]

Prepared from 1-isopropyl-azetidin-3-ol. MS (ESI): mass calcd. for $C_{15}H_{21}ClN_2O_2$, 296.1; m/z found, 297.0 [M+H]+. 1H NMR (MeOD): 7.70 (dd, J=8.7, 2.5 Hz, 1H), 6.78-6.67 (m, 2H), 5.04-4.97 (m, 1H), 4.76-4.67 (m, 1H), 3.98-3.92 (m, 2H), 3.80-3.67 (m, 4H), 3.34-3.26 (m, 2H), 2.53-2.46 (m, 1H), 0.98 (d, J=6.3 Hz, 6H).

Example 225

3-[5-Chloro-2-(1-benzhydryl-azetidin-3-ol)-phenoxy]-azetidine

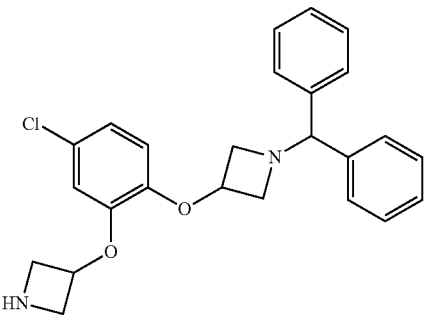 [SMILES: Clc1ccc(OC2CN(C(c3ccccc3)c3ccccc3)C2)c(OC2CNC2)c1]

Prepared from 1-benzhydryl-azetidin-3-ol. MS (ESI): mass calcd. for $C_{25}H_{25}ClN_2O_2$, 420.2; m/z found, 421.0 [M+H]$^+$. $^1$H NMR (MeOD): 7.58-7.39 (m, 10H), 7.02-6.81 (m, 3H), 5.81 (s, 1H), 5.19-5.10 (m, 2H), 4.67-4.50 (m, 4H), 4.39-4.31 (m, 2H), 4.23-4.16 (m, 2H).

Example 226

3-[5-Chloro-2-(1-azetidin-3-ol)-phenoxy]-azetidine

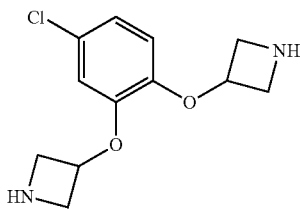 [SMILES: Clc1ccc(OC2CNC2)c(OC2CNC2)c1]

Prepared according to the procedure of Example 222 Step B using 3-hydroxy-azetidine-1-carboxylic acid tert-butyl ester. MS (ESI): mass calcd. for $C_{12}H_{15}ClN_2O_2$, 254.1; m/z found, 255.1 [M+H]$^+$. $^1$H NMR (MeOD): 7.00 (dd, J=8.6, 2.4 Hz, 1H). 6.91 (d, J=2.4 Hz, 1H), 6.83 (d, J=8.6 Hz, 1H), 5.22-5.11 (m, 2H), 4.62-4.53 (m, 4H), 4.31-4.22 (m, 4H).

Example 227

3-[5-Chloro-2-(1-Isopropyl-azetidin-3-ol)-phenoxy]-1-isopropyl-azetidine

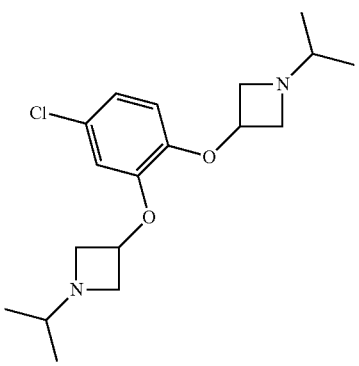 [SMILES: CC(C)N1CC(Oc2ccc(Cl)cc2OC2CN(C(C)C)C2)C1]

To the title compound of Step 226 (100 mg) in CH$_2$Cl$_2$ (50 mL) was added acetone (100 µL) and NaBH$_3$CN (1 mL, 1M in CH$_2$Cl$_2$). The mixture was stirred at rt for 16 h. Then, NaOH solution (2 mL, 1M in H$_2$O) was added. After 1 h, the organic layer was separated and concentrated. PTLC provided the title compound (20 mg). MS (ESI): mass calcd. for $C_{18}H_{27}ClN_2O_2$, 338.2; m/z found, 339.3 [M+H]$^+$. $^1$H NMR (CDCl$_3$): 6.85 (dd, J=8.6, 2.4 Hz, 1H). 6.63 (d, J=2.4 Hz, 1H), 6.58 (d, J=8.6 Hz, 1H), 4.83-4.67 (m, 2H), 3.96-3.76 (m, 4H), 3.26-3.05 (m, 4H), 2.47-2.38 (m, 2H), 1.00 (d, J=6.1 Hz, 12H).

Example 228

3-[5-Chloro-2-(3-phenyl-cyclobutoxy)-phenoxy]-azetidine

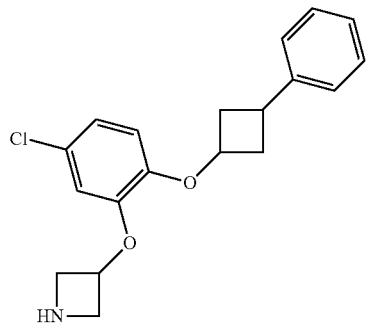 [SMILES: Clc1ccc(OC2CC(c3ccccc3)C2)c(OC2CNC2)c1]

Step A: Preparation of 3-phenyl-cyclobutanol. To the solution of 3-phenyl-cyclobutanone (100 mg) in THF (10 mL) was added LiAlH$_4$ (0.2 mL, 2M in THF). The mixture was stirred at rt for 2 h, then 2M NaOH (1 mL) was added. The organic layer was concentrated and purified by PTLC providing the title compound (80 mg).

Step B: Preparation of 3-[5-Chloro-2-(3-phenyl-cyclobutoxy)-phenoxy]-azetidine. The mixture of the title compound of Step A (80 mg), 3-(5-chloro-2-hydroxy-phenoxy)-azetidine-1-carboxylic acid tert-butyl ester (200 mg) and cyanomethylenetri-n-butylphosphorane (1.0 mmol) in toluene (2 mL) was heated at 120° C. in a microwave reactor for 1 h. The mixture was cooled to rt and purified via PTLC providing 3-[5-chloro-2-(3-phenyl-cyclobutoxy)-phenoxy]-azetidine-1-carboxylic acid tert-butyl ester (120 mg). The ester was re-dissolved into CH$_2$Cl$_2$ (10 mL), and TFA (2 mL) was added. The mixture was stirred at rt for 4 h then concentrated to give the title compound (168 mg). MS (ESI): mass calcd. for $C_{19}H_{20}ClNO_2$, 329.1; m/z found, 330.1 [M+H]$^+$. $^1$H NMR (MeOD): 7.26-6.64 (m, 8H), 5.30-5.15 (m, 2H), 4.95-4.83 (m, 2H), 4.60-4.52 (m, 1H), 3.78-3.65 (m, 1H), 2.68-2.58 (m, 4H).

Example 229

3-[5-Bromo-2-(3-fluoro-benzyloxy)-phenoxy]-1-tert-butyl-azetidine

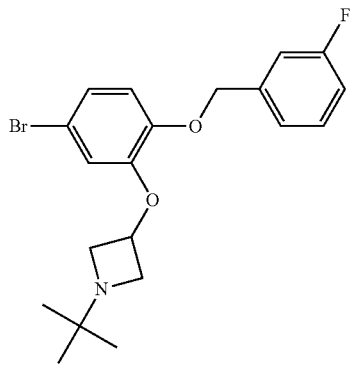 [SMILES: CC(C)(C)N1CC(Oc2cc(Br)ccc2OCc2cccc(F)c2)C1]

Step A: Preparation of 1-tert-butyl-azetidin-3-ol: To a solution of tert-butylamine (10 mmol) in isopropylalcohol (20 mL) was added dropwise epichlorohydrine (10 mmol). The mixture was stirred at 25° C. for 16 h. After concentration, the residue was re-dissolved in acetonitrile (20 mL) and triethylamine (20 mmol) was added. The mixture was heated at 100° C. for 24 h, cooled to rt and filtered. The filtrate was concentrated providing 1-tert-butyl-azetidin-3-ol (1.1 g). MS (ESI): mass calcd. for $C_7H_{15}NO$, 129.1; m/z found, 130.1 $[M+H]^+$. $^1$H NMR (CDCl$_3$): 6.15-5.70 (br s, 1H), 4.84-4.72 (m, 1H), 4.24-4.12 (m, 2H), 4.03-3.87 (m, 2H), 1.37 (s, 9H).

Step B: Preparation of 3-[5-Bromo-2-(3-fluoro-benzyloxy)-phenoxy]-1-tert-butyl-azetidine: To a solution of the title compound of Step A (3 mmol), and triethylamine (6 mmol) in CH$_2$Cl$_2$ (50 mL), was added MeSO$_3$Cl (4 mmol). The mixture was stirred at 25° C. for 16 h. After concentration, ⅓ of the residue was dissolved in MeCN (20 mL). Next, 5-bromo-2-(3-fluoro-benzyloxy)-phenol (0.5 mmol) and K$_2$CO$_3$ (2 mmol) were added. The mixture was stirred at 100° C. for 16 h, concentrated and purified via PTLC providing the title compound (189 mg). MS (ESI): mass calcd. for $C_{20}H_{23}BrFNO_2$, 407.1; m/z found, 408.0 $[M+H]^+$. $^1$H NMR (CDCl$_3$): 7.37-7.28 (m, 1H), 7.19-7.12 (m, 2H), 7.04-6.95 (m, 2H), 6.84-6.63 (m, 2H), 5.08 (s, 2H), 4.78-4.48 (m, 1H), 3.68-3.62 (m, 2H), 3.35-3.26 (m, 2H), 1.00 (s, 9H).

Example 230-231 was prepared by the procedure of Example 229 using the appropriately substituted phenols.

Example 230

1-tert-Butyl-3-[5-chloro-2-(3-trifluoromethyl-benzyloxy)-phenoxy]-azetidine

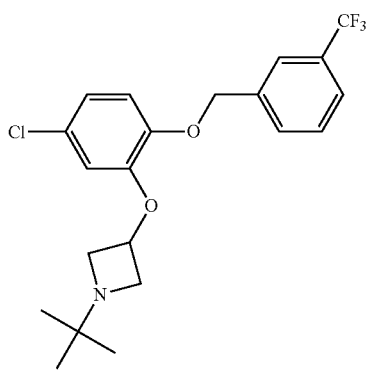 [SMILES: CC(C)(C)N1CC(Oc2cc(Cl)ccc2OCc2cccc(C(F)(F)F)c2)C1]

MS (ESI): mass calcd. for $C_{21}H_{23}ClF_3NO_2$, 413.1; m/z found, 413.9 $[M+H]^+$. $^1$H NMR (CDCl$_3$): 7.75-7.46 (m, 4H), 6.90-6.65 (m, 3H), 5.12 (s, 2H), 4.80-4.71 (m, 1H), 3.71-3.62 (m, 2H), 3.35-3.26 (m, 2H), 0.99 (s, 9H).

Example 231

1-tert-Butyl-3-[5-chloro-2-[1-(3-trifluoromethyl-phenyl)-ethoxy]-phenoxy]-azetidine

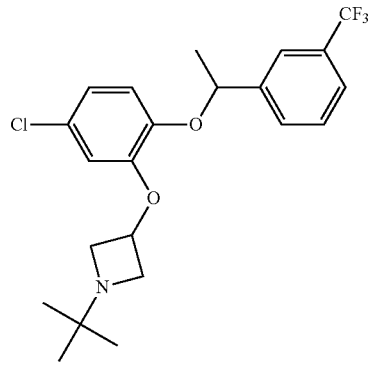 [SMILES: CC(Oc1ccc(Cl)cc1OC1CN(C(C)(C)C)C1)c1cccc(C(F)(F)F)c1]

MS (ESI): mass calcd. for $C_{22}H_{25}ClF_3NO_2$, 427.2; m/z found, 428.3 $[M+H]^+$. $^1$H NMR (CDCl$_3$): 7.68-7.42 (m, 4H), 6.78-6.62 (m, 3H), 5.32-5.23 (m, 1H), 4.78-4.68 (m, 1H), 3.70-3.62 (m, 2H), 3.33-3.25 (m, 2H), 1.65 (d, J=6.4 Hz, 3H), 0.99 (s, 9H).

Example 232

3-[5-Bromo-2-(5-trifluoromethyl-furan-2-yl-methoxy)-benzyl]-azetidine

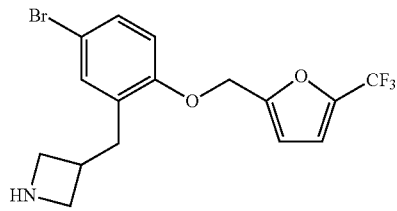

Step A: Preparation of 3-(Methoxy-methyl-carbamoyl)-azetidine-1-carboxylic acid tert-butyl ester. To a solution of azetidine-1,3-dicarboxylic acid mono-tert-butyl ester (3.5 g, 17 mmol) in DMF (50 mL) was added O,N-dimethyl-hydroxylamine hydrochloride (3.4 g, 34 mmol), triethylamine (9.6 mL, 69 mmol), HATU (13.4 g, 34.6 mmol) and DCM (125 mL). After stirring for 16 h, saturated NaHCO$_3$ solution and ethyl acetate were added. The aqueous portion was extracted three times with ethyl acetate. The combined organic fractions were dried (Na$_2$SO$_4$) and concentrated and the crude product was purified using RP HPLC (basic conditions) to provide the title compound (3.5 g, 83%) MS (ESI): mass calcd. for $C_{11}H_{20}N_2O_4$, 244.1; m/z found, 189.1 [M-t-Bu]$^+$. $^1$H NMR (CDCl$_3$): 4.14-4.03 (m, 2H), 4.05 (t, J=8.7 Hz, 2H), 3.66 (s, 3H), 3.63-3.59 (m, 1H), 3.21 (s, 1H), 1.43 (s, 9H).

Step B: Preparation of 3-(2-Methoxy-benzoyl)-azetidine-1-carboxylic acid tert-butyl ester. To a solution of 3-(methoxy-methyl-carbamoyl)-azetidine-1-carboxylic acid tert-butyl ester (3.48 g, 14.2 mmol) in dry ether (150 mL) at 0° C. was added 2-methoxylphenylmagnesium bromide (1.0 M in THF, 17 mL, 17 mmol). The reaction was allowed to slowly warm to rt and stirred for 36 h. Then a solution of 1M KHSO$_4$ and EtOAc were added and the aqueous portion was extracted once with EtOAc. The combined organic fractions were dried (Na$_2$SO$_4$) and concentrated to provide the title compound.

This material was used in subsequent reactions without additional purifications. MS (ESI): mass calcd. for $C_{16}H_{21}NO_4$, 291.1; m/z found, 236.1 [M-t-Bu]+. 1H NMR (CDCl3): 7.83 (dd, J=7.8, 1.8 Hz, 1H), 7.51 (ddd, J=8.5, 7.3, 1.8 Hz, 1H), 7.06-6.95 (m, 2H), 4.13-4.03 (m, 5H), 3.90 (s, 3H), 1.44 (s, 9H).

Step C: Preparation of 3-(2-Methoxy-benzyl)-azetidine-1-carboxylic acid tert-butyl ester. To a solution of 3-(2-methoxy-benzoyl)-azetidine-1-carboxylic acid tert-butyl ester (2.1 g, 7.2 mmol) in methanol (50 mL) was added sodium borohydride (1.08 g, 28.8 mmol). After stirring for 36 h, saturated sodium bicarbonate solution and EtOAc were added. The aqueous portion was extracted three times with EtOAc and the combined organic were dried ($Na_2SO_4$) and concentrated. To a solution of this material in ethanol (50 mL) was added 10% Pd/C. This reaction was then placed on a Parr hydrogenation apparatus with 60 psi of hydrogen gas. After 72 h, the reaction mixture was filtered through a pad of Celite and the filtrate concentrated. The crude product was purified by RP HPLC (basic conditions) to provide the title compound (370 mg, 19%). MS (ESI): mass calcd. for $C_{16}H_{23}NO_3$, 277.2; m/z found, 222.2 [M-t-Bu]+. 1H NMR (CDCl3): 7.23-7.10 (m, 1H), 7.06 (d, J=7.3 Hz, 1H), 6.92-6.77 (m, 2H), 3.96 (t, J=8.0 Hz, 2H), 3.81 (s, 3H), 3.65-3.63 (m, 2H), 2.94-2.78 (m, 5H), 1.44 (s, 9H).

Step D: Preparation of 2,2,2-Trifluoro-1-[3-(2-methoxy-benzyl)-azetidin-1-yl]-ethanone. To a solution of 3-(2-methoxy-benzyl)-azetidine-1-carboxylic acid tert-butyl ester (370 mg, 1.3 mmol) in DCM (10 mL) was added TFA (3 mL). After stirring for 16 h, TLC analysis indicated complete consumption of the starting material. To quench the reaction, saturated NaHCO3 solution and EtOAc were added. The aqueous portion was extracted twice with EtOAc and the combined organic extracts were dried ($Na_2SO_4$) and concentrated. To a solution of this material in DCM (20 mL) was added triethylamine (370 μL, 2.60 mmol) followed by trifluoroacetic anhydride (204 μL, 1.50 mmol). After 1 h, saturated NaHCO3 solution and EtOAc were added. The aqueous portion was extracted twice with EtOAc and the combined organic extracts were dried ($Na_2SO_4$) and concentrated to provide the title compound (274 mg, 75%). MS (ESI): mass calcd. for $C_{13}H_{14}F_3NO_2$, 273.1; m/z found, 274.2 [M+H]+. 1H NMR (CDCl3): 7.26-7.20 (m, 1H), 7.07 (dd, J=7.4, 1.6 Hz, 1H), 6.94-6.82 (m, 2H), 4.41 (dd, J=9.6, 8.4 Hz, 1H), 4.23-4.14 (m, 1H), 4.12-4.08 (m, 1H), 3.93-3.84 (m, 1H), 3.82 (s, 3H), 3.18-3.00 (m, 1H), 2.95-2.91 (m, 2H).

Step E: Preparation of 1-[3-(5-Bromo-2-methoxy-benzyl)-azetidin-1-yl]-2,2,2-trifluoro-ethanone. To a solution of 2,2,2-trifluoro-1-[3-(2-methoxy-benzyl)-azetidin-1-yl]-ethanone (95 mg, 0.35 mmol) in acetone (2 mL) and water (2 mL) was added NaBr (143 mg, 1.40 mmol) followed by Oxone (210 mg, 0.35 mmol). After 5 h, 10% sodium metabisulfite solution was added. After 1 h, EtOAc was added and the aqueous portion extracted twice with EtOAc. The combined organics were dried ($Na_2SO_4$) and concentrated. The crude product was purified by RP HPLC (basic conditions) to provide the title compound (66 mg, 53%). MS (ESI): mass calcd. for $C_{13}H_{13}BrF_3NO_2$, 352.1; m/z found, 354.1 [M+H]+. 1H NMR (CDCl3): 7.32 (dd, J=8.7, 2.5 Hz, 1H), 7.17 (d, J=2.5 Hz, 1H), 6.75 (t, J=10.2 Hz, 1H), 4.43 (dd, J=9.6, 8.4 Hz, 1H), 4.26-4.14 (m, 1H), 4.09 (dd, J=9.6, 5.7 Hz, 1H), 3.89 (dd, J=10.7, 5.7 Hz, 1H), 3.81 (s, 3H), 3.14-2.96 (m, 1H), 2.90 (d, J=7.8 Hz, 2H).

Step F: Preparation of 1-[3-(5-Bromo-2-hydroxy-benzyl)-azetidin-1-yl]-2,2,2-trifluoro-ethanone. To a solution of 1-[3-(5-bromo-2-methoxy-benzyl)-azetidin-1-yl]-2,2,2-trifluoro-ethanone (66 mg, 0.19 mmol) in dry DCM (10 mL) at 0° C. was added BBr3 (1.0 M in DCM, 370 mL, 0.37 mmol). After warming to rt overnight, saturated NaHCO3 solution and EtOAc were added. The aqueous portion was extracted twice with EtOAc and the combined organic extracts were dried ($Na_2SO_4$) and concentrated to provide the title compound (59 mg, 92%). MS (ESI): mass calcd. for $C_{12}H_{11}BrF_3NO_2$, 337.0; m/z found, 338.0 [M+H]+. 1H NMR (CDCl3): 7.23-7.10 (m, 2H), 6.70 (t, J=8.7 Hz, 1H), 4.53-4.40 (m, 1H), 4.27-4.11 (m, 2H), 3.97 (dd, J=10.7, 6.0 Hz, 1H), 3.17-3.01 (m, 1H), 3.01-2.78 (m, 2H).

Step G: Preparation of 1-{3-[5-Bromo-2-(5-trifluoromethyl-furan-2-ylmethoxy)-benzyl]-azetidin-1-yl}-2,2,2-trifluoro-ethanone. To a solution of 1-[3-(5-bromo-2-hydroxy-benzyl)-azetidin-1-yl]-2,2,2-trifluoro-ethanone (59 mg, 0.17 mmol) in DMF (10 mL) was added KI (40 mg, 0.24 mmol), $Cs_2CO_3$ (170 mg, 0.51 mmol) and 2-bromomethyl-5-trifluoromethyl-furan (56 mg, 0.24 mmol). After 16 h, saturated sodium bicarbonate solution and EtOAc were added. The aqueous portion was extracted three times with EtOAc and the combined organic were dried ($Na_2SO_4$) and concentrated. The crude product was purified by RP HPLC (basic conditions) to provide the title compound (76 mg, 91%). MS (ESI): mass calcd. for $C_{18}H_{14}BrF_6NO_3$, 486.2; m/z found, 488.1 [M+H]+. 1H NMR (CDCl3): 7.34 (dd, J=8.7, 2.5 Hz, 1H), 7.21 (d, J=2.5 Hz, 1H), 6.89-6.76 (m, 2H), 6.48 (d, J=3.4 Hz, 1H), 5.02 (s, 2H), 4.40 (dd, J=9.6, 8.4 Hz, 1H), 4.22-4.11 (m, 1H), 4.08-4.02 (m, 1H), 3.84 (dd, J=10.7, 5.7 Hz, 1H), 3.11-2.97 (m, 1H), 2.97-2.82 (m, 2H).

Step H: Preparation of 3-[5-Bromo-2-(5-trifluoromethyl-furan-2-ylmethoxy)-benzyl]-azetidine. To a solution of 1-{3-[5-bromo-2-(5-trifluoromethyl-furan-2-ylmethoxy)-benzyl]-azetidin-1-yl}-2,2,2-trifluoro-ethanone (76 mg, 0.16 mmol) in methanol (10 mL) was added $K_2CO_3$ (94 mg, 0.70 mmol). After 1 h, TLC analysis indicated complete consumption of the starting material. Brine and EtOAc were added to the reaction mixture and the aqueous portion was extracted with EtOAc (3×). The combined organic layers were dried. The crude product was purified by RP HPLC (basic conditions) to provide the title compound (50 mg, 76%). MS (ESI): mass calcd. for $C_{16}H_{15}BrF_3NO_2$, 390.2; m/z found, 393.2 [M+H]+. 1H NMR (CDCl3): 7.50-7.41 (m, 1H), 7.35-7.26 (m, 1H), 6.89-6.79 (m, 2H), 6.53 (s, 1H), 5.05 (s, 2H), 4.43-4.20 (m, 1H), 3.63 (t, J=8.2 Hz, 2H), 3.44 (t, J=7.7 Hz, 2H), 2.85 (d, J=7.6 Hz, 2H).

Example 233

3-[5-Bromo-2-(3-chloro-benzyloxy)-phenoxymethyl]-azetidine

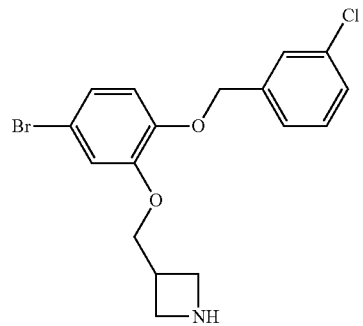 [SMILES: Clc1cccc(COc2ccc(Br)cc2OCC2CNC2)c1]

Prepared similar to Example 1 using 3-hydroxymethyl-azetidine-1-carboxylic acid tert-butyl ester. MS (ESI): mass calcd. for $C_{17}H_{17}BrClNO_2$, 381.0; m/z found, 382.1 [M+H]+.

¹H NMR (CDCl₃): 7.45 (s, 1H), 7.35-7.21 (m, 3H), 7.15-6.96 (m, 2H), 6.77 (d, J=8.5, 1H), 5.04 (s, 2H), 4.16 (d, J=6.4, 2H), 3.81 (m, 2H), 3.63 (m, 1H), 3.62-3.52 (m, 1H), 3.21 (m, 1H), 2.17 (m, 1H).

Example 234

3-[5-Bromo-2-(3-chloro-benzyloxy)-phenoxymethyl]-1-methyl-azetidine

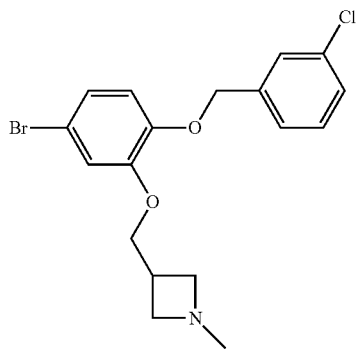 [SMILES: CN1CC(COc2cc(Br)ccc2OCc2cccc(Cl)c2)C1]

Prepared from Example 233 using general procedure 5. MS (ESI): mass calcd. for C₁₈H₁₉BrClNO₂, 395.0; m/z found, 396.1 [M+H]⁺. ¹H NMR (CDCl₃): 7.52 (d, J=2.5, 1H), 7.40 (s, 1H), 7.36-7.22 (m, 4H), 6.74 (d, J=8.7, 1H), 5.04 (s, 2H), 4.45 (s, 2H), 4.23-4.15 (m, 1H), 3.64 (s, 2H), 2.93 (s, 2H), 2.35 (s, 3H).

Example 235

3-[5-Bromo-2-(3-chloro-benzyloxy)-phenoxymethyl]-azetidin-3-ol

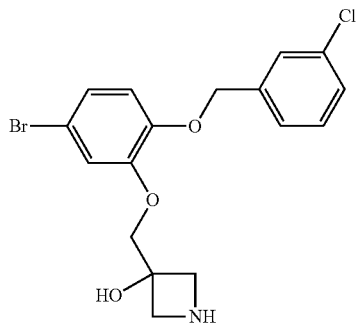 [SMILES: OC1(COc2cc(Br)ccc2OCc2cccc(Cl)c2)CNC1]

Step A: Preparation of 1-Boc-3-[5-bromo-2-(3-chloro-benzyloxy)-phenoxymethyl]-azetidin-3-ol. The mixture of the title compound of Example 215 Step B (2.3 mmol), 5-bromo-2-(3-chloro-benzyloxy)-phenol (1.3 mmol), and cyanomethylenetri-n-butylphosphorane (2 mmol) in toluene (5 mL) was heated at 150° C. in a microwave reactor for 1 h. The mixture was cooled to rt and purified by PTLC providing the title compound (580 mg). MS (ESI): mass calcd. for C₂₂H₂₅BrClNO₅, 497.1; m/z found, 504.2 [M-OH+Na]⁺. ¹H NMR (CDCl₃): 7.52-7.23 (m, 4H), 6.99-6.68 (m, 3H), 5.70-5.10 (br S, 1H), 5.04 (s, 2H), 4.99-4.97 (m, 2H), 4.50-4.46 (m, 4H), 1.45 (s, 9H).

Step B: 3-[5-Bromo-2-(3-chloro-benzyloxy)-phenoxymethyl]-azetidin-3-ol. The title compound of Step A (160 mg) was dissolved in CH₂Cl₂ (20 mL), and TFA (3 mL) was added. The mixture was stirred at rt for 4 h and concentrated. The resulting residue was dissolved into MeOH (20 mL), and Dowex 66 ion-exchange resin (Dowex hydroxide, weakly basic anion, Macroporous) was added to adjust the pH to 7. The resin was filtered and the filtrate concentrated providing the title compound (120 mg). MS (ESI): mass calcd. for C₁₇H₁₇BrClNO₃, 397.0; m/z found, 382.2 [M-OH+H]⁺. ¹H NMR (MeOD): 7.52-7.28 (m, 4H), 6.97-6.81 (m, 3H), 5.18-5.15 (m, 2H), 5.12 (s, 2H), 4.73-4.68 (m, 4H).

Example 236

3-[1-[5-Bromo-2-(3-chloro-benzyloxy)-phenoxy]-ethyl]-azetidin-3-ol

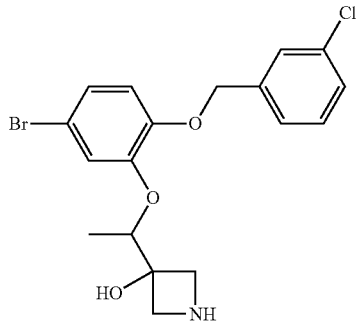 [SMILES: CC(Oc1cc(Br)ccc1OCc1cccc(Cl)c1)C1(O)CNC1]

Prepared according to Example 235 using 3-ethyl-3-hydroxy-azetidine-1-carboxylic acid tert-butyl ester. MS (ESI): mass calcd. for C₁₈H₁₉BrClNO₃, 411.0; m/z found, 396.0 [M-OH+H]⁺. ¹H NMR (MeOD): 7.52-7.27 (m, 4H), 6.98-6.80 (m, 3H), 5.57-5.48 (m, 1H), 5.12 (s, 2H), 4.73-4.61 (br s, 4H), 1.63-1.57 (m, 3H).

Example 237

3-[5-Bromo-2-(3-chloro-benzyloxy)-benzyloxy]-azetidine

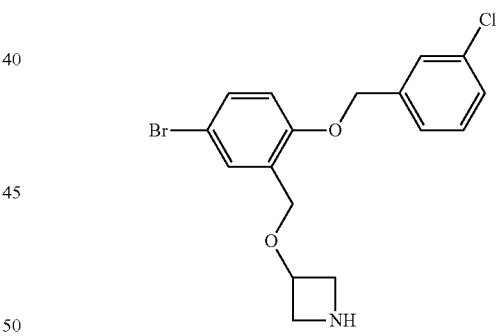

Step A: Preparation of [5-Bromo-2-(3-chloro-benzyloxy)-phenyl]-methanol. To a solution of 5-bromo-2-(3-chloro-benzyloxy)-benzaldehyde (6.0 g, 18.4 mmol) in MeOH (90 mL) at rt was added NaBH₄ (1.07 g, 27.7 mmol) over 1 h. After 18 h at rt, H₂O was added (5 mL) and the reaction concentrated to a residual mass, which was dissolved into EtOAc (150 mL). This EtOAc solution was washed with H₂O (2×100 mL) and dried to yield the title compound as a light yellow (6.0 g, 100%). MS (ESI): mass calcd. for C₁₄H₁₂BrClO, 327.6; m/z found, 328.3 [M+H]⁺. ¹H NMR (CDCl₃) 7.48 (d, J=2.5 Hz, 1H), 7.42-7.20 (m, 5H), 6.76 (d, J=8.7 Hz, 1H), 5.07 (d, J=19.2 Hz, 2H), 4.69 (d, J=17.5 Hz, 2H), 2.15 (t, J=10.0 Hz, 1H).

Step B. 5-Bromo-2-(3-chloro-benzyloxy)-benzyl chloride. The title compound of Step A was dissolved into CH₂Cl₂ (8 mL) and thionyl chloride (114 mg, 0.95 mmol) was added at rt. The reaction mixture was stirred for 2 h and concentrated to yield the title compound (300 mg). $^1$H NMR (CDCl$_3$): 7.51 (d, J=2.5 Hz, 1H), 7.48-7.22 (m, 6H), 6.76 (t, J=11.1 Hz, 1H), 5.14-4.99 (m, 2H), 4.65 (d, J=14.7 Hz, 2H).

Step C. 3-[5-Bromo-2-(3-chloro-benzyloxy)-benzyloxy]-azetidine. To a DMF (5 mL) solution of 3-hydroxy-azetidine-1-carboxylic acid tert-butyl ester (150 mg, 0.87 mmol) at rt was added 60% NaH (36 mg, 0.91 mmol). The reaction mixture was stirred at rt for 0.5 h. Then a DMF solution of the title compound of Step B (300 mg, 0.87 mmol) was added. After 18 h, the reaction mixture was partitioned between EtOAc and H$_2$O. The organic phase was dried and concentrated to yield the title compound (380 mg). This material was purified by chromatography (SiO$_2$) using 0-25% EtOAc in hexanes to give 3-[5-bromo-2-(3-chloro-benzyloxy)-benzyloxy]-azetidine-1-carboxylic acid tert-butyl ester (70 mg, 37%). This compound was treated with 4M HCl in dioxane and stirred 6 h at rt and concentrated. Purification by RP HPLC (basic system) gave the title compound (26 mg, 7%) MS (ESI): mass calcd. for C$_{17}$H$_{17}$BrClNO$_2$, 381.7; m/z found, 383.0 [M+H]$^+$. $^1$H NMR (CDCl$_3$): 7.52 (d, J=2.5 Hz, 1H), 7.41 (s, 1H), 7.36-7.21 (m, 4H), 6.74 (d, J=8.7 Hz, 1H), 5.03 (s, 2H), 4.49-4.39 (m, 3H), 3.68 (m, 4H), 1.75 (s, 1H).

Example 238

3-[5-Chloro-2-(3-chloro-benzyloxy)-benzyloxy]-azetidine

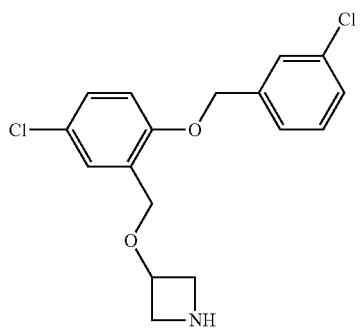 [SMILES: Clc1cccc(COc2ccc(Cl)cc2COC2CNC2)c1]

Prepared according to Example 237 using 5-chloro-2-(3-chloro-benzyloxy)-benzaldehyde. MS (ESI): mass calcd. for C$_{17}$H$_{17}$Cl$_2$NO$_2$, 337.06; m/z found, 338.2 [M+H]$^+$. $^1$H NMR (CDCl$_3$): 7.43-7.15 (m, 6H), 6.79 (d, J=8.7 Hz, 1H), 5.04 (s, 2H), 4.49-4.39 (m, 3H), 3.71-3.67 (m, 3H), 1.92 (m, 1H), 1.90-1.83 (m, 1H).

Example 239

5-[2-(Azetidin-3-yloxy)-4-chloro-phenoxymethyl]-3-methyl-[1,2,4]oxadiazole

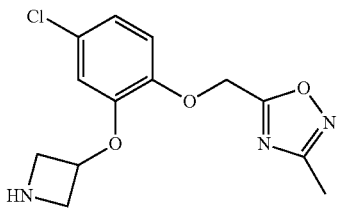 [SMILES: Cc1noc(COc2ccc(Cl)cc2OC2CNC2)n1]

Step A: Preparation of 3-(5-Chloro-2-ethoxycarbonyl-methoxy-phenoxy)-azetidine-1-carboxylic acid tert-butyl ester. To 3-(5-Chloro-2-hydroxy-phenoxy)-azetidine-1-carboxylic acid tert-butyl ester (1.5 g, 5.0 mmol) in DMF (20 mL) was added Cs$_2$CO$_3$ (2.1 g, 6.4 mmol), KI (0.84 g, 5.0 mmol) and bromoethyl acetate (0.84 g, 0.55 mL, 5.0 mmol). After 18 h, H$_2$O was added and the mixture extracted with EtOAc (2×). The combined organics were washed with brine and dried. Silica gel chromatography (5-30% EtOAc in hexanes) gave 1.95 g (99%) of the title compound as a clear oil. $^1$H NMR (CDCl$_3$): 6.91 (dd, J=8.7, 2.4 Hz, 1H), 6.79 (d, J=8.7 Hz, 1H), 6.58 (d, J=2.4 Hz, 1H), 4.91-4.87 (m, 1H), 4.65 (s, 2H), 4.32-4.25 (m, 4H), 4.01 (dd, J=10.5, 4.2 Hz, 2H), 1.44 (s, 9H), 1.30 (t, J=7.1 Hz, 3H).

Step B: Preparation of 3-(2-Carboxymethoxy-5-chloro-phenoxy)-azetidine-1-carboxylic acid tert-butyl ester. To the title compound from Step A (1.70 g, 4.40 mmol) in MeOH (10 mL) was added 4N NaOH (10 mL). After 2 h, CH$_2$Cl$_2$ was added and the mixture acidified with 1N KHSO$_4$ (50 mL) then extracted with CH$_2$Cl$_2$ (2×). The combined organics were dried to give a 0.90 g (57%) of the title compound as a white solid that was used without further purification. MS (ESI): mass calcd. for C$_{16}$H$_{20}$ClNO$_6$, 357.1; m/z found, 380.1 [M+Na]$^+$. $^1$H NMR (400 MHz): 6.92 (dd, J=8.6, 2.3 Hz, 1H), 6.85 (d, J=8.7 Hz, 1H), 6.59 (d, J=2.3 Hz, 1H), 4.92-4.86 (m, 1H), 4.67 (s, 2H), 4.31 (dd, J=9.9, 6.5 Hz, 2H), 4.07 (dd, J=10.0, 4.1 Hz, 2H), 1.45 (s, 9H).

Step C: Preparation of 3-[5-Chloro-2-(3-methyl-[1,2,4]oxadiazol-5-ylmethoxy)-phenoxy]-azetidine-1-carboxylic acid tert-butyl ester. To the title compound of Step B (0.15 g, 0.42 mmol) in CH$_2$Cl$_2$ (4 mL) was added DMF (catalytic) and 2M COCl$_2$ in CH$_2$Cl$_2$ (0.3 mL, 0.6 mmol). After 2 h, the reaction was concentrated and THF (2 mL) was added. This solution was added to N-hydroxy-acetamidine (0.035 g, 0.46 mmol) and N,N-diisopropylethylamine (0.065 g, 0.088 mL, 0.50 mmol) in THF (2 mL). The mixture was then heated for 20 min at 155° C. in a microwave reactor, cooled to rt and concentrated. Silica gel chromatography (5-30% EtOAc in hexanes) gave 0.155 g (93%) of the title compound as a clear oil. MS (ESI): mass calcd. for C$_{18}$H$_{22}$ClN$_3$O$_6$, 395.1; m/z found, 295.3 [M-100]$^+$. $^1$H NMR (400 MHz): 6.94 (d, J=8.6 Hz, 1H), 6.91 (dd, J=8.6, 2.2 Hz, 1H), 6.57 (d, J=2.1 Hz, 1H), 5.27 (s, 2H), 4.89-4.85 (m, 1H), 4.32-4.29 (m, 2H), 4.04 (dd, J=10.4, 4.2 Hz, 2H), 2.43 (s, 3H), 1.45 (s, 9H).

Step D: Preparation of 5-[2-(Azetidin-3-yloxy)-4-chloro-phenoxymethyl]-3-methyl-[1,2,4]oxadiazole hydrochloride. Prepared from the title compound of Step B using general procedure 1. MS (ESI): mass calcd. for C$_{13}$H$_{14}$ClN$_3$O$_3$, 295.1; m/z found, 296.2 [M+H]$^+$. $^1$H NMR (DMSO-D$_6$): 9.30 (s, 2H), 7.14 (d, J=8.7 Hz, 1H), 7.05 (dd, J=8.7, 2.4 Hz, 1H), 6.96 (d, J=2.4 Hz, 1H), 5.52 (s, 2H), 5.10-5.05 (m, 1H), 4.42 (dd, J=12.5, 6.7 Hz, 2H), 4.01 (dd, J=12.5, 4.8 Hz, 2H) 2.36 (s, 3H).

The compounds in Examples 240-243 were synthesized according to Example 239 using the appropriately substituted N-hydroxyamidine.

Example 240

5-[2-(Azetidin-3-yloxy)-4-chloro-phenoxymethyl]-3-cyclobutyl-[1,2,4]oxadiazole

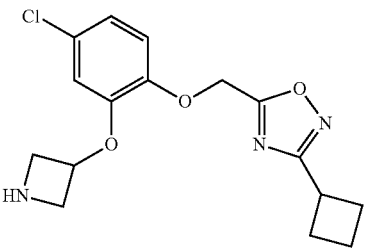 [SMILES: Clc1ccc(OCc2nc(C3CCC3)no2)c(OC2CNC2)c1]

MS (ESI): mass calcd. for C$_{16}$H$_{18}$ClN$_3$O$_3$, 335.1; m/z found, 336.2 [M+H]$^+$. $^1$H NMR (CDCl$_3$): 6.95 (d, J=8.6 Hz, 1H), 6.87 (dd, J=8.6, 2.3 Hz, 1H), 6.62 (s, 1H), 5.28 (s, 2H), 4.99-4.89 (m, 1H), 3.98-3.66 (m, 5H), 2.41-2.36 (m, 4H), 2.17-1.98 (m, 2H).

Example 241

5-[2-(Azetidin-3-yloxy)-4-chloro-phenoxymethyl]-3-cyclopropyl-[1,2,4]oxadiazole hydrochloride

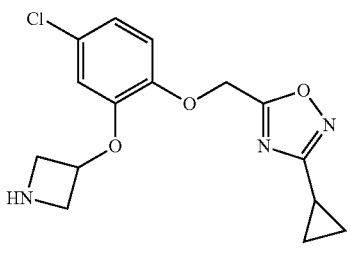 [SMILES: Clc1ccc(OCc2nc(C3CC3)no2)c(OC2CNC2)c1]

MS (ESI): mass calcd. for $C_{15}H_{16}ClN_3O_3$, 321.1; m/z found, 322.2 [M+H]$^+$. $^1$H NMR (DMSO-D$_6$): 9.31 (s, 2H), 7.12 (d, J=8.8 Hz, 1H), 7.05 (dd, J=8.7, 2.4 Hz, 1H), 6.96 (d, J=2.4 Hz, 1H), 5.49 (s, 2H), 5.09-5.04 (m, 1H), 4.42 (dd, J=12.2, 6.6 Hz, 2H), 4.03-3.99 (m, 2H), 2.17-2.13 (m, 1H), 1.11-1.07 (m, 2H), 0.90-0.87 (m, 2H).

Example 242

5-[2-(Azetidin-3-yloxy)-4-chloro-phenoxymethyl]-3-isopropyl-[1,2,4]oxadiazole hydrochloride

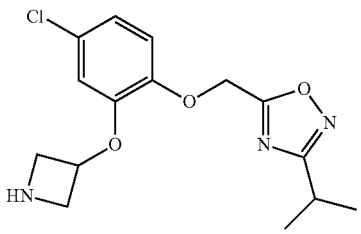 [SMILES: CC(C)c1noc(COc2ccc(Cl)cc2OC2CNC2)n1]

MS (ESI): mass calcd. for $C_{15}H_{18}ClN_3O_3$, 323.1; m/z found, 324.2 [M+H]$^+$. $^1$H NMR (DMSO-D$_6$): 9.28 (s, 2H), 7.14 (d, J=8.7 Hz, 1H), 7.06 (dd, J=8.7, 2.4 Hz, 1H), 6.97 (d, J=2.4 Hz, 1H), 5.51 (s, 2H), 5.10-5.05 (m, 1H), 4.43 (dd, J=12.3, 6.6 Hz, 2H), 4.02 (dd, J=12.3, 4.7 Hz, 2H), 3.12-3.07 (m, 1H), 1.28 (d, J=6.9 Hz, 6H).

Example 243

5-[2-(Azetidin-3-yloxy)-4-chloro-phenoxymethyl]-3-ethyl-[1,2,4]oxadiazole hydrochloride

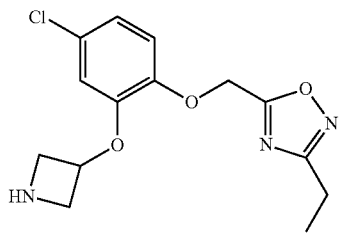 [SMILES: CCc1noc(COc2ccc(Cl)cc2OC2CNC2)n1]

MS (ESI): mass calcd. for $C_{14}H_{16}ClN_3O_3$, 309.1; m/z found, 310.2 [M+H]$^+$. $^1$H NMR (DMSO-D$_6$): 9.34 (s, 2H), 7.14 (d, J=8.7 Hz, 1H), 7.06 (dd, J=8.7, 2.4 Hz, 1H), 6.97 (d, J=2.4 Hz, 1H), 5.51 (s, 2H), 5.10-5.05 (m, 1H), 4.42 (dd, J=12.6, 6.7 Hz, 2H), 4.02 (dd, J=12.5, 4.9 Hz, 2H), 2.75 (q, J=7.6 Hz, 2H), 1.26 (t, J=7.6 Hz, 2H).

Compounds in Examples 244-278 were synthesized according to general procedure 6.

Example 244

3-(5-Bromo-2-phenoxy-phenoxy)-azetidine

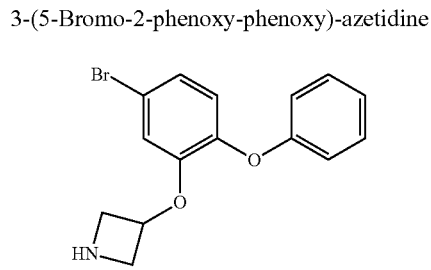

MS (ESI): mass calcd. for $C_{15}H_{14}BrNO_2$, 320.2; m/z found, 322.1 [M+H]$^+$. $^1$H NMR (CDCl$_3$): 7.32-7.28 (m, 2H), 7.07-7.05 (m, 2H), 6.94-6.92 (m, 2H), 6.88-6.84 (m, 2H), 4.97-4.91 (m, 1H), 3.85-3.81 (m, 2H), 3.71-3.67 (m, 2H).

Example 245

3-[5-Bromo-2-(3-bromo-phenoxy)-phenoxy]-azetidine

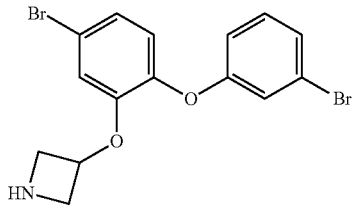 [SMILES: Brc1cccc(Oc2ccc(Br)cc2OC2CNC2)c1]

MS (ESI): mass calcd. for $C_{15}H_{13}Br_2NO_2$, 399.1; m/z found, 401.0 [M+H]$^+$. $^1$H NMR (CDCl$_3$): 7.21-7.12 (m, 2H), 7.09 (dd, J=8.5, 2.2 Hz, 1H), 7.04-6.98 (m, 1H), 6.91 (d, J=8.5, 1H), 6.88-6.77 (m, 2H), 4.96-4.92 (m, 1H), 3.90-3.78 (m, 2H), 3.72-3.60 (m, 2H).

Example 246

3-[5-Bromo-2-(3-fluoro-phenoxy)-phenoxy]-azetidine

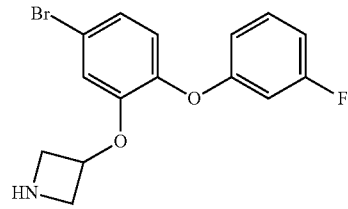 [SMILES: Fc1cccc(Oc2ccc(Br)cc2OC2CNC2)c1]

MS (ESI) mass calcd. for $C_{15}H_{13}BrFNO_2$, 337.01; m/z found, 338.3 [M+H]$^+$. $^1$H NMR (CD$_3$OD) 7.37-7.21 (m, 2H), 7.18 (d, J=2.2 Hz, 1H), 7.03 (d, J=8.6 Hz, 1H), 6.83 (t, J=8.4, 2.4 Hz, 1H), 6.75-6.63 (m, 2H), 5.15 (m, 1H), 4.47 (dd, J=12.4, 6.6 Hz, 2H), 4.05 (dd, J=12.4, 4.7 Hz, 2H).

Example 247

3-(5-Bromo-2-m-tolyloxy-phenoxy)-azetidine

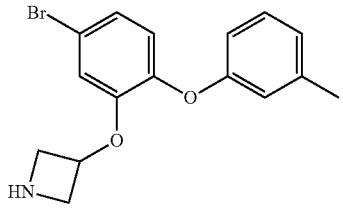 [SMILES: Cc1cccc(Oc2ccc(Br)cc2OC2CNC2)c1]

MS (ESI) mass calcd. for $C_{16}H_{16}BrFNO_2$, 333.04; m/z found, 334.1 [M+H]$^+$. $^1$H NMR (CD$_3$OD) 7.25-7.10 (m, 3H), 6.92 (dd, J=12.9, 8.1 Hz, 2H), 6.80-6.64 (m, 2H), 5.19-5.03 (m, 1H), 4.45 (dd, J=12.7, 6.7 Hz, 2H), 4.09 (dd, J=12.6, 4.9 Hz, 2H).

Example 248

3-[5-Bromo-2-(3-methoxy-phenoxy)-phenoxy]-azetidine

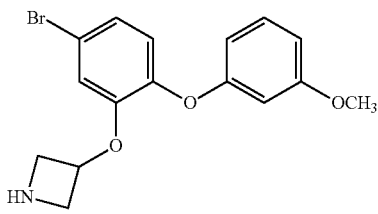 [SMILES: COc1cccc(Oc2ccc(Br)cc2OC2CNC2)c1]

MS (ESI): mass calcd. for $C_{16}H_{16}BrNO_3$, 350.2; m/z found, 351.1 [M+H]$^+$.

$^1$H NMR (CDCl$_3$): 7.18 (t, J=8.1 Hz, 1H), 7.06 (dd, J=8.5, 2.2 Hz, 1H), 6.88 (d, J=8.5 Hz, 1H), 6.83 (d, J=2.2 Hz, 1H), 6.62 (dd, J=8.2, 1.7 Hz, 1H), 6.53-6.45 (m, 2H), 5.00-4.90 (m, 1H), 3.95-3.62 (m, 7H).

Example 249

3-[5-Bromo-2-(4-fluoro-phenoxy)-phenoxy]-azetidine

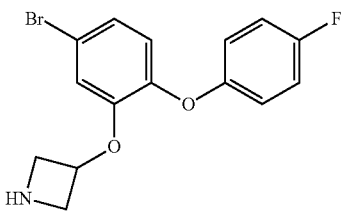 [SMILES: Fc1ccc(Oc2ccc(Br)cc2OC2CNC2)cc1]

MS (ESI): mass calcd. for $C_{15}H_{13}BrFNO_2$, 338.2; m/z found, 339.1 [M+H]$^+$. $^1$H NMR (CDCl$_3$): 7.05 (dd, J=8.5, 2.2 Hz, 1H), 7.01-6.97 (m, 2H), 6.90-6.88 (m, 2H), 6.82 (dd, J=5.4, 3.1 Hz, 2H), 4.99-4.90 (m, 1H), 3.92-3.64 (m, 4H).

Example 250

3-[5-Bromo-2-(4-bromo-phenoxy)-phenoxy]-azetidine

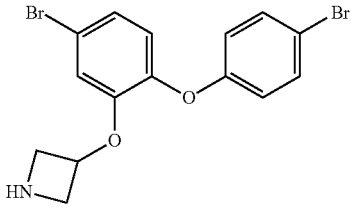 [SMILES: Brc1ccc(Oc2ccc(Br)cc2OC2CNC2)cc1]

MS (ESI): mass calcd. for $C_{15}H_{13}Br_2NO_2$, 399.1; m/z found, 401.0 [M+H]$^+$. $^1$H NMR (CDCl$_3$): 7.43-7.33 (m, 2H), 7.08 (dd, J=8.5, 2.3 Hz, 1H), 6.88 (d, J=8.5 Hz, 1H), 6.83-6.78 (m, 3H), 4.99-4.90 (m, 1H), 3.95-3.55 (m, 4H).

Example 251

3-[5-Bromo-2-(4-chloro-phenoxy)-phenoxy]-azetidine

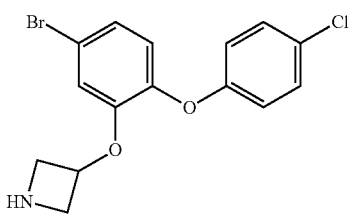 [SMILES: Clc1ccc(Oc2ccc(Br)cc2OC2CNC2)cc1]

MS (ESI): mass calcd. for $C_{15}H_{13}BrClNO_2$, 354.6; m/z found, 355.0 [M+H]$^+$. $^1$H NMR (MeOD): 7.34-7.22 (m, 2H), 7.18 (d, J=2.2 Hz, 1H), 7.10 (dd, J=8.0, 1.9 Hz, 1H), 7.02 (d, J=8.6 Hz, 1H), 6.94 (t, J=2.2 Hz, 1H), 6.85 (dd, J=8.3, 2.4 Hz, 1H), 5.18-5.10 (m, 1H), 4.50-4.41 (m, 2H), 4.07-4.04 (m, 2H).

Example 252

3-[5-Bromo-2-(3-chloro-phenoxy)-phenoxy]-azetidine

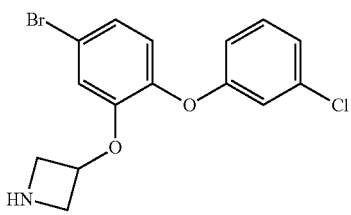 [SMILES: Clc1cccc(Oc2ccc(Br)cc2OC2CNC2)c1]

MS (ESI): mass calcd. for $C_{15}H_{13}BrClNO_2$, 354.6; m/z found, 355.0 [M+H]$^+$. $^1$H NMR (MeOD): 7.34-7.22 (m, 2H), 7.18 (d, J=2.2 Hz, 1H), 7.10 (dd, J=8.0, 1.9 Hz, 1H), 7.02 (d, J=8.6 Hz, 1H), 6.94 (t, J=2.2 Hz, 1H), 6.85 (dd, J=8.3, 2.4 Hz, 1H), 5.18-5.10 (m, 1H), 4.50-4.41 (m, 2H), 4.07-4.04 (m, 2H).

Example 253

3-[5-Bromo-2-(3-trifluoromethoxy-phenoxy)-phenoxy]-azetidine

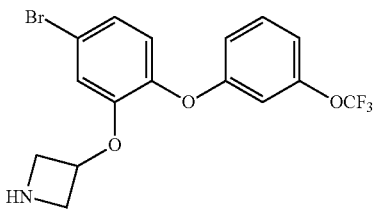 [SMILES: FC(F)(F)Oc1cccc(Oc2ccc(Br)cc2OC2CNC2)c1]

MS (ESI): mass calcd. for C$_{16}$H$_{13}$BrF$_3$NO$_3$, 403.0; m/z found, 404.1 [M+H]$^+$. $^1$H NMR (MeOD): 7.41 (t, J=8.3 Hz, 1H), 7.31-7.13 (m, 2H), 7.06-7.02 (m, 1H), 7.02-6.97 (m, 1H), 6.93-6.78 (m, 2H), 5.21-5.09 (m, 1H), 4.50-4.47 (m, 2H), 4.06-4.03 (m, 2H), 3.34-3.24 (m, 1H).

Example 254

3-[5-Bromo-2-(naphthalen-2-yloxy)-phenoxy]-azetidine

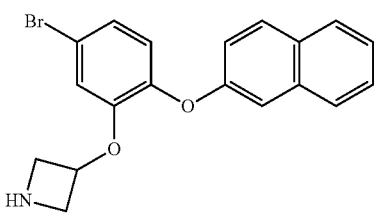

MS (ESI): mass calcd. for C$_{19}$H$_{16}$BrNO$_2$, 369.0; m/z found, 370.1 [M+H]$^+$. $^1$H NMR (MeOD): 7.92-7.77 (m, 2H), 7.70 (d, J=8.1 Hz, 1H), 7.49-6.97 (m, 7H), 5.20-5.12 (m, 1H), 4.44 (dd, J=12.5, 6.6 Hz, 2H), 4.05 (dd, J=12.5, 5.0 Hz, 2H).

Example 255

3-[5-Bromo-2-(naphthalen-1-yloxy)-phenoxy]-azetidine

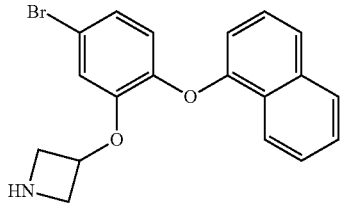 [SMILES: Brc1ccc(Oc2cccc3ccccc23)c(OC2CNC2)c1]

MS (ESI): mass calcd. for C$_{19}$H$_{16}$BrNO$_2$, 369.0; m/z found, 370.1 [M+H]$^+$. $^1$H NMR (MeOD): 8.25-8.16 (m, 1H), 7.95-7.85 (m, 1H), 7.65-7.16 (m, 6H), 6.95-6.72 (m, 2H), 5.21-5.12 (m, 1H), 4.42 (m, 2H), 4.05 (dd, J=12.5, 5.0 Hz, 2H).

Example 256

3-(5-Chloro-2-phenoxy-phenoxy)-azetidine

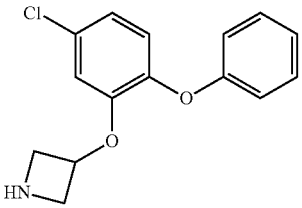 [SMILES: Clc1ccc(Oc2ccccc2)c(OC2CNC2)c1]

MS (ESI): mass calcd. for C$_{15}$H$_{14}$ClNO$_2$, 275.1; m/z found, 276.1 [M+H]$^+$. $^1$H NMR (CDCl$_3$): 7.33-7.26 (m, 2H), 7.11-6.99 (m, 1H), 6.99-6.84 (m, 4H), 6.70 (d, J=1.3 Hz, 1H), 4.97-4.91 (m, 1H), 3.88-3.79 (m, 2H), 3.75-3.64 (m, 2H).

Example 257

3-[5-Chloro-2-(3-chloro-phenoxy)-phenoxy]-azetidine maleate

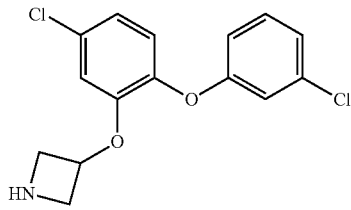 [SMILES: Clc1cccc(Oc2ccc(Cl)cc2OC2CNC2)c1]

MS (ESI): mass calcd. for C$_{15}$H$_{13}$Cl$_2$NO$_2$, 309.0; m/z found, 310.1 [M+H]$^+$. $^1$H NMR (CDCl$_3$): 7.22 (t, J=8.2 Hz, 1H), 7.04 (d, J=8.1 Hz, 1H), 7.01 (dd, J=8.6 Hz, 2.3 Hz, 1H), 6.93 (d, J=8.6 Hz, 1H), 6.89 (t, J=2.1 Hz, 1H), 6.80 (dt, J=5.2, 2.5 Hz, 2H), 6.29 (s, 2H), 5.18-5.08 (m, 1H), 4.44 (d, J=6.7 Hz, 2H), 4.21 (s, 2H).

Example 258

3-[5-Chloro-2-(4-chloro-phenoxy)-phenoxy]-azetidine trifluoroacetate

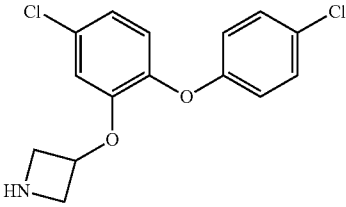 [SMILES: Clc1ccc(Oc2ccc(Cl)cc2OC2CNC2)cc1]

MS (ESI): mass calcd. for C$_{15}$H$_{13}$Cl$_2$NO$_2$, 309.0; m/z found, 310.8 [M+H]$^+$. $^1$H NMR (CDCl$_3$): 7.31-7.27 (m, 2H), 7.02 (dd, J=8.7, 2.4 Hz, 1H), 6.91 (d, J=8.6 Hz, 1H), 6.88-6.83 (m, 2H), 6.79 (d, J=2.3 Hz, 1H), 5.11-5.06 (m, 1H), 4.34 (dd, J=11.8, 6.8 Hz, 2H), 4.14 (dd, J=11.7, 5.5 Hz, 2H).

Example 259

3-(5-Chloro-2-o-tolyloxy-phenoxy)-azetidine trifluoroacetate

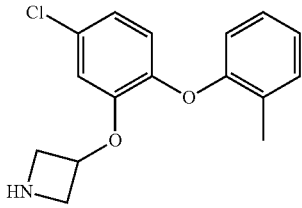 [SMILES: Cc1ccccc1Oc1ccc(Cl)cc1OC1CNC1]

MS (ESI): mass calcd. for $C_{16}H_{16}ClNO_2$, 289.1; m/z found, 290.2 [M+H]$^+$. $^1$H NMR (CDCl$_3$): 7.25 (d, J=7.5 Hz, 1H), 7.15 (t, J=7.0 Hz, 1H), 7.07 (t, J=7.4 Hz, 1H), 6.95 (dd, J=8.7, 2.4 Hz, 1H), 6.81 (d, J=2.4 Hz, 1H), 6.75 (d, J=8.0 Hz, 1H), 6.68 (d, J=8.7 Hz, 1H), 5.10 (s, 1H), 4.34 (s, 2H), 4.19 (s, 2H), 2.24 (s, 3H).

Example 260

3-[5-Chloro-2-(naphthalen-2-yloxy)-phenoxy]-azetidine

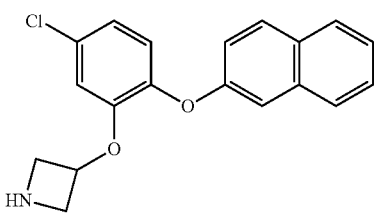 [SMILES: Clc1ccc(Oc2ccc3ccccc3c2)c(OC2CNC2)c1]

MS (ESI): mass calcd. for $C_{19}H_{16}ClNO_2$, 325.1; m/z found, 326.2 [M+H]$^+$. $^1$H NMR (MeOD): 7.90-7.79 (m, 2H), 7.70 (d, J=8.0 Hz, 1H), 7.48-7.03 (m, 7H), 5.20-5.12 (m, 1H), 4.44 (dd, J=12.6, 6.6 Hz, 2H), 4.05 (dd, J=12.6, 5.0 Hz, 2H).

Example 261

2-[2-(Azetidin-3-yloxy)-4-chloro-phenoxy]-benzothiazole

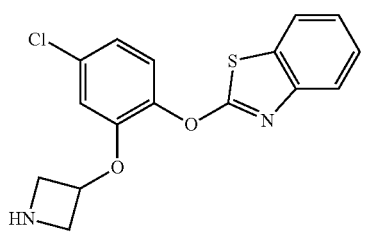 [SMILES: Clc1ccc(Oc2nc3ccccc3s2)c(OC2CNC2)c1]

A mixture of 3-(5-chloro-2-hydroxy-phenoxy)-azetidine-1-carboxylic acid tert-butyl ester (0.5 mmol), 2-chloro-benzothiazole (0.5 mmol), and K$_2$CO$_3$ (1 mmol) in CH$_3$CN (3 mL) was heated at 120-150° C. via Microwave for 1 h. The mixture was cooled down and separated through PTLC providing 3-[2-(benzothiazol-2-yloxy)-5-chloro-phenoxy]-azetidine-1-carboxylic acid tert-butyl ester (180 mg). The ester was re-dissolved into CH$_2$Cl$_2$ (20 mL), and CF$_3$COOH (3 mL) was added. The mixture was stirred at 25° C. for 4 h. After concentration, the title compound was obtained (192 mg). MS (ESI): mass calcd. for $C_{16}H_{13}ClN_2O_2S$, 332.0; m/z found, 333.1 [M+H]$^+$. $^1$H NMR (MeOD): 7.23-7.07 (m, 4H), 6.92-6.81 (m, 3H), 5.14-5.08 (m, 1H), 4.51 (dd, J=12.5, 6.6 Hz, 2H), 4.23 (dd, J=12.5, 5.0 Hz, 2H).

Example 262

2-[2-(Azetidin-3-yloxy)-4-chloro-phenoxy]-benzooxazole

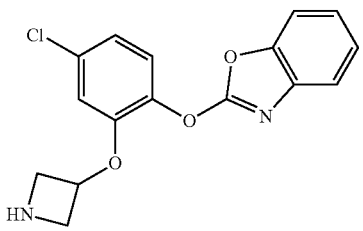 [SMILES: Clc1ccc(Oc2nc3ccccc3o2)c(OC2CNC2)c1]

MS (ESI): mass calcd. for $C_{16}H_{13}ClN_2O_3$, 316.1; m/z found, 317.1 [M+H]$^+$. $^1$H NMR (MeOD): 7.83-7.78 (m, 1H), 7.67-7.62 (m, 1H), 7.46-7.41 (m, 2H), 7.26-7.21 (m, 1H), 7.20 (dd, J=8.6, 2.3 Hz, 1H), 7.11 (d, J=2.3 Hz, 1H), 5.26-5.21 (m, 1H), 4.50 (dd, J=12.7, 6.6 Hz, 2H), 4.07 (dd, J=12.7, 4.8 Hz, 2H).

Example 263

2-[2-(Azetidin-3-yloxy)-4-chloro-phenoxy]-[1,8] naphthyridine

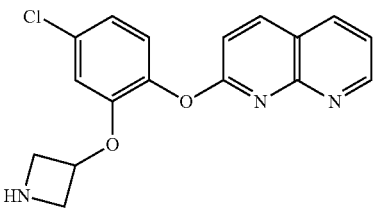 [SMILES: Clc1ccc(Oc2ccc3cccnc3n2)c(OC2CNC2)c1]

MS (ESI): mass calcd. for $C_{17}H_{14}ClN_3O_2$, 327.1; m/z found, 328.1 [M+H]$^+$. $^1$H NMR (MeOD): 9.06-9.04 (m, 1H), 8.97 (d, J=4.7 Hz, 1H), 8.74 (d, J=8.9 Hz, 1H), 7.92 (dd, J=8.1, 5.4 Hz, 1H), 7.70 (d, J=8.9 Hz, 1H), 7.25 (d, J=8.6 Hz, 1H), 7.20 (dd, J=8.6, 2.3 Hz, 1H), 7.08 (d, J=2.3 Hz, 1H), 5.27-5.18 (m, 1H), 4.46 (dd, J=12.7, 6.6 Hz, 2H), 3.97 (dd, J=12.7, 4.8 Hz, 2H).

Example 264

2-[2-(Azetidin-3-yloxy)-4-chloro-phenoxy]-quinoline

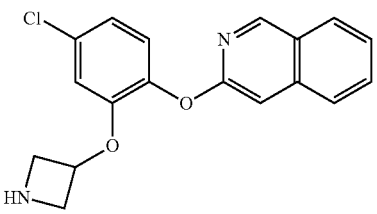 [SMILES: Clc1ccc(Oc2cc3ccccc3cn2)c(OC2CNC2)c1]

MS (ESI): mass calcd. for $C_{18}H_{15}ClN_2O_2$, 327.1; m/z found, 328.1 [M+H]$^+$. $^1$H NMR (CDCl$_3$): 8.75 (s, 1H), 8.12-8.06 (m, 1H), 7.65-7.58 (m, 3H), 7.20 (d, J=8.6 Hz, 1H), 7.04 (dd, J=8.6, 2.3 Hz, 1H), 6.73 (d, J=2.3 Hz, 1H), 4.99-4.88 (m, 1H), 3.86-3.72 (m, 2H), 3.61-3.47 (m, 2H).

Example 265

4-(5-Chloro-2-phenoxy-phenoxy)-piperidine

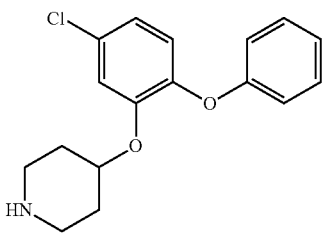 [SMILES: Clc1ccc(Oc2ccccc2)c(OC2CCNCC2)c1]

MS (ESI): mass calcd. for $C_{17}H_{18}ClNO_2$, 303.8; m/z found, 304.2 [M+H]$^+$. $^1$H NMR (CDCl$_3$): 7.29-7.26 (m, 2H), 7.04-7.01 (m, 1H), 6.99-6.97 (m, 2H), 6.93-6.89 (m, 3H), 4.35-4.30 (m, 2H), 2.95-2.91 (m, 2H), 2.62 (ddd, J=12.3, 8.6, 3.3 Hz, 2H), 1.88-1.82 (m, 2H), 1.57-1.45 (m, 2H).

Example 266

(S)-3-(4-Chloro-2-p-tolyloxy-phenoxy)-pyrrolidine

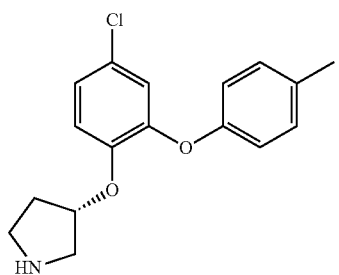 [SMILES: Cc1ccc(Oc2cc(Cl)ccc2O[C@H]2CCNC2)cc1]

MS (ESI): mass calcd. for $C_{17}H_{18}ClNO_2$, 303.1; m/z found, 304.2 [M+H]$^+$. $^1$H NMR (CDCl$_3$): 7.09 (t, J=7.7 Hz, 2H), 7.04 (dd, J=8.7, 2.5 Hz, 1H), 6.99 (d, J=2.5 Hz, 1H), 6.87 (d, J=8.7 Hz, 1H), 6.84-6.78 (m, 2H), 4.79 (dd, J=5.7, 4.4 Hz, 1H), 3.06 (d, J=12.8 Hz, 1H), 2.98-2.89 (m, 1H), 2.82-2.71 (m, 2H), 2.32 (s, 3H), 1.99-1.89 (m, 1H), 1.87-1.78 (m, 1H).

Example 267

(R)-3-(4-Chloro-2-p-tolyloxy-phenoxy)-pyrrolidine

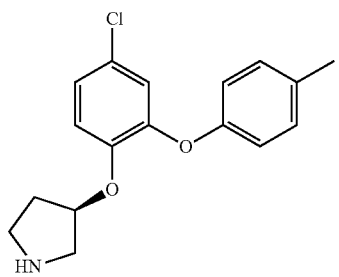 [SMILES: Cc1ccc(Oc2cc(Cl)ccc2O[C@@H]2CCNC2)cc1]

MS (ESI): mass calcd. for $C_{17}H_{18}ClNO_2$, 303.1; m/z found, 304.2 [M+H]$^+$. $^1$H NMR (CDCl$_3$): 7.09 (d, J=8.3 Hz, 2H), 7.04 (dd, J=8.7, 2.5 Hz, 1H), 6.98 (d, J=2.5 Hz, 1H), 6.86 (d, J=8.7 Hz, 1H), 6.83-6.79 (m, 2H), 4.79 (t, J=4.8 Hz, 1H), 3.05 (d, J=12.8 Hz, 1H), 2.97-2.89 (m, 1H), 2.78 (d, J=9.3 Hz, 2H), 2.31 (s, 3H), 1.99-1.89 (m, 1H), 1.86-1.77 (m, 1H).

Example 268

(R)-3-(4-Chloro-2-p-tolyloxy-phenoxy)-1-methyl-pyrrolidine

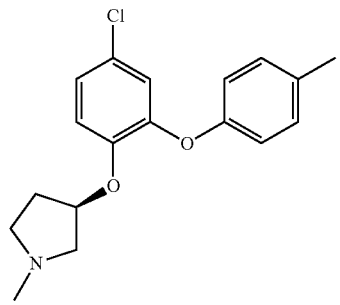 [SMILES: Cc1ccc(Oc2cc(Cl)ccc2O[C@@H]2CCN(C)C2)cc1]

Prepared from Example 261 using general procedure 5. MS (ESI): mass calcd. for $C_{18}H_{20}ClNO_2$, 317.1; m/z found, 318.2 [M+H]$^+$. $^1$H NMR (CDCl$_3$): 7.10 (d, J=8.4 Hz, 2H), 7.00 (dd, J=8.7, 2.5 Hz, 1H), 6.90 (d, J=2.5 Hz, 1H), 6.87-6.79 (m, 3H), 4.84-4.74 (m, 1H), 2.91 (dd, J=10.6, 6.1 Hz, 1H), 2.58 (dd, J=6.9, 6.3 Hz, 2H), 2.54-2.48 (m, 1H), 2.32 (d, J=4.5 Hz, 6H), 2.23-2.16 (m, 1H), 1.98-1.86 (m, 1H).

Example 269

(S)-3-[4-Chloro-2-(4-fluoro-phenoxy)-phenoxy]-pyrrolidine

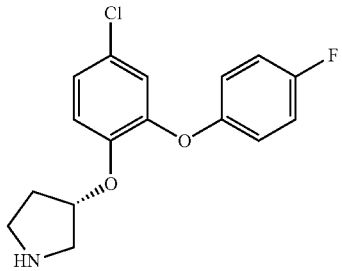 [SMILES: Fc1ccc(Oc2cc(Cl)ccc2O[C@H]2CCNC2)cc1]

MS (ESI): mass calcd. for $C_{16}H_{15}ClFNO_2$, 307.1; m/z found, 308.2 [M+H]$^+$. $^1$H NMR (CDCl$_3$): 7.07 (dd, J=8.7, 2.5 Hz, 1H), 7.03-6.96 (m, 3H), 6.92-6.84 (m, 3H), 4.78 (dd, J=5.9, 4.5 Hz, 1H), 3.04 (d, J=12.8 Hz, 1H), 2.95 (dt, J=11.3, 7.4 Hz, 1H), 2.89-2.75 (m, 2H), 2.02-1.92 (m, 1H), 1.85-1.77 (m, 1H).

Example 270

(R)-3-[4-Chloro-2-(4-fluoro-phenoxy)-phenoxy]-pyrrolidine

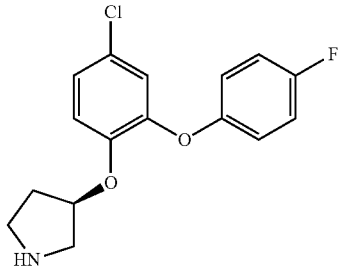 [SMILES: Fc1ccc(Oc2cc(Cl)ccc2O[C@@H]2CCNC2)cc1]

MS (ESI): mass calcd. for $C_{16}H_{15}ClFNO_2$, 307.1; m/z found, 308.2 $[M+H]^+$. $^1H$ NMR ($CDCl_3$): 7.06 (dd, J=8.7, 2.5 Hz, 1H), 7.02-6.96 (m, 3H), 6.91-6.84 (m, 3H), 4.78 (dd, J=5.8, 4.5 Hz, 1H), 3.05 (d, J=12.8 Hz, 1H), 2.96 (dt, J=11.3, 7.4 Hz, 1H), 2.90-2.74 (m, 2H), 2.03-1.92 (m, 1H), 1.85-1.77 (m, 1H).

Example 271

(R)-3-[4-Chloro-2-(4-fluoro-phenoxy)-phenoxy]-1-methyl-pyrrolidine

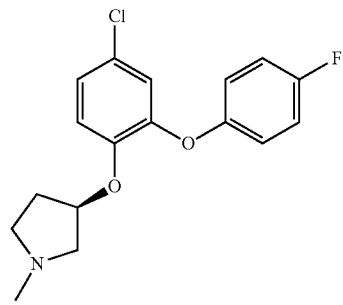 [SMILES: CN1CC[C@@H](Oc2ccc(Cl)cc2Oc2ccc(F)cc2)C1]

Prepared from Example 264 using general procedure 5. MS (ESI): mass calcd. for $C_{17}H_{17}ClFNO_2$, 321.1; m/z found, 322.2 $[M+H]^+$. $^1H$ NMR ($CDCl_3$): 7.05-6.96 (m, 3H), 6.94-6.86 (m, 3H), 6.81 (d, J=8.7 Hz, 1H), 4.93-4.53 (m, 1H), 2.91 (dd, J=10.6, 6.1 Hz, 1H), 2.63-2.41 (m, 3H), 2.32 (s, 3H), 2.23-2.16 (m, 1H), 1.90-1.81 (m, 1H).

Example 272

(S)-3-(4-Chloro-2-o-tolyloxy-phenoxy)-pyrrolidine

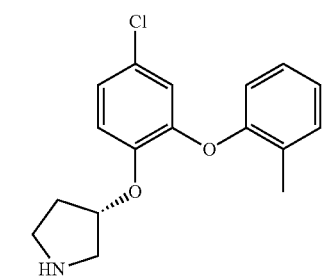 [SMILES: Cc1ccccc1Oc1cc(Cl)ccc1O[C@H]1CCNC1]

MS (ESI): mass calcd. for $C_{17}H_{18}ClNO_2$, 303.1; m/z found, 304.2 $[M+H]^+$. $^1H$ NMR ($CDCl_3$): 7.23 (d, J=6.8 Hz, 1H), 7.11-7.06 (m, 1H), 7.04-6.98 (m, 2H), 6.91 (d, J=2.5 Hz, 1H), 6.86 (d, J=8.7 Hz, 1H), 6.69 (d, J=8.0 Hz, 1H), 4.79 (dd, J=5.6, 4.4 Hz, 1H), 3.04 (d, J=12.9 Hz, 1H), 2.89 (dt, J=11.4, 7.4 Hz, 1H), 2.81-2.71 (m, 2H), 2.29 (s, 3H), 1.98-1.89 (m, 1H), 1.85-1.75 (m, 1H).

Example 273

(S)-3-(4-Chloro-2-m-tolyloxy-phenoxy)-pyrrolidine

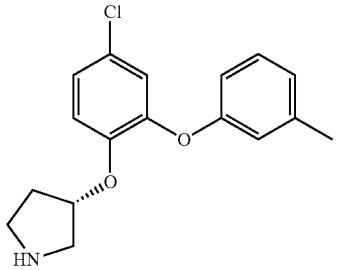 [SMILES: Cc1cccc(Oc2cc(Cl)ccc2O[C@H]2CCNC2)c1]

MS (ESI): mass calcd. for $C_{17}H_{18}ClNO_2$, 303.1; m/z found, 304.2 $[M+H]^+$. $^1H$ NMR ($CDCl_3$): 7.17 (t, J=7.8 Hz, 1H), 7.08-7.02 (m, 2H), 7.04-7.00 (m, 1H), 6.91-6.85 (m, 2H), 6.76-6.66 (m, 2H), 4.81-4.75 (m, 1H), 3.03 (d, J=12.8 Hz, 1H), 2.89 (dt, J=11.3, 7.5 Hz, 1H), 2.80-2.70 (m, 2H), 2.31 (s, 3H), 1.96-1.88 (m, 1H), 1.85-1.74 (m, 1H).

Example 274

(S)-3-[4-Chloro-2-(4-fluoro-3-methyl-phenoxy)-phenoxy]-pyrrolidine

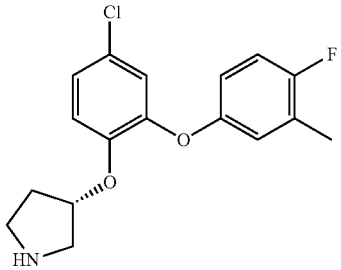 [SMILES: Cc1cc(Oc2cc(Cl)ccc2O[C@H]2CCNC2)ccc1F]

MS (ESI): mass calcd. for $C_{17}H_{17}ClFNO_2$, 321.1; m/z found, 322.2 $[M+H]^+$. $^1H$ NMR ($CDCl_3$): 7.05 (dd, J=8.7, 2.5 Hz, 1H), 6.95 (d, J=2.5 Hz, 1H), 6.92 (d, J=8.9 Hz, 1H), 6.88 (d, J=8.7 Hz, 1H), 6.75 (dd, J=6.2, 3.0 Hz, 1H), 6.72-6.65 (m, 1H), 4.79 (dd, J=5.8, 4.5 Hz, 1H), 3.07 (d, J=12.8 Hz, 1H), 2.98 (dt, J=11.4, 7.4 Hz, 1H), 2.88-2.76 (m, 2H), 2.24 (d, J=1.8 Hz, 3H), 2.00-1.93 (m, 1H), 1.88-1.79 (m, 1H).

Example 275

(S)-3-[4-Chloro-2-(4-chloro-phenoxy)-phenoxy]-pyrrolidine

MS (ESI): mass calcd. for $C_{16}H_{15}Cl_2NO_2$, 323.1; m/z found, 324.1 $[M+H]^+$. $^1H$ NMR ($CDCl_3$): 7.27-7.22 (m, 2H), 7.09 (dd, J=8.7, 2.5 Hz, 1H), 7.03 (d, J=2.5 Hz, 1H), 6.88 (d, J=8.7 Hz, 1H), 6.86-6.75 (m, 2H), 4.76 (dd, J=5.7, 4.5 Hz, 1H), 3.01 (d, J=12.8 Hz, 1H), 2.96-2.74 (m, 3H), 2.01-1.89 (m, 1H), 1.85-1.71 (m, 1H).

Example 276

(S)-3-[4-Chloro-2-(3-chloro-phenoxy)-phenoxy]-pyrrolidine

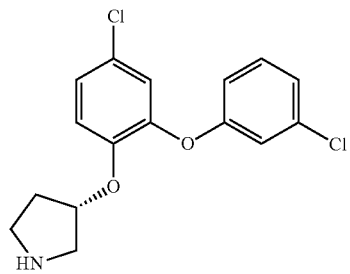 [SMILES: Clc1cccc(Oc2cc(Cl)ccc2O[C@H]2CCNC2)c1]

MS (ESI): mass calcd. for $C_{16}H_{15}Cl_2NO_2$, 323.1; m/z found, 324.1 [M+H]+. 1H NMR (CDCl3): 7.21 (t, J=8.1 Hz, 1H), 7.12 (dd, J=8.7, 2.6 Hz, 1H), 7.08 (d, J=2.5 Hz, 1H), 7.03 (ddd, J=8.0, 1.9, 0.9 Hz, 1H), 6.89 (d, J=8.7 Hz, 1H), 6.85 (t, J=2.2 Hz, 1H), 6.80 (ddd, J=8.3, 2.4, 0.9 Hz, 1H), 4.87-4.51 (m, 1H), 3.00 (d, J=12.8 Hz, 1H), 2.94-2.70 (m, 3H), 2.00-1.89 (m, 1H), 1.82-1.71 (m, 1H).

Example 277

(S)-3-[2-(4-Bromo-phenoxy)-4-chloro-phenoxy]-pyrrolidine

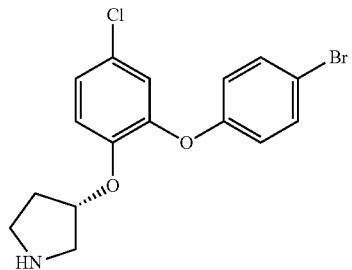 [SMILES: Clc1ccc(O[C@H]2CCNC2)c(Oc2ccc(Br)cc2)c1]

MS (ESI): mass calcd. for $C_{16}H_{15}BrClNO_2$, 367.0; m/z found, 368.1 [M+H]+. 1H NMR (CDCl3): 7.43-7.35 (m, 2H), 7.10 (dd, J=8.7, 2.6 Hz, 1H), 7.03 (dd, J=8.7, 2.5 Hz, 1H), 6.88 (d, J=8.7 Hz, 1H), 6.80-6.73 (m, 2H), 4.76 (dd, J=5.9, 4.4 Hz, 1H), 3.01 (d, J=12.8 Hz, 1H), 2.92 (dt, J=11.4, 7.4 Hz, 1H), 2.87-2.72 (m, 2H), 2.02-1.89 (m, 1H), 1.84-1.72 (m, 1H).

Example 278

(S)-3-[4-Chloro-2-(4-isopropyl-phenoxy)-phenoxy]-pyrrolidine

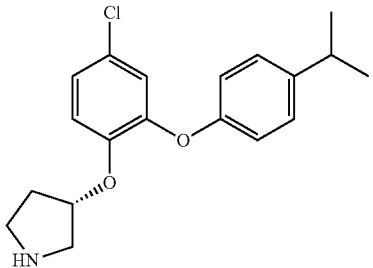 [SMILES: CC(C)c1ccc(Oc2cc(Cl)ccc2O[C@H]2CCNC2)cc1]

MS (ESI): mass calcd. for $C_{19}H_{22}ClNO_2$, 331.1; m/z found, 332.2 [M+H]+. 1H NMR (CDCl3): 7.15 (d, J=8.5 Hz, 2H), 7.07-7.00 (m, 2H), 6.85 (dd, J=11.0, 8.6 Hz, 3H), 4.77 (d, J=4.6 Hz, 1H), 3.04 (d, J=12.8 Hz, 1H), 2.92-2.81 (m, 2H), 2.76-2.70 (m, 2H), 1.95-1.87 (m, 1H), 1.82-1.73 (m, 1H), 1.24 (d, J=6.9 Hz, 6H).

Example 279

(±)-3-[5-Bromo-2-(4-bromo-phenoxy)-phenoxy]-1-ethyl-pyrrolidine

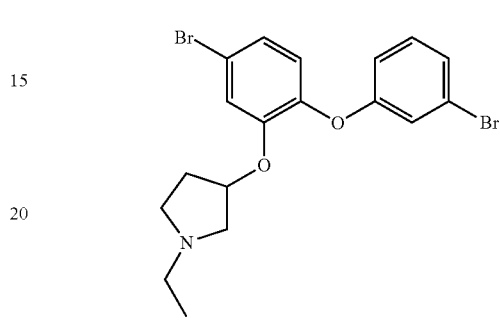

Prepared using 5-bromo-2-(3-bromo-phenoxy)-phenol and (±)-1-ethyl-pyrrolidin-3-ol according to general procedure 7. MS (ESI): mass calcd. for $C_{18}H_{19}Br_2NO_2$, 439.1; m/z found, 441.0 [M+H]+. 1H NMR (CDCl3): 7.16-7.12 (m, 2H), 7.08 (dd, J=8.4, 2.2 Hz, 1H), 7.02 (d, J=2.2 Hz, 1H), 7.01-6.98 (m, 1H), 6.93 (d, J=8.5 Hz, 1H), 6.87-6.82 (m, 1H), 4.74 (m, 1H), 3.02 (dd, J=10.7, 6.2 Hz, 1H), 2.69-2.54 (m, 1H), 2.44 (m, 4H), 2.17 (m, 1H), 1.88-1.77 (m, 1H), 1.07 (t, J=7.2 Hz, 3H).

Example 280

2-(Azetidin-3-yloxy)-4-bromo-phenyl]-phenyl-methanone

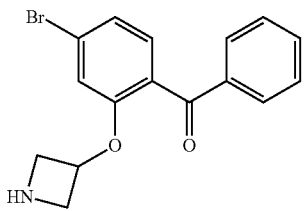 [SMILES: O=C(c1ccccc1)c1ccc(Br)cc1OC1CNC1]

Step A: Preparation of 3-[5-Bromo-2-(hydroxy-phenyl-methyl)-phenoxy]-azetidine-1-carboxylic acid tert-butyl ester. To a solution of 3-(5-bromo-2-formyl-phenoxy)-azetidine-1-carboxylic acid tert-butyl ester (0.25 g, 0.70 mmol) in CH2Cl2 (10 mL) was added a solution of PhMgBr (1M in THF, 1 mL). The reaction was allowed to stir for 15 h then quenched with 1N HCl (4 mL). After 10 min, the mixture was made basic with 1N NaOH (10 mL), and extracted with CH2Cl2 (3×20 mL). The organic layers were combined and dried. Chromatography of the resulting residue (SiO2; EtOAc/Hexanes) gave the title compound (0.24 g, 79%). MS (ESI): mass calcd. for $C_{21}H_{24}BrNO_4$, 433.1; m/z found, 434.4 [M+H]+. 1H NMR (CDCl3): 7.41-7.23 (m, 6H), 7.17 (dd, J=8.2, 1.7, 1H), 6.61 (d, J=1.7, 1H), 6.04 (s, 1H), 4.90-4.68 (m, 1H), 4.32-4.01 (m, 2H), 3.95-3.68 (m, 2H), 2.04-2.10, 1H), 1.44 (s, 9H).

Step B: Preparation of 3-(2-Benzoyl-5-bromo-phenoxy)-azetidine-1-carboxylic acid tert-butyl ester. A solution of the title compound of Step A (0.12 g, 0.28 mmol) and Dess-Martin periodane (0.17 g, 0.39 mmol) in CH$_2$Cl$_2$ (15 mL) was stirred at rt for 15 h and filtered. The resulting filtrate was concentrated and purified (SiO$_2$; EtOAc/Hexanes) providing the title compound (0.10 g, 84%). MS (ESI): mass calcd. for C$_{21}$H$_{22}$BrNO$_4$, 431.1; m/z found, 432.4 [M+H]$^+$. $^1$H NMR (CDCl$_3$): 7.70-7.64 (m, 2H), 7.55-7.45 (m, 1H), 7.40-7.31 (m, 2H), 7.27 (d, J=8.1 Hz, 1H), 7.18 (dd, J=8.0, 1.7 Hz, 1H), 6.69 (d, J=1.6 Hz, 1H), 4.72 (tt, J=6.4, 4.2 Hz, 1H), 4.16-3.97 (m, 2H), 3.59 (dd, J=10.6, 4.1 Hz, 2H), 1.46-1.25 (m, 9H).

Step C: Preparation of 2-(azetidin-3-yloxy)-4-bromo-phenyl]-phenyl-methanone. To a solution of 3-(2-benzoyl-5-bromo-phenoxy)-azetidine-1-carboxylic acid tert-butyl ester (0.10 g, 0.23 mmol) in CH$_2$Cl$_2$ (10 mL) was added 2M HCl in Et$_2$O (0.5 mL). After 15 h, the reaction was concentrated to give the title compound as the hydrochloride salt which was neutralized with 1N NaOH (5 mL) and extracted with CH$_2$Cl$_2$ (3×15 mL). The organic layers were combined and dried to give the title compound (0.07 g, 90%). MS (ESI): mass calcd. for C$_{16}$H$_{14}$BrNO$_2$, 331.0; m/z found 332.2, [M+H]$^+$. $^1$H NMR (CD$_3$OD): 7.82-7.74 (m, 2H), 7.67 (t, J=7.4 Hz, 1H), 7.54 (t, J=7.8 Hz, 2H), 7.43-7.32 (m, 2H), 5.47-5.36 (m, 1H), 4.46 (dd, J=12.4, 6.7 Hz, 2H), 3.94-3.81 (m, 2H).

Examples 275-292 were synthesized according to Example 274 using the appropriately substituted aryl magnesium halide and aldehyde.

Example 281

[2-(Azetidin-3-yloxy)-4-bromo-phenyl]-(4-chloro-phenyl)-methanone

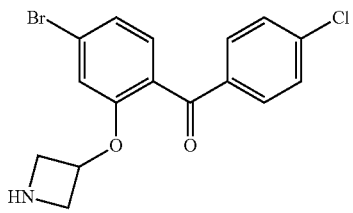 [SMILES: O=C(c1ccc(Cl)cc1)c1ccc(Br)cc1OC1CNC1]

MS (ESI): mass calcd. for C$_{16}$H$_{13}$BrClNO$_2$, 365.0; m/z found, 366.0 [M+H]$^+$. $^1$H NMR (CD$_3$OD): 7.91-7.79 (m, 2H), 7.68-7.55 (m, 2H), 7.52-7.41 (m, 2H), 5.39-5.26 (m, 1H), 4.65-4.47 (m, 2H), 4.01 (d, J=7.4 Hz, 2H).

Example 282

[2-(Azetidin-3-yloxy)-4-bromo-phenyl]-(3-chloro-phenyl)-methanone

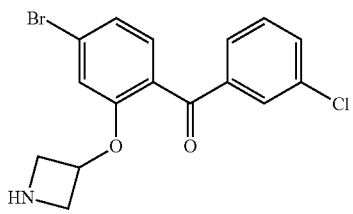 [SMILES: O=C(c1cccc(Cl)c1)c1ccc(Br)cc1OC1CNC1]

MS (ESI): mass calcd. for C$_{16}$H$_{13}$BrClNO$_2$, 365.0; m/z found, 366.0 [M+H]$^+$. $^1$H NMR (CD$_3$OD): 7.77 (t, J=1.8, 1H), 7.71-7.61 (m, 2H), 7.51 (t, J=7.9, 1H), 7.44-7.34 (m, 2H), 7.17 (d, J=1.3, 1H), 5.19 (t, J=4.9, 1H), 4.45 (dd, J=12.7, 6.6, 2H), 3.89 (dd, J=12.6, 4.8, 2H).

Example 283

[4-Bromo-2-(1-methyl-azetidin-3-yloxy)-phenyl]-(3-chloro-phenyl)-methanone

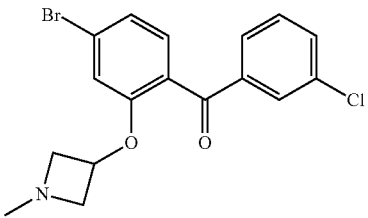 [SMILES: CN1CC(Oc2cc(Br)ccc2C(=O)c2cccc(Cl)c2)C1]

Prepared according to general procedure 5 using the title compound from Example 276. MS (ESI): mass calcd. for C$_{17}$H$_{15}$BrClNO$_2$, 379.0; m/z found, 380.1 [M+H]$^+$. $^1$H NMR (CD$_3$OD): 7.74 (t, J=1.7, 1H), 7.71-7.60 (m, 2H), 7.51 (t, J=7.9, 1H), 7.44-7.34 (m, 2H), 7.17 (d, J=1.3, 1H), 5.19 (t, J=4.9, 1H), 4.50-4.40 (m, 2H), 3.90-3.82 (m, 2H). 2.19 (s, 3H).

Example 284

[2-(Azetidin-3-yloxy)-4-bromo-phenyl]-m-tolyl-methanone

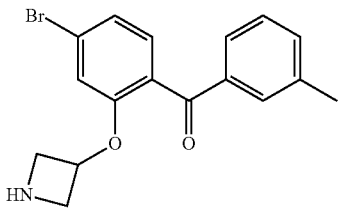 [SMILES: Cc1cccc(C(=O)c2ccc(Br)cc2OC2CNC2)c1]

MS (ESI): mass calcd. for C$_{17}$H$_{16}$BrNO$_2$, 345.0; m/z found, 346.1 [M+H]$^+$. $^1$H NMR (CDCl$_3$): 7.67-7.48 (m, 2H), 7.43-7.13 (m, 4H), 6.90-6.74 (m, 1H), 4.98-4.86 (m, 1H), 3.80 (s, 1H), 3.52 (s, 1H), 2.40 (s, 2H), 2.02 (s, 3H).

Example 285

[2-Azetidin-3-yloxy)-4-bromo-phenyl]-o-tolyl-methanone

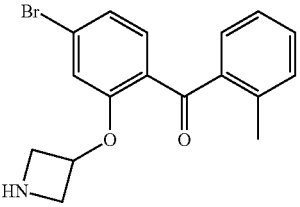 [SMILES: Cc1ccccc1C(=O)c1ccc(Br)cc1OC1CNC1]

MS (ESI): mass calcd. for C$_{17}$H$_{16}$BrNO$_2$, 345.0; m/z found, 346.1 [M+H]$^+$. $^1$H NMR (CDCl$_3$): 7.46 (d, J=8.2, 1H), 7.36 (s, 1H), 7.27 (s, 3H), 7.23-7.10 (m, 2H), 6.75 (s, 1H), 4.81 (s, 1H), 3.69 (s, 2H), 3.32 (s, 2H), 2.44 (s, 3H).

Example 286

[2-(Azetidin-3-yloxy)-4-bromo-phenyl]-(3-methoxy-phenyl)-methanone

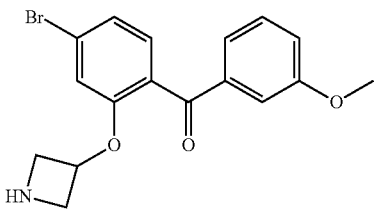 [SMILES: COc1cccc(C(=O)c2ccc(Br)cc2OC2CNC2)c1]

MS (ESI): mass calcd. for C₁₇H₁₆BrNO₃, 361.0; m/z found, 362.1 [M+H]⁺. ¹H NMR (CDCl₃): 7.39-7.07 (m, 6H), 6.91-6.79 (m, 1H), 4.66 (s, 1H), 3.84 (s, 3H), 3.50 (s, 2H), 2.97 (s, 2H).

Example 287

[2-(Azetidin-3-yloxy)-4-bromo-phenyl]-naphthalen-2-yl-methanone

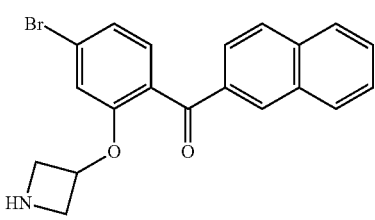

MS (ESI): mass calcd. for C₂₀H₁₆BrNO₂, 381.0; m/z found, 382.1 [M+H]⁺. ¹H NMR (CDCl₃): 8.19 (s, 1H), 7.96-7.85 (m, 4H), 7.65-7.50 (m, 2H), 7.39-7.21 (m, 2H), 6.85 (d, J=1.6 Hz, 1H), 4.95-4.89 m, 1H), 3.77-3.66 (m, 2H), 3.51-3.40 (m, 2H).

Example 288

[4-Bromo-2-(1-isopropyl-azetidin-3-yloxy)-phenyl]-naphthalen-2-yl-methanone

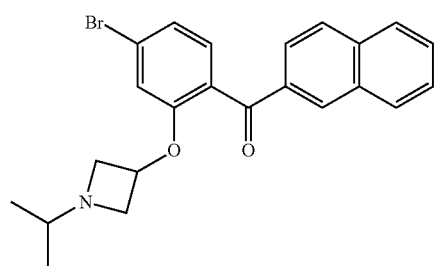 [SMILES: CC(C)N1CC(Oc2cc(Br)ccc2C(=O)c2ccc3ccccc3c2)C1]

Prepared according to general procedure 3 or 4 using the title compound from Example 281. MS (ESI): mass calcd. for C₂₃H₂₂BrNO₂, 423.1; m/z found, 426.1 [M+H]⁺. ¹H NMR (CDCl₃): 8.16-8.10 (m, 1H), 7.95-7.85 (m, 4H), 7.65-7.50 (m, 2H), 7.39-7.21 (m, 2H), 6.90-6.82 (m, 4H), 4.96-4.80 (m, 1H), 3.77-3.66 (m, 2H), 3.51-3.40 (m, 2H), 2.34-2.20 (m, 1H), 0.91 (d, J=6.1 Hz, 6H).

Example 289

[2-(Azetidin-3-yloxy)-4-bromo-phenyl]-benzo[1,3]dioxol-5-yl-methanone

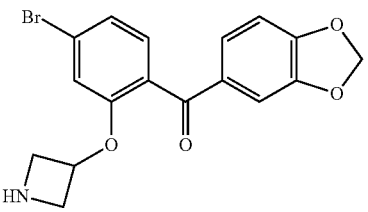 [SMILES: O=C(c1ccc2c(c1)OCO2)c1ccc(Br)cc1OC1CNC1]

MS (ESI): mass calcd. for C₁₇H₁₄BrNO₄, 375.1; m/z found, 376.1 [M+H]⁺. ¹H NMR (CDCl₃): 7.38-7.11 (m, 4H), 6.81 (d, J=8.0 Hz, 2H), 6.06 (s, 2H), 4.94 (s, 1H), 3.81 (s, 2H), 3.59 (s, 2H).

Example 290

Benzo[1,3]dioxol-5-yl-[4-bromo-2-(1-isopropyl-azetidin-3-yloxy)-phenyl]-methanone

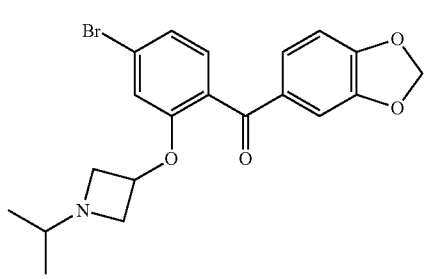

Prepared according to general procedure 3 or 4 using the title compound from Example 283. MS (ESI): mass calcd. for C₂₀H₂₀BrNO₄, 417.1; m/z found, 418.1 [M+H]⁺. ¹H NMR (CDCl₃): 7.36-7.15 (m, 4H), 6.76-6.61 (m, 2H), 6.06 (d, J=4.1 Hz, 2H), 4.76-4.61 (m, 1H), 3.79-3.63 (m, 2H), 2.87-2.75 (m, 2H), 2.34-2.18 (m, 1H), 0.90 (d, J=6.2 Hz, 6H).

Example 291

[2-(Azetidin-3-yloxy)-4-bromo-phenyl]-(4-methoxy-phenyl)-methanone

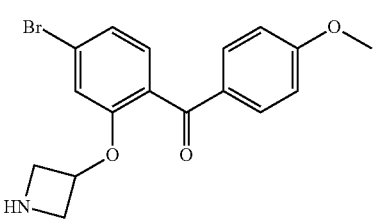 [SMILES: COc1ccc(C(=O)c2ccc(Br)cc2OC2CNC2)cc1]

MS (ESI): mass calcd. for C₁₇H₁₆BrNO₃, 361.0; m/z found, 362.1 [M+H]⁺. ¹H NMR (CDCl₃): 7.38-7.12 (m, 6H), 6.96-6.83 (m, 1H), 4.65 (s, 1H), 3.84 (s, 3H), 3.54 (s, 2H), 2.99 (s, 2H).

Example 292

[2-(Azetidin-3-yloxy)-4-bromo-phenyl]-(4-chloro-3-fluoro-phenyl)-methanone

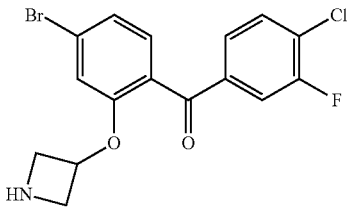 [SMILES: O=C(c1ccc(Cl)c(F)c1)c1ccc(Br)cc1OC1CNC1]

MS (ESI): mass calcd. for $C_{16}H_{12}BrClFNO_2$, 383.0; m/z found, 384.2 [M+H]$^+$. $^1$H NMR (CDCl$_3$): 7.63-7.40 (m, 3H), 7.38-7.15 (m, 2H), 6.88-6.67 (m, 1H), 4.91 (s, 1H), 3.80 (s, 2H), 3.50 (s, 2H).

Example 293

[2-(Azetidin-3-yloxy)-4-bromo-phenyl]-(3,4-dichloro-phenyl)-methanone

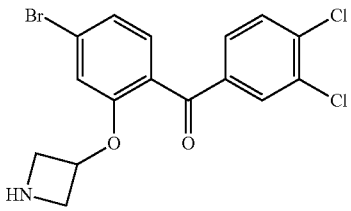 [SMILES: O=C(c1ccc(Cl)c(Cl)c1)c1ccc(Br)cc1OC1CNC1]

MS (ESI): mass calcd. for $C_{16}H_{12}BrCl_2NO_2$, 399.0; m/z found, 400.1 [M+H]$^+$. $^1$H NMR (CDCl$_3$): 7.83 (d, J=1.9 Hz, 1H), 7.63-7.51 (m, 2H), 7.35-7.19 (m, 2H), 6.82 (d, J=1.6 Hz, 1H), 5.00-4.85 (m, 1H), 4.02-3.31 (m, 4H).

Example 294

[2-(Azetidin-3-yloxy)-4-chloro-phenyl]-naphthalen-2-yl-methanone

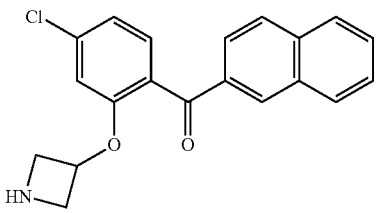 [SMILES: O=C(c1ccc2ccccc2c1)c1ccc(Cl)cc1OC1CNC1]

MS (ESI): mass calcd. for $C_{20}H_{16}ClNO_2$, 337.1; m/z found, 338.2 [M+H]$^+$. $^1$H NMR (CDCl$_3$): 8.19 (s, 1H), 7.98-7.85 (m, 3H), 7.63-7.37 (m, 4H), 7.10 (dd, J=8.1, 1.7 Hz, 1H), 6.70 (d, J=1.6 Hz, 1H), 4.97-4.84 (m, 1H), 3.74 (s, 2H), 3.50-3.37 (m, 2H).

Example 295

[2-(Azetidin-3-yloxy)-4-chloro-phenyl]-benzo[1,3]dioxol-5-yl-methanone

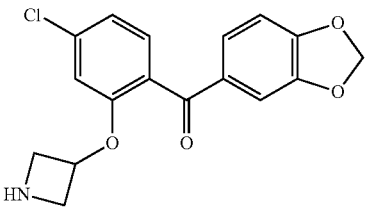 [SMILES: O=C(c1ccc2c(c1)OCO2)c1ccc(Cl)cc1OC1CNC1]

MS (ESI): mass calcd. for $C_{17}H_{14}ClNO_4$, 331.1; m/z found, 332.2 [M+H]$^+$. $^1$H NMR (CDCl$_3$): 7.35-7.21 (m, 3H), 7.04 (dd, J=8.1, 1.8 Hz, 1H), 6.82 (d, J=8.1 Hz, 1H), 6.65 (d, J=1.7 Hz, 1H), 6.05 (d, J=8.9 Hz, 2H), 5.02-4.87 (m, 1H), 3.86 (s, 2H), 3.62 (s, 2H).

Example 296

Benzo[1,3]dioxol-5-yl-[4-chloro-2-(1-isopropyl-azetidin-3-yloxy)-phenyl]-methanone

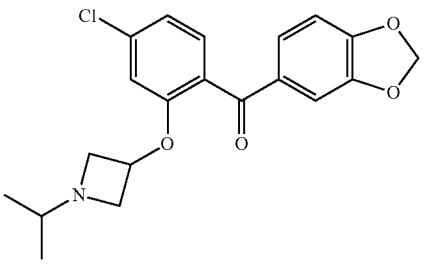

Prepared according to general procedure 3 or 4 using the title compound from Example 289. MS (ESI): mass calcd. for $C_{20}H_{20}ClNO_4$, 373.1; m/z found, 374.2 [M+H]$^+$. $^1$H NMR (CDCl$_3$): 7.40-7.25 (m, 4H), 6.76-6.61 (m, 2H), 6.10-6.04 (m, 2H), 4.81-4.64 (m, 1H), 3.75-3.63 (m, 2H), 2.85-2.74 (m, 2H), 2.28-2.18 (m, 1H), 0.96 (d, J=6.1 Hz, 6H).

Example 297

[2-(Azetidin-3-yloxy)-4-chloro-phenyl]-(4-chloro-phenyl)-methanone

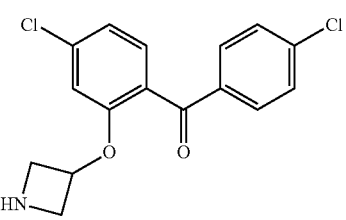

MS (ESI): mass calcd. for $C_{16}H_{13}Cl_2NO_2$, 321.0; m/z found, 322.2 [M+H]$^+$. $^1$H NMR (CD$_3$OD): 7.79-7.62 (m, 2H), 7.56-7.35 (m, 3H), 7.16 (s, 1H), 7.00-6.76 (m, 1H), 5.19-5.08 (m, 1H), 4.16 (s, 2H), 3.87 (s, 1H), 3.49 (s, 1H).

Example 298

[2-(Azetidin-3-yloxy)-4-chloro-phenyl]-(3-chloro-phenyl)-methanone

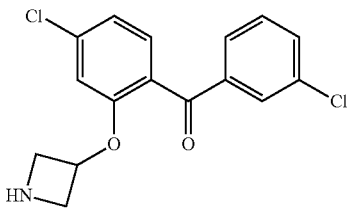 [SMILES: O=C(c1cccc(Cl)c1)c1ccc(Cl)cc1OC1CNC1]

MS (ESI): mass calcd. for $C_{16}H_{13}Cl_2NO_2$, 321.0; m/z found, 322.2 [M+H]$^+$. $^1$H NMR (CDCl$_3$): 7.70 (t, J=1.7, 1H), 7.62 (dd, J=7.8, 1.3 Hz, 1H), 7.58-7.51 (m, 1H), 7.47-7.34 (m, 2H), 7.12 (dd, J=8.2, 1.8 Hz, 1H), 6.61 (d, J=1.7 Hz, 1H), 4.87-4.68 (m, 1H), 4.21-4.13 (m, 2H), 3.67 (dd, J=9.9, 4.0 Hz, 2H).

Biological Assays r5-HT$_7$ Binding Assay

Receptor binding was performed using membrane fractions prepared from the HEK-293 cell line recombinantly expressing rat 5-HT$_7$ receptors (NCBI accession NM 022938). Compound affinity for the rat 5-HT$_7$ receptor subtype was evaluated by competitive radioligand binding assays using 5-carboxamido[$^3$H]tryptamine ([$^3$H]5-CT) (Amersham Biosciences, cat. 90000403) detection. HitHunter™ cAMP assays are in-vitro based competitive immunoassays. The assay was performed on the HEK-293 cell line stably transfected with r5-HT$_7$ receptor. Cells were pre-incubated with test compounds for 10 minutes. For antagonist testing, the cells were then challenged with 100 nM 5-CT for 20 minutes. Cells were then lysed and cAMP measured according to manufacturers protocol (Amersham, cat. NET791250UC) or [$^3$H]mesulergine (Amersham, cat. TRK1041). The assay was performed on membranes prepared from HEK-293 cells stably transfected with h5-HT$_6$. Following centrifugation, membranes were resuspended and incubated for 60 min at room temperature with 1.7 nM [$^3$H] LSD in the presence of increasing concentration of test compounds. Nonspecific binding was defined in the presence of 10 μM clozapine (Tocris, cat. TRK1068). Homogenized HEK-293 membranes expressing the human SERT were incubated in 50 mM Tris-HCl (pH 7.5), 120 mM NaCl, 5 mM KCl with [$^3$H]-citalopram (3 nM) with or without test compounds. Nonspecific binding was determined in the presence of 10 μM fluoxetine. Radioactivity readouts and K$_i$ values were performed as previously described for r5-HT$_7$. Table 1 shows assay results for exemplified compounds of the invention. Compounds were assayed in their free form or as salts, as indicated in the Examples section above.

TABLE 1

| EX. | 5HT7-RAT Ki (uM) | hSERT binding Ki (uM) | h5HT6 binding K$_i$ (uM) | h5HT2$_A$ binding K$_i$ (uM) | h5HT2$_B$ binding K$_i$ (uM) | h5HT2$_C$ binding K$_i$ (uM) | R5HT7 cAMP pK$_b$ |
|---|---|---|---|---|---|---|---|
| 1 | 0.009 | 0.048 | ND | ND | ND | ND | 7.9 |
| 2 | 0.012 | 0.001 | 0.047 | 0.042 | 0.074 | 0.760 | 7.5 |
| 3 | 0.018 | 0.381 | ND | ND | ND | ND | 8.6 |
| 4 | 0.008 | ND | ND | ND | ND | ND | 9.2 |
| 5 | 0.008 | 0.194 | ND | ND | ND | ND | 8.3 |
| 6 | 0.006 | 0.249 | ND | ND | ND | ND | 8.4 |
| 7 | 0.010 | 0.023 | ND | ND | ND | ND | 7.2 |
| 8 | 0.006 | 0.004 | ND | ND | ND | ND | 8.1 |
| 9 | 0.011 | 0.002 | ND | ND | ND | ND | 7.7 |
| 10 | 0.007 | 0.039 | 0.050 | ND | ND | ND | 8.2 |
| 11 | 0.053 | ND | ND | ND | ND | ND | ND |
| 12 | 0.011 | 0.006 | ND | ND | ND | ND | 8.5 |
| 13 | 0.004 | 0.006 | ND | ND | ND | ND | 8.4 |
| 14 | 0.012 | 0.052 | ND | ND | ND | ND | 6.8 |
| 15 | 0.017 | 0.005 | 0.045 | ND | ND | ND | 6.2 |
| 16 | 0.100 | ND | ND | ND | ND | ND | ND |
| 17 | 0.010 | 0.004 | 0.039 | ND | ND | ND | 7.3 |
| 18 | 0.005 | 0.435 | ND | ND | ND | ND | 8.8 |
| 19 | 0.004 | 0.396 | ND | ND | ND | ND | 8.7 |
| 20 | 0.008 | ND | ND | ND | ND | ND | ND |
| 21 | 0.020 | ND | ND | ND | ND | ND | ND |
| 22 | 0.125 | 0.028 | ND | ND | ND | ND | ND |
| 23 | 0.121 | ND | ND | ND | ND | ND | ND |
| 24 | 0.190 | ND | ND | ND | ND | ND | ND |
| 25 | 0.018 | 0.019 | ND | ND | ND | ND | 7.4 |
| 26 | 0.025 | 0.013 | ND | ND | ND | ND | ND |
| 27 | 0.229 | 1.679 | ND | ND | ND | ND | ND |
| 28 | 0.049 | 0.683 | ND | ND | ND | ND | ND |
| 29 | 0.083 | 0.027 | ND | 0.225 | 0.529 | 1.109 | 6.9 |
| 30 | 0.105 | ND | ND | ND | ND | ND | ND |
| 31 | 0.100 | 0.090 | ND | ND | ND | ND | ND |
| 32 | 0.053 | 0.029 | ND | ND | ND | ND | ND |
| 33 | 0.007 | 0.008 | ND | ND | ND | ND | 7.8 |
| 34 | 0.029 | 0.001 | ND | ND | ND | ND | 7.4 |
| 35 | 0.023 | 0.003 | ND | ND | ND | ND | 6.0 |
| 36 | 0.015 | 0.036 | ND | ND | ND | ND | 6.1 |
| 37 | 0.008 | 0.007 | 0.089 | ND | ND | ND | 6.9 |
| 38 | 0.006 | 0.100 | 0.036 | ND | ND | ND | 8.0 |
| 39 | 0.007 | 0.004 | ND | ND | ND | ND | 8.5 |
| 40 | 0.009 | 0.043 | ND | ND | ND | ND | 7.4 |
| 41 | 0.130 | ND | ND | ND | ND | ND | ND |
| 42 | 0.035 | 0.578 | ND | ND | ND | ND | ND |
| 43 | 0.015 | 0.086 | ND | ND | ND | ND | ND |
| 44 | 0.087 | ND | ND | ND | ND | ND | ND |
| 45 | 3.159 | 0.197 | ND | ND | ND | ND | ND |
| 46 | 0.102 | ND | ND | ND | ND | ND | ND |
| 47 | 0.011 | 0.021 | ND | ND | ND | ND | ND |
| 48 | 0.088 | ND | ND | ND | ND | ND | ND |
| 49 | 0.013 | 0.040 | ND | ND | ND | ND | 7.6 |
| 50 | 0.010 | 0.005 | ND | ND | ND | ND | 7.5 |
| 51 | 0.387 | 0.086 | ND | ND | ND | ND | ND |
| 52 | 0.110 | 0.089 | ND | ND | ND | ND | ND |
| 53 | 0.260 | 0.464 | ND | ND | ND | ND | ND |
| 54 | 0.006 | 0.028 | 0.077 | ND | ND | ND | 8.1 |
| 55 | 0.171 | ND | ND | ND | ND | ND | ND |
| 56 | 8.999 | ND | ND | ND | ND | ND | ND |
| 57 | 0.042 | ND | ND | ND | ND | ND | ND |
| 58 | 0.120 | ND | ND | ND | ND | ND | ND |
| 59 | 0.027 | 0.353 | 0.084 | ND | ND | ND | 7.8 |
| 60 | 0.250 | ND | ND | ND | ND | ND | ND |
| 61 | 0.036 | ND | ND | ND | ND | ND | ND |
| 62 | 0.034 | ND | ND | ND | ND | ND | ND |
| 63 | 0.007 | 0.048 | ND | ND | ND | ND | 7.6 |
| 64 | 0.017 | 0.043 | ND | ND | ND | ND | ND |
| 65 | 0.011 | 0.014 | 0.041 | ND | ND | ND | 6.9 |
| 66 | 0.010 | ND | ND | ND | ND | ND | 7.3 |
| 67 | 0.013 | ND | ND | ND | ND | ND | 6.4 |
| 68 | 0.017 | ND | ND | ND | ND | ND | 6.2 |
| 69 | 0.094 | ND | ND | ND | ND | ND | ND |
| 70 | 0.174 | ND | ND | ND | ND | ND | ND |
| 71 | 0.143 | ND | ND | ND | ND | ND | ND |
| 72 | 0.270 | ND | ND | ND | ND | ND | ND |
| 73 | 0.023 | 2.177 | 0.012 | ND | ND | ND | 6.6 |
| 74 | 0.011 | ND | ND | ND | ND | ND | ND |
| 75 | 8.999 | ND | ND | ND | ND | ND | ND |
| 76 | 5.000 | ND | ND | ND | ND | ND | ND |
| 77 | 0.153 | 5.000 | ND | ND | ND | ND | ND |
| 78 | 0.710 | ND | ND | ND | ND | ND | ND |
| 79 | 0.026 | 0.003 | ND | 0.069 | 0.248 | 0.290 | 7.3 |
| 80 | >10 | ND | ND | ND | ND | ND | ND |
| 81 | 0.097 | 1.170 | ND | 0.076 | 0.367 | 0.590 | ND |
| 82 | 0.198 | ND | ND | ND | ND | ND | ND |
| 83 | 0.016 | 0.024 | ND | ND | ND | ND | ND |
| 84 | 0.034 | 0.061 | ND | ND | ND | ND | ND |

TABLE 1-continued

| EX. | 5HT7-RAT Ki (uM) | hSERT binding Ki (uM) | h5HT6 binding $K_i$ (uM) | h5HT2$_A$ binding $K_i$ (uM) | h5HT2$_B$ binding $K_i$ (uM) | h5HT2$_C$ binding $K_i$ (uM) | R5HT7 cAMP p$K_b$ |
|---|---|---|---|---|---|---|---|
| 85 | 0.095 | 0.404 | ND | ND | ND | ND | ND |
| 86 | 0.038 | 0.121 | ND | ND | ND | ND | ND |
| 87 | 0.240 | ND | ND | ND | ND | ND | ND |
| 88 | 0.681 | ND | ND | ND | ND | ND | ND |
| 89 | 0.025 | 0.242 | ND | ND | ND | ND | ND |
| 90 | 0.920 | ND | ND | 0.020 | 0.083 | 0.160 | ND |
| 91 | 0.500 | ND | ND | 0.005 | 0.050 | 0.120 | ND |
| 92 | 0.260 | ND | ND | 0.014 | 0.028 | 0.110 | ND |
| 93 | 0.140 | ND | ND | 0.003 | 0.013 | 0.051 | ND |
| 94 | >2.499 | ND | ND | 0.032 | 0.250 | 0.069 | ND |
| 95 | 0.009 | ND | ND | ND | ND | ND | ND |
| 96 | 0.013 | ND | ND | ND | ND | ND | ND |
| 97 | 0.034 | ND | ND | ND | ND | ND | ND |
| 98 | 0.023 | ND | ND | ND | ND | ND | ND |
| 99 | 0.005 | ND | ND | ND | ND | ND | ND |
| 100 | 0.150 | ND | ND | ND | ND | ND | ND |
| 101 | 0.005 | 0.152 | 0.746 | 0.317 | 0.203 | 0.933 | ND |
| 102 | 0.376 | 0.954 | ND | ND | ND | ND | ND |
| 103 | 0.027 | ND | ND | ND | ND | ND | ND |
| 104 | 0.166 | ND | ND | ND | ND | ND | ND |
| 105 | 0.023 | 0.193 | ND | ND | ND | ND | 7.3 |
| 106 | 0.075 | ND | ND | ND | ND | ND | ND |
| 107 | 0.090 | ND | ND | ND | ND | ND | ND |
| 108 | 0.036 | 5 | ND | ND | ND | ND | ND |
| 109 | 0.005 | 2.900 | ND | ND | ND | ND | ND |
| 110 | 0.090 | 0.554 | ND | ND | ND | ND | ND |
| 111 | 0.010 | 0.118 | 0.268 | 0.073 | 0.069 | 0.331 | ND |
| 112 | 0.023 | 0.138 | ND | ND | ND | ND | 7.5 |
| 113 | 0.011 | 0.058 | 0.496 | 0.206 | 0.122 | 0.490 | ND |
| 114 | 0.014 | 0.075 | ND | ND | ND | ND | 7.5 |
| 115 | 0.033 | 0.202 | ND | ND | ND | ND | ND |
| 116 | 0.068 | ND | ND | ND | ND | ND | ND |
| 117 | 0.041 | 0.071 | ND | ND | ND | ND | ND |
| 118 | 0.090 | ND | ND | ND | ND | ND | ND |
| 119 | 0.288 | ND | ND | ND | ND | ND | ND |
| 120 | 0.040 | ND | ND | ND | ND | ND | ND |
| 121 | 0.033 | 0.164 | ND | ND | ND | ND | ND |
| 122 | 0.210 | ND | ND | ND | ND | ND | ND |
| 123 | 0.042 | 0.025 | ND | ND | ND | ND | ND |
| 124 | 0.043 | 0.020 | ND | ND | ND | ND | ND |
| 125 | 0.104 | ND | ND | ND | ND | ND | ND |
| 126 | 0.038 | ND | ND | ND | ND | ND | ND |
| 127 | 0.063 | ND | ND | ND | ND | ND | ND |
| 128 | 0.127 | ND | ND | ND | ND | ND | ND |
| 129 | 0.903 | ND | ND | ND | ND | ND | ND |
| 130 | 0.371 | ND | ND | ND | ND | ND | ND |
| 131 | 0.073 | 1.355 | ND | ND | ND | ND | ND |
| 132 | 0.456 | ND | ND | ND | ND | ND | ND |
| 133 | 0.591 | ND | ND | ND | ND | ND | ND |
| 134 | 3.827 | ND | ND | ND | ND | ND | ND |
| 135 | 0.015 | 0.096 | 1.275 | 0.140 | 0.027 | 0.755 | ND |
| 136 | 0.029 | 0.098 | ND | ND | ND | ND | ND |
| 137 | 0.472 | ND | ND | ND | ND | ND | ND |
| 138 | 0.042 | ND | ND | ND | ND | ND | ND |
| 139 | 0.189 | ND | ND | ND | ND | ND | ND |
| 140 | 0.230 | ND | ND | ND | ND | ND | ND |
| 141 | 0.450 | ND | ND | ND | ND | ND | ND |
| 142 | 0.091 | 0.613 | ND | ND | ND | ND | ND |
| 143 | 0.215 | ND | ND | ND | ND | ND | ND |
| 144 | 0.304 | ND | ND | ND | ND | ND | ND |
| 145 | 0.040 | 0.773 | ND | ND | ND | ND | ND |
| 146 | 0.012 | 0.059 | 0.558 | ND | ND | ND | 8.1 |
| 147 | 0.211 | ND | ND | ND | ND | ND | ND |
| 148 | 2.000 | ND | ND | ND | ND | ND | ND |
| 149 | >10 | ND | ND | ND | ND | ND | ND |
| 150 | 0.010 | 0.013 | ND | ND | ND | ND | 8.0 |
| 151 | 0.040 | ND | ND | ND | ND | ND | 7.5 |
| 152 | 0.019 | 0.025 | ND | ND | ND | ND | 7.4 |
| 153 | 0.084 | ND | ND | ND | ND | ND | 7.2 |
| 154 | 0.018 | 0.013 | ND | ND | ND | ND | 7.7 |
| 155 | 0.019 | 0.045 | ND | ND | ND | ND | ND |
| 156 | 0.252 | ND | ND | ND | ND | ND | <5 |
| 157 | 0.010 | 0.181 | ND | ND | ND | ND | 8.3 |
| 158 | 0.015 | 0.067 | ND | 0.008 | 0.036 | 0.146 | 8.0 |
| 159 | 0.017 | 0.021 | ND | 0.006 | 0.041 | 0.196 | 8.1 |
| 160 | 0.015 | 0.210 | ND | 0.005 | 0.025 | 0.146 | 8.3 |
| 161 | 0.028 | 0.060 | ND | ND | ND | ND | 7.8 |
| 162 | 5.000 | ND | ND | ND | ND | ND | ND |
| 163 | 0.766 | ND | ND | ND | ND | ND | ND |
| 164 | 0.033 | 0.008 | ND | 0.024 | 0.030 | 0.181 | ND |
| 165 | 0.016 | 0.095 | ND | ND | ND | ND | ND |
| 166 | 1.269 | ND | ND | ND | ND | ND | ND |
| 167 | 0.167 | ND | ND | ND | ND | ND | ND |
| 168 | 0.130 | ND | ND | 0.008 | 0.021 | 0.048 | ND |
| 169 | 0.119 | ND | ND | ND | ND | ND | ND |
| 170 | 5.000 | ND | ND | ND | ND | ND | ND |
| 171 | 0.007 | 0.234 | ND | ND | ND | ND | ND |
| 172 | 5.000 | ND | ND | ND | ND | ND | ND |
| 173 | 0.007 | 0.056 | ND | ND | ND | ND | 8.1 |
| 174 | 0.006 | 0.042 | ND | ND | ND | ND | 8.2 |
| 175 | 0.011 | 0.004 | ND | ND | ND | ND | ND |
| 176 | 0.024 | 0.075 | ND | ND | ND | ND | ND |
| 177 | 0.012 | 0.262 | 0.123 | 0.035 | 0.056 | 0.140 | ND |
| 178 | 0.017 | 0.131 | ND | ND | ND | ND | ND |
| 179 | 0.360 | ND | ND | ND | ND | ND | ND |
| 180 | 0.813 | ND | ND | ND | ND | ND | ND |
| 181 | 0.019 | 0.967 | ND | ND | ND | ND | 7.7 |
| 182 | 0.076 | 0.514 | ND | ND | ND | ND | ND |
| 183 | 0.110 | ND | ND | ND | ND | ND | ND |
| 184 | 0.023 | 0.124 | ND | 0.005 | 0.012 | 0.038 | 7.3 |
| 185 | 0.006 | 0.029 | 0.177 | 0.008 | 0.007 | 0.091 | ND |
| 186 | 0.005 | 0.053 | 0.033 | 0.014 | 0.008 | 0.079 | ND |
| 187 | 0.036 | 0.340 | ND | ND | ND | ND | ND |
| 188 | 0.034 | 0.065 | ND | 0.008 | 0.028 | 0.143 | ND |
| 189 | 0.138 | ND | ND | ND | ND | ND | ND |
| 190 | 0.008 | 0.211 | ND | 0.014 | 0.069 | 0.056 | ND |
| 191 | 0.008 | 0.007 | ND | 0.008 | 0.011 | 0.053 | ND |
| 192 | 0.008 | 0.088 | ND | 0.009 | 0.022 | 0.140 | ND |
| 193 | 0.005 | 0.009 | ND | 0.011 | 0.014 | 0.071 | ND |
| 194 | 0.004 | 0.141 | ND | 0.004 | 0.195 | 0.081 | ND |
| 195 | 0.002 | 0.060 | 0.027 | 0.010 | 0.004 | 0.042 | ND |
| 196 | 0.359 | 0.053 | ND | ND | ND | ND | ND |
| 197 | 1.421 | ND | ND | ND | ND | ND | ND |
| 198 | 1.462 | ND | ND | ND | ND | ND | ND |
| 199 | 0.018 | 0.128 | ND | 0.103 | 1.223 | 0.526 | 7.4 |
| 200 | 0.031 | 0.224 | ND | 0.605 | 7.568 | 5.000 | 6.8 |
| 201 | 0.031 | 0.056 | ND | 0.067 | 0.184 | 0.498 | 7.3 |
| 202 | 0.066 | ND | ND | ND | ND | ND | ND |
| 203 | 0.024 | 0.271 | ND | ND | ND | ND | 7.7 |
| 204 | 0.027 | ND | ND | ND | ND | ND | ND |
| 205 | 0.027 | ND | ND | ND | ND | ND | ND |
| 206 | 0.021 | ND | ND | ND | ND | ND | ND |
| 207 | 0.020 | ND | ND | ND | ND | ND | 7.8 |
| 208 | 0.365 | 0.303 | ND | ND | ND | ND | ND |
| 209 | 0.013 | 0.020 | ND | ND | ND | ND | 7.7 |
| 210 | 0.506 | ND | ND | ND | ND | ND | ND |
| 211 | 8.999 | ND | ND | ND | ND | ND | ND |
| 212 | 0.053 | 0.041 | ND | ND | ND | ND | ND |
| 213 | 4.589 | ND | ND | ND | ND | ND | ND |
| 214 | 8.999 | 1.693 | ND | ND | ND | ND | ND |
| 215 | 0.011 | 0.044 | ND | 0.006 | 0.017 | 0.026 | ND |
| 216 | 0.016 | 0.036 | ND | ND | ND | ND | ND |
| 217 | 0.034 | 0.113 | ND | ND | ND | ND | ND |
| 218 | 0.069 | ND | ND | ND | ND | ND | ND |
| 219 | 0.009 | 0.068 | ND | ND | ND | 0.031 | ND |
| 220 | 0.493 | 0.789 | ND | ND | ND | ND | ND |
| 221 | 0.147 | 5 | ND | ND | ND | ND | ND |
| 222 | 0.018 | 2.114 | ND | ND | ND | 1.009 | ND |
| 223 | 0.145 | 8.999 | ND | ND | ND | ND | ND |
| 224 | 0.068 | ND | ND | ND | ND | ND | ND |
| 225 | 2.669 | ND | ND | ND | ND | ND | ND |
| 226 | 0.840 | ND | ND | ND | ND | ND | ND |
| 227 | 0.336 | ND | ND | ND | ND | ND | ND |
| 228 | 0.009 | 0.072 | ND | ND | ND | ND | ND |
| 229 | 0.003 | 0.925 | ND | ND | ND | ND | ND |
| 230 | 0.006 | 1.203 | ND | ND | ND | ND | ND |
| 231 | 0.015 | 4.481 | ND | ND | ND | ND | ND |
| 232 | 0.003 | 0.001 | ND | ND | ND | ND | ND |
| 233 | 0.027 | 0.023 | ND | ND | ND | ND | ND |
| 234 | 0.130 | ND | ND | ND | ND | ND | ND |
| 235 | 0.665 | ND | ND | ND | ND | ND | ND |
| 236 | 0.831 | ND | ND | ND | ND | ND | ND |

TABLE 1-continued

| EX. | 5HT7-RAT Ki (uM) | hSERT binding Ki (uM) | h5HT6 binding $K_i$ (uM) | h5HT2$_A$ binding $K_i$ (uM) | h5HT2$_B$ binding $K_i$ (uM) | h5HT2$_C$ binding $K_i$ (uM) | R5HT7 cAMP pK$_b$ |
|---|---|---|---|---|---|---|---|
| 237 | 0.120 | ND | ND | ND | ND | ND | ND |
| 238 | 0.200 | ND | ND | ND | ND | ND | ND |
| 239 | 0.233 | ND | ND | ND | ND | ND | ND |
| 240 | 0.252 | ND | ND | ND | ND | ND | ND |
| 241 | 0.263 | ND | ND | ND | ND | ND | ND |
| 242 | 0.273 | ND | ND | ND | ND | ND | ND |
| 243 | 0.461 | ND | ND | ND | ND | ND | ND |
| 244 | 0.020 | 5.000 | 0.046 | ND | ND | ND | 6.6 |
| 245 | 0.009 | ND | ND | ND | ND | ND | 6.7 |
| 248 | 0.043 | ND | ND | ND | ND | ND | ND |
| 249 | 0.020 | ND | ND | ND | ND | ND | ND |
| 250 | 0.017 | ND | ND | ND | ND | ND | ND |
| 251 | 0.011 | ND | ND | ND | ND | ND | 6.8 |
| 252 | 0.007 | 0.060 | ND | ND | ND | ND | 7.2 |
| 253 | 0.018 | ND | ND | ND | ND | ND | 6.3 |
| 254 | 0.019 | ND | ND | ND | ND | ND | ND |
| 255 | 0.196 | ND | ND | ND | ND | ND | ND |
| 256 | 0.160 | ND | ND | ND | ND | ND | ND |
| 257 | 0.021 | ND | ND | ND | ND | ND | 6.3 |
| 258 | 0.023 | ND | ND | ND | ND | ND | 6.3 |
| 259 | 0.460 | ND | ND | ND | ND | ND | ND |
| 260 | 0.016 | 0.002 | ND | ND | ND | ND | 6.0 |
| 261 | 1.604 | ND | ND | ND | ND | ND | ND |
| 262 | 0.031 | 0.112 | ND | ND | ND | ND | ND |
| 263 | 0.544 | ND | ND | ND | ND | ND | ND |
| 264 | 1.097 | ND | ND | ND | ND | ND | ND |
| 265 | 0.130 | ND | ND | ND | ND | ND | ND |
| 266 | >10 | ND | ND | 0.150 | 0.130 | 0.230 | ND |
| 267 | 2.300 | ND | ND | 0.120 | 0.065 | 0.210 | ND |
| 268 | 0.820 | ND | ND | 0.150 | 0.130 | 0.380 | ND |
| 269 | >10 | ND | ND | 0.190 | 0.500 | 0.400 | ND |
| 270 | 1.000 | ND | ND | 0.120 | 0.075 | 0.240 | ND |
| 271 | 0.660 | ND | ND | 0.078 | 0.098 | 0.350 | ND |
| 272 | >10 | ND | ND | 0.220 | 0.310 | 0.330 | ND |
| 273 | >5 | ND | ND | 0.082 | 0.160 | 0.150 | ND |
| 274 | 8.600 | ND | ND | 0.100 | 0.170 | 0.230 | ND |
| 275 | >10 | ND | ND | 0.530 | 0.910 | 0.220 | ND |
| 276 | >10 | ND | ND | 0.084 | 0.190 | 0.120 | ND |
| 277 | 5.500 | ND | ND | 0.410 | 0.270 | 0.120 | ND |
| 278 | >10 | ND | ND | 1.400 | 1.300 | 0.330 | ND |
| 279 | 0.025 | ND | ND | ND | ND | ND | ND |
| 280 | 0.098 | ND | ND | ND | ND | ND | ND |
| 281 | 0.048 | ND | ND | ND | ND | ND | 6.5 |
| 282 | 0.039 | ND | ND | ND | ND | ND | 6.7 |
| 283 | 0.050 | ND | ND | ND | ND | ND | ND |
| 284 | 0.019 | ND | ND | ND | ND | ND | ND |
| 285 | 3.000 | ND | ND | ND | ND | ND | ND |
| 286 | 0.039 | ND | ND | ND | ND | ND | ND |
| 287 | 0.015 | 0.014 | ND | ND | ND | ND | 7.2 |
| 288 | 0.059 | ND | ND | ND | ND | ND | ND |
| 289 | 0.034 | 0.437 | ND | ND | ND | ND | 7.4 |
| 290 | 0.143 | ND | ND | ND | ND | ND | ND |
| 291 | 0.034 | ND | ND | ND | ND | ND | ND |
| 292 | 0.074 | ND | ND | ND | ND | ND | ND |
| 293 | 0.051 | ND | ND | ND | ND | ND | ND |
| 294 | 0.072 | ND | ND | ND | ND | ND | ND |
| 295 | 0.226 | ND | ND | ND | ND | ND | ND |
| 296 | 0.181 | ND | ND | ND | ND | ND | ND |
| 297 | 0.150 | ND | ND | ND | ND | ND | ND |
| 298 | 0.102 | ND | ND | ND | ND | ND | ND |

*ND symbolizes not determined.

While the invention has been illustrated by reference to exemplary and preferred embodiments, it will be understood that the invention is intended not to be limited by the foregoing detailed description, but to be defined by the appended claims as properly construed under principles of patent law.

What is claimed is:

1. A compound selected from the group consisting of (a) compounds of Formula (I):

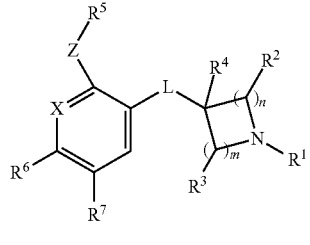

(I)

wherein

R$^1$ is —H, —C$_{1-4}$alkyl, monocyclic cycloalkyl, phenyl, or benzyl;

m is 1;

n is 1;

R$^2$ and R$^3$ are each independently —H or —C$_{1-4}$alkyl;

R$^4$ is —H, F, C$_{1-4}$alkyl, or R$^4$ is —OH when L is —CH$_2$—, —CF$_2$—, —CHF—, —OCH$_2$—, or —OCH(CH$_3$)—;

L is —O—, —CH$_2$—, —OCH$_2$—, —OCH(CH$_3$)—, —CH$_2$O—, —CF$_2$—, or —CHF—;

Z is —O—, —C(O)—, —OCH(R$^b$)—, or —OCH$_2$C(R$^c$)(R$^d$)—;

where R$^b$ is —H; a —C$_{1-4}$alkyl group unsubstituted or substituted with OH or halo: —CO$_2$C$_{1-4}$alkyl; or —CO$_2$H; and R$^c$ and R$^d$ are each independently —H, —C$_{1-4}$alkyl, —O—C$_{1-4}$alkyl, or halo;

or R$^c$ and R$^d$ taken together form an oxime, a C$_{1-4}$alkyl oxime, or a carbonyl group;

or R$^c$ and R$^d$ taken together with the carbon to which they are attached form a C$_{3-6}$cycloalkyl group;

R$^5$ is:

i) a phenyl, unsubstituted or substituted with one, two, or three R$^g$ substituents;

where each R$^g$ substituent is selected from the group consisting of: —C$_{1-6}$alkyl, —OH, —OC$_{1-6}$alkyl, —CN, —NO$_2$, —C(O)C$_{1-6}$alkyl, —S(O)$_{0-2}$—C$_{1-6}$alkyl, —OS(O)$_{0-2}$—C$_{1-6}$alkyl, —SO$_2$CF$_3$, —SCF$_3$, halo, —CF$_3$, —OCF$_3$, —CO$_2$H, —CO$_2$C$_{1-6}$alkyl, —CH$_2$OH, monocyclic cycloalkyl, phenyl, thiophenyl, benzhydryl, and oxadiazolyl;

or two R$^g$ substituents taken together form —OCH$_2$O—, —OCF$_2$O—, or —OCH$_2$CH$_2$O—;

ii) a naphthyl group, unsubstituted or substituted with C$_{1-4}$alkyl or halo;

iii) a monocyclic heteroaryl group, unsubstituted or substituted with one, two, or three R$^g$ substituents;

iv) a fused bicyclic heteroaryl group, unsubstituted or substituted with C$_{1-4}$alkyl or halo;

v) a monocyclic cycloalkyl group, optionally fused to a phenyl ring, and unsubstituted or substituted with one or two substituents selected from the group consisting of: —C$_{1-4}$alkyl, —OC$_{1-4}$alkyl, halo, —CF$_3$, oxime, —C$_{1-4}$alkyl oxime, or phenyl; and vi) a monocyclic heterocycloalkyl group, optionally fused to or substituted with phenyl;

X is C;

R$^6$ or R$^7$ are each independently —H, halo, —CF$_3$, or —C(O)N(R$^x$)R$^y$;

wherein R$^x$ and R$^y$ are each independently —H or —C$_{1-4}$alkyl;

and (b) pharmaceutically acceptable salts of the compounds of Formula (I).

2. A compound as defined in claim 1, wherein $R^1$ is —H, —CH$_3$, —CH$_2$CH$_3$, —CH$_2$CH$_2$CH$_3$, —CH(CH$_3$)$_2$, —C(CH$_3$)$_3$, cyclopropyl, cyclobutyl, or benzyl.

3. A compound as defined in claim 2, wherein $R^1$ is —H.

4. A compound as defined in claim 1, wherein $R^2$ is —H or —CH$_3$.

5. A compound as defined in claim 1, wherein $R^3$ is —H or —CH$_3$.

6. A compound as defined in claim 1, wherein $R^2$ and $R^3$ are each —H.

7. A compound as defined in claim 1, wherein $R^4$ is —H.

8. A compound as defined in claim 1, wherein L is —O—, —CH$_2$—, —OCH$_2$—, —OCH(CH$_3$)—, —CH$_2$O—, —CHF—, or —CF$_2$—.

9. A compound as defined in claim 1, wherein L is —O—.

10. A compound as defined in claim 1, wherein Z is —O—, —C(O)—, —OCH$_2$—, —OCH(CH$_3$)—, —OCH(CH$_2$CH$_3$)—, —OCH(CH$_2$OH)—, —OCH(CO$_2$H)—, —OCH(CH$_2$F)—, —OCH$_2$CH$_2$—, —OCH$_2$CH(F)—, —OCH$_2$CH(OCH$_3$)—, —OCH$_2$C(NOH)—, —OCH$_2$C(NOCH$_3$)—, —OCH$_2$CF$_2$—, —OCH$_2$C(O)—, or

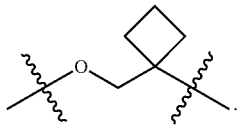

11. A compound as defined in claim 1, wherein Z is —O—, —OCH$_2$—, —OCH$_2$CH$_2$—, or —OCH(CH$_3$)—.

12. A compound as defined in claim 1, wherein $R^5$ is phenyl, optionally substituted with halo, —OCH$_3$, —OSO$_2$CH$_3$, CF$_3$.

13. A compound as defined in claim 1, wherein $R^5$ is cyclohexyl, 2-indanyl, or furanyl optionally substituted with one or more substituents individually selected from halo, —CH$_3$, —CF$_3$, —OCF$_3$, or —CN.

14. A compound as defined in claim 1, wherein $R^5$ is selected from the group consisting of:
i) cyclopropyl, cyclobutyl, 3-phenyl-cyclobutyl, cyclopentyl, cyclohexyl, phenyl, 3- or 4-bromo-phenyl, 2-, 3- or 4-chloro-phenyl, 3,4-dichloro-phenyl, 3- or 4-cyano-phenyl, 2-, 3- or 4-fluoro-phenyl, 3-chloro-4-fluoro-phenyl, 4-chloro-3-fluoro-phenyl, 4-chloro-3-trifluoromethyl-phenyl, 3-chloro-4-trifluoromethoxy-phenyl, 2,4-difluoro-phenyl, 2-fluoro-4-trifluoromethyl-phenyl, 3-fluoro-4-trifluoromethyl-phenyl, 4-fluoro-3-trifluoromethyl-phenyl, 3- or 4-methyl-phenyl, 3- or 4-methylsulfanyl-phenyl, 3- or 4-methoxy-phenyl, 3-chloro-4-methoxy-phenyl, 3-methanesulfonyloxy-phenyl, 3- or 4-methoxy-phenyl, 3-trifluoromethoxy-phenyl, 2-, 3- or 4-trifluoromethyl-phenyl, 4-fluoro-3-trifluoromethyl-phenyl, 3- or 4-trifluoromethylsulfanyl-phenyl, 3-trifluoromethoxy-phenyl,

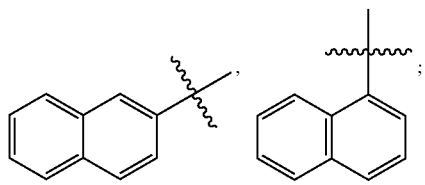 [SMILES: *c1ccc2ccccc2c1 ; *c1cccc2ccccc12]

and ii) 3-azetidinyl, 1-benzyl-azetidin-3-yl, 1-benzhydryl-azetidin-3-yl, 1-isopropyl-azetidin-3-yl, benzo[1,3]dioxol-5-yl, 2,2-difluoro-benzo[1,3]dioxol-5-yl, 2-benzofuranyl, 5-benzofuranyl, 2,3-dihydro-benzofuran-2-yl, 2-benzothiazolyl, 6-benzothiazolyl, 1H-benzotriazole-6-yl, 1-methyl-1H-benzotriazole-6-yl, 2- or 3-chromanyl, 2- or 3-furanyl, 5-trifluoromethyl-2-furanyl, 2-indanyl, tetrahydro-3-furanyl, 1-Hydroxyimino-indan-2-yl, 4-methoxy-2-indanyl, 5-fluoro-1-indanyl, 5-methyl-1-indanyl, 5- or 6-chloro-1-indanyl, 6-fluoro-1-indanyl, 6-trifluoromethyl-1-indanyl, 6-methyl-1-indanyl, 5-fluoro-2-indanyl, 5-methoxy-2-indanyl, [1,2,4]oxadiazole-5-yl, 3-cyclopropyl-[1,2,4]oxadiazole-5-yl, 3-cyclobutyl-[1,2,4]oxadiazole-5-yl, 3-isopropyl-[1,2,4]oxadiazole-5-yl, phenoxy, 4-piperidinyl, 2- or 3-pyrrolidinyl, 3-methyl-[1,2,4]oxadiazole-5-yl, 5-oxazolyl, 3-, 4- or 5-pyrazolyl, 4-trifluoromethyl-2-pyridinyl, 2-, 3- or 4-pyridinyl, 6-trifluoromethyl-2-pyridinyl, 1,2,3,4-tetrahydro-naphthalen-1-yl, 1,2,3,4-tetrahydro-naphthalen-2-yl, 1-phenyl-3-azetidinyl, 4- or 5-thiazolyl, 2-methyl-thiazole-4-yl, 2-thiophen-2-yl-thiazole-4-yl

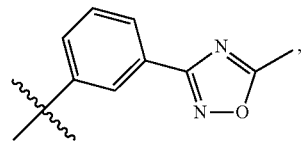 [SMILES: *c1cccc(-c2noc(C)n2)c1]

5-methyl-isoxazole-3-yl.

15. A compound as defined in claim 1, wherein $R^6$ and $R^7$ are each independently —H, halo, —CF$_3$, or N,N-dimethyl-formamidyl.

16. A compound as defined in claim 1, wherein $R^6$ is —H or halo.

17. A compound as defined in claim 1, wherein $R^6$ is —H or halo and $R^7$ is —H, halo, —CF$_3$, or N,N-dimethyl-formamidyl.

18. A compound as defined in claim 1, selected from the group consisting of:
3-(2-Benzyloxy-5-bromo-phenoxy)-azetidine;
3-[5-Bromo-2-(3-chloro-benzyloxy)-phenoxy]-azetidine;
3-[5-Bromo-2-(3-chloro-benzyloxy)-phenoxy]-1-cyclobutyl-azetidine;
3-[5-Bromo-2-(3-chloro-benzyloxy)-phenoxy]-1-propyl-azetidine;
3-[5-Bromo-2-(3-chloro-benzyloxy)-phenoxy]-1-isopropyl-azetidine;
3-[5-Bromo-2-(3-chloro-benzyloxy)-phenoxy]-1-ethyl-azetidine;
3-[5-Bromo-2-(3-trifluoromethoxy-benzyloxy)-phenoxy]-azetidine;
3-[5-Bromo-2-(3-trifluoromethyl-benzyloxy)-phenoxy]-azetidine;
3-[2-(Azetidin-3-yloxy)-4-bromo-phenoxymethyl]-benzonitrile;
3-[5-Bromo-2-(5-trifluoromethyl-furan-2-ylmethoxy)-phenoxy]-azetidine;
3-[5-Bromo-2-(3-chloro-4-trifluoromethoxy-benzyloxy)-phenoxy]-azetidine;
3-[5-Bromo-2-(3-chloro-4-fluoro-benzyloxy)-phenoxy]-azetidine;
3-[5-Bromo-2-(3-chloro-4-methoxy-benzyloxy)-phenoxy]-azetidine;
3-[5-Bromo-2-(4-chloro-benzyloxy)-phenoxy]-azetidine;
3-[5-Bromo-2-(2-chloro-benzyloxy)-phenoxy]-azetidine;

3-[5-Bromo-2-(2-chloro-benzyloxy)-phenoxy]-1-methyl-azetidine;
3-[5-Bromo-2-(3-fluoro-benzyloxy)-phenoxy]-azetidine;
3-[5-Bromo-2-(3-fluoro-benzyloxy)-phenoxy]-1-ethyl-azetidine;
3-[5-Bromo-2-(3-fluoro-benzyloxy)-phenoxy]-1-propyl-azetidine;
3-[5-Bromo-2-(3-fluoro-benzyloxy)-phenoxy]-1-isopropyl-azetidine;
3-[5-Bromo-2-(3-fluoro-benzyloxy)-phenoxy]-1-cyclobutyl-azetidine;
3-[4-Bromo-2-(3-chloro-benzyloxy)-phenoxy]-azetidine;
3-[4-Bromo-2-(3-chloro-benzyloxy)-phenoxy]-1-cyclobutyl-azetidine;
3-[4-Bromo-2-(3-chloro-benzyloxy)-phenoxy]-1-isopropyl-azetidine;
3-[5-Chloro-2-(4-fluoro-benzyloxy)-phenoxy]-azetidine;
3-[5-Chloro-2-(3-methylsulfanyl-benzyloxy)-phenoxy]-azetidine;
3-[5-Chloro-2-(3-methanesulfonyl-benzyloxy)-phenoxy]-azetidine;
4-[2-(Azetidin-3-yloxy)-4-chloro-phenoxymethyl]-2-thiophen-2-yl-thiazole;
4-[2-(Azetidin-3-yloxy)-4-chloro-phenoxymethyl]-2-methyl-thiazole;
3-[2-(Azetidin-3-yloxy)-4-chloro-phenoxymethyl]-5-methyl-isoxazole;
3-[3-[2-(Azetidin-3-yloxy)-4-chloro-phenoxymethyl]-phenyl]-5-methyl-[1,2,4]oxadiazole;
3-[5-Chloro-2-(2-trifluoromethyl-benzyloxy)-phenoxy]-azetidine;
3-[5-Chloro-2-(3-methoxy-benzyloxy)-phenoxy]-azetidine;
3-[2-(Azetidin-3-yloxy)-4-chloro-phenoxymethyl]-benzonitrile;
3-[5-Chloro-2-(2-chloro-benzyloxy)-phenoxy]-azetidine;
3-[5-Chloro-2-(4-chloro-benzyloxy)-phenoxy]-azetidine;
3-[5-Chloro-2-(3-chloro-benzyloxy)-phenoxy]-azetidine;
3-[5-Chloro-2-(3-chloro-benzyloxy)-phenoxy]-1-methyl-azetidine;
3-[5-Chloro-2-(3-trifluoromethyl-benzyloxy)-phenoxy]-azetidine;
3-(2-Benzyloxy-5-chloro-phenoxy)-azetidine;
3-[5-Chloro-2-(3-chloro-4-trifluoromethoxy-benzyloxy)-phenoxy]-azetidine;
3-[5-Chloro-2-(4-trifluoromethoxy-benzyloxy)-phenoxy]-azetidine;
3-[5-Chloro-2-(4-trifluoromethyl-benzyloxy)-phenoxy]-azetidine;
4-[2-(Azetidin-3-yloxy)-4-chloro-phenoxymethyl]-benzonitrile;
3-[2-(2,4-Bis-trifluoromethyl-benzyloxy)-5-chloro-phenoxy]-azetidine;
3-[5-Chloro-2-(4-trifluoromethylsulfanyl-benzyloxy)-phenoxy]-azetidine;
3-[5-Chloro-2-(4-fluoro-3-trifluoromethyl-benzyloxy)-phenoxy]-azetidine;
3-[5-Chloro-2-(2-fluoro-4-trifluoromethyl-benzyloxy)-phenoxy]-azetidine;
3-[5-Chloro-2-(4-chloro-3-trifluoromethyl-benzyloxy)-phenoxy]-azetidine;
3-[5-Chloro-2-(3,4-dichloro-benzyloxy)-phenoxy]-azetidine;
2-[2-(Azetidin-3-yloxy)-4-chloro-phenoxymethyl]-pyridine;
3-[2-(Azetidin-3-yloxy)-4-chloro-phenoxymethyl]-pyridine;
4-[2-(Azetidin-3-yloxy)-4-chloro-phenoxymethyl]-pyridine;
3-[5-Chloro-2-(5-trifluoromethyl-furan-2-ylmethoxy)-phenoxy]-azetidine;
5-[2-(Azetidin-3-yloxy)-4-chloro-phenoxymethyl]-furan-2-carboxylic acid ethyl ester;
3-[5-Chloro-2-(4-chloro-2-methanesulfonyl-benzyloxy)-phenoxy]-azetidine;
3-[5-Chloro-2-(2,4-difluoro-benzyloxy)-phenoxy]-azetidine;
3-(5-Chloro-2-cyclopentyloxy-phenoxy)-azetidine;
3-(5-Chloro-2-cyclohexylmethoxy-phenoxy)-azetidine;
3-(5-Bromo-2-cyclohexylmethoxy-phenoxy)-azetidine;
5-[2-(Azetidin-3-yloxy)-4-chloro-phenoxymethyl]-2-trifluoromethyl-furan-3-carboxylic acid;
5-[2-(Azetidin-3-yloxy)-4-chloro-phenoxymethyl]-2-trifluoromethyl-furan-3-carboxylic acid ethyl ester;
5-[4-Chloro-2-(1-methyl-azetidin-3-yloxy)-phenoxymethyl]-2-trifluoromethyl-furan-3-yl]-methanol;
3-[5-Chloro-2-(5-methyl-2-trifluoromethyl-furan-3-ylmethoxy)-phenoxy]-azetidine;
2-[2-(Azetidin-3-yloxy)-4-chloro-phenoxymethyl]-6-trifluoromethyl-pyridine;
3-[2-(Azetidin-3-yloxy)-4-chloro-phenoxymethyl]-2-methyl-6-trifluoromethyl-pyridine;
2-[2-(Azetidin-3-yloxy)-4-chloro-phenoxymethyl]-4-trifluoromethyl-pyridine;
5-[2-(Azetidin-3-yloxy)-4-chloro-phenoxymethyl]-2-trifluoromethyl-pyridine;
3-[2-(Benzofuran-5-ylmethoxy)-5-chloro-phenoxy]-azetidine;
6-[2-(Azetidin-3-yloxy)-4-chloro-phenoxymethyl]-benzothiazole;
6-[2-(Azetidin-3-yloxy)-4-chloro-phenoxymethyl]-1-methyl-1H-benzotriazole;
3-[5-Chloro-2-(2,2-difluoro-benzo[1,3]dioxol-5-ylmethoxy)-phenoxy]-azetidine;
5-[2-(Azetidin-3-yloxy)-4-chloro-phenoxymethyl]-oxazole;
2-[2-(Azetidin-3-yloxy)-4-chloro-phenoxymethyl]-thiazole;
3-[2-(Benzofuran-2-ylmethoxy)-5-chloro-phenoxy]-azetidine;
(S)-3-[5-Chloro-2-[1-(3-trifluoromethyl-phenyl)-ethoxy]-phenoxy]-azetidine;
(S)-3-[5-Chloro-2-[1-(3-trifluoromethyl-phenyl)-ethoxy]-phenoxy]-azetidine;
(S)-3-[5-Chloro-2-[1-(3-trifluoromethyl-phenyl)-ethoxy]-phenoxy]-1-methyl-azetidine;
(S)-1-Benzyl-3-[5-chloro-2-[1-(3-trifluoromethyl-phenyl)-ethoxy]-phenoxy]-azetidine;
(±)-3-[5-Chloro-2-[1-(3-trifluoromethyl-phenyl)-ethoxy]-phenoxy]-azetidine;
(±)-3-[5-Chloro-2-[1-(3-trifluoromethyl-phenyl)-ethoxy]-phenoxy]-1-isopropyl-azetidine;
(±)-3-[5-Chloro-2-[1-(3-trifluoromethyl-phenyl)-ethoxy]-phenoxy]-1-cyclobutyl-azetidine;
(±)-1-Benzyl-3-[5-chloro-2-[1-(3-trifluoromethyl-phenyl)-ethoxy]-phenoxy]-azetidine;
(±)-3-[5-Chloro-2-[1-(3-trifluoromethyl-phenyl)-ethoxy]-phenoxy]-1-methyl-azetidine;
(±)-3-[5-Bromo-2-[1-(3-trifluoromethoxy-phenyl)-ethoxy]-phenoxy]-azetidine;
(±)-3-[5-Bromo-2-[1-(3-chloro-phenyl)-ethoxy]-phenoxy]-azetidine;
(±)-3-[5-Bromo-2-[1-(3-trifluoromethyl-phenyl)-ethoxy]-phenoxy]-azetidine;

(R)-3-[5-Bromo-2-[1-(3-trifluoromethyl-phenyl)-ethoxy]-phenoxy]-azetidine;
(±)-3-[5-Chloro-2-[1-(3-chloro-phenyl)-ethoxy]-phenoxy]-azetidine;
(±)-3-[5-Chloro-2-[1-(3-fluoro-phenyl)-ethoxy]-phenoxy]-azetidine;
(±)-3-[5-Chloro-2-[1-(2-chloro-phenyl)-ethoxy]-phenoxy]-azetidine;
(±)-3-[5-Chloro-2-[1-(4-fluoro-3-trifluoromethyl-phenyl)-ethoxy]-phenoxy]-azetidine;
(±)-3-[5-Chloro-2-[1-(3-fluoro-4-trifluoromethyl-phenyl)-ethoxy]-phenoxy]-azetidine;
(±)-3-[5-Chloro-2-[1-(3-fluoro-5-trifluoromethyl-phenyl)-ethoxy]-phenoxy]-azetidine;
(±)-3-[5-Chloro-2-[1-(3-trifluoromethylsulfanyl-phenyl)-ethoxy]-phenoxy]-azetidine;
(±)-3-[5-Chloro-2-[1-(2-fluoro-phenyl)-ethoxy]-phenoxy]-azetidine;
(±)-3-[5-Chloro-2-[1-(2-trifluoromethyl-phenyl)-ethoxy]-phenoxy]-azetidine;
(±)-3-[5-Chloro-2-[1-(4-chloro-phenyl)-ethoxy]-phenoxy]-azetidine;
(±)-3-[5-Chloro-2-[1-(4-fluoro-phenyl)-ethoxy]-phenoxy]-azetidine;
(±)-3-[1-[2-(Azetidin-3-yloxy)-4-chloro-phenoxy]-ethyl]-benzonitrile;
(±)-3-[5-Chloro-2-[1-(3,4-dichloro-phenyl)-ethoxy]-phenoxy]-azetidine;
(±)-3-[5-Chloro-2-[1-(3-trifluoromethoxy-phenyl)-ethoxy]-phenoxy]-azetidine;
(±)-3-[5-Chloro-2-[1-(3,4-difluoro-phenyl)-ethoxy]-phenoxy]-azetidine;
(±)-3-[5-Chloro-2-[1-(2,5-dichloro-phenyl)-ethoxy]-phenoxy]-azetidine;
(±)-3-[5-Chloro-2-[1-(2,5-difluoro-phenyl)-ethoxy]-phenoxy]-azetidine;
2-[1-[2-(Azetidin-3-yloxy)-4-chloro-phenoxy]-ethyl]-benzothiazole;
5-[1-[2-(Azetidin-3-yloxy)-4-chloro-phenoxy]-ethyl]-thiazole;
2-[1-[2-(Azetidin-3-yloxy)-4-chloro-phenoxy]-ethyl]-thiazole;
5-[1-[2-(Azetidin-3-yloxy)-4-chloro-phenoxy]-ethyl]-2,4-dimethyl-thiazole;
(±)-3-[5-Chloro-2-[1-(3-trifluoromethyl-phenyl)-propoxy]-phenoxy]-azetidine;
3-[5-Bromo-2-(2-fluoro-1-phenyl-ethoxy)-phenoxy]-azetidine;
3-[5-Chloro-2-(2-fluoro-1-phenyl-ethoxy)-phenoxy]-azetidine;
(±)-3-[5-Chloro-2-(1-phenyl-ethoxy)-phenoxy]-azetidine;
(±)-3-[5-Chloro-2-[1-(5-trifluoromethyl-furan-2-yl)-ethoxy]-phenoxy]-azetidine;
3-[5-Chloro-2-(1-phenyl-propoxy)-phenoxy]-azetidine;
2-[2-(Azetidin-3-yloxy)-4-chloro-phenoxy]-2-phenyl-ethanol;
[2-(Azetidin-3-yloxy)-4-chloro-phenoxy]-phenyl-acetic acid;
(±)-3-[5-Chloro-2-(6-fluoro-indan-1-yloxy)-phenoxy]-azetidine;
(±)-3-[5-Bromo-2-(indan-1-yloxy)-phenoxy]-azetidine;
(±)-3-[5-Bromo-2-(5-chloro-indan-1-yloxy)-phenoxy]-azetidine;
(±)-3-[5-Bromo-2-(6-chloro-indan-1-yloxy)-phenoxy]-azetidine;
(±)-3-[5-Bromo-2-(5-fluoro-indan-1-yloxy)-phenoxy]-azetidine;
(±)-3-[5-Bromo-2-(5-methyl-indan-1-yloxy)-phenoxy]-azetidine;
(±)-3-[5-Bromo-2-(6-methyl-indan-1-yloxy)-phenoxy]-azetidine;
(±)-3-[5-Bromo-2-(6-trifluoromethyl-indan-1-yloxy)-phenoxy]-azetidine;
(±)-3-[5-Chloro-2-(6-methyl-indan-1-yloxy)-phenoxy]-azetidine;
(±)-3-[5-Chloro-2-(6-chloro-indan-1-yloxy)-phenoxy]-azetidine;
3-[5-Chloro-2-(6-trifluoromethyl-indan-1-yloxy)-phenoxy]-azetidine;
3-[5-Chloro-2-(1,2,3,4-tetrahydro-naphthalen-1-yloxy)-phenoxy]-azetidine;
3-[5-Bromo-2-(5-tert-butyl-indan-1-yloxy)-phenoxy]-azetidine;
3-[5-Chloro-2-(tetrahydro-furan-3-ylmethoxy)-phenoxy]-azetidine;
3-[5-Chloro-2-(1,2,3,4-tetrahydro-naphthalen-2-yloxy)-phenoxy]-azetidine;
3-[5-Chloro-2-(chroman-2-ylmethoxy)-phenoxy]-azetidine;
3-[5-Chloro-2-(tetrahydro-furan-2-ylmethoxy)-phenoxy]-azetidine;
3-[5-Chloro-2-(chroman-3-ylmethoxy)-phenoxy]-azetidine;
3-[5-Chloro-2-(2-methoxy-2-phenyl-ethoxy)-phenoxy]-azetidine;
3-[5-Chloro-2-(2,3-dihydro-benzofuran-2-ylmethoxy)-phenoxy]-azetidine;
5-[2-(Azetidin-3-yloxy)-4-chloro-phenoxymethyl]-1,3-dimethyl-1H-pyrazole;
3-[5-Chloro-2-(2-phenoxy-ethoxy)-phenoxy]-azetidine;
3-[5-Bromo-2-(3-fluoro-benzyloxy)-phenoxy]-1-phenyl-azetidine;
3-[5-Chloro-2-(indan-2-yloxy)-phenoxy]-azetidine;
3-[5-Bromo-2-(indan-2-yloxy)-phenoxy]-azetidine;
3-[5-Chloro-2-(5-fluoro-indan-2-yloxy)-phenoxy]-azetidine;
3-[5-Chloro-2-(5-chloro-indan-2-yloxy)-phenoxy]-azetidine;
3-[5-Chloro-2-(5-methoxy-indan-2-yloxy)-phenoxy]-azetidine;
3-[5-Chloro-2-(4-methoxy-indan-2-yloxy)-phenoxy]-azetidine;
2-[2-(Azetidin-3-yloxy)-4-chloro-phenoxy]-indan-1-one oxime;
2-[2-(Azetidin-3-yloxy)-4-chloro-phenoxy]-indan-1-one O-methyl-oxime;
2-[2-(Azetidin-3-yloxy)-4-chloro-phenoxy]-1-phenyl-ethanone oxime;
2-[2-(Azetidin-3-yloxy)-4-chloro-phenoxy]-1-phenyl-ethanone O-methyl-oxime;
2-[2-(Azetidin-3-yloxy)-4-chloro-phenoxy]-1-(4-chloro-phenyl)-ethanone;
3-[5-Chloro-2-(2,2-difluoro-2-phenyl-ethoxy)-phenoxy]-azetidine;
3-[5-Chloro-2-[2-(3-chloro-phenyl)-ethoxy]-phenoxy]-azetidine;
3-[5-Chloro-2-(3-chloro-benzyloxy)-phenoxy]-azetidine;
3-[5-Chloro-2-(2-fluoro-2-phenyl-ethoxy)-phenoxy]-azetidine;
3-[5-Chloro-2-[1-(4-chloro-phenyl)-cyclobutylmethoxy]-phenoxy]-azetidine;

3-[5-Chloro-2-[1-(3-chloro-phenyl)-cyclobutylmethoxy]-phenoxy]-azetidine;
3-[5-Chloro-2-[2-(3-methoxy-phenyl)-ethoxy]-phenoxy]-azetidine;
3-[5-Chloro-2-[2-(3-fluoro-phenyl)-ethoxy]-phenoxy]-azetidine;
3-[5-Chloro-2-[2-(4-chloro-phenyl)-ethoxy]-phenoxy]-azetidine;
3-[5-Chloro-2-[2-(4-fluoro-phenyl)-ethoxy]-phenoxy]-azetidine;
3-[5-Chloro-2-[2-(4-methoxy-phenyl)-ethoxy]-phenoxy]-azetidine;
3-(5-Bromo-2-phenethyloxy-phenoxy)-azetidine;
3-(2-Benzyloxy-5-chloro-3-fluoro-phenoxy)-azetidine;
3-[5-Chloro-3-fluoro-2-(5-trifluoromethyl-furan-2-yl-methoxy)-phenoxy]-azetidine;
3-[5-Tri fluoromethyl-2-(5-trifluoromethyl-furan-2-yl-methoxy)-phenoxy]-azetidine;
3-[5-Trifluoromethyl-2-[1-(3-trifluoromethyl-phenyl)-ethoxy]-phenoxy]-azetidine;
3-[2-(1-Phenyl-ethoxy)-5-trifluoromethyl-phenoxy]-azetidine;
3-[2-(3-Chloro-benzyloxy)-5-fluoro-phenoxy]-azetidine;
3-[2-(3-Chloro-benzyloxy)-5-fluoro-phenoxy]-1-methyl-azetidine;
3-[2-(3-Chloro-benzyloxy)-5-fluoro-phenoxy]-1-isopropyl-azetidine;
3-[2-(3-Chloro-benzyloxy)-5-fluoro-phenoxy]-1-cyclobutyl-azetidine;
3-[2-(3-Chloro-benzyloxy)-5-fluoro-phenoxy]-1-propyl-azetidine;
3-[2-(3-Chloro-benzyloxy)-5-fluoro-phenoxy]-1-ethyl-azetidine;
3-[5-Fluoro-2-(5-trifluoromethyl-furan-2-ylmethoxy)-phenoxy]-azetidine;
3-[5-Fluoro-2-(5-trifluoromethyl-furan-2-ylmethoxy)-phenoxy]-1-isopropyl-azetidine;
3-(Azetidin-3-yloxy)-4-(3-Chloro-benzyloxy)-N,N-dimethyl-benzamide;
3-[5-Bromo-2-(3-chloro-benzyloxy)-phenoxy]-3-methyl-azetidine;
3-[5-Bromo-2-(3-chloro-benzyloxy)-phenoxy]-3-ethyl-azetidine;
3-[5-Bromo-2-(3-chloro-benzyloxy)-phenoxy]-3-isopropyl-azetidine;
3-(5-Bromo-2-phenethyloxy-phenoxy)-3-methyl-azetidine;
3-[5-Bromo-2-(5-trifluoromethyl-furan-2-ylmethoxy)-phenoxy]-azetidine;
3-[5-Bromo-2-(3-trifluoromethyl-benzyloxy)-phenoxy]-azetidine;
3-(5-Bromo-2-phenoxy-phenoxy)-3-methyl-azetidine;
(±)-trans-3-[5-Bromo-2-(3-fluoro-benzyloxy)-phenoxy]-2-methyl-azetidine;
cis-1-Benzyl-3-[5-bromo-2-(3-fluoro-benzyloxy)-phenoxy]-2-methyl-azetidine;
trans-1-Benzyl-3-[5-bromo-2-(3-fluoro-benzyloxy)-phenoxy]-2-methyl-azetidine;
3-[5-Chloro-2-(1-phenyl-azetidin-3-ol)-phenoxy]-azetidine;
(±)-3-[5-Chloro-2-(trans-1-benzyl-2-methyl-azetidin-3-ol)-phenoxy]-azetidine;
3-[5-Chloro-2-(1-Isopropyl-azetidin-3-ol)-phenoxy]-azetidine;
3-[5-Chloro-2-(1-benzhydryl-azetidin-3-ol)-phenoxy]-azetidine;
3-[5-Chloro-2-(1-azetidin-3-ol)-phenoxy]-azetidine;
3-[5-Chloro-2-(1-Isopropyl-azetidin-3-ol)-phenoxy]-1-isopropyl-azetidine;
3-[5-Chloro-2-(3-phenyl-cyclobutoxy)-phenoxy]-azetidine;
3-[5-Bromo-2-(3-fluoro-benzyloxy)-phenoxy]-1-tert-butyl-azetidine;
1-tert-Butyl-3-[5-chloro-2-(3-trifluoromethyl-benzyloxy)-phenoxy]-azetidine
1-tert-Butyl-3-[5-chloro-2-[1-(3-trifluoromethyl-phenyl)-ethoxy]-phenoxy]-azetidine;
3-[5-Bromo-2-(5-trifluoromethyl-furan-2-ylmethoxy)-benzyl]-azetidine;
3-[5-Bromo-2-(3-chloro-benzyloxy)-phenoxymethyl]-azetidine;
3-[5-Bromo-2-(3-chloro-benzyloxy)-phenoxymethyl]-1-methyl-azetidine;
3-[5-Bromo-2-(3-chloro-benzyloxy)-phenoxymethyl]-azetidin-3-ol;
3-[1-[5-Bromo-2-(3-chloro-benzyloxy)-phenoxy]-ethyl]-azetidin-3-ol;
3-[5-Bromo-2-(3-chloro-benzyloxy)-benzyloxy]-azetidine;
3-[5-Chloro-2-(3-chloro-benzyloxy)-benzyloxy]-azetidine;
5-[2-(Azetidin-3-yloxy)-4-chloro-phenoxymethyl]-3-methyl-[1,2,4]oxadiazole;
5-[2-(Azetidin-3-yloxy)-4-chloro-phenoxymethyl]-3-cyclobutyl-[1,2,4]oxadiazole;
5-[2-(Azetidin-3-yloxy)-4-chloro-phenoxymethyl]-3-cyclopropyl-[1,2,4]oxadiazole;
5-[2-(Azetidin-3-yloxy)-4-chloro-phenoxymethyl]-3-isopropyl-[1,2,4]oxadiazole;
5-[2-(Azetidin-3-yloxy)-4-chloro-phenoxymethyl]-3-ethyl-[1,2,4]oxadiazole;
3-(5-Bromo-2-phenoxy-phenoxy)-azetidine;
3-[5-Bromo-2-(3-bromo-phenoxy)-phenoxy]-azetidine;
3-[5-Bromo-2-(3-fluoro-phenoxy)-phenoxy]-azetidine;
3-(5-Bromo-2-m-tolyloxy-phenoxy)-azetidine;
3-[5-Bromo-2-(3-methoxy-phenoxy)-phenoxy]-azetidine;
3-[5-Bromo-2-(4-fluoro-phenoxy)-phenoxy]-azetidine;
3-[5-Bromo-2-(4-bromo-phenoxy)-phenoxy]-azetidine;
3-[5-Bromo-2-(4-chloro-phenoxy)-phenoxy]-azetidine;
3-[5-Bromo-2-(3-chloro-phenoxy)-phenoxy]-azetidine;
3-[5-Bromo-2-(3-trifluoromethoxy-phenoxy)-phenoxy]-azetidine;
3-[5-Bromo-2-(naphthalen-2-yloxy)-phenoxy]-azetidine;
3-[5-Bromo-2-(naphthalen-1-yloxy)-phenoxy]-azetidine;
3-(5-Chloro-2-phenoxy-phenoxy)-azetidine;
3-[5-Chloro-2-(3-chloro-phenoxy)-phenoxy]-azetidine;
3-[5-Chloro-2-(4-chloro-phenoxy)-phenoxy]-azetidine;
3-(5-Chloro-2-o-tolyloxy-phenoxy)-azetidine;
3-[5-Chloro-2-(naphthalen-2-yloxy)-phenoxy]-azetidine;
2-[2-(Azetidin-3-yloxy)-4-chloro-phenoxy]-benzothiazole;
2-[2-(Azetidin-3-yloxy)-4-chloro-phenoxy]-benzooxazole;
2-[2-(Azetidin-3-yloxy)-4-chloro-phenoxy]-[1,8]naphthyridine;
2-[2-(Azetidin-3-yloxy)-4-chloro-phenoxy]-quinoline;
2-(Azetidin-3-yloxy)-4-bromo-phenyl]-phenyl-methanone;
[2-(Azetidin-3-yloxy)-4-bromo-phenyl]-(4-chloro-phenyl)-methanone;
[2-(Azetidin-3-yloxy)-4-bromo-phenyl]-(3-chloro-phenyl)-methanone;

[4-Bromo-2-(1-methyl-azetidin-3-yloxy)-phenyl]-(3-chloro-phenyl)-methanone;
[2-(Azetidin-3-yloxy)-4-bromo-phenyl]-m-tolyl-methanone;
[2-(Azetidin-3-yloxy)-4-bromo-phenyl]-o-tolyl-methanone;
[2-(Azetidin-3-yloxy)-4-bromo-phenyl]-(3-methoxy-phenyl)-methanone;
[2-(Azetidin-3-yloxy)-4-bromo-phenyl]-naphthalen-2-yl-methanone;
[4-Bromo-2-(1-isopropyl-azetidin-3-yloxy)-phenyl]-naphthalen-2-yl-methanone;
[2-(Azetidin-3-yloxy)-4-bromo-phenyl]-benzo[1,3]dioxol-5-yl-methanone;
Benzo[1,3]dioxol-5-yl-[4-bromo-2-(1-isopropyl-azetidin-3-yloxy)-phenyl]-methanone;
[2-(Azetidin-3-yloxy)-4-bromo-phenyl]-(4-methoxy-phenyl)-methanone;
[2-(Azetidin-3-yloxy)-4-bromo-phenyl]-(4-chloro-3-chloro-phenyl)-methanone;
[2-(Azetidin-3-yloxy)-4-bromo-phenyl]-(3,4-dichloro-phenyl)-methanone;
[2-(Azetidin-3-yloxy)-4-chloro-phenyl]-naphthalen-2-yl-methanone;
[2-(Azetidin-3-yloxy)-4-chloro-phenyl]-benzo[1,3]dioxol-5-yl-methanone;
Benzo[1,3]dioxol-5-yl-[4-chloro-2-(1-isopropyl-azetidin-3-yloxy)-phenyl]-methanone;
[2-(Azetidin-3-yloxy)-4-chloro-phenyl]-(4-chloro-phenyl)-methanone; and
[2-(Azetidin-3-yloxy)-4-chloro-phenyl]-(3-chloro-phenyl)-methanone;
and pharmaceutically acceptable salts thereof.

19. A pharmaceutical composition, comprising an effective amount of at least one compound selected from compounds of Formula (I):

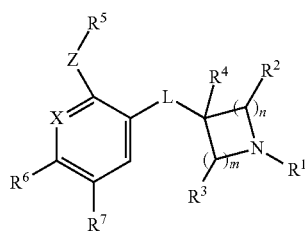

(I)

wherein
$R^1$ is —H, —$C_{1-4}$alkyl, monocyclic cycloalkyl, phenyl, or benzyl;
m is 1;
n is 1;
$R^2$ and $R^3$ are each independently —H or —$C_{1-4}$alkyl;
$R^4$ is —H, F, $C_{1-4}$alkyl, or $R^4$ is —OH when L is —$CH_2$—, —$CF_2$—, —CHF—, —$OCH_2$—, or —$OCH(CH_3)$—;
L is —O—, —$CH_2$—, —$OCH_2$—, —$OCH(CH_3)$—, —$CH_2$—, —$CF_2$—, or —CHF—;
Z is —O—, —C(O)—, —$OCH(R^b)$—, or —$OCH_2C(R^c)(R^d)$—;
 where
  where $R^b$ is —H; a —$C_{1-4}$alkyl group unsubstituted or substituted with OH or halo; —$CO_2C_{1-4}$alkyl; or —$CO_2H$; and
  $R^c$ and $R^d$ are each independently —H, —$C_{1-4}$alkyl, —O—$C_{1-4}$alkyl, or halo;

or $R^c$ and $R^d$ taken together form an oxime, a $C_{1-4}$alkyl oxime, or a carbonyl group;
 or $R^c$ and $R^d$ taken together with the carbon to which they are attached form a $C_{3-6}$cycloalkyl group;
$R^5$ is:
 i) a phenyl, unsubstituted or substituted with one, two, or three $R^g$ substituents;
  where each $R^g$ substituent is selected from the group consisting of: —$C_{1-6}$alkyl, —OH, —$OC_{1-6}$alkyl, —CN, —$NO_2$, —$C(O)C_{1-6}$alkyl, —$S(O)_{0-2}$—$C_{1-6}$alkyl, —$OS(O)_{0-2}$—$C_{1-6}$alkyl, —$SO_2CF_3$, —$SCF_3$, halo, —$CF_3$, —$OCF_3$, —$CO_2H$, —$CO_2C_{1-6}$alkyl, —$CH_2OH$, monocyclic cycloalkyl, phenyl, thiophenyl, benzhydryl, and oxadiazolyl;
  or two $R^g$ substituents taken together form —$OCH_2O$—, —$OCF_2O$—, or —$OCH_2CH_2O$—;
 ii) a naphthyl group, unsubstituted or substituted with $C_{1-4}$alkyl or halo;
 iii) a monocyclic heteroaryl group, unsubstituted or substituted with one, two, or three $R^g$ substituents;
 iv) a fused bicyclic heteroaryl group, unsubstituted or substituted with $C_{1-4}$alkyl or halo;
 v) a monocyclic cycloalkyl group, optionally fused to a phenyl ring, and unsubstituted or substituted with one or two substituents selected from the group consisting of: —$C_{1-4}$alkyl —$OC_{1-4}$alkyl, halo, —$CF_3$, oxime, —$C_{1-4}$alkyl oxime, or phenyl; and
 vi) a monocyclic heterocycloalkyl group, optionally fused to or substituted with phenyl;
X is C;
$R^6$ or $R^7$ are each independently —H, halo, —$CF_3$, or —$C(O)N(R^x)R^y$;
 wherein $R^x$ and $R^y$ are each independently —H or —$C_{1-4}$alkyl;
and (b) pharmaceutically acceptable salts of the compounds of Formula (I).

20. A pharmaceutical composition according to claim 19, wherein said at least one compound is selected from the group consisting of:
3-(2-Benzyloxy-5-bromo-phenoxy)-azetidine;
3-[5-Bromo-2-(3-chloro-benzyloxy)-phenoxy]-azetidine;
3-[5-Bromo-2-(3-chloro-benzyloxy)-phenoxy]-1-cyclobutyl-azetidine;
3-[5-Bromo-2-(3-chloro-benzyloxy)-phenoxy]-1-propyl-azetidine;
3-[5-Bromo-2-(3-chloro-benzyloxy)-phenoxy]-1-isopropyl-azetidine;
3-[5-Bromo-2-(3-chloro-benzyloxy)-phenoxy]-1-ethyl-azetidine;
3-[5-Bromo-2-(3-trifluoromethoxy-benzyloxy)-phenoxy]-azetidine;
3-[5-Bromo-2-(3-trifluoromethyl-benzyloxy)-phenoxy]-azetidine;
3-[2-(Azetidin-3-yloxy)-4-bromo-phenoxymethyl]-benzonitrile;
3-[5-Bromo-2-(5-trifluoromethyl-furan-2-ylmethoxy)-phenoxy]-azetidine;
3-[5-Bromo-2-(3-chloro-4-trifluoromethoxy-benzyloxy)-phenoxy]-azetidine;
3-[5-Bromo-2-(3-chloro-4-fluoro-benzyloxy)-phenoxy]-azetidine;
3-[5-Bromo-2-(3-chloro-4-methoxy-benzyloxy)-phenoxy]-azetidine;
3-[5-Bromo-2-(4-chloro-benzyloxy)-phenoxy]-azetidine;
3-[5-Bromo-2-(2-chloro-benzyloxy)-phenoxy]-azetidine;

3-[5-Bromo-2-(2-chloro-benzyloxy)-phenoxy]-1-methyl-azetidine;
3-[5-Bromo-2-(3-fluoro-benzyloxy)-phenoxy]-azetidine;
3-[5-Bromo-2-(3-fluoro-benzyloxy)-phenoxy]-1-ethyl-azetidine;
3-[5-Bromo-2-(3-fluoro-benzyloxy)-phenoxy]-1-propyl-azetidine;
3-[5-Bromo-2-(3-fluoro-benzyloxy)-phenoxy]-1-isopropyl-azetidine;
3-[5-Bromo-2-(3-fluoro-benzyloxy)-phenoxy]-1-cyclobutyl-azetidine
3-[4-Bromo-2-(3-chloro-benzyloxy)-phenoxy]-azetidine;
3-[4-Bromo-2-(3-chloro-benzyloxy)-phenoxy]-1-cyclobutyl-azetidine;
3-[4-Bromo-2-(3-chloro-benzyloxy)-phenoxy]-1-isopropyl-azetidine;
3-[5-Chloro-2-(4-fluoro-benzyloxy)-phenoxy]-azetidine;
3-[5-Chloro-2-(3-methylsulfanyl-benzyloxy)-phenoxy]-azetidine;
3-[5-Chloro-2-(3-methanesulfonyl-benzyloxy)-phenoxy]-azetidine;
4-[2-(Azetidin-3-yloxy)-4-chloro-phenoxymethyl]-2-thiophen-2-yl-thiazole;
4-[2-(Azetidin-3-yloxy)-4-chloro-phenoxymethyl]-2-methyl-thiazole;
3-[2-(Azetidin-3-yloxy)-4-chloro-phenoxymethyl]-5-methyl-isoxazole;
3-[3-[2-(Azetidin-3-yloxy)-4-chloro-phenoxymethyl]-phenyl]-5-methyl-[1,2,4]oxadiazole;
3-[5-Chloro-2-(2-trifluoromethyl-benzyloxy)-phenoxy]-azetidine;
3-[5-Chloro-2-(3-methoxy-benzyloxy)-phenoxy]-azetidine;
3-[2-(Azetidin-3-yloxy)-4-chloro-phenoxymethyl]-benzonitrile;
3-[5-Chloro-2-(2-chloro-benzyloxy)-phenoxy]-azetidine;
3-[5-Chloro-2-(4-chloro-benzyloxy)-phenoxy]-azetidine;
3-[5-Chloro-2-(3-chloro-benzyloxy)-phenoxy]-azetidine;
3-[5-Chloro-2-(3-chloro-benzyloxy)-phenoxy]-1-methyl-azetidine;
3-[5-Chloro-2-(3-trifluoromethyl-benzyloxy)-phenoxy]-azetidine;
3-(2-Benzyloxy-5-chloro-phenoxy)-azetidine;
3-[5-Chloro-2-(3-chloro-4-trifluoromethoxy-benzyloxy)-phenoxy]-azetidine;
3-[5-Chloro-2-(4-trifluoromethoxy-benzyloxy)-phenoxy]-azetidine;
3-[5-Chloro-2-(4-trifluoromethyl-benzyloxy)-phenoxy]-azetidine;
4-[2-(Azetidin-3-yloxy)-4-chloro-phenoxymethyl]-benzonitrile;
3-[2-(2,4-Bis-trifluoromethyl-benzyloxy)-5-chloro-phenoxy]-azetidine;
3-[5-Chloro-2-(4-trifluoromethylsulfanyl-benzyloxy)-phenoxy]-azetidine;
3-[5-Chloro-2-(4-fluoro-3-trifluoromethyl-benzyloxy)-phenoxy]-azetidine;
3-[5-Chloro-2-(2-fluoro-4-trifluoromethyl-benzyloxy)-phenoxy]-azetidine;
3-[5-Chloro-2-(4-chloro-3-trifluoromethyl-benzyloxy)-phenoxy]-azetidine;
3-[5-Chloro-2-(3,4-dichloro-benzyloxy)-phenoxy]-azetidine;
2-[2-(Azetidin-3-yloxy)-4-chloro-phenoxymethyl]-pyridine;
3-[2-(Azetidin-3-yloxy)-4-chloro-phenoxymethyl]-pyridine;
4-[2-(Azetidin-3-yloxy)-4-chloro-phenoxymethyl]-pyridine;
3-[5-Chloro-2-(5-trifluoromethyl-furan-2-ylmethoxy)-phenoxy]-azetidine;
5-[2-(Azetidin-3-yloxy)-4-chloro-phenoxymethyl]-furan-2-carboxylic acid ethyl ester;
3-[5-Chloro-2-(4-chloro-2-methanesulfonyl-benzyloxy)-phenoxy]-azetidine;
3-[5-Chloro-2-(2,4-difluoro-benzyloxy)-phenoxy]-azetidine;
3-(5-Chloro-2-cyclopentyloxy-phenoxy)-azetidine;
3-(5-Chloro-2-cyclohexylmethoxy-phenoxy)-azetidine;
3-(5-Bromo-2-cyclohexylmethoxy-phenoxy)-azetidine;
5-[2-(Azetidin-3-yloxy)-4-chloro-phenoxymethyl]-2-trifluoromethyl-furan-3-carboxylic acid;
5-[2-(Azetidin-3-yloxy)-4-chloro-phenoxymethyl]-2-trifluoromethyl-furan-3-carboxylic acid ethyl ester;
5-[4-Chloro-2-(1-methyl-azetidin-3-yloxy)-phenoxymethyl]-2-trifluoromethyl-furan-3-yl]-methanol;
3-[5-Chloro-2-(5-methyl-2-trifluoromethyl-furan-3-ylmethoxy)-phenoxy]-azetidine;
2-[2-(Azetidin-3-yloxy)-4-chloro-phenoxymethyl]-6-trifluoromethyl-pyridine;
3-[2-(Azetidin-3-yloxy)-4-chloro-phenoxymethyl]-2-methyl-6-trifluoromethyl-pyridine;
2-[2-(Azetidin-3-yloxy)-4-chloro-phenoxymethyl]-4-trifluoromethyl-pyridine;
5-[2-(Azetidin-3-yloxy)-4-chloro-phenoxymethyl]-2-trifluoromethyl-pyridine;
3-[2-(Benzofuran-5-ylmethoxy)-5-chloro-phenoxy]-azetidine;
6-[2-(Azetidin-3-yloxy)-4-chloro-phenoxymethyl]-benzothiazole;
6-[2-(Azetidin-3-yloxy)-4-chloro-phenoxymethyl]-1-methyl-1H-benzotriazole;
3-[5-Chloro-2-(2,2-difluoro-benzo[1,3]dioxol-5-ylmethoxy)-phenoxy]-azetidine;
5-[2-(Azetidin-3-yloxy)-4-chloro-phenoxymethyl]-oxazole;
2-[2-(Azetidin-3-yloxy)-4-chloro-phenoxymethyl]-thiazole;
3-[2-(Benzofuran-2-ylmethoxy)-5-chloro-phenoxy]-azetidine;
(S)-3-[5-Cloro-2-[1-(3-trifluoromethyl-phenyl)-ethoxy]-phenoxy]-azetidine;
(S)-3-[5-Chloro-2-[1-(3-trifluoromethyl-phenyl)-ethoxy]-phenoxy]-azetidine;
(S)-3-[5-Chloro-2-[1-(3-trifluoromethyl-phenyl)-ethoxy]-phenoxy]-1-methyl-azetidine;
(S)-1-Benzyl-3-[5-chloro-2-[1-(3-trifluoromethyl-phenyl)-ethoxy]-phenoxy]-azetidine;
(±)-3-[5-Chloro-2-[1-(3-trifluoromethyl-phenyl)-ethoxy]-phenoxy]-azetidine;
(±)-3-[5-Chloro-2-[1-(3-trifluoromethyl-phenyl)-ethoxy]-phenoxy]-1-isopropyl-azetidine;
(±)-3-[5-Chloro-2-[1-(3-trifluoromethyl-phenyl)-ethoxy]-phenoxy]-1-cyclobutyl-azetidine;
(±)-1-Benzyl-3-[5-chloro-2-[1-(3-trifluoromethyl-phenyl)-ethoxy]-phenoxy]-azetidine;
(±)-3-[5-Chloro-2-[1-(3-trifluoromethyl-phenyl)-ethoxy]-phenoxy]-1-methyl-azetidine;
(±)-3-[5-Bromo-2-[1-(3-trifluoromethoxy-phenyl)-ethoxy]-phenoxy]-azetidine;
(±)-3-[5-Bromo-2-[1-(3-chloro-phenyl)-ethoxy]-phenoxy]-azetidine;
(±)-3-[5-Bromo-2-[1-(3-trifluoromethyl-phenyl)-ethoxy]-phenoxy]-azetidine;

(R)-3-[5-Bromo-2-[1-(3-trifluoromethyl-phenyl)-ethoxy]-phenoxy]-azetidine;
(±)-3-[5-Chloro-2-[1-(3-chloro-phenyl)-ethoxy]-phenoxy]-azetidine;
(±)-3-[5-Chloro-2-[1-(3-fluoro-phenyl)-ethoxy]-phenoxy]-azetidine;
(±)-3-[5-Chloro-2-[1-(2-chloro-phenyl)-ethoxy]-phenoxy]-azetidine;
(±)-3-[5-Chloro-2-[1-(4-fluoro-3-trifluoromethyl-phenyl)-ethoxy]-phenoxy]-azetidine;
(±)-3-[5-Chloro-2-[1-(3-fluoro-4-trifluoromethyl-phenyl)-ethoxy]-phenoxy]-azetidine;
(±)-3-[5-Chloro-2-[1-(3-fluoro-5-trifluoromethyl-phenyl)-ethoxy]-phenoxy]-azetidine;
(±)-3-[5-Chloro-2-[1-(3-trifluoromethylsulfanyl-phenyl)-ethoxy]-phenoxy]-azetidine;
(±)-3-[5-Chloro-2-[1-(2-fluoro-phenyl)-ethoxy]-phenoxy]-azetidine;
(±)-3-[5-Chloro-2-[1-(2-trifluoromethyl-phenyl)-ethoxy]-phenoxy]-azetidine;
(±)-3-[5-Chloro-2-[1-(4-chloro-phenyl)-ethoxy]-phenoxy]-azetidine;
(±)-3-[5-Chloro-2-[1-(4-fluoro-phenyl)-ethoxy]-phenoxy]-azetidine;
(±)-3-[1-[2-(Azetidin-3-yloxy)-4-chloro-phenoxy]-ethyl]-benzonitrile;
(±)-3-[5-Chloro-2-[1-(3,4-dichloro-phenyl)-ethoxy]-phenoxy]-azetidine;
(±)-3-[5-Chloro-2-[1-(3-trifluoromethoxy-phenyl)-ethoxy]-phenoxy]-azetidine;
(±)-3-[5-Chloro-2-[1-(3,4-difluoro-phenyl)-ethoxy]-phenoxy]-azetidine;
(±)-3-[5-Chloro-2-[1-(2,5-dichloro-phenyl)-ethoxy]-phenoxy]-azetidine;
(±)-3-[5-Chloro-2-[1-(2,5-difluoro-phenyl)-ethoxy]-phenoxy]-azetidine;
2-[1-[2-(Azetidin-3-yloxy)-4-chloro-phenoxy]-ethyl]-benzothiazole;
5-[1-[2-(Azetidin-3-yloxy)-4-chloro-phenoxy]-ethyl]-thiazole;
2-[1-[2-(Azetidin-3-yloxy)-4-chloro-phenoxy]-ethyl]-thiazole;
5-[1-[2-(Azetidin-3-yloxy)-4-chloro-phenoxy]-ethyl]-2,4-dimethyl-thiazole;
(±)-3-[5-Chloro-2-[1-(3-trifluoromethyl-phenyl)-propoxy]-phenoxy]-azetidine;
3-[5-Bromo-2-(2-fluoro-1-phenyl-ethoxy)-phenoxy]-azetidine;
3-[5-Chloro-2-(2-fluoro-1-phenyl-ethoxy)-phenoxy]-azetidine;
(±)-3-[5-Chloro-2-(1-phenyl-ethoxy)-phenoxy]-azetidine;
(±)-3-[5-Chloro-2-[1-(5-trifluoromethyl-furan-2-yl)-ethoxy]-phenoxy]-azetidine;
3-[5-Chloro-2-(1-phenyl-propoxy)-phenoxy]-azetidine;
2-[2-(Azetidin-3-yloxy)-4-chloro-phenoxy]-2-phenyl-ethanol;
[2-(Azetidin-3-yloxy)-4-chloro-phenoxy]-phenyl-acetic acid;
(±)-3-[5-Chloro-2-(6-fluoro-indan-1-yl oxy)-phenoxy]-azetidine;
(±)-3-[5-Bromo-2-(indan-1-yloxy)-phenoxy]-azetidine;
(±)-3-[5-Bromo-2-(5-chloro-indan-1-yloxy)-phenoxy]-azetidine;
(±)-3-[5-Bromo-2-(6-chloro-indan-1-yloxy)-phenoxy]-azetidine;
(±)-3-[5-Bromo-2-(5-fluoro-indan-1-yloxy)-phenoxy]-azetidine;
(±)-3-[5-Bromo-2-(5-methyl-indan-1-yloxy)-phenoxy]-azetidine;
(±)-3-[5-Bromo-2-(6-methyl-indan-1-yloxy)-phenoxy]-azetidine;
(±)-3-[5-Bromo-2-(6-trifluoromethyl-indan-1-yloxy)-phenoxy]-azetidine;
(±)-3-[5-Chloro-2-(6-methyl-indan-1-yloxy)-phenoxy]-azetidine;
(±)-3-[5-Chloro-2-(6-chloro-indan-1-yloxy)-phenoxy]-azetidine;
3-[5-Chloro-2-(6-trifluoromethyl-indan-1-yloxy)-phenoxy]-azetidine;
3-[5-Chloro-2-(1,2,3,4-tetrahydro-naphthalen-1-yloxy)-phenoxy]-azetidine;
3-[5-Bromo-2-(5-tert-butyl-indan-1-yloxy)-phenoxy]-azetidine;
3-[5-Chloro-2-(tetrahydro-furan-3-ylmethoxy)-phenoxy]-azetidine;
3-[5-Chloro-2-(1,2,3,4-tetrahydro-naphthalen-2-yloxy)-phenoxy]-azetidine;
3-[5-Chloro-2-(chroman-2-ylmethoxy)-phenoxy]-azetidine;
3-[5-Chloro-2-(tetrahydro-furan-2-ylmethoxy)-phenoxy]-azetidine;
3-[5-Chloro-2-(chroman-3-ylmethoxy)-phenoxy]-azetidine;
3-[5-Chloro-2-(2-methoxy-2-phenyl-ethoxy)-phenoxy]-azetidine;
3-[5-Chloro-2-(2,3-dihydro-benzofuran-2-ylmethoxy)-phenoxy]-azetidine;
5-[2-(Azetidin-3-yloxy)-4-chloro-phenoxymethyl]-1,3-dimethyl-1H-pyrazole;
3-[5-Chloro-2-(2-phenoxy-ethoxy)-phenoxy]-azetidine;
3-[5-Bromo-2-(3-fluoro-benzyloxy)-phenoxy]-1-phenyl-azetidine;
3-[5-Chloro-2-(indan-2-yloxy)-phenoxy]-azetidine;
3-[5-Bromo-2-(indan-2-yloxy)-phenoxy]-azetidine;
3-[5-Chloro-2-(5-fluoro-indan-2-yloxy)-phenoxy]-azetidine;
3-[5-Chloro-2-(5-chloro-indan-2-yloxy)-phenoxy]-azetidine;
3-[5-Chloro-2-(5-methoxy-indan-2-yloxy)-phenoxy]-azetidin;
3-[5-Chloro-2-(4-methoxy-indan-2-yloxy)-phenoxy]-azetidine;
2-[2-(Azetidin-3-yloxy)-4-chloro-phenoxy]-indan-1-one oxime;
2-[2-(Azetidin-3-yloxy)-4-chloro-phenoxy]-indan-1-one O-methyl-oxime;
2-[2-(Azetidin-3-yloxy)-4-chloro-phenoxy]-1-phenyl-ethanone oxime;
2-[2-(Azetidin-3-yloxy)-4-chloro-phenoxy]-1-phenyl-ethanone O-methyl-oxime;
2-[2-(Azetidin-3-yloxy)-4-chloro-phenoxy]-1-(4-chloro-phenyl)-ethanone;
3-[5-Chloro-2-(2,2-difluoro-2-phenyl-ethoxy)-phenoxy]-azetidine;
3-[5-Chloro-2-[2-(3-chloro-phenyl)-ethoxy]-phenoxy]-azetidine;
3-[5-Chloro-2-(3-chloro-benzyloxy)-phenoxy]-azetidine;
3-[5-Chloro-2-(2-fluoro-2-phenyl-ethoxy)-phenoxy]-azetidine;
3-[5-Chloro-2-[1-(4-chloro-phenyl)-cyclobutylmethoxy]-phenoxy]-azetidine;

3-[5-Chloro-2-[1-(3-chloro-phenyl)-cyclobutylmethoxy]-phenoxy]-azetidine;
3-[5-Chloro-2-[2-(3-methoxy-phenyl)-ethoxy]-phenoxy]-azetidine;
3-[5-Chloro-2-[2-(3-fluoro-phenyl)-ethoxy]-phenoxy]-azetidine;
3-[5-Chloro-2-[2-(4-chloro-phenyl)-ethoxy]-phenoxy]-azetidine;
3-[5-Chloro-2-[2-(4-fluoro-phenyl)-ethoxy]-phenoxy]-azetidine;
3-[5-Chloro-2-[2-(4-methoxy-phenyl)-ethoxy]-phenoxy]-azetidine;
3-(5-Bromo-2-phenethyloxy-phenoxy)-azetidine;
3-(2-Benzyloxy-5-chloro-3-fluoro-phenoxy)-azetidine;
3-[5-Chloro-3-fluoro-2-(5-trifluoromethyl-furan-2-ylmethoxy)-phenoxy]-azetidin;
3-[5-Tri fluoromethyl-2-(5-trifluoromethyl-furan-2-ylmethoxy)-phenoxy]-azetidine;
3-[5-Trifluoromethyl-2-[1-(3-trifluoromethyl-phenyl)-ethoxy]-phenoxy]-azetidine;
3-[2-(1-Phenyl-ethoxy)-5-trifluoromethyl-phenoxy]-azetidine;
3-[2-(3-Chloro-benzyloxy)-5-fluoro-phenoxy]-azetidine;
3-[2-(3-Chloro-benzyloxy)-5-fluoro-phenoxy]-1-methyl-azetidine;
3-[2-(3-Chloro-benzyloxy)-5-fluoro-phenoxy]-1-isopropyl-azetidine;
3-[2-(3-Chloro-benzyloxy)-5-fluoro-phenoxy]-1-cyclobutyl-azetidine;
3-[2-(3-Chloro-benzyloxy)-5-fluoro-phenoxy]-1-propyl-azetidine;
3-[2-(3-Chloro-benzyloxy)-5-fluoro-phenoxy]-1-ethyl-azetidine;
3-[5-Fluoro-2-(5-trifluoromethyl-furan-2-ylmethoxy)-phenoxy]-azetidine;
3-[5-Fluoro-2-(5-trifluoromethyl-furan-2-ylmethoxy)-phenoxy]-1-isopropyl-azetidine;
3-(Azetidin-3-yloxy)-4-(3-chloro-benzyloxy)-N,N-dimethyl-benzamide;
3-[5-Bromo-2-(3-chloro-benzyloxy)-phenoxy]-3-methyl-azetidine;
3-[5-Bromo-2-(3-chloro-benzyloxy)-phenoxy]-3-ethyl-azetidine;
3-[5-Bromo-2-(3-chloro-benzyloxy)-phenoxy]-3-isopropyl-azetidine;
3-(5-Bromo-2-phenethyloxy-phenoxy)-3-methyl-azetidine;
3-[5-Bromo-2-(5-trifluoromethyl-furan-2-ylmethoxy)-phenoxy]-azetidine;
3-[5-Bromo-2-(3-trifluoromethyl-benzyloxy)-phenoxy]-azetidine;
3-(5-Bromo-2-phenoxy-phenoxy)-3-methyl-azetidine;
(±)-trans-3-[5-Bromo-2-(3-fluoro-benzyloxy)-phenoxy]-2-methyl-azetidine;
cis-1-Benzyl-3-[5-bromo-2-(3-fluoro-benzyloxy)-phenoxy]-2-methyl-azetidine;
trans-1-Benzyl-3-[5-bromo-2-(3-fluoro-benzyloxy)-phenoxy]-2-methyl-azetidine;
3-[5-Chloro-2-(1-phenyl-azetidin-3-ol)-phenoxy]-azetidine;
(±)-3-[5-Chloro-2-(trans-1-benzyl-2-methyl-azetidin-3-ol)-phenoxy]-azetidine;
3-[5-Chloro-2-(1-Isopropyl-azetidin-3-ol)-phenoxy]-azetidine;
3-[5-Chloro-2-(1-benzhydryl-azetidin-3-ol)-phenoxy]-azetidine;
3-[5-Chloro-2-(1-azetidin-3-ol)-phenoxy]-azetidine;
3-[5-Chloro-2-(1-Isopropyl-azetidin-3-ol)-phenoxy]-1-isopropyl-azetidine;
3-[5-Chloro-2-(3-phenyl-cyclobutoxy)-phenoxy]-azetidine;
3-[5-Bromo-2-(3-fluoro-benzyloxy)-phenoxy]-1-tert-butyl-azetidine;
1-tert-Butyl-3-[5-chloro-2-(3-trifluoromethyl-benzyloxy)-phenoxy]-azetidine
1-tert-Butyl-3-[5-chloro-2-[1-(3-trifluoromethyl-phenyl)-ethoxy]-phenoxy]-azetidine;
3-[5-Bromo-2-(5-trifluoromethyl-furan-2-ylmethoxy)-benzyl]-azetidine;
3-[5-Bromo-2-(3-chloro-benzyloxy)-phenoxymethyl]-azetidine;
3-[5-Bromo-2-(3-chloro-benzyloxy)-phenoxymethyl]-1-methyl-azetidine;
3-[5-Bromo-2-(3-chloro-benzyloxy)-phenoxymethyl]-azetidin-3-ol;
3-[1-[5-Bromo-2-(3-chloro-benzyloxy)-phenoxy]-ethyl]-azetidin-3-ol;
3-[5-Bromo-2-(3-chloro-benzyloxy)-benzyloxy]-azetidine;
3-[5-Chloro-2-(3-chloro-benzyloxy)-benzyloxy]-azetidine;
5-[2-(Azetidin-3-yloxy)-4-chloro-phenoxymethyl]-3-methyl-[1,2,4]oxadiazole;
5-[2-(Azetidin-3-yloxy)-4-chloro-phenoxymethyl]-3-cyclobutyl-[1,2,4]oxadiazole;
5-[2-(Azetidin-3-yloxy)-4-chloro-phenoxymethyl]-3-cyclopropyl-[1,2,4]oxadiazole;
5-[2-(Azetidin-3-yloxy)-4-chloro-phenoxymethyl]-3-isopropyl-[1,2,4]oxadiazole;
5-[2-(Azetidin-3-yloxy)-4-chloro-phenoxymethyl]-3-ethyl-[1,2,4]oxadiazole;
3-(5-Bromo-2-phenoxy-phenoxy)-azetidine;
3-[5-Bromo-2-(3-bromo-phenoxy)-phenoxy]-azetidine;
3-[5-Bromo-2-(3-fluoro-phenoxy)-phenoxy]-azetidine;
3-(5-Bromo-2-m-tolyloxy-phenoxy)-azetidine;
3-[5-Bromo-2-(3-methoxy-phenoxy)-phenoxy]-azetidine;
3-[5-Bromo-2-(4-fluoro-phenoxy)-phenoxy]-azetidine;
3-[5-Bromo-2-(4-bromo-phenoxy)-phenoxy]-azetidine;
3-[5-Bromo-2-(4-chloro-phenoxy)-phenoxy]-azetidine;
3-[5-Bromo-2-(4-chloro-phenoxy)-phenoxy]-azetidine;
3-[5-Bromo-2-(3-trifluoromethoxy-phenoxy)-phenoxy]-azetidine;
3-[5-Bromo-2-(naphthalen-2-yloxy)-phenoxy]-azetidine;
3-[5-Bromo-2-(naphthalen-1-yloxy)-phenoxy]-azetidine;
3-(5-Chloro-2-phenoxy-phenoxy)-azetidine;
3-[5-Chloro-2-(3-chloro-phenoxy)-phenoxy]-azetidine;
3-[5-Chloro-2-(4-chloro-phenoxy)-phenoxy]-azetidine;
3-(5-Chloro-2-o-tolyloxy-phenoxy)-azetidine;
3-[5-Chloro-2-(naphthalen-2-yloxy)-phenoxy]-azetidine;
2-[2-(Azetidin-3-yloxy)-4-chloro-phenoxy]-benzothiazole;
2-[2-(Azetidin-3-yloxy)-4-chloro-phenoxy]-benzooxazole;
2-[2-(Azetidin-3-yloxy)-4-chloro-phenoxy]-[1,8]naphthyridine;
2-[2-(Azetidin-3-yloxy)-4-chloro-phenoxy]-quinoline;
2-(Azetidin-3-yloxy)-4-bromo-phenyl]-phenyl-methanone;
[2-(Azetidin-3-yloxy)-4-bromo-phenyl]-(4-chloro-phenyl)-methanone;
[2-(Azetidin-3-yloxy)-4-bromo-phenyl]-(3-chloro-phenyl)-methanone;

[4-Bromo-2-(1-methyl-azetidin-3-yloxy)-phenyl]-(3-chloro-phenyl)-methanone;
[2-(Azetidin-3-yloxy)-4-bromo-phenyl]-m-tolyl-methanone;
[2-(Azetidin-3-yloxy)-4-bromo-phenyl]-o-tolyl-methanone;
[2-(Azetidin-3-yloxy)-4-bromo-phenyl]-(3-methoxy-phenyl)-methanone;
[2-(Azetidin-3-yloxy)-4-bromo-phenyl]-naphthalen-2-yl-methanone;
[4-Bromo-2-(1-isopropyl-azetidin-3-yloxy)-phenyl]-naphthalen-2-yl-methanone;
[2-(Azetidin-3-yloxy)-4-bromo-phenyl]-benzo[1,3]dioxol-5-yl-methanone;
Benzo[1,3]dioxol-5-yl-[4-bromo-2-(1-isopropyl-azetidin-3-yloxy)-phenyl]-methanone;
[2-(Azetidin-3-yloxy)-4-bromo-phenyl]-(4-methoxy-phenyl)-methanone;
[2-(Azetidin-3-yloxy)-4-bromo-phenyl]-(4-chloro-3-fluoro-phenyl)-methanone;
[2-(Azetidin-3-yloxy)-4-bromo-phenyl]-(3,4-dichloro-phenyl)-methanone;
[2-(Azetidin-3-yloxy)-4-chloro-phenyl]-naphthalen-2-yl-methanone;
[2-(Azetidin-3-yloxy)-4-chloro-phenyl]-benzo[1,3]dioxol-5-yl-methanone;
Benzo[1,3]dioxol-5-yl-[4-chloro-2-(1-isopropyl-azetidin-3-yloxy)-phenyl]-methanone;
[2-(Azetidin-3-yloxy)-4-chloro-phenyl]-(4-chloro-phenyl)-methanone; and
[2-(Azetidin-3-yloxy)-4-chloro-phenyl]-(3-chloro-phenyl)-methanone;

and pharmaceutically acceptable salts thereof.

21. A method of treating a subject suffering from or diagnosed with a disease, disorder selected from the group consisting of depression, anxiety, schizophrenia, bipolar disorders, Alzheimer's disease, Parkinson's disease, hypotension, peripheral vascular disorders, cardiovascular shock, renal disorders, gastric motility, diarrhea, spastic colon, irritable bowel disorders, ischemias, septic shock, urinary incontinence, glaucoma, optic neuritis, diabetic retinopathy, retinal edema, and age-related macular degeneration, comprising administering to the subject an effective amount of at least one agent selected from compounds of Formula (I) and pharmaceutically acceptable salts of said compounds of Formula (I):

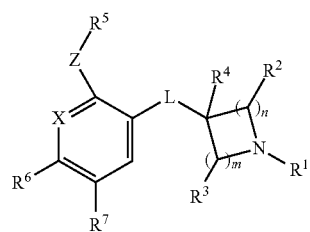

(I)

wherein
$R^1$ is —H, —$C_{1-4}$alkyl, monocyclic cycloalkyl, phenyl, or benzyl;
m is 1;
n is 1;
$R^2$ and $R^3$ are each independently —H or —$C_{1-4}$alkyl;
$R^4$ is —H, F, $C_{1-4}$alkyl, or $R^4$ is —OH when L is —$CH_2$—, —$CF_2$—, —CHF—, —$OCH_2$—, or —$OCH(CH_3)$—;
L is —O—, —$CH_2$—, —$OCH_2$—, —$OCH(CH_3)$—, —$CH_2O$—, —$CF_2$—, or —CHF—;
Z is —O—, —C(O)—, —$OCH(R^b)$—, or —$OCH_2C(R^c)(R^d)$—;
  where
    where $R^b$ is —H; a —$C_{1-4}$alkyl group unsubstituted or substituted with OH or halo; —$CO_2C_{1-4}$alkyl; or —$CO_2H$; and
    $R^c$ and $R^d$ are each independently —H, —$C_{1-4}$alkyl, —O—$C_{1-4}$alkyl, or halo;
    or $R^c$ and $R^d$ taken together form an oxime, a $C_{1-4}$alkyl oxime, or a carbonyl group;
    or $R^c$ and $R^d$ taken together with the carbon to which they are attached form a $C_{3-6}$cycloalkyl group;
$R^5$ is:
  i) a phenyl, unsubstituted or substituted with one, two, or three $R^g$ substituents;
    where each $R^g$ substituent is selected from the group consisting of: —$C_{1-6}$alkyl, —OH, —$OC_{1-6}$alkyl, —CN, —$NO_2$, —$C(O)C_{1-6}$alkyl, —$S(O)_{0-2}$—$C_{1-6}$alkyl, —$OS(O)_{0-2}$—$C_{1-6}$alkyl, —$SO_2CF_3$, —$SCF_3$, halo, —$CF_3$, —$OCF_3$, —$CO_2H$, —$CO_2C_{1-6}$alkyl, —$CH_2OH$, monocyclic cycloalkyl, phenyl, thiophenyl, benzhydryl, and oxadiazolyl;
    or two $R^g$ substituents taken together form —$OCH_2O$—, —$OCF_2O$—, or —$OCH_2CH_2O$—;
  ii) a naphthyl group, unsubstituted or substituted with $C_{1-4}$alkyl or halo;
  iii) a monocyclic heteroaryl group, unsubstituted or substituted with one, two, or three $R^g$ substituents;
  iv) a fused bicyclic heteroaryl group, unsubstituted or substituted with $C_{1-4}$alkyl or halo;
  v) a monocyclic cycloalkyl group, optionally fused to a phenyl ring, and unsubstituted or substituted with one or two substituents selected from the group consisting of: —$C_{1-4}$alkyl, —$OC_{1-4}$alkyl, halo, —$CF_3$, oxime, —$C_{1-4}$alkyl oxime, or phenyl; and
  vi) a monocyclic heterocycloalkyl group, optionally fused to or substituted with phenyl;
X is C;
$R^6$ or $R^7$ are each independently —H, halo, —$CF_3$, or —$C(O)N(R^x)R^y$;
wherein $R^x$ and $R^y$ are each independently —H or —$C_{1-4}$alkyl;
and (b) pharmaceutically acceptable salts of the compounds of Formula (I).

* * * * *